US010940051B2

(12) United States Patent
Gross et al.

(10) Patent No.: US 10,940,051 B2
(45) Date of Patent: Mar. 9, 2021

(54) ABSORBENT ARTICLES WITH COLOR EFFECTS

(71) Applicant: The Procter & Gamble Company, Cincinnati, OH (US)

(72) Inventors: Sarah Beth Gross, Harrison, OH (US); Stephanie Niezgoda Moss, Cincinnati, OH (US); Kelyn Anne Arora, Cincinnati, OH (US); John Lee Hammons, Hamilton, OH (US)

(73) Assignee: The Procter & Gamble Company, Cincinnati, OH (US)

(*) Notice: Subject to any disclaimer, the term of this patent is extended or adjusted under 35 U.S.C. 154(b) by 565 days.

(21) Appl. No.: 14/933,017

(22) Filed: Nov. 5, 2015

(65) Prior Publication Data

US 2016/0278986 A1    Sep. 29, 2016

Related U.S. Application Data

(60) Provisional application No. 62/190,000, filed on Jul. 8, 2015, provisional application No. 62/076,043, filed on Nov. 6, 2014.

(51) Int. Cl.
*A61F 13/15* (2006.01)
*A61F 13/537* (2006.01)
(Continued)

(52) U.S. Cl.
CPC ........ *A61F 13/15203* (2013.01); *A61F 13/47* (2013.01); *A61F 13/513* (2013.01);
(Continued)

(58) Field of Classification Search
CPC ............... A61F 13/15203; A61F 13/47; A61F 13/51104; A61F 13/513; A61F 13/51394;
(Continued)

(56) References Cited

U.S. PATENT DOCUMENTS 4,324,246 A    4/1982 Mullane et al.
4,629,643 A    12/1986 Curro et al.
(Continued)

FOREIGN PATENT DOCUMENTS

CN    1729097 A    2/2006
CN    2897211       5/2007
(Continued)

OTHER PUBLICATIONS

Search Report and Written Opinion for PCT/US2015/059202 dated Nov. 5, 2015.

*Primary Examiner* — Michele M Kidwell
(74) *Attorney, Agent, or Firm* — George H. Leal

(57) ABSTRACT

Disposable absorbent articles having color effects and materials thereof are disclosed. Disposable absorbent articles include a topsheet; a backsheet; an absorbent core between the topsheet and the backsheet; and a layer between the absorbent core and the topsheet. The topsheet has a generally planar first surface having a plurality of out-of-plane features and a first color. The layer has a second color. And, the plurality of out-of-plane features have a feature color different than the first color and the second color.

22 Claims, 112 Drawing Sheets
(51 of 112 Drawing Sheet(s) Filed in Color)

(51) Int. Cl.
  *A61F 13/511* (2006.01)
  *A61F 13/513* (2006.01)
  *A61F 13/47* (2006.01)
  *A61F 13/84* (2006.01)

(52) U.S. Cl.
  CPC .. *A61F 13/51104* (2013.01); *A61F 13/51394* (2013.01); *A61F 13/537* (2013.01); *A61F 13/84* (2013.01); *A61F 2013/15243* (2013.01); *A61F 2013/51377* (2013.01); *A61F 2013/8497* (2013.01)

(58) Field of Classification Search
  CPC ............ A61F 13/84; A61F 2013/15243; A61F 2013/51377; A61F 2013/8497; A61F 13/537
  See application file for complete search history.

(56) References Cited

U.S. PATENT DOCUMENTS

| | | | |
|---|---|---|---|
| 4,741,941 A | 5/1988 | Englebert et al. | |
| 4,780,352 A | 10/1988 | Palumbo | |
| 4,801,494 A | 1/1989 | Datta et al. | |
| 4,834,735 A | 5/1989 | Alemany et al. | |
| 4,840,829 A | 6/1989 | Suzuki et al. | |
| 4,950,264 A * | 8/1990 | Osborn, III | A61F 13/15203 604/385.08 |
| H1377 H | 11/1994 | Perry | |
| 5,437,653 A | 8/1995 | Gilman et al. | |
| 5,536,555 A | 7/1996 | Zelazoski et al. | |
| 5,628,097 A | 5/1997 | Benson et al. | |
| 5,660,788 A | 8/1997 | Gray et al. | |
| 5,704,101 A | 1/1998 | Majors et al. | |
| H1732 H | 6/1998 | Johnson | |
| 5,824,352 A | 10/1998 | Yang et al. | |
| 5,895,380 A | 4/1999 | Turi et al. | |
| 5,916,661 A | 6/1999 | Benson et al. | |
| 5,968,025 A * | 10/1999 | Roe | A61F 13/8405 604/364 |
| 5,998,696 A | 12/1999 | Schone | |
| 6,015,936 A | 1/2000 | Takai et al. | |
| 6,093,871 A | 7/2000 | Takai et al. | |
| 6,114,595 A | 9/2000 | Moore et al. | |
| 6,117,524 A | 9/2000 | Hisanaka et al. | |
| 6,228,462 B1 | 5/2001 | Lee et al. | |
| 6,410,823 B1 | 6/2002 | Daley et al. | |
| 6,468,626 B1 | 10/2002 | Takai et al. | |
| 6,479,130 B1 | 11/2002 | Takai et al. | |
| 6,610,391 B2 | 8/2003 | Molee | |
| 6,632,504 B1 | 10/2003 | Gillespie et al. | |
| 6,676,646 B2 | 1/2004 | Bast et al. | |
| 6,719,742 B1 | 4/2004 | McCormack et al. | |
| 6,780,270 B2 | 8/2004 | Andersson | |
| 6,849,319 B2 | 2/2005 | Cree et al. | |
| 6,932,798 B2 | 8/2005 | Kudo et al. | |
| 7,005,558 B1 | 2/2006 | Johansson et al. | |
| 7,033,340 B1 | 4/2006 | Muscat et al. | |
| 7,118,639 B2 | 10/2006 | DeLucia et al. | |
| 7,371,919 B1 | 5/2008 | Busam et al. | |
| 8,022,267 B2 | 9/2011 | Hellstrom et al. | |
| 8,186,296 B2 | 5/2012 | Brown et al. | |
| 8,226,625 B2 | 7/2012 | Turner et al. | |
| 8,226,626 B2 | 7/2012 | Turner et al. | |
| 8,231,595 B2 | 7/2012 | Turner et al. | |
| 8,251,965 B2 * | 8/2012 | Costea | A61F 13/42 604/361 |
| 8,324,444 B2 | 12/2012 | Hansson et al. | |
| 8,387,530 B2 | 3/2013 | Larson et al. | |
| 8,388,594 B2 | 3/2013 | Turner et al. | |
| 2001/0005540 A1 | 6/2001 | Hisanaka et al. | |
| 2001/0053901 A1 | 12/2001 | Mizutani et al. | |
| 2002/0013563 A1 | 1/2002 | Lassen et al. | |
| 2002/0028624 A1 | 3/2002 | Mizutani et al. | |
| 2002/0062113 A1 | 5/2002 | Thomas et al. | |
| 2002/0062115 A1 | 5/2002 | Wada et al. | |
| 2003/0003269 A1 | 1/2003 | Lee et al. | |
| 2003/0004481 A1 | 1/2003 | Matsuoka et al. | |
| 2003/0021951 A1 | 1/2003 | Desai et al. | |
| 2003/0109839 A1 | 6/2003 | Costea et al. | |
| 2003/0145517 A1 | 8/2003 | Miller | |
| 2003/0149412 A1 | 8/2003 | Damaghi et al. | |
| 2003/0187415 A1 * | 10/2003 | Kudo | A61F 13/15203 604/367 |
| 2004/0043189 A1 | 3/2004 | Huang | |
| 2004/0092902 A1 | 5/2004 | Hoffman et al. | |
| 2004/0118811 A1 | 6/2004 | Stone et al. | |
| 2004/0122396 A1 | 6/2004 | Maldonado et al. | |
| 2004/0127128 A1 | 7/2004 | Thomas | |
| 2004/0127875 A1 | 7/2004 | Hammons et al. | |
| 2004/0161586 A1 | 8/2004 | Cree et al. | |
| 2004/0162536 A1 | 8/2004 | Becker et al. | |
| 2004/0170813 A1 * | 9/2004 | Digiacomantonio | A61F 13/511 428/195.1 |
| 2004/0181199 A1 | 9/2004 | Moberg-Alehammar et al. | |
| 2004/0209042 A1 | 10/2004 | Peacock | |
| 2005/0027270 A1 | 2/2005 | Cree et al. | |
| 2005/0096614 A1 | 5/2005 | Perez et al. | |
| 2005/0103434 A1 | 5/2005 | Andersson et al. | |
| 2005/0143699 A1 | 6/2005 | Linder | |
| 2005/0148971 A1 | 7/2005 | Kuroda et al. | |
| 2005/0202208 A1 | 9/2005 | Kelly | |
| 2005/0244619 A1 | 11/2005 | Kauschke et al. | |
| 2005/0256475 A1 | 11/2005 | Komatsu et al. | |
| 2005/0288647 A1 | 12/2005 | Ellingson et al. | |
| 2006/0019063 A1 | 1/2006 | Kelly | |
| 2006/0069361 A1 | 3/2006 | Olson | |
| 2006/0141885 A1 | 6/2006 | Cobbs et al. | |
| 2007/0048498 A1 | 3/2007 | Cree | |
| 2007/0073254 A1 | 3/2007 | Ponomarenko et al. | |
| 2007/0088307 A1 | 4/2007 | Arizti et al. | |
| 2007/0135787 A1 | 6/2007 | Raidel et al. | |
| 2007/0191802 A1 * | 8/2007 | Gubernick | A61F 13/472 604/385.01 |
| 2007/0256286 A1 | 11/2007 | Ngai | |
| 2008/0138574 A1 | 6/2008 | Maschino et al. | |
| 2008/0294135 A1 | 11/2008 | Hara et al. | |
| 2008/0294138 A1 | 11/2008 | Andersson et al. | |
| 2008/0312622 A1 | 12/2008 | Hundorf et al. | |
| 2009/0030390 A1 | 1/2009 | Hammons et al. | |
| 2009/0030391 A1 | 1/2009 | Hammons et al. | |
| 2009/0082746 A1 | 3/2009 | Thomas et al. | |
| 2009/0104831 A1 | 4/2009 | Bornemann et al. | |
| 2009/0131896 A1 | 5/2009 | Ebitsuka et al. | |
| 2009/0233046 A1 | 9/2009 | Iulianetti | |
| 2009/0247978 A1 | 10/2009 | Boissier | |
| 2009/0299316 A1 | 12/2009 | Seyler | |
| 2010/0004615 A1 | 1/2010 | Boissier | |
| 2010/0019415 A1 | 1/2010 | Stone et al. | |
| 2010/0035014 A1 | 2/2010 | Hammons et al. | |
| 2010/0036338 A1 | 2/2010 | Hammons et al. | |
| 2010/0036346 A1 | 2/2010 | Hammons et al. | |
| 2010/0130952 A1 | 5/2010 | Murai | |
| 2010/0196653 A1 | 8/2010 | Curro et al. | |
| 2010/0233438 A1 * | 9/2010 | Stone | B26F 1/26 428/172 |
| 2010/0280471 A1 | 11/2010 | Shah | |
| 2010/0330326 A1 | 12/2010 | Turner et al. | |
| 2011/0087185 A1 | 4/2011 | Wohlke et al. | |
| 2011/0106036 A1 | 5/2011 | Stahl et al. | |
| 2011/0184370 A1 | 7/2011 | Seyler et al. | |
| 2011/0264064 A1 * | 10/2011 | Arora | A61F 13/51496 604/367 |
| 2011/0305870 A1 | 12/2011 | Curro et al. | |
| 2012/0003423 A1 | 1/2012 | Cree | |
| 2012/0095426 A1 | 4/2012 | Visscher et al. | |
| 2012/0150136 A1 | 6/2012 | Ueminami et al. | |
| 2012/0177886 A1 * | 7/2012 | Kanya | A61F 13/51476 428/156 |
| 2012/0296304 A1 | 11/2012 | Choo et al. | |
| 2012/0323204 A1 | 12/2012 | Poole et al. | |
| 2013/0012898 A1 | 1/2013 | Bergendahl et al. | |
| 2013/0178811 A1 | 7/2013 | Kikuchi et al. | |

(56) References Cited

U.S. PATENT DOCUMENTS

| | | | |
|---|---|---|---|
| 2014/0087130 A1 | 3/2014 | Seyler et al. | |
| 2014/0148774 A1 | 5/2014 | Brown et al. | |
| 2014/0151934 A1 | 6/2014 | Thomas et al. | |
| 2014/0163500 A1 | 6/2014 | Roe et al. | |
| 2014/0163506 A1 | 6/2014 | Roe et al. | |
| 2014/0163511 A1 | 6/2014 | Roe et al. | |
| 2014/0228795 A1* | 8/2014 | Castanares | A61F 13/51394 604/385.01 |
| 2014/0324009 A1 | 10/2014 | Lee et al. | |
| 2014/0336605 A1 | 11/2014 | Hardie et al. | |
| 2017/0151103 A1* | 6/2017 | Bianchi | A61F 13/51394 |

FOREIGN PATENT DOCUMENTS

| | | | | |
|---|---|---|---|---|
| CN | 201505226 | | 6/2010 | |
| CN | 201618014 | | 11/2010 | |
| CN | 201855363 | | 6/2011 | |
| CN | 101940514 B | | 12/2013 | |
| DE | 2806401 | | 8/1979 | |
| DE | 19647459 A1 | | 5/1998 | |
| DE | 19846857 C1 | | 10/1998 | |
| EP | 0165807 A1 | | 12/1985 | |
| EP | 0359501 A2 | | 3/1990 | |
| EP | 0495212 A1 | | 7/1992 | |
| EP | 0535579 A1 | | 4/1993 | |
| EP | 0589224 A1 | | 3/1994 | |
| EP | 0545423 B1 | | 8/1997 | |
| EP | 0934737 A1 | | 8/1999 | |
| EP | 0749737 B1 | | 11/1999 | |
| EP | 0749738 B1 | | 11/1999 | |
| EP | 0749736 B1 | | 1/2000 | |
| EP | 0983758 A1 | | 3/2000 | |
| EP | 0749739 B1 | | 11/2000 | |
| EP | 1086676 A1 | | 3/2001 | |
| EP | 0749740 B1 | | 12/2001 | |
| EP | 1022007 B1 | | 3/2006 | |
| EP | 2227385 A1 | | 9/2010 | |
| EP | 2347872 A3 | | 1/2015 | |
| GB | 2103933 B | | 9/1985 | |
| GB | 2225724 B | | 7/1992 | |
| GB | 2284384 | * | 6/1995 | B32B 7/14 |
| GB | 2296464 A | | 7/1996 | |
| GB | 2310606 B | | 9/1999 | |
| JP | 06038818 | | 2/1994 | |
| JP | 2587116 B2 | | 3/1997 | |
| JP | H10272152 | | 10/1998 | |
| JP | 2006181294 A | | 7/2006 | |
| JP | 4919759 A | | 4/2008 | |
| JP | 2010269029 | | 12/2010 | |
| JP | 2011135979 | | 7/2011 | |
| JP | 2011239835 | | 12/2011 | |
| JP | 2012050548 A2 | | 3/2012 | |
| KR | 20010064584 A | | 7/2001 | |
| WO | WO199110415 A2 | | 7/1991 | |
| WO | WO199311726 A1 | | 6/1993 | |
| WO | WO199315701 A1 | | 8/1993 | |
| WO | WO199513773 A1 | | 5/1995 | |
| WO | WO199610481 A1 | | 4/1996 | |
| WO | WO199611107 A1 | | 4/1996 | |
| WO | WO199619313 A1 | | 6/1996 | |
| WO | WO199702133 A2 | | 1/1997 | |
| WO | WO199703818 A1 | | 2/1997 | |
| WO | WO200001334 A1 | | 1/2000 | |
| WO | WO200037249 A1 | | 1/2000 | |
| WO | WO200028929 A1 | | 5/2000 | |
| WO | WO2000062826 A1 | | 10/2000 | |
| WO | WO200172251 A1 | | 10/2001 | |
| WO | WO2002007662 A1 | | 1/2002 | |
| WO | WO2002100632 A1 | | 12/2002 | |
| WO | WO2003015681 A1 | | 2/2003 | |
| WO | WO2003071019 A1 | | 8/2003 | |
| WO | WO2004009009 A1 | | 1/2004 | |
| WO | WO2004098474 A1 | | 11/2004 | |
| WO | WO2005095713 A1 | | 10/2005 | |
| WO | WO2010017353 A1 | | 2/2010 | |
| WO | WO2011000419 A1 | | 1/2011 | |
| WO | WO2012051467 A1 | | 4/2012 | |
| WO | WO2012052172 A1 | | 4/2012 | |
| WO | WO2012129026 A1 | | 9/2012 | |
| WO | 2016/065503 A1 | * | 5/2016 | A61F 13/511 |
| WO | 2017/082834 A1 | * | 5/2017 | A61F 13/513 |

* cited by examiner

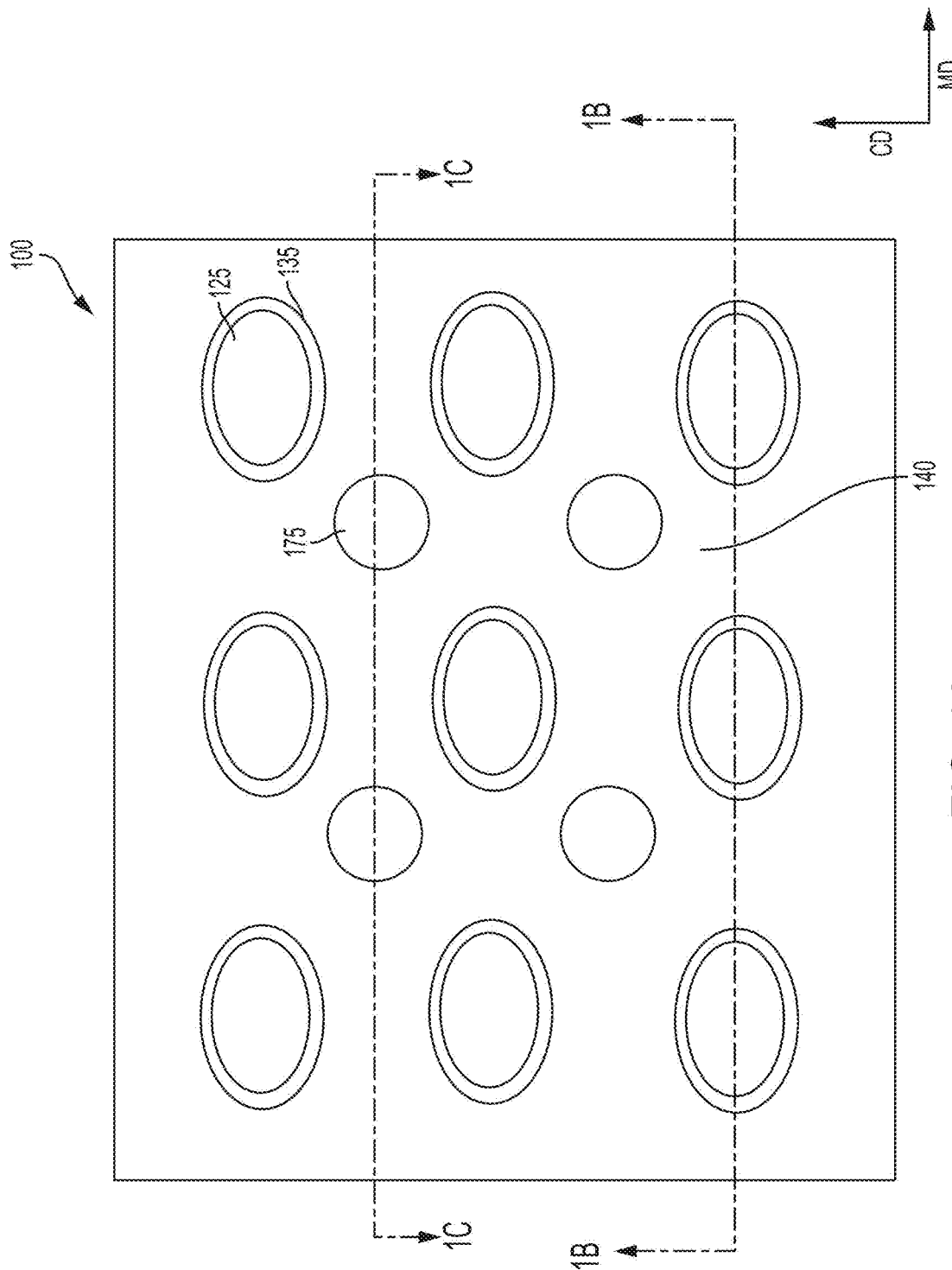

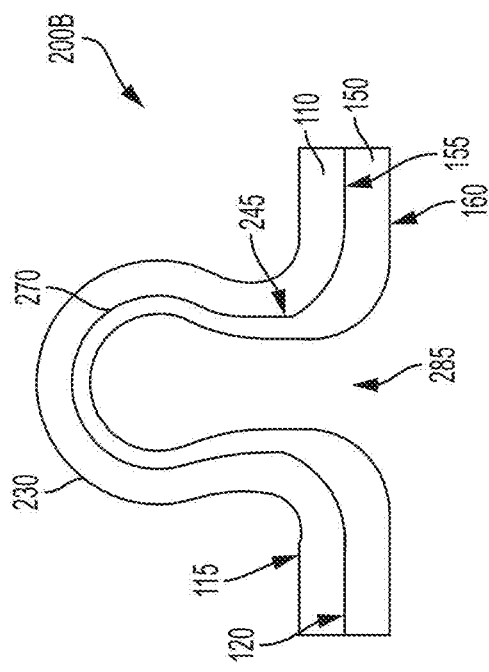
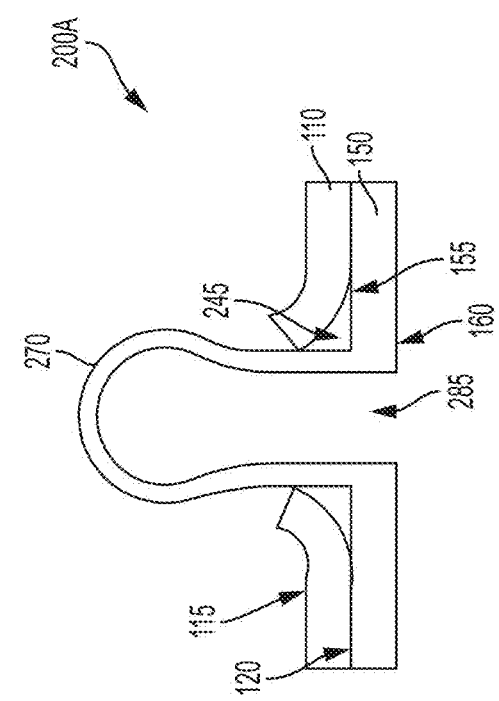
FIG. 2B
FIG. 2A

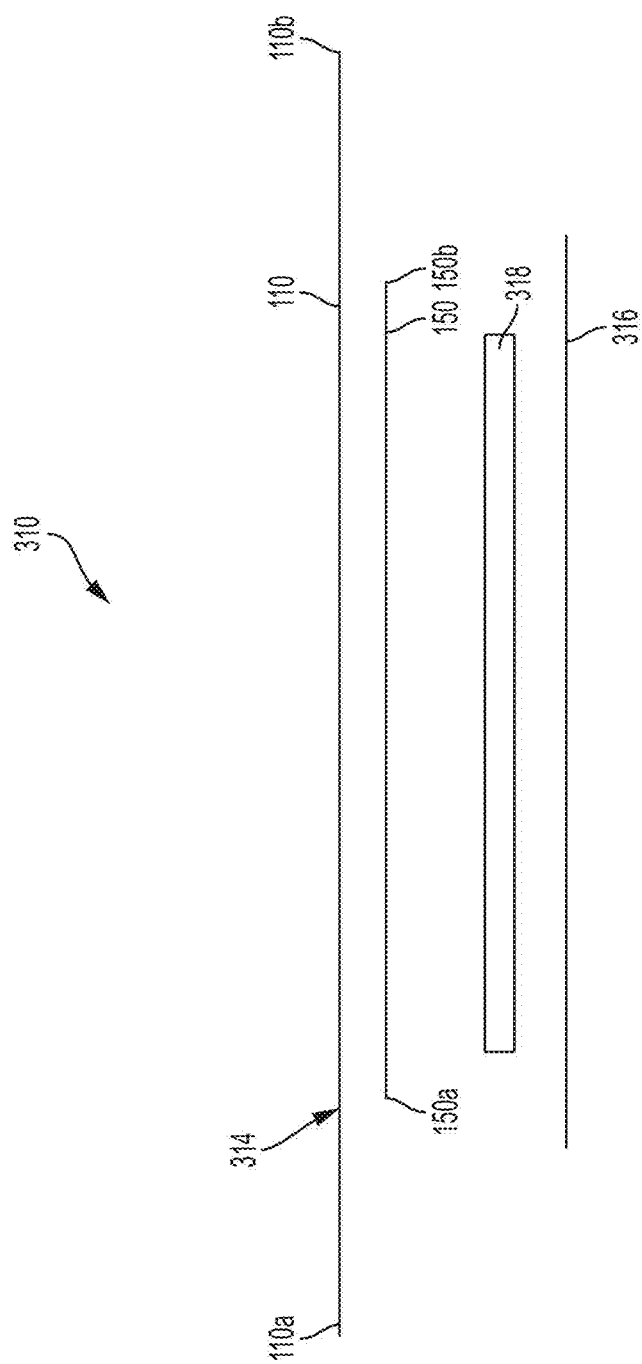

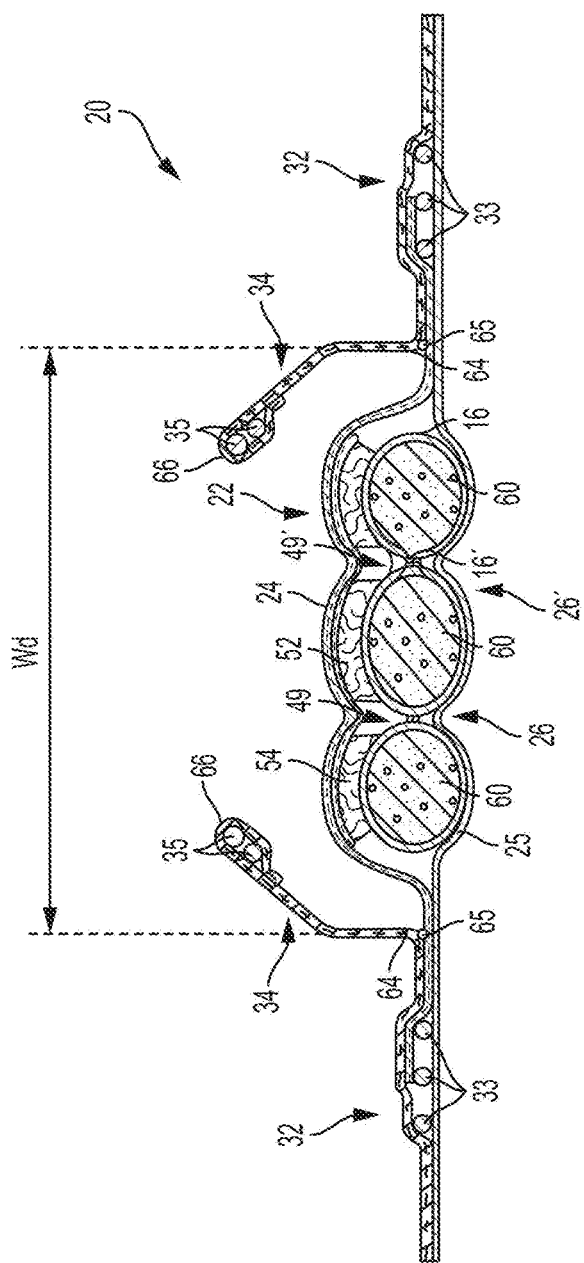

ABSORBENT ARTICLES WITH COLOR EFFECTS

FIELD OF THE INVENTION

The disclosure herein relates generally to disposable absorbent articles exhibiting color effects.

BACKGROUND OF THE INVENTION

Many disposable absorbent articles currently on the market include printing, graphics or other indicia which can provide assistance to a user in donning the article, e.g. indication of front versus rear of the article. Additionally, printing can sometimes be used to highlight areas of the absorbent article which would otherwise not be noticed by the user. For example, printing can be used to highlight areas of an absorbent core which have enhanced absorbency capability. Printing can even be used to highlight features of the absorbent article which may or may not otherwise be visible, e.g. apertures. However, highlighting these features can introduce manufacturing complexities, i.e. registration. In general, causing printing or color on the absorbent article to coincide with a desired feature can be difficult—particularly at high processing speeds.

Based on the foregoing, there is a need for a material and process which facilitates registration of color effects as well as a need for features which can enhance the experience of a user.

SUMMARY OF THE INVENTION

Disclosed herein are webs/laminates and disposable absorbent articles having visible color effects. Disposable absorbent articles of the present invention may comprise colorants on one or more layers of the disposable absorbent article. Such colored layers or other layers of the disposable absorbent article may be mechanically manipulated to provide visible color effects derived from the colorant on the one or more layers. Suitable materials for such visible color effects include single layer materials of nonwoven or film; laminates of nonwoven and film, laminates of film layers, laminates of films and nonwovens. These laminates may comprise more than two layers of material. When the materials of the present invention are utilized as a topsheet of a feminine hygiene article, they may provide a good masking benefit.

In those forms of the present invention where the disposable absorbent article comprises a laminate, the laminate may comprise a first layer having a first color and a second layer having a second color. In some forms, the first color and the second color are different. In other forms, the first color and the second color may be the same color. In addition to the preceding, disposable absorbent articles of the present disclosure may also comprise patterns of apertures, patterns of tufts, patterns of bonds and/or printing patterns are disclosed herein. Each of these patterns may be coordinated with one another as described herein.

In some forms, a disposable absorbent article comprises: a topsheet having a generally planar first surface comprising a plurality of out-of-plane features and wherein the topsheet has a first color; a backsheet; an absorbent core disposed between the topsheet and the backsheet; and a layer disposed between the topsheet and the absorbent core, the layer comprising a second color. The plurality of out-of-plane features have a feature color different than the first color and the second color.

In some forms, a disposable absorbent article comprises: a topsheet having a first color; a backsheet; an absorbent core disposed between the topsheet and the backsheet; a layer disposed between the topsheet and the absorbent core, the layer comprising a second color; and at least two of the following: a plurality of apertures having an aperture color which is different than the first color and the second color; a plurality of melt lips comprising a melt lip color different than the first color and the second color, a plurality of out-of-plane features comprising a feature color different than the first color and the second color, a plurality of bond sites comprising a bond color which is different than the first color and the second color, an embossed area comprising an embossed color which is different than the first color and the second color, or wing color which is different than the first color and the second color.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

While the specification concludes with claims particularly pointing out and distinctly claiming the subject matter of the present invention, it is believed that the invention can be more readily understood from the following description taken in connection with the accompanying drawings, in which:

FIG. 1A is a schematic representation of a laminate of the present invention shown in plan view;

FIG. 2A is a schematic representation of a laminate of the present invention shown in cross section;

FIG. 2B is a schematic representation of a laminate of the present invention shown in cross section;

FIG. 3B is an exploded cross section of the feminine hygiene article of FIG. 3A;

FIG. 6 is a view of the absorbent article of FIG. 5 where the absorbent article has been at least partially loaded with fluid in accordance with the present disclosure;

DETAILED DESCRIPTION OF THE INVENTION

Figure 1B:
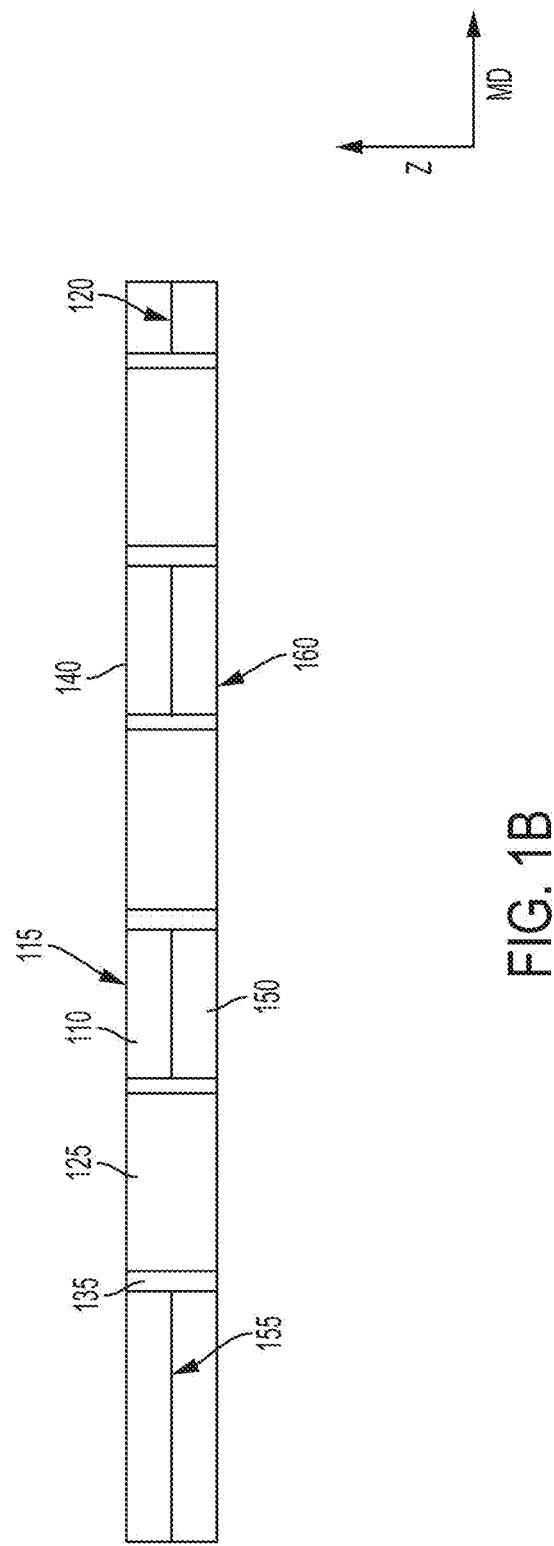
FIG. 1B is a schematic representation of the laminate of FIG. 1A shown in cross section along line 1B-1B.

The present invention pertains to disposable absorbent articles having color effects. Constituent portions of the disposable absorbent articles can be mechanically manipulated to provide a plurality of color effects. In this regard, features of the absorbent article may be highlighted.

Constituent portions of disposable absorbent articles can include a topsheet, a backsheet, and an absorbent core disposed between the topsheet and the backsheet. Additional layers may be disposed between the topsheet and the absorbent core and/or between the backsheet and the absorbent core. In some forms of the present disclosure, the topsheet may be manipulated to produce the color effects described herein. In some forms, the backsheet may be manipulated to produce the color effects. In other forms, a layer between the topsheet and the absorbent core may be manipulated to provide the color effects. In some particular forms of the present disclosure, combinations of portions may be manipulated. For example, a topsheet and the layer between the topsheet and the absorbent core may be manipulated in combination to provide color effects. In some forms, constituent portions of the absorbent article may also comprise barrier leg cuffs.

Portions of the absorbent articles, e.g. topsheet, backsheet, absorbent core, barrier leg cuffs, additional layers (disposed between topsheet and backsheet) may comprise a variety of materials. In some forms of the present invention, for example, topsheets, may comprise a laminate structure. The laminate structure may comprise a plurality of nonwoven layers, a plurality of film layers, or a combination thereof. Backsheets, barrier leg cuffs, and/or additional layers (disposed between the topsheet and backsheet) may be configured similarly.

For the production of color effects, two adjacent layers within an absorbent article may comprise a first material layer and a second material layer. At least one of the first material layer and the second material layer comprise printed ink and/or pigment(s) in and/or on the layer. Mechanical manipulation of the first layer and/or second layer can produce color effects which correspond to the mechanical manipulation and in effect register the color effects with the mechanical manipulation. Examples of two adjacent layers in absorbent articles include a topsheet and an acquisition layer; a topsheet and a secondary topsheet, a topsheet and a distribution layer; a topsheet and a dusting layer; a topsheet and an absorbent core; a topsheet and a backsheet outboard of the absorbent core; a backsheet and an absorbent core, a backsheet and a distribution layer; and a backsheet and a layer between the absorbent core and backsheet.

A topsheet for example, may comprise a colorant in the form of printed ink and/or pigment(s) such that the topsheet comprises a first color. Mechanical manipulation of the material of the topsheet can produce a variety of color effects as provided herein such that the topsheet comprises additional colors which are different than the first color. In other forms, a layer disposed between the topsheet and the absorbent core may comprise a colorant in the form of printed ink and/or pigment(s) and the topsheet may be a color different than that of the layer. Mechanical manipulation of the topsheet and the layer can produce a variety of color effects as provided herein. Similarly, mechanical manipulation of the topsheet alone or the layer alone may produce a variety of color effects. Still in other forms, the topsheet may comprise a laminate structure having a first layer and a second layer. The first layer and/or second layer may comprise a color in the form of printed ink and/or pigment(s). Mechanical manipulation of the laminate can produce a variety of color effects as provided herein. The layers of the laminate structure may comprise different colors. For example, a first layer may comprise a first color and a second layer a second color, wherein the first color and the second color are different. Mechanical manipulation of the laminate structure may produce a variety of color effects as provided herein. In some forms of the present invention, absorbent articles may comprise backsheets, barrier leg cuffs, and/or additional layers (disposed between the topsheet and the backsheet) configured similarly.

Portions of the absorbent article may be mechanically manipulated as described herein. The mechanical manipulations can create visible color differences in the areas of manipulation. For example, webs/laminates, and subsequently absorbent articles incorporating the webs/laminates, may exhibit a plurality of colors in addition to those of the first color and the second color because of the mechanical manipulations. As another example, mechanical manipulations of the webs/laminates of the present invention can create color effects with regard to printing.

"Absorbent articles" as referred to herein can be diapers, including taped diapers—refastenable; diaper pants—prefastened refastenable or pre-fastened non-refastenable; feminine sanitary napkins/pads; adult incontinence products, e.g. pants or pads; baby wipes, sanitary wipes, cleansing wipes, tampons, and/or the like. Absorbent articles can be disposable absorbent articles. Hereafter, the terms "sanitary pad" or "sanitary pads" are used for the sake of convenience; however, such terms serve as a proxy for absorbent articles unless otherwise noted. The term "absorbent article" also encompasses cleaning or dusting pads or substrates that have some absorbency.

The term "color" as referred to herein includes any primary color, i.e., white, black, red, blue, violet, orange, yellow, green, and indigo as well as any declination thereof or mixture thereof. The term "color" includes conventional white (defined below) unless otherwise noted. "Conventional white" is further defined as those colors having an $L^*$ value of at least 80, can a $a^*$ value equal to $0\pm 2$, and a $b^*$ value equal to $0\pm 3$.

Absorbent articles of the present disclosure may comprise a plurality of portions as disclosed above. And, each of the portions, e.g. topsheet, backsheet, barrier leg cuffs may comprise a plurality of features. Some exemplary features include tufts, apertures, aperture perimeters, e.g. melt lips, bond sites, embossed areas, and land areas, and, where the absorbent articles include sanitary pads, wings. In some forms of the present invention, with sufficient color contrast between a first layer and an adjacent second layer in an absorbent article, color effects can be created with regard to each of the above features or with a few of the above. For example, a $\Delta E^*$ of 25 or greater between the first color and the second color of a first layer and a second layer, respectively, may produce color differences for each of the above features with respect to each other. And, in some forms a $\Delta E^*$ of 10 or greater may provide visibly distinct differences among/between a plurality of features. Additionally, where these features coincide with printing, visible color effects can also occur. In some forms, a $\Delta E^*$ between the first color and the second color may be about 3 to about 10, from about 5 to about 15, from about 7 to about 20, from about 10 to about 25 or as noted above greater than about 25 including all values within these ranges and any ranges created thereby.

For the purposes of this application, a visible color effects shall have a $\Delta E^*=2.5$ or greater. Samples and data of some exemplary laminates are discussed hereafter. While laminates are discussed throughout the specification, as noted above, forms of the present invention are contemplated where portions of an absorbent article, e.g. topsheet, backsheet, barrier leg cuffs, combinations thereof, etc., are configured as single layers/single webs rather than laminates. As such, many of the color effects described herein may be achieved via the utilization of a single layer/single web in a similar manner to the effect achieved by a laminate unless otherwise expressed. The laminates/webs of the present invention may be utilized as any component of a disposable absorbent article.

Color Features

Referring to FIGS. 1A-1E, laminates/webs of the present invention have a machine direction (MD), a cross machine direction (CD), and a Z direction, as is commonly known in the art of web manufacture. Each of the at least two material layers are referred to herein as generally planar, two-dimensional webs. While the primary discussion herein centers around laminates comprising a first layer and second layer, similar visible effects as described herein may be achieved where the first layer and second layer are adjacent layers in an absorbent article and not necessarily a laminate structure.

FIGS. 1A and 1B show a laminate 100 of the present invention. The laminate 100 comprises a first layer 110 having a first surface 115 and a second surface 120, each of which are generally planar. The laminate 100 further comprises a second layer 150 having a first surface 155 and a second surface 160 each of which are generally planar. The first surfaces 115 and 155 of the first layer 110 and the second layer 150, respectively, can be body-facing surfaces and the second surfaces 120 and 160 of the first layer 110 and the second layer 150, respectively, can be garment-facing surfaces.

As noted previously, the first layer 110 comprises a first color and the second layer 150 comprises a second color. In some forms of the present invention, the first color and the second color may be different. In some forms, first layer may be conventional white while the second layer comprises a different second color. In other forms, the second layer may be conventional white while the first layer comprises a different first color. Still in other forms, the first layer and the second layer may each comprise the same color. In some forms, the first layer may comprise a first color excluding conventional white and the second layer may comprise a second color excluding conventional white, and the first color and the second color are different. For example, a first color may be green while a second color is blue.

The laminate 100 may comprise a plurality of features described herein. Still referring to FIGS. 1A through 1C and 1E, some exemplary features include apertures 125, melt lip 135, bond sites 175, land areas 140, and embossed areas 180. As shown, in some forms of the present invention, the laminate 100 may comprise a plurality of apertures 125 that extend through the first layer 110 and the second layer 150. The second layer 150, in some forms, may not include apertures. In some forms, the plurality of apertures 125 may be formed in the first layer 110 and the second layer 150 contemporaneously such that the apertures 125 are substantially aligned in the first layer 110 and the second layer 150. In other forms, apertures may be formed in the first layer 110 and subsequently in the second layer 150. And, when the first layer 110 and second layer 150 are subsequently laminated, the apertures may substantially align. Substantially aligned, in the context of the apertures herein, means that the majority of the apertures in the first layer 110, i.e. at least 51%, comprise a reciprocal aperture in the second layer 150, and of those apertures in the first layer 110 comprising a reciprocal aperture in the second layer 150, at least 51% of the open area of each of those apertures in the first layer 110 corresponds to open area of an aperture in the second layer 150.

When the laminate 100 of the present invention is utilized as a topsheet in an absorbent article, subjacent layers may be visible through the apertures 125. For example, where the laminate 100 is utilized as a topsheet for a sanitary pad and where the apertures 125 extend through both the first layer 110 and second layer 150, respective colors of underlying layers, e.g. absorbent core, dusting layer, secondary topsheets, etc., may show through the apertures 125. The subjacent layers may be conventional white or some other color and such color may be visible through the apertures 125—"aperture color".

In some forms of the present invention, the first layer 110 may represent the topsheet of a disposable absorbent article and the second layer 150 may represent a subjacent layer of a disposable absorbent article. Suitable subjacent layers include secondary topsheets, acquisition layers, distribution layers, etc.

The disposable absorbent article may be configured such that the color visible through the apertures is different than the first color and the second color. For example, where the first layer has a first color that is conventional white, e.g. L*=99, a*=−1, b*=−3, and is an outer-facing layer of a disposable absorbent article, the second layer comprises a second color excluding conventional white and is disposed subjacent to the first layer, and a subjacent layer beneath the second layer has a color of conventional white, a visible color difference between the apertures 125 and the land area 140 may occur where a ΔE* of 10 or greater exists between the first color and the second color. However, a visible color difference between the land area 140 and the aperture 125 may occur for ΔE* of 10 or lower in some forms of the present invention. For example, ΔE*'s of greater than about 3, 4, 6, or 8, specifically including any numbers within these values may produce a visible color difference. And, as discussed hereafter, the size of the apertures can impact the color difference that is created by the first layer and second layer.

As another example, forms of the present invention are contemplated where the first layer 110 is apertured and the second layer 150 is not apertured. Where the first color and the second color are different, the second color may be visible through the apertures 125 in the first layer 110 if the ΔE* between the first color and the second color was at least 2.5.

In yet another form of the present invention, where the first color nor the second color comprise the same color excluding conventional white, a visible color difference between the apertures 125 and the land area 140 may occur. For example, where the first layer comprises a first color and the second layer comprises a second color each of which has an L*=69; a*=48; and b*=−29, the ΔE* between the first layer and second layer is equal to zero. In this form though, the color visible through the apertures 125 compared to the land area 140 may be visibly distinct and provide a color difference assuming a subjacent layer has a color which has a ΔE* equal to or greater than 2.5 with regard to the first layer and second layer, e.g. white subjacent layer. However, other features, e.g. bond sites, melt lips, etc. may not be visibly distinct with respect to the land area 140 in this particular form as the ΔE* between the colors of the first layer and the second layer would be zero.

Another example of a feature of the present invention is the melt lip 135. In some forms of the present invention, the first layer 110 and the second layer 150, may be joined about the periphery of each of the plurality of apertures 125 via the melt lip 135. For example, melt lips 135 may be created, in part, by melting/fusing fibers of the first layer 110 and second layer 150. During the melting/fusing, the melted fiber material can form bonds with surrounding fibers of the first layer 110 and the second layer 150, thereby forming a thin film like area. Similarly, where the first layer 110 or the second layer 150 are apertured separately, the constituent fibers of the first layer 110 or second layer 150 can form a thin film like areas respectively.

The thin film like areas are subsequently broken. The breaking apart of the thin film like areas forms the aperture 125 and the melt lip 135. Generally, to break apart the melted areas, the laminate is stretched in the CD direction. This stretching causes a portion of the thin film like areas to break apart and form apertures 125. A remaining portion of the film like area remains unbroken forming a melt lip. Additionally, during the aperturing process, the nonwoven is generally under tension in the MD direction. As such, the manipulation of material of the first layer 110 and the second layer 150 in the MD and/or CD direction can create color effects as described below. Note that while the formation of the thin film like areas is also the result of bonding as described above (generally in the Z-direction), the apertures 125 and melt lips 135 are created due to the stretching of the laminate 100 in the MD and/or CD directions. As the resulting structure, i.e. apertures 125 and melt lips 135 are disposed between the first surface 115 of the first layer 110 and the second surface 160 of the second layer 150, the apertures 125 and melt lip 135 are considered to be derived from an MD/CD manipulation of material. Methods for the formation of apertures 125 are described hereafter. Additional benefits created by the CD stretching are hereafter with regard to the Examples.

The melt lip 135 may comprise a color—"melt lip color"—different than that of the first layer 110, second layer 150, of the land area 140, and of the aperture color. For example, a visible difference in the melt lip 135 compared to the land area 140 may occur when the first color and the second color have a ΔE* of at least about 10.00. So for those forms where the ΔE* of at least about 10.00 exists between the first color and the second color, the melt lip color may be different than the first color and the second color and different than a color of the land area 140.

However, without wishing to be bound by theory, it is believed that a color difference can be achieved between the melt lip color and the first color and second color even when ΔE* between the first color and second color is zero. It is believed that during the formation of the melt lips 135, pigment on the constituent fibers is consolidated in the melt lip. The consolidation of the pigment in the melt lip 135 can create a color contrast between the melt lip 135 and the land area 140.

Another example of a feature which can be utilized in conjunction with the present invention is the land area 140. In some forms, land areas 140 are disposed between adjacent apertures 125 and do not include tufts, bond sites 175, or melt lips 135. The land areas 140 of the laminate 100 comprise a land color which can be different than the first color and second color and can be different than the melt lip color. For example, where the first layer comprises a color which is conventional white and the second layer comprises a color excluding conventional white, the resulting color of the land area 140 may be different than the first color and second color. In one particular example, a color difference between the land color and the first color and second color may be obtained where a ΔE* of about 10 or greater exists between the first color and the second color. Similar effects may be achieved where the first layer and second layer represent adjacent layers in a disposable absorbent article.

The resultant color of the land area may depend on the opacity of the first layer 110. For those forms where the first layer 110 and the second layer 150 comprise different colors, the first layer 110 with a low opacity may allow more of the color of the second layer 150 to bleed through. In such forms, the color of the land areas 140 may appear closer to the color of the second layer 150. However, where the first layer 110 has high opacity, the color of the second layer 150 is impacted to a larger extent, and the color of the land area 140 may appear closer to the color of the first layer 110.

In some forms, at least one of the first layer 110 or second layer 150 comprise a high opacity nonwoven or film. In some forms, the high opacity can enable an aperture pattern to be more easily distinguished, can provide contrast to any colors and materials underneath, and in the case of a diaper or feminine care article, can mask the presence of bodily fluids contained within the absorbent core, providing a cleaner appearance to the wearer. To achieve this benefit, a material with an opacity of 30, 40, 50 or 60 may be utilized. Increases in opacity can be achieved via any known suitable product/process. Some suitable examples include adding fillers (e.g. TiO2), fiber shape (e.g. Trilobal vs. round), smaller fiber diameters (including microfibers and/or nano fibers), etc. A specific example of nonwoven web having high opacity is an SMS construction. Another specific example is a nonwoven comprising nano fibers, such as those produced by melt film fibrillation as described in U.S. Pat. No. 8,487,156 and U.S. Patent Application Publication No. 2004/0266300.

Still another example of a feature of the laminates of the present invention includes bond sites 175. In general, the bond sites 175 are formed when the laminate 100 is passed through a nip between a pair of adjacent rolls. At least one of the rolls comprises nubs which compress the laminate 100 at the bond site 175. As shown, in some forms of the present invention, the nubs may engage the first surface 115 of the first layer 110 and compress the laminate along with a subjacent layer 170. The compression can be in the negative Z-direction and may generally thin the material of the first layer 110 and the second layer 150 which make up the bond site 175. This compression, which can be coupled with the application of heat in some forms, can cause the constituent material of the first layer 110 and the second layer 150 at the bond site 175 to fuse together. The constituent material of the first layer 110 and the second layer 150 are compressed as is the material of the subjacent layer 170. And, for those forms where there is a subjacent layer 170 being subjected to the bonding process, the constituent material of the subjacent layer 170 may be fused with the constituent material of the first layer 110 and the second layer 150. The fusing of the constituent material of the first layer 110, second layer 150, and/or subjacent layer 170 can create a thin film like area.

Figure 1C:
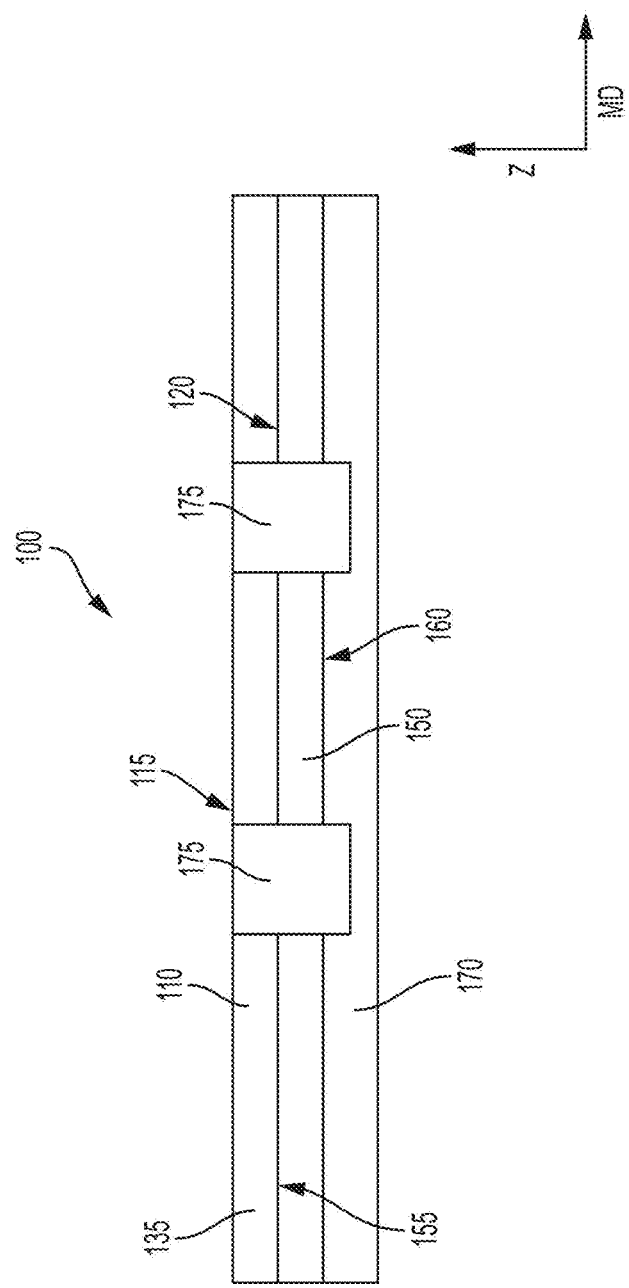
FIG. 1C is a schematic representation of the laminate of FIG. 1A shown in cross-section along line 1C-1C.

The compression of the first layer 110 and second layer 150 at the bond site 175 can, similar to the above features, create a color difference as described below. As shown in FIG. 1C, the bond sites 175 of the laminate 100 can join the laminate 100 to the subjacent layer 170. In some forms, bond sites 175 are contemplated where the bonds are formed only with regard to the first layer 110 and the second layer 150. The formation of bond sites 175 is disclosed further in U.S. patent application Ser. No. 14/135,687, filed on Dec. 20, 2013.

The bond sites 175 may comprise a bond site color which is different than the first color, second color, land area color, aperture color, and melt lip color. For example, the bond site color may be different than the land area color when the first color and the second color have a ΔE* of at least about 25.00. So for those forms where the ΔE* of at least about 25.00 exists between the first color and the second color, the bond sites 175 may exhibit a bond site color which is different than the first color, the second color, the land color, and the melt lip color. In contrast, a ΔE* of at least about 10.00 between the first color and the second color may produce color differences between the bond color and the melt lip color. Similarly, a color difference between the bond site color and the aperture color may occur where a ΔE* of at least 11 exists between the first color and the second color.

Figure 1D:
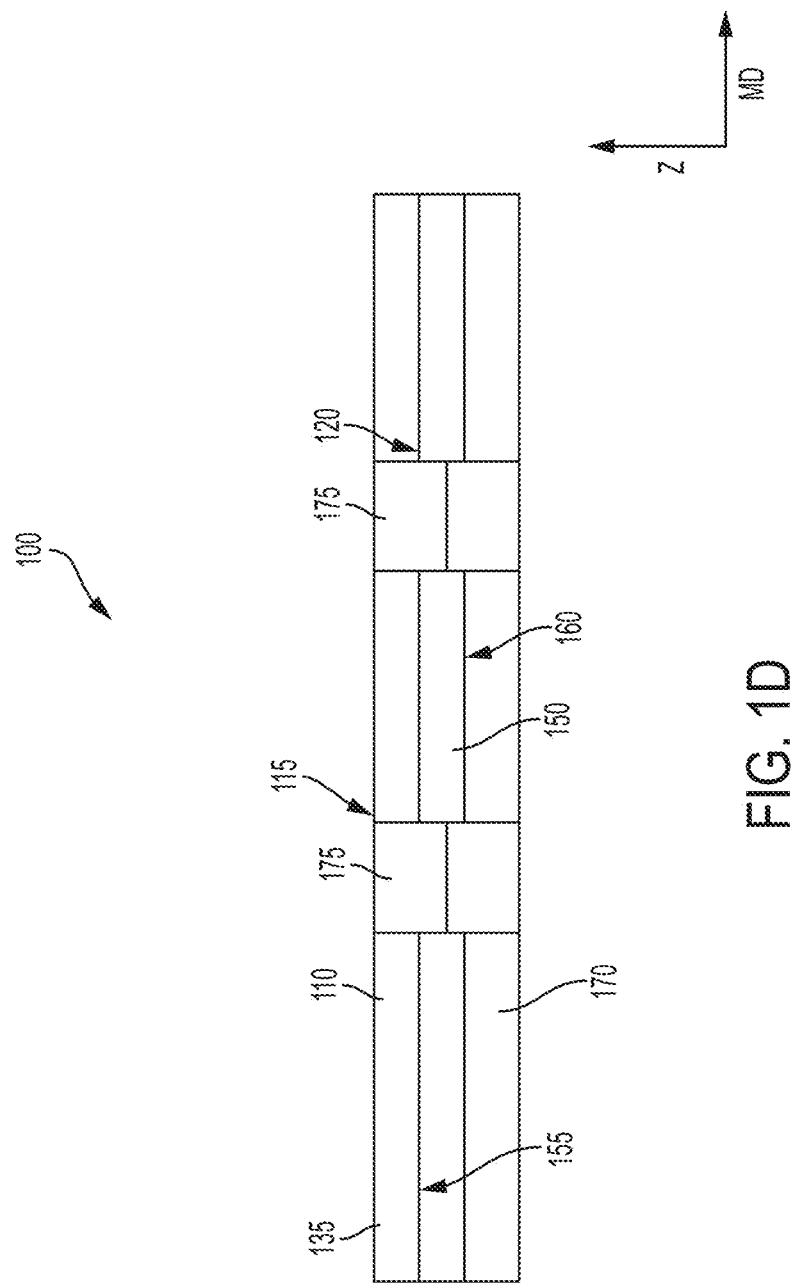
FIG. 1D is a schematic representation of another form of the laminate of FIG. 1A.

Referring to FIG. 1D, alternate forms of bonds 175 may exist. Recall that the formation of the bonds may be derived from a pair of rolls, one of which comprises nubs. Forms of the present invention are contemplated, where each of the pair of rolls comprises nubs and as the nubs engage the laminate 100, a first nub from a first roll may compress the laminate 100 plus the subjacent layer 170 in the negative Z-direction, and a second nub from a second roll may compress the laminate 100 plus the subjacent layer 170 in the positive-Z direction. In such forms of the present invention, the resulting bond 175 may be an out-of-plane feature—bonds 175 depicted in FIG. 1C.

Figure 1E:
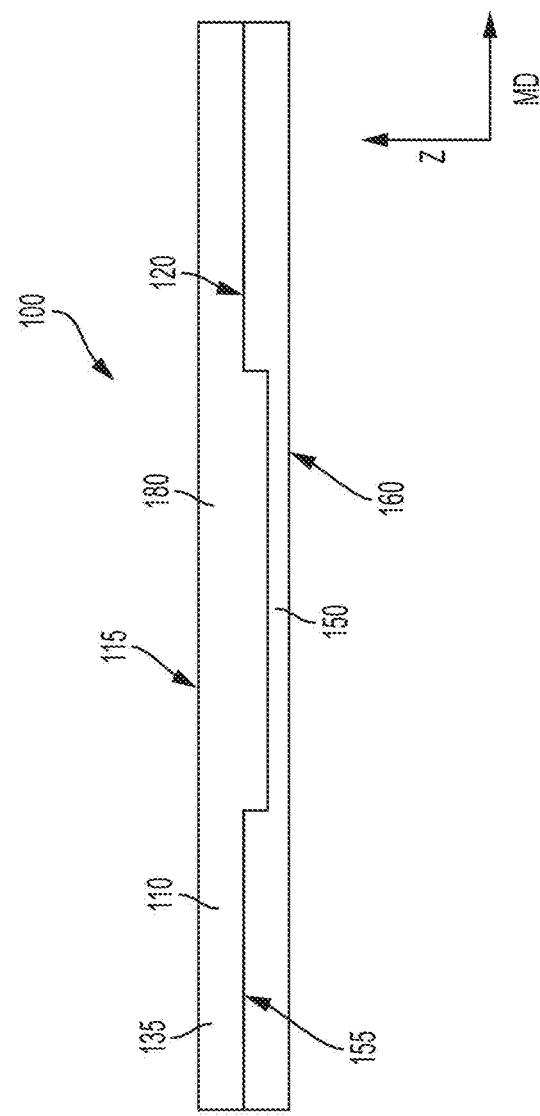
FIG. 1E is a schematic representation of another form of the laminate of FIG. 1A.

Embossing of absorbent articles generally results in thinned out areas in the absorbent article. The thinned out areas may provide a color effect as well. Namely, where the first layer and second layer comprise contrasting colors, a color effect can be exhibited by the area of the sanitary pad that is embossed. Embossing, similar to bonding, involves the manipulation of material in the first layer 110 and the second layer 150 in the positive and/or negative Z-direction. Generally, embossing does not result in the fusion of layers. Embossing can result in an out-of-plane feature. As shown in FIG. 1E, the laminate 100 of the present invention may comprise an embossed area 180. As noted in FIGS. 1D and 1C, the thinned out areas can provide a color effect without resulting in out-of-laminate manipulation. Embossed areas may comprise embossed color.

With regard to FIGS. 1A-1C, the apertures 125 and/or bond sites 175 may be positioned in any suitable manner. For example, in some forms, the apertures 125 and/or bond sites 175 may be arranged in patterns as disclosed herein. Additionally, in some forms, individual bond sites may comprise patterns themselves—also disclosed herein.

With regard to FIG. 2A, laminates of the present invention may comprise additional features which are out-of-plane features. One example of an out-of-plane feature is a tuft 270 depicted in FIG. 2A. FIG. 2A is a schematic representation of a laminate 200A constructed in accordance with the present invention. As shown, the laminate 200A comprises the first layer 110 and the second layer 150, and may comprise the tuft 270.

As shown, in some forms of the present invention, the second surface 120 of the first layer 110 may comprise a first plurality of discontinuities 245, and the second surface 260 of the second layer 150 may comprise a second plurality of discontinuities 285. The first plurality of discontinuities 245 as well as the second plurality of discontinuities 285 may be formed when localized areas of constituent material of the first layer 110 and the second layer 150 are urged in the positive Z-direction such that material of the first layer 210 and second layer 255 may be disposed superjacent to the first surface 115 of the first layer 110 and superjacent to the first surface 155 of the second layer 150, respectively. The disposition of the material of the first layer 110 may, in some forms, create a tuft 230—shown in FIG. 2B. Similarly, the disposition of the constituent material of the second layer 150 may form the tuft 270. And, as shown in FIG. 2A, in some forms, the material of the first layer 110 may break under the urging in the Z-direction. In such forms, the tufts 270 may extend through the discontinuity 245. Each tuft 270 extends through a corresponding discontinuity 245 in the first layer 110. The plurality of tufts 270 may be positioned above the first surface 115. Each of the plurality of tufts 270 can partially overlie at least one of the first plurality of discontinuities 245. For example, a first tuft may at least partially overlay a first discontinuity, and a second tuft may at least partially overlay a second discontinuity and so on. In such forms, where the constituent material of the first layer 110 breaks, a $\Delta E^*$ between the feature color and the second color may be less than a $\Delta E^*$ between the feature color and the first color.

As shown in FIG. 2B, a laminate 200B of the present invention is shown. The material of the first layer 110 when urged in the Z-direction may form tufts 230 within which tufts 270 are disposed. In some forms, laminates of the present invention may comprise a plurality of tufts 270 for which there are no corresponding tufts 230 and/or similarly may comprise a plurality of tufts 270 each of which are disposed within a corresponding tuft 230. In such forms, where the constituent material of the first layer 110, a $\Delta E^*$ between the feature color and the second color may be less than a $\Delta E^*$ between the feature color and the first color. However, depending on the level of opacity of the first layer, the opposite may be true. For example, where the opacity of the first layer is high, the $\Delta E^*$ between the feature color and the first color may be lower than a $\Delta E^*$ between the feature color and the second color.

Based on the above, for those forms where the laminates comprise tufts and the second layer 150 comprises pigmented fibers, a portion of the pigmented fibers will be urged into a tuft 270. As such, colored fibers are pushed into the tuft 270. Where the first layer 110 comprises a film, it may be beneficial to create laminate 200A. While tufts 270 are possible with a film as the constituent material, the film may have adverse effects with regard to user feel. As such, tufts 270 comprising a nonwoven may counteract—to some extent—the effect of the film first layer 110.

Figure 2D:
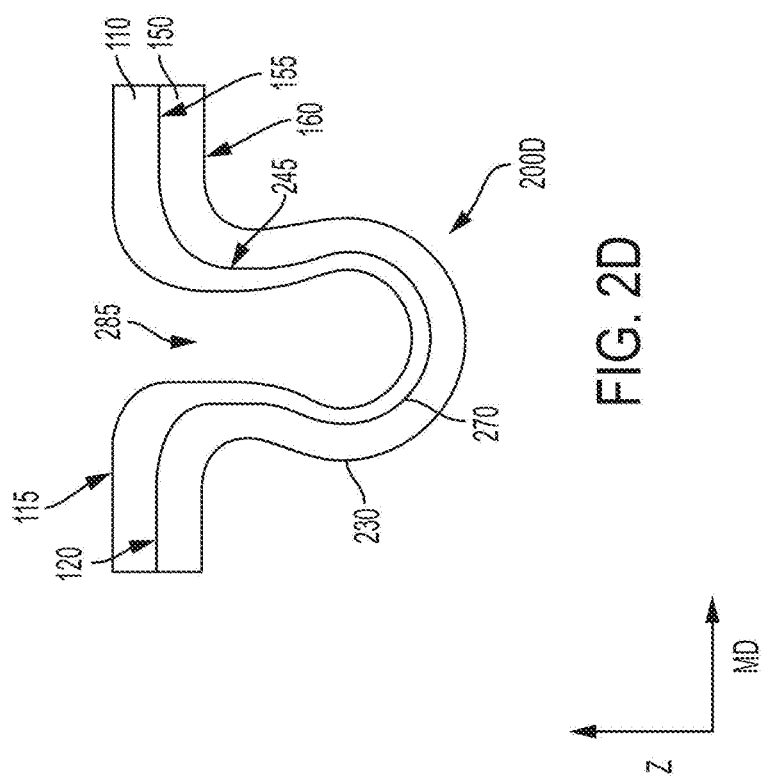
FIG. 2D is a schematic representation of a laminate of the present invention shown in cross section.
Figure 2C:
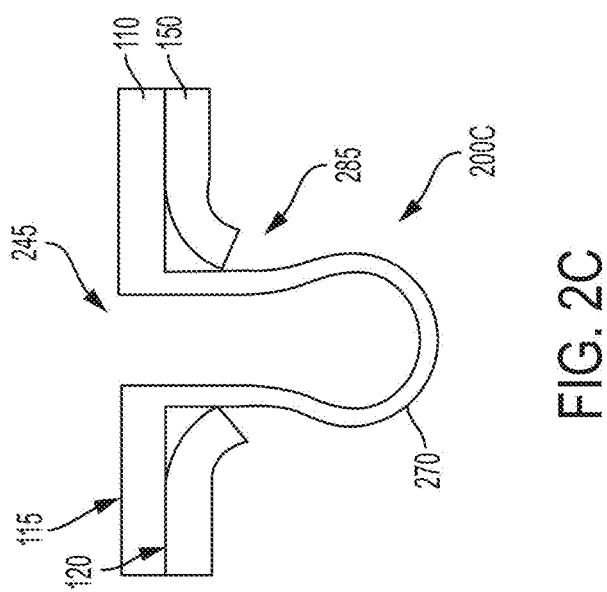
FIG. 2C is a schematic representation of a laminate of the present invention shown in cross section.

Additional arrangements of tufts are provided with respect to FIGS. 2C-2D. As shown, each laminate 200C and 200D comprise the first layer 110 and the second layer 150. As shown, the second surface 120 of the first layer 110 may comprise the first plurality of discontinuities 245. However, instead being urged in the positive Z-direction, urging of the material of the first layer 110 and second layer 150 may be in the negative Z-direction. And, similar to FIG. 2A, material of the second layer 150 may break as shown in FIG. 2C or may form a tuft 230 as shown in FIG. 2D.

Figure 2E:
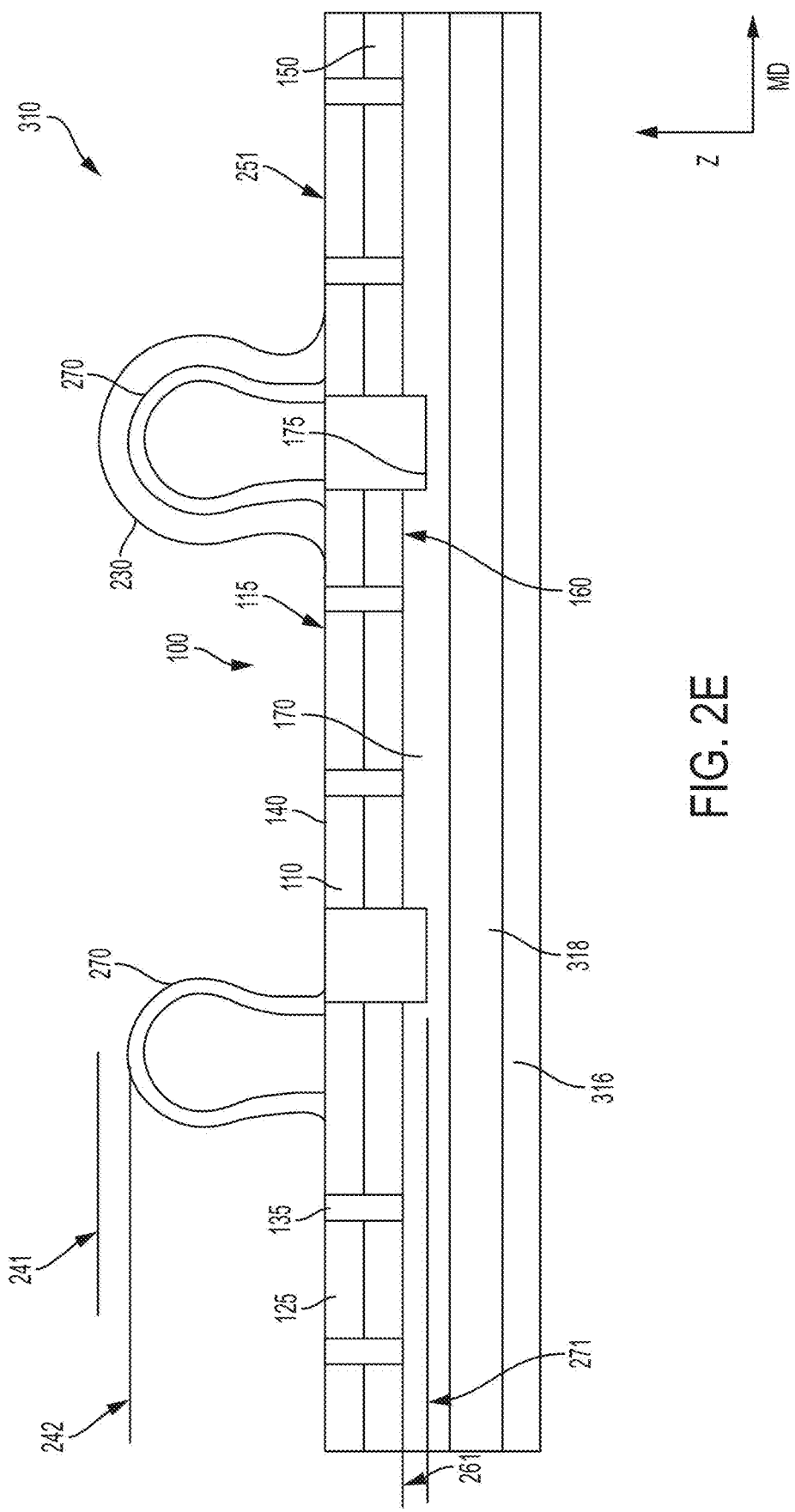
FIG. 2E is a schematic representation showing a cross section of a sanitary pad constructed in accordance with the present invention.

Referring to FIG. 2E, regarding color, the color difference produced by the tufts 270 can depend on the location of the tuft 270. For example, where laminates of the present invention are utilized as topsheets of disposable absorbent articles, tufts 270 may be positioned above an absorbent core 318 (traditionally white) whereas other tufts 270 may be positioned outboard of the absorbent core 318, e.g. on a wing of a sanitary napkin 310. The absorbent core 318 may comprise longitudinal side edges 318a and 318b (shown in FIG. 3A). For those tufts positioned inboard or within the longitudinal side edges 318a and 318b, these tufts are considered to be positioned above the absorbent core 318. For those tufts which are disposed outboard of the longitudinal side edges 318a and 318b, these tufts are considered to be positioned outboard of the absorbent core 318. For those tufts which straddle, at least in part, the longitudinal side edges 318a or 318b, these may exhibit the color effects of tufts within the longitudinal sides edges 318a/318b of the absorbent core 318 and/or the color effects of tufts outboard of the longitudinal side edges 318a/318b of the absorbent core 318.

In some forms of the present invention, the wings may comprise a portion of the topsheet which is joined to the backsheet. In other forms, wings may comprise a portion of the topsheet or a portion of the backsheet. Still in other forms, the wings may comprise material from a layer which is subjacent or superjacent to the topsheet.

In some forms, disposable absorbent articles incorporating the laminates of the present invention may comprise features which include out-of-plane-core features and out-of-plane-non-core features. Based on the above, tufts 270 positioned above the absorbent core 318 would be included in the out-of-plane-core features, and tufts 270 positioned outboard of the core 318 and out-of-plane-non-core features. In such forms, the out-of-plane-core features may comprise a core feature color, and the out-of-plane-non-core features may comprise a non-core feature color. The term "feature color" will include both core feature color and non-core feature color.

In some forms, the core feature color may be different than the first color, second color, melt lip color, bond site color, land area color, and/or non-core feature color. Similarly, in some forms, the non-core feature color may be different than the first color, second color, melt lip color, bond site color, land area color, and/or core feature color. For example, where the first color and the second color have a $\Delta E^*$ of greater than about 10, out-of-plane features, e.g. tufts, disposed above an absorbent core can exhibit a core feature color which is different than the first color, the second color, the melt lip color, the aperture color, bond color, non-core feature color, and color of wings. It is worth noting that for a $\Delta E^*$ of about 63 between the first color and the second color, the $\Delta E^*$ between the core feature color and the bond site color may be about 2.36 which is below the threshold of visibly different.

While the above discussion regarding core feature color and non-core feature color are with regard to discrete tufts 230/270, forms are contemplated where materials of the first layer and second layer are urged in the positive or negative Z-direction to form ridges which extend over a length or a width of the entire laminate or a large portion thereof. Ridges are another example of an out-of-plane feature of the present invention. Forms of the present invention are contemplated where the ridges extend the full length (or a large portion thereof) of a disposable absorbent article. As another example, forms are contemplated where ridges extend the full width (or a large portion thereof) of a disposable absorbent article. The ridges can be either laterally spaced or longitudinally spaced. It is believed however, that the urging of the material of the first layer and the second layer in the positive or negative Z-direction would produce similar results as the tufts with regard to color. Exemplary forms of ridges and methods of forming the same are discussed in U.S. Pat. No. 7,954,213; and U.S. Patent Application Publication Nos. 2012/0045620; 2012/0141742; 2012/0196091; 2012/20321839; and 2013/0022784.

Additional out-of-plane features include nubs. Some suitable processes for creating nubs on a web and the resulting structures are described in U.S. Pat. Nos. 7,713,683; 6,852,475; 7,303,861; 8,057,729; 8,287,800; and U.S. Patent Application Publication No. 2004/0121120.

The out-of-plane features of the present invention are thought to mask or partially mask fluid that is collected by the laminate and remains in the capillaries between fibers of the tufts/ridges. Such laminates employed in an absorbent article such as a wipe, a sanitary napkin, a tampon, or a diaper can be appealing to the user (or caregiver) in that potentially unsightly fluids retained in the capillaries between fibers of the tufts/ridges will be obscured or partially obscured from the viewer. The tufts/ridges which cover or partially cover other tufts/ridges in which fluids can be held and can make the laminate appear less soiled.

Additional color effects may be provided via out-of-plane features. For example, laminates of the present invention may comprise tufts which include a corresponding outer tuft and may comprise tufts without a corresponding outer tuft. Tufts with corresponding outer tufts may provide a first color while tufts without a corresponding cap may provide a different color.

Tufts may be spaced apart from adjacent tufts. Each of the spaced apart tufts have generally parallel longitudinal axes L. The number of tufts per unit area of a laminate of the present invention, i.e., the area density of tufts and/or caps, can be varied from one tuft per unit area, e.g., square centimeter to as high as 100 tufts per square centimeter. There can be at least 10, or at least 20 tufts per square centimeter, depending on the end use. In general, the area density need not be uniform across the entire area of laminates of the present invention, and, in some embodiments, tufts can be only in certain regions of laminates of the present invention, such as in regions having predetermined shapes, such as lines, stripes, bands, circles, and the like.

Figure 3A:
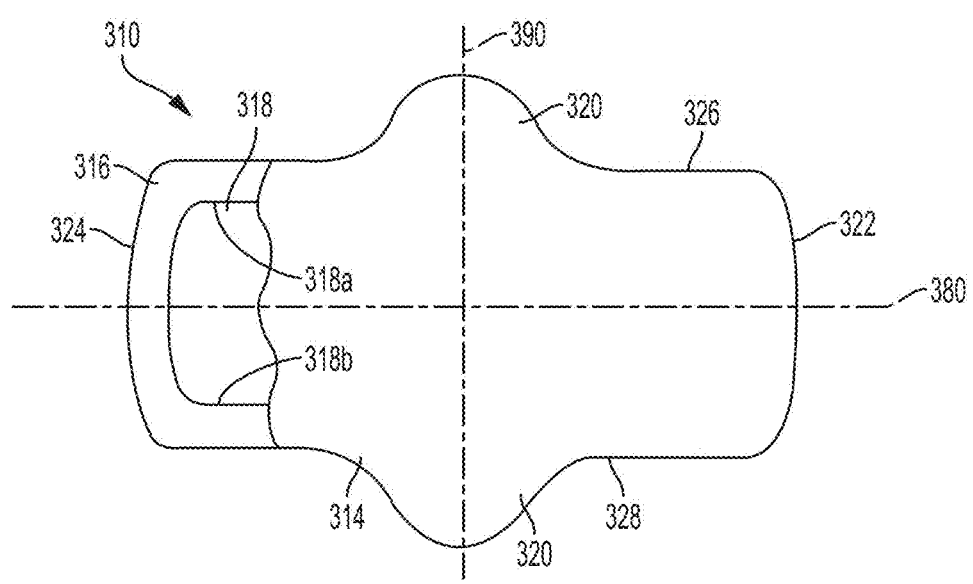
FIG. 3A is a top view of a feminine hygiene article, i.e. sanitary napkin, constructed in accordance with the present invention.

Another feature of the present invention may include wings (item 320 in FIG. 3A). For those forms where the absorbent article is a sanitary pad including wings and where the first color is different than the second color, the wings may exhibit a color which is different than the first color, second color, aperture color, melt lip color, land area color, bond site color, core feature color, and non-core feature color.

As noted previously, the laminates of the present invention may be utilized in disposable absorbent articles. Examples of some disposable absorbent articles comprising the laminates of the present invention are provided with regard to FIGS. 59-85. Additionally, a schematic representation of a partial cross section of the sanitary pad 310 is shown in FIG. 2E. As shown, the sanitary pad 310 may comprise the laminate 100 as a topsheet and may further comprise a backsheet 316. Between the topsheet and the backsheet 316 is disposed the subjacent layer 170 and the absorbent core 318. As shown, the sanitary pad 310 may comprise a plurality of the features discussed heretofore, e.g. tufts 230/270, apertures 125, melt lips 135, land areas 140, and bond sites 175. The partial cross section shown is taken parallel to a longitudinal axis 380 (shown in FIG. 3A) and the features depicted may be laterally spaced apart on the sanitary pad 310. For example, the tufts 230/270 may be laterally spaced from the bond 175.

In accordance with the disclosure herein, the sanitary pad 310 may comprise a plurality of colors which, in some forms of the present invention, are derived from a single colored layer, e.g. the first layer 110 and/or second layer 150. For example, in a first plane 241, the sanitary pad 310 may comprise one color, e.g. feature color, or in some forms, two colors derived from a plurality of out-of-plane features, e.g. a core feature color and a non-core feature color. Forms of the invention are contemplated where the sanitary pad 310 comprises one color at the first plane 241 which is provided by a feature color which may comprise either a core feature color or a non-core feature color.

In a second plane 251—generally co-planar with the first surface 115 of the first layer 110—the sanitary pad 310 may comprise two colors derived from non-elevated regions, e.g. melt lip color and land area color. In a third plane 261—generally co-planar with the second surface 160 of the second layer 150—the sanitary pad 310 may comprise a color derived from a depressed regions, e.g. aperture color. In a fourth plane 271, the sanitary pad 310 may comprise a color derived from depressed regions, e.g. bond site color. The fourth plane 271 is subjacent to the third plane 261 and is co-planar with the bond 175.

As shown, in some forms of the present invention, tufts 270 may not have a corresponding outer tuft 230 which covers tuft 270. In such forms, the tuft 270, because it is uncovered, may provide a third color to the first plane 241 or may provide one color on a plane 242, subjacent to the first plane 241.

In some forms of the present invention, the colors associated with the features in the first plane 241 may have a ΔE* with respect to the colors in the second plane 251 ranging from about 3 to about 15, specifically including all numbers within this range or any ranges created thereby. In some forms of the present invention, the colors associated with the features in the second plane can have a ΔE* of from about 4 to about 12, specifically including all numbers within this range or any ranges created thereby. In some forms of the present invention, colors associated with third plane 261, can have a ΔE* with regard to features in the second plane 251 ranging from about 3 to about 30, specifically including all numbers within this range and any ranges created thereby. In some forms of the present invention, the colors associated with features in the fourth plane 271 with respect to the features of the second plane 261 may have a ΔE* ranging from about 3 to about 13, specifically including all numbers within this range and any ranges created thereby. In some forms, the ΔE* between the first color and the second color may be between about 10 to about 63, specifically including all numbers within this range and any ranges created thereby. Height difference between the first plane 241 and the fourth plane 271 (apex of tuft/ridge to lowest point in bond) can be about 1.2 mm to about 3.2 mm.

One of the benefits of the creation of visible color effects as above is that the registration of the effects coincides with the feature desired to be highlighted. For example, regarding the formation of tufts, the first layer and the second layer can be urged in the positive or negative Z-direction. For those forms of the present invention where at least one of the first layer and second layer are colored, the colored fibers (or colored material in the case of a film) are also urged in the positive or negative Z-direction. So, the color effect is registered with the tuft. Similarly, the creation of bonds, apertures, melt lips with respect to those forms of the present invention where at least one of the first layer and the second layer are colored, involves the manipulation of colored fibers (or colored material in the case of the film).

Similar benefits may be achieved with regard to printing. Referring back to FIG. 1C, where printing is provided on the subjacent layer 170, various printing effects can be achieved with the above features. For example, where bonds overlap with printing, a visible color difference may be exhibited. It is believed that similar color effects could be achieved with printing on the second layer 150 and/or printing on the second surface 120 of the first layer 110 and with regard to the features described herein.

Sanitary pads constructed in accordance with the present invention are further discussed in the Examples section of this application. Said exemplary sanitary pads include a plurality of sanitary pads which include colored laminate topsheets, a plurality of sanitary pads which include printing effects and a plurality of sanitary pads which include a combination thereof.

As noted previously, the color effects discussed above can be achieved via a single web as opposed to a laminate. For example, where a single web is utilized as a topsheet, a subjacent layer, e.g. acquisition, distribution and/or secondary topsheet, may be manipulated as described herein along with the single web. Where the color difference between the subjacent layer and the single web comprises the requisite ΔE* as described herein, a visible color effect may be achieved. Similarly, where the single web is manipulated as described above, color effects may also be created.

Precursor Materials

Referring back to FIG. 1A, the webs/laminates of the present invention begin with constituent layers, e.g. the first layer 110 and the second layer 150. Similarly, the webs of the present invention begin with the constituent material. Where the first layer 110 and the second layer 150 or web comprise nonwoven materials, the plurality of randomly oriented fibers of the nonwoven layers may comprise any suitable thermoplastic polymer. Some suitable thermoplastic polymers, as used in the disclosed compositions, are polymers that melt and then, upon cooling, crystallize or harden, but can be re-melted upon further heating. Suitable thermoplastic polymers used herein have a melting temperature (also referred to as solidification temperature) from about 60° C. to about 300° C., from about 80° C. to about 250° C., or from 100° C. to 215° C. And, the molecular weight of the thermoplastic polymer should be sufficiently high to enable entanglement between polymer molecules and yet low enough to be melt spinnable.

The thermoplastic polymers can be derived any suitable material including renewable resources (including bio-based and recycled materials), fossil minerals and oils, and/or biodegradeable materials. Some suitable examples of thermoplastic polymers include polyolefins, polyesters, polyamides, copolymers thereof, and combinations thereof. Some exemplary polyolefins include polyethylene or copolymers thereof, including low density, high density, linear low density, or ultra low density polyethylenes such that the polyethylene density ranges between 0.90 grams per cubic centimeter to 0.97 grams per cubic centimeter, between 0.92 and 0.95 grams per cubic centimeter or any values within these ranges or any ranges within these values. The density of the polyethylene may be determined by the amount and type of branching and depends on the polymerization technology and co-monomer type. Polypropylene and/or polypropylene copolymers, including atactic polypropylene; isotactic polypropylene, syndiotactic polypropylene, and combination thereof can also be used. Polypropylene copolymers, especially ethylene can be used to lower the melting temperature and improve properties. These polypropylene polymers can be produced using metallocene and Ziegler-Natta catalyst systems. These polypropylene and polyethylene compositions can be combined together to optimize end-use properties. Polybutylene is also a useful polyolefin and may be used in some embodiments. Other suitable polymers include polyamides or copolymers thereof, such as Nylon 6, Nylon 11, Nylon 12, Nylon 46, Nylon 66; polyesters or copolymers thereof, such as maleic anhydride polypropylene copolymer, polyethylene terephthalate; olefin carboxylic acid copolymers such as ethylene/acrylic acid copolymer, ethylene/maleic acid copolymer, ethylene/meth-acrylic acid copolymer, ethylene/vinyl acetate copolymers or combinations thereof; polyacrylates, polymethacrylates, and their copolymers such as poly(methyl methacrylates).

Non-limiting examples of suitable commercially available polypropylene or polypropylene copolymers include Basell Profax PH-835 (a 35 melt flow rate Ziegler-Natta isotactic polypropylene from Lyondell-Basell), Basell Metocene MF-650W (a 500 melt flow rate metallocene isotactic polypropylene from Lyondell-Basell), Polybond 3200 (a 250 melt flow rate maleic anhydride polypropylene copolymer from Crompton), Exxon Achieve 3854 (a 25 melt flow rate metallocene isotactic polypropylene from Exxon-Mobil Chemical), Mosten NB425 (a 25 melt flow rate Ziegler-Natta isotactic polypropylene from Unipetrol), Danimer 27510 (a polyhydroxyalkanoate polypropylene from Danimer Scientific LLC), Dow Aspun 6811A (a 27 melt index polyethylene polypropylene copolymer from Dow Chemical), Eastman 9921 (a polyester terephthalic homopolymer with a nominally 0.81 intrinsic viscosity from Eastman Chemical), Achieve 3155 (a 35 melt flow rate zinc isotactic polypropylene from Exxon Mobil), Moplen HP561R and Moplen HP552R, both of which are 25 melt flow rate Ziegler-Natta isotactic polypropylene from Lyondell-Basell).

The thermoplastic polymer component can be a single polymer species as described above or a blend of two or more thermoplastic polymers as described above, e.g. two different polypropylene resins. As an example, the constituent fibers of the first nonwoven layer can be comprised of polymers such as polypropylene and blends of polypropylene and polyethylene. The second nonwoven layer may comprise fibers selected from polypropylene, polypropylene/polyethylene blends, and polyethylene/polyethylene teraphthalate blends. In some embodiments, the second nonwoven layer may comprise fibers selected from cellulose rayon, cotton, other hydrophilic fiber materials, or combinations thereof. The fibers can also comprise a super absorbent material such as polyacrylate or any combination of suitable materials.

The fibers of the first nonwoven layer and/or the second nonwoven layer can be monocomponent, bi-component, and/or bi-constituent, round or non-round (e.g., capillary channel fibers), and can have major cross-sectional dimensions (e.g., diameter for round fibers) ranging from 0.1-500 microns. The constituent fibers of the nonwoven precursor web may also be a mixture of different fiber types, differing in such features as chemistry (e.g. polyethylene and polypropylene), components (mono- and bi-), denier (micro denier and >2 denier), shape (i.e. capillary and round) and the like. The constituent fibers can range from about 0.1 denier to about 100 denier.

As used herein, the term "monocomponent" fiber refers to a fiber formed from one extruder using one or more polymers. This is not meant to exclude fibers formed from one polymer to which small amounts of additives have been added for coloration, antistatic properties, lubrication, hydrophilicity, etc.

As used herein, the term "bi-component fibers" refers to fibers which have been formed from at least two different polymers extruded from separate extruders but spun together to form one fiber. Bi-component fibers are also sometimes referred to as conjugate fibers or multicomponent fibers. The polymers are arranged in substantially constantly positioned distinct zones across the cross-section of the bi-component fibers and extend continuously along the length of the bi-component fibers. The configuration of such a bi-component fiber may be, for example, a sheath/core arrangement wherein one polymer is surrounded by another, or may be a side-by-side arrangement, a pie arrangement, or an "islands-in-the-sea" arrangement. Some specific examples of fibers which can be used in the first nonwoven layer include polyethylene/polypropylene side-by-side bi-component fibers. Another example, is a polypropylene/polyethylene bi-component fiber where the polyethylene is configured as a sheath and the polypropylene is configured as a core within the sheath. Still another example, is a polypropylene/polypropylene bi-component fiber where two different propylene polymers are configured in a side-by-side configuration.

Bi-component fibers may comprise two different resins, e.g. a first polypropylene resin and a second polypropylene resin. The resins may have different melt flow rates, molecular weights, or molecular weight distributions. Ratios of the 2 different polymers may be about 50/50, 60/40, 70/30 or any ratio within these ratios. The ratio may be selected to control the amount of crimp, strength of the nonwoven layer, softness, bonding or the like.

As used herein, the term "bi-constituent fibers" refers to fibers which have been formed from at least two polymers extruded from the same extruder as a blend. Bi-constituent fibers do not have the various polymer components arranged in relatively constantly positioned distinct zones across the cross-sectional area of the fiber and the various polymers are usually not continuous along the entire length of the fiber, instead usually forming fibrils which start and end at random. Bi-constituent fibers are sometimes also referred to as multi-constituent fibers. In other examples, a bi-component fiber may comprise a multiconstituent components.

As used herein, the term "non-round fibers" describes fibers having a non-round cross-section, and includes "shaped fibers" and "capillary channel fibers." Such fibers can be solid or hollow, and they can be tri-lobal, delta-shaped, and can be fibers having capillary channels on their outer surfaces. The capillary channels can be of various cross-sectional shapes such as "U-shaped", "H-shaped", "C-shaped" and "V-shaped". One practical capillary channel fiber is T-401, designated as 4DG fiber available from Fiber Innovation Technologies, Johnson City, Tenn. T-401 fiber is a polyethylene terephthalate (PET polyester).

The fibers of the first nonwoven layer and/or the second nonwoven layer may comprise additives in addition to their constituent chemistry. For example, suitable additives include additives for coloration, antistatic properties, lubrication, softness, hydrophilicity, hydrophobicity and the like and combinations thereof.

Further regarding coloration, the first layer and/or the second layer may comprise pigments, inks or dyes to achieve any color difference as provided herein. The fibers of the first layer and the fibers of the second layer may differ from each other in pigmentation. As used herein, to "differ in pigmentation" or "difference in pigmentation" means (a) the fibers of the first layer comprise a pigment which is different from the pigment of the second layer; or (b) the fibers of the first layer comprise a different combination of pigments; or (c) the fibers of the first layer comprise different amounts of the same pigment(s) versus the second layer; or (d) combinations of any of options a) to c). The pigment or colorant may be added uniformly throughout the fibers within each layer or may be added to one or both components in same or different type/amount within multicomponent fibers.

A pigment is a material, which can be organic or inorganic and may include activatable, structural and or special effects pigments. A pigment changes the color of reflected or transmitted light as the result of wavelength-selective absorption. This physical process differs from fluorescence, phosphorescence, and other forms of luminescence, in which a material emits light. A pigment is a generally insoluble powder, which differs from a dye, which either is itself a liquid or is soluble in a solvent (resulting in a solution). Dyes are often used to provide a print on the surface of a nonwoven web, such as graphics, pattern or images. Hence, these dyes do not form a part of the fibers of the nonwoven web but are rather applied on the web surface. In the present invention the pigments may be comprised within the fibers of the multilayered nonwoven web, which eliminates the risk of rub-off or wash-off of the color(s) imparted to the multilayered nonwoven web by the pigment.

For the present invention, the pigment will typically be mixed with the thermoplastic material, of which the fibers are made. Often, the pigment is added to the thermoplastic material in the form of a master batch or concentrate at the time of formation of the fibers. Colored master batches useful for the present invention include polypropylene based custom color master batches e.g. supplied by Ampacet; Lufilen and Luprofil supplied by BASF; Remafin for polyolefin fibers, Renol-AT for polyester fibers, Renol-AN for polyamide fibers and CESA for renewable polymers supplied by Clariant. Hence, the pigment will be suspended in the molten thermoplastic material prior to the thermoplastic material being forced through the spinnerets to form and lay down the fibers which form the nonwoven web.

To increase the whiteness and/or opacity of the fibers in either or both layers, titanium dioxide (TiO2) may be used. Different crystal forms are available, however most preferred are rutile or anatase TiO2. Other white pigments include zinc oxide, zinc sulfide, lead carbonate or calcium carbonate. To create a black color, carbon black or any other suitable colorant may be used. Various colored inorganic pigments may be used depending upon the desired color and may include metal oxides, hydroxides and sulfides or any other suitable material. Non-limiting examples of inorganic pigments include cadmium orange, iron oxide, ultramarine, chrome oxide green. One or more pigments may be combined to create the desired color. Non-limiting examples of organic colorants include anthraquinone pigments, azo pigments, benzimidazolone pigments, BONA Lakes, Dioxazine, Naphthol, Perylene, Perinone, Phthalocyanine, Pyranthrone, Quinacridones. Effects pigments including metal, pearlescent and fluorescent may also be used. Various colorants are described in *Plastics Additives Handbook,* 5th Edition The basis weight of nonwoven materials is usually expressed in grams per square meter (gsm). The basis weight of a single layer nonwoven material can range from about 8 gsm to about 100 gsm, depending on the ultimate use of the material. For example, each layer of a laminate may have a basis weight from about 8 to about 40 gsm or from about 8 to about 30 gsm. The basis weight of a multi-layer material is the combined basis weight of the constituent layers and any other added components. The basis weight of multi-layer materials of interest herein can range from about 20 gsm to about 150 gsm, depending on the ultimate use of the material.

The layers of the laminates of the present invention may be selected from any suitable type of nonwoven. Some suitable examples include spunbond nonwoven webs, thermally point bonded spunbond, carded nonwoven webs, through air bonded or hydroentangled nonwoven webs.

Where laminates of the present invention comprise a film layer, any suitable film may be utilized. Exemplary films are discussed in U.S. Pat. Nos. 7,410,683; 8,440,286 and 8,697,218.

Disposable Absorbent Articles

Disposable absorbent articles of the present invention may utilize the laminates described herein in any suitable location. And, the laminates described herein may be incorporated into any suitable disposable absorbent article. Some suitable uses for the webs/laminates of the present invention in some absorbent articles include a topsheet, a backsheet, a secondary layer between the topsheet and backsheet, combinations thereof, etc.

Referring to FIGS. 3A and 3B, an absorbent article which may utilize the webs/laminates described herein may be the sanitary napkin/sanitary pad/feminine hygiene pad 310. As shown, the sanitary pad 310 may comprise a liquid permeable topsheet 314, the liquid impermeable, or substantially liquid impermeable, backsheet 316, and the absorbent core 318 positioned intermediate the topsheet 314 and the backsheet 316. The sanitary pad 310 may comprise wings 320 extending outwardly with respect to the longitudinal axis 380 of the sanitary napkin 310. The sanitary pad 310 may also comprise a lateral axis 390. The wings 320 may be joined to the topsheet 314, the backsheet 316, and/or the absorbent core 318. As shown, the absorbent core 318 may comprise the longitudinal side edges 318a and 318b.

As shown, the topsheet 314 may comprise the first layer 110 and the second layer 150. The second layer 150 may comprise ends 150a and 150b which are disposed laterally inboard of ends 110a and 110b of the first layer 150. In some forms, the second layer 150 and the first layer 110 may be coterminous. In other forms, the ends 150a and 150b of the second layer 150 may be disposed laterally outboard of the ends 110a and 110b of the first layer 110. The sanitary pad 310 may also comprise a front edge 322, a rear edge 324 longitudinally opposing the front edge 322, a first side edge 326, and a second side edge 328 laterally opposing the first side edge 326. The longitudinal axis 380 may extend from a midpoint of the front edge 322 to a midpoint of the rear edge 324. The lateral axis 390 may extend from a midpoint of the first side edge 328 to a midpoint of the second side edge 328. The sanitary pad 310 may also be provided with additional features commonly found in sanitary pads as is known in the art.

As shown, the topsheet 314 forms a portion of a wearer-facing surface of the sanitary pad 310. In some forms, the topsheet 314 may be unitary, e.g. the first layer 110 forms a portion of the wearer-facing surface. In some forms, the topsheet 314 may form a portion of the laterally opposing edges 326 and 328. In some forms, the topsheet 314 may be unitary and form a portion of the laterally opposing edges 326 and 328. In other forms, the topsheet 314 may comprise a plurality of discrete materials which form a wearer-facing surface.

In some forms, the topsheet 314 may comprise a single layer which may comprise a color excluding conventional white. In other forms, the single layer may be conventional white and a subjacent layer comprises printing and/or a different color.

Any suitable absorbent core known in the art may be utilized. The absorbent core 318 may be any absorbent member which is generally compressible, conformable, non-irritating to the wearer's skin, and capable of absorbing and retaining liquids such as urine, menses, and/or other body exudates. The absorbent core 318 may be manufactured from a wide variety of liquid-absorbent materials commonly used in disposable absorbent articles such as comminuted wood pulp which is generally referred to as airfelt. The absorbent core 318 may comprise superabsorbent polymers (SAP) and less than 15%, less than 10%, less than 5%, less than 3%, or less than 1% of airfelt, or be completely free of airfelt. Examples of other suitable absorbent materials comprise creped cellulose wadding, meltblown polymers including coform, chemically stiffened, modified or cross-linked cellulosic fibers, tissue including tissue wraps and tissue laminates, absorbent foams, absorbent sponges, superabsorbent polymers, absorbent gelling materials, or any equivalent material or combinations of materials.

The configuration and construction of the absorbent core 318 may vary (e.g., the absorbent core may have varying caliper zones, a hydrophilic gradient, a superabsorbent gradient, or lower average density and lower average basis weight acquisition zones; or may comprise one or more layers or structures). In some forms, the absorbent core 318 may comprise one or more channels, such as two, three, four, five, or six channels.

The absorbent core 318 of the present disclosure may comprise one or more adhesives, for example, to help immobilize the SAP or other absorbent materials within a core wrap and/or to ensure integrity of the core wrap, in particular when the core wrap is made of two or more substrates. The core wrap may extend to a larger area than required for containing the absorbent material(s) within.

Absorbent cores comprising relatively high amounts of SAP with various core designs are disclosed in U.S. Pat. No. 5,599,335 to Goldman et al., EP 1,447,066 to Busam et al., WO 95/11652 to Tanzer et al., U.S. Pat. Publ. No. 2008/0312622A1 to Hundorf et al., and WO 2012/052172 to Van Malderen.

Other forms and more details regarding channels and pockets that are free of, or substantially free of absorbent materials, such as SAP, within absorbent cores are discussed in greater detail in U.S. Patent Application Publication Nos. 2014/0163500, 2014/0163506, and 2014/0163511, all published on Jun. 12, 2014.

The sanitary napkin 310 may comprise additional layers between the topsheet 314 and the absorbent core 318. For example, the sanitary napkin 310 may comprise a secondary topsheet and/or an acquisition layer positioned between the topsheet 314 and the absorbent core 318.

The backsheet can comprise a liquid impervious film. The backsheet can be impervious to liquids (e.g., body fluids) and can be typically manufactured from a thin plastic film. However, typically the backsheet can permit vapours to escape from the disposable article. In an embodiment, a microporous polyethylene film can be used for the backsheet. A suitable microporous polyethylene film is manufactured by Mitsui Toatsu Chemicals, Inc., Nagoya, Japan and marketed in the trade as PG-P.

One suitable material for the backsheet can be a liquid impervious thermoplastic film having a thickness of from about 0.012 mm (0.50 mil) to about 0.051 mm (2.0 mils), for example including polyethylene or polypropylene. Typically, the backsheet can have a basis weight of from about 5 g/m² to about 35 g/m². However, it should be noted that other flexible liquid impervious materials may be used as the backsheet. Herein, "flexible" refers to materials which are compliant and which will readily conform to the general shape and contours of the wearer's body.

The backsheet can be typically positioned adjacent an outer-facing surface of the absorbent core and can be joined thereto by any suitable attachment device known in the art. For example, the backsheet may be secured to the absorbent core by a uniform continuous layer of adhesive, a patterned layer of adhesive, or an array of separate lines, spirals, or spots of adhesive. Illustrative, but non-limiting adhesives, include adhesives manufactured by H. B. Fuller Company of St. Paul, Minn., U.S.A., and marketed as HL-1358J. An example of a suitable attachment device including an open pattern network of filaments of adhesive is disclosed in U.S. Pat. No. 4,573,986 entitled "Disposable Waste-Containment Garment", which issued to Minetola et al. on Mar. 4, 1986. Another suitable attachment device including several lines of adhesive filaments swirled into a spiral pattern is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Alternatively, the attachment device may include heat bonds, thermal fusion bonds, pressure bonds, ultrasonic bonds, dynamic mechanical bonds, or any other suitable attachment device or combinations of these attachment devices. The backsheet may be additionally secured to the topsheet by any of the above-cited attachment devices/methods.

Forms of the present invention are contemplated where the backsheet comprises the first layer and/or second layer described herein. For example, the backsheet may comprise printing and/or a color. The color in some forms may be conventional white, while in other forms may exclude conventional white.

As stated previously, sanitary napkins of the present invention, may comprise the laminates described herein. Options for utilization of the laminates described herein as topsheets are discussed hereafter.

Still another example of a disposable absorbent article which may utilize the laminates of the present invention are diapers which include non-refastenable pants and/or re-fastenable diapers. Diapers have can have a similar construction to that of sanitary napkins. An exemplary diaper is described below.

Figure 4:
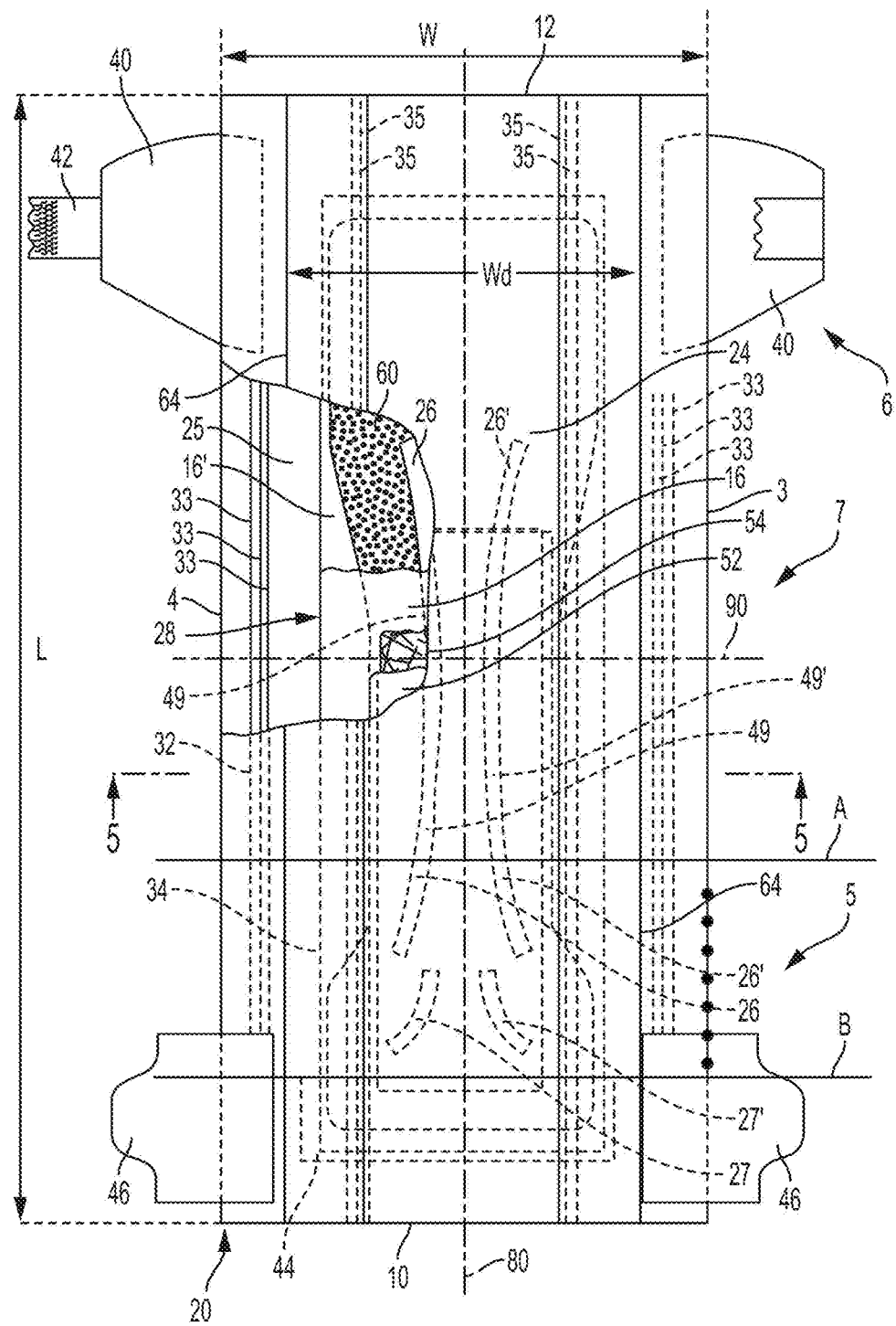
FIG. 4 is a top view of an absorbent article with some layers partially removed in accordance with the present disclosure.
Figure 5:
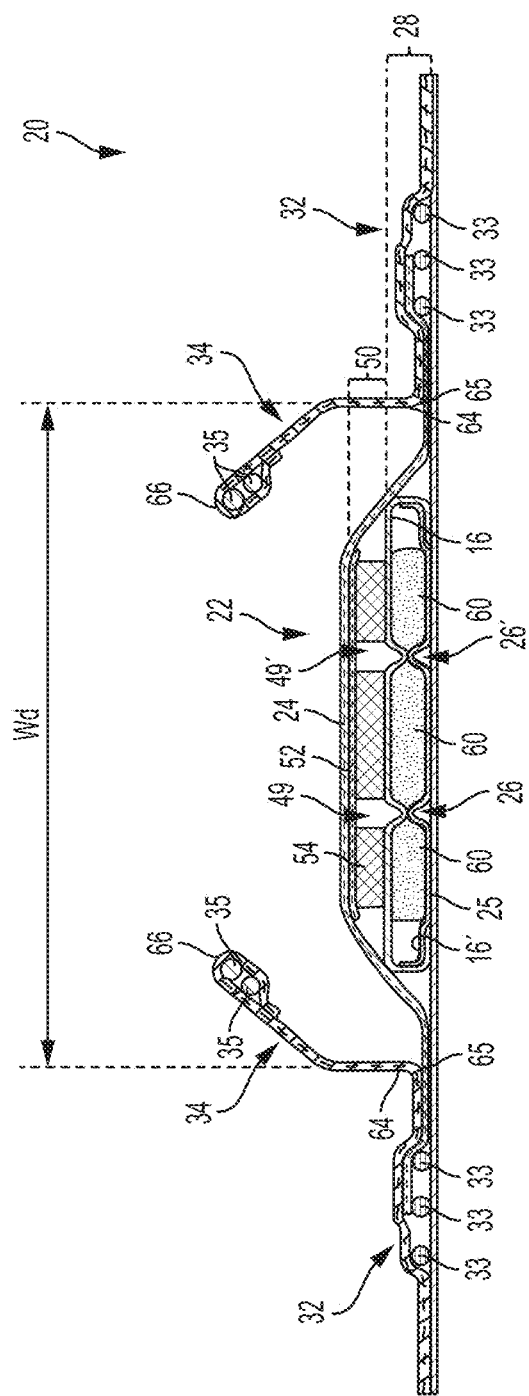
FIG. 5 is a cross-sectional view of the absorbent article taken about line 5-5 of FIG. 4 in accordance with the present disclosure.

Referring to FIGS. 4-6, an example absorbent article that is a diaper 20 in its flat-out, uncontracted state (i.e., with elastic induced contraction pulled out—FIG. 4) with portions of the structure being cut-away to more clearly show the construction of the diaper 20 and with its wearer-facing surface toward the viewer. This diaper is shown for illustration purpose only as the present disclosure may be used for making a wide variety of diapers and other absorbent articles.

The absorbent article may comprise a liquid permeable topsheet 24, a liquid impermeable backsheet 25, an absorbent core 28 positioned at least partially intermediate the topsheet 24 and the backsheet 25, and barrier leg cuffs 34. The absorbent article may also comprise a liquid management system ("LMS") 50 (shown in FIG. 28), which, in the example represented, comprises a distribution layer 54 and an acquisition layer 52 that will both be further discussed below. In various forms, the acquisition layer 52 may instead distribute bodily exudates and the distribution layer 54 may instead acquire bodily exudates or both layers may distribute and/or acquire bodily exudates. The LMS 50 may also be provided as a single layer or two or more layers. The absorbent article may also comprise elasticized gasketing cuffs 32 joined to the chassis of the absorbent article, typically via the topsheet and/or backsheet, and substantially planar with the chassis of the diaper.

The Figures also show typical taped diaper components such as a fastening system comprising adhesive tabs 42 or other mechanical fasteners attached towards the rear edge of the absorbent article 20 and cooperating with a landing zone 44 on the front of the absorbent article 20. The absorbent article may also comprise other typical elements, which are not represented, such as a rear elastic waist feature and a front elastic waist feature, for example.

The absorbent article 20 may comprise a front waist edge 10, a rear waist edge 12 longitudinally opposing the front waist edge 10, a first side edge 3, and a second side edge 4 laterally opposing the first side edge 3. The front waist edge 10 is the edge of the absorbent article 20 which is intended to be placed towards the front of the user when worn, and the rear waist edge 12 is the opposite edge. Together the front waist edge 10 and the rear waist edge form waist opening when the absorbent article 20 is donned on a wearer. The absorbent article 20 may have a longitudinal axis 80 extending from the lateral midpoint of the front waist edge 10 to a lateral midpoint of the rear waist edge 12 of the absorbent article 20 and dividing the absorbent article 20 in two substantially symmetrical halves relative to the longitudinal axis 80, with article placed flat and viewed from the wearer-facing surface as illustrated FIG. 5. The absorbent article may also have a lateral axis 90 extending from the longitudinal midpoint of the first side edge 3 to the longitudinal midpoint of the second side edge 4. The length L of the absorbent article 20 may be measured along the longitudinal axis 80 from the front waist edge 10 to the rear waist edge 12. The crotch width of the absorbent article 20 may be measured along the lateral axis 90 from the first side edge 3 to the second side edge 4. The absorbent article 20 may comprise a front waist region 5, a rear waist region 6, and a crotch region 7. The front waist region, the rear waist region, and the crotch region each define ⅓ of the longitudinal length of the absorbent article. Front and back portions may also be defined on opposite sides of the lateral axis 90.

The topsheet 24, the backsheet 25, the absorbent core 28, and the other article components may be assembled in a variety of configurations, in particular by gluing or heat embossing, for example. Example diaper configurations are described generally in U.S. Pat. Nos. 3,860,003, 5,221,274, 5,554,145, 5,569,234, 5,580,411, and 6,004,306.

The absorbent core 28 may comprise an absorbent material comprising 75% to 100%, at least 80%, at least 85%, at least 90%, at least 95%, or at least 99%, all by weight, of the absorbent material, specifically reciting all 0.1% increments within the above-specified ranges and all ranges formed therein or thereby, and a core wrap enclosing the absorbent material. The core wrap may typically comprise two materials, substrates, or nonwoven materials 16 and 16' for the top side and bottom side of the core.

The absorbent core 28 may comprises one or more channels, represented in FIG. 5 as the four channels 26, 26' and 27, 27'. Additionally or alternative, the LMS 50 may comprises one or more channels, represented in FIGS. 5-6 as channels 49, 49'. In some forms, the channels of the LMS 50 may be positioned within the absorbent article 20 such they aligned with, substantially aligned with, overlap, or at least partially overlap, the channels of the absorbent core 28. These and other components of the absorbent articles will now be discussed in more details.

The topsheet 24 is the part of the absorbent article that is directly in contact with the wearer's skin. The topsheet 24 may be joined to the backsheet 25, the core 28 and/or any other layers as is known to those of skill in the art. Usually, the topsheet 24 and the backsheet 25 are joined directly to each other in some locations (e.g., on or close to the periphery of the article) and are indirectly joined together in other locations by directly joining them to one or more other elements of the absorbent article 20.

The backsheet 25 is generally that portion of the absorbent article 20 positioned adjacent the garment-facing surface of the absorbent core 28 and which prevents, or at least inhibits, the bodily exudates absorbed and contained therein from soiling articles such as bedsheets and undergarments. The backsheet 25 is typically impermeable, or at least substantially impermeable, to liquids (e.g., urine, running BM), but permeable to vapors to allow the diaper to "breath". The backsheet may, for example, be or comprise a thin plastic film such as a thermoplastic film having a thickness of about 0.012 mm to about 0.051 mm. Example backsheet films include those manufactured by Tredegar Corporation, based in Richmond, Va., and sold under the trade name CPC2 film. Other suitable backsheet materials may include breathable materials which permit vapors to escape from the absorbent article 20 while still preventing, or at least inhibiting, bodily exudates from passing through the backsheet 25. Example breathable materials may include materials such as woven webs, nonwoven webs, composite materials such as film-coated nonwoven webs, microporous films, and monolithic films.

The backsheet 25 may be joined to the topsheet 24, the absorbent core 28, and/or any other element of the absorbent article 20 by any attachment methods known to those of skill in the art. Suitable attachment methods are described above with respect to methods for joining the topsheet 24 to other elements of the absorbent article 20.

As used herein, the term "absorbent core" refers to the individual component of the absorbent article having the most absorbent capacity and that comprises an absorbent material. The absorbent core may comprise a core wrap or core bag (hereafter "core wrap") enclosing the absorbent material. The term "absorbent core" does not include the LMS or any other component of the absorbent article which is not either integral part of the core wrap or placed within the core wrap. The absorbent core may comprise, consist essentially of, or consist of, a core wrap, absorbent material as defined below, and glue enclosed within the core wrap. Pulp or air-felt may also be present within the core wrap and may form a portion of the absorbent material. The absorbent core periphery, which may be the periphery of the core wrap, may define any suitable shape, such as a "T," "Y," "hour-glass," or "dog-bone" shape, for example. An absorbent core periphery having a generally "dog bone" or "hour-glass" shape may taper along its width towards the middle or "crotch" region of the core. In this way, the absorbent core may have a relatively narrow width in an area of the absorbent core intended to be placed in the crotch region of an absorbent article.

The absorbent core 28 of the present disclosure may comprise an absorbent material with a high amount of superabsorbent polymers (herein abbreviated as "SAP") enclosed within a core wrap. The SAP content may represent 70% to 100% or at least 70%, 75%, 80%, 85%, 90%, 95%, 99%, or 100% by weight of the absorbent material contained in the core wrap. The SAP useful with the present disclosure may include a variety of water-insoluble, but water-swellable polymers capable of absorbing large quantities of fluids. The core wrap is not considered as absorbent material for the purpose of assessing the percentage of SAP in the absorbent core. The remainder of the absorbent material in the core 28 may be air-felt.

"Absorbent material" means a material which has some absorbency property or liquid retaining properties, such as SAP, cellulosic fibers as well as synthetic fibers. Typically, glues used in making absorbent cores have no absorbency properties and are not considered as absorbent material. The SAP content may be higher than 80%, for example at least 85%, at least 90%, at least 95%, at least 99%, and even up to and including 100% of the weight of the absorbent material contained within the core wrap, as stated above. This provides a relatively thin core compared to conventional cores typically comprising between 40-60% SAP, for example, and high content of cellulose fibers or airfelt. The absorbent material may comprise less than 15% or less than 10% weight percent of natural or synthetic fibers, less than 5% weight percent, less than 3% weight percent, less than 2% weight percent, less than 1% weight percent, or may even be substantially free of, or free of, natural and/or synthetic fibers, specifically reciting all 0.1% increments within the specified ranges and all ranges formed therein or thereby. The absorbent material may comprise little or no airfelt (cellulose) fibers, in particular the absorbent core may comprise less than 15%, 10%, 5%, 3%, 2%, 1% airfelt (cellulose) fibers by weight, or may even be substantially free of, or free of, cellulose fibers, specifically reciting all 0.1% increments within the specified ranges and all ranges formed therein or thereby.

The absorbent core 28 may also comprise a generally planar top side and a generally planar bottom side. The core 28 may have a longitudinal axis 80' corresponding substantially to the longitudinal axis 80 of the absorbent article, as seen from the top in a planar view as in FIG. 4. The absorbent material may be distributed in higher amount towards the front side than towards the rear side as more absorbency may be required at the front in particular articles. The absorbent material may have a non-uniform basis weight or a uniform basis weight across any portion of the core. The core wrap may be formed by two nonwoven materials, substrates, laminates, or other materials, 16, 16' which may be at least partially sealed along the sides of the absorbent core. The core wrap may be at least partially sealed along its front side, rear side, and two longitudinal sides so that substantially no absorbent material leaks out of the absorbent core wrap. The first material, substrate, or nonwoven 16 may at least partially surround the second material, substrate, or nonwoven 16' to form the core wrap. The first material 16 may surround a portion of the second material 16' proximate to the first and second side edges 284 and 286.

Cores comprising relatively high amount of SAP with various core designs are disclosed in U.S. Pat. No. 5,599,335 (Goldman), EP 1,447,066 (Busam), WO 95/11652 (Tanzer), U.S. Pat. Publ. No. 2008/0312622A1 (Hundorf), and WO 2012/052172 (Van Malderen).

The absorbent material may be one or more continuous layers present within the core wrap. Alternatively, the absorbent material may be comprised of individual pockets or stripes of absorbent material enclosed within the core wrap. In the first case, the absorbent material may be, for example, obtained by the application of a single continuous layer of absorbent material. The continuous layer of absorbent material, in particular of SAP, may also be obtained by combining two or more absorbent layers having discontinuous absorbent material application pattern, wherein the resulting layer is substantially continuously distributed across the absorbent particulate polymer material area, as disclosed in U.S. Pat. Appl. Publ. No. 2008/0312622A1 (Hundorf), for example. The absorbent core 28 may comprise a first absorbent layer and a second absorbent layer. The first absorbent layer may comprise the first material 16 and a first layer 61 of absorbent material, which may be 100% or less of SAP. The second absorbent layer may comprise the second material 16' and a second layer 62 of absorbent material, which may also be 100% or less of SAP.

The fibrous thermoplastic adhesive material 51 may be at least partially in contact with the absorbent material 61, 62 in the land areas and at least partially in contact with the materials 16 and 16' in the junction areas. This imparts an essentially three-dimensional structure to the fibrous layer of thermoplastic adhesive material 51, which in itself is essentially a two-dimensional structure of relatively small thickness, as compared to the dimension in length and width directions. Thereby, the fibrous thermoplastic adhesive material may provide cavities to cover the absorbent material in the land area, and thereby immobilizes this absorbent material, which may be 100% or less of SAP.

The core wrap may be made of a single substrate, material, or nonwoven folded around the absorbent material, or may comprise two (or more) substrates, materials, or nonwovens which are attached to another. Typical attachments are the so-called C-wrap and/or sandwich wrap. In a C-wrap, the longitudinal and/or transversal edges of one of the substrates are folded over the other substrate to form flaps. These flaps are then bonded to the external surface of the other substrate, typically by gluing. Other techniques may be used to form a core wrap. For example, the longitudinal and/or transversal edges of the substrates may be bonded together and then folded underneath the absorbent core 28 and bonded in that position.

The core wrap may be at least partially sealed along all the sides of the absorbent core so that substantially no absorbent material leaks out of the core. By "substantially no absorbent material" it is meant that less than 5%, less than 2%, less than 1%, or about 0% by weight of absorbent material escape the core wrap. The term "seal" is to be understood in a broad sense. The seal does not need to be continuous along the whole periphery of the core wrap but may be discontinuous along part or the whole of it, such as formed by a series of seal points spaced on a line. A seal may be formed by gluing and/or thermal bonding.

The core wrap may also be formed by a single substrate which may enclose as in a parcel wrap the absorbent material and be sealed along the front side and rear side of the core and one longitudinal seal.

The absorbent article may comprise a pair of barrier leg cuffs 34. Each barrier leg cuff may be formed by a piece of material which is bonded to the absorbent article so it can extend upwards from the inner surface of the absorbent article and provide improved containment of liquids and other bodily exudates approximately at the junction of the torso and legs of the wearer. The barrier leg cuffs 34 are delimited by a proximal edge 64 joined directly or indirectly to the topsheet 24 and/or the backsheet 25 and a free terminal edge 66, which is intended to contact and form a seal with the wearer's skin. The barrier leg cuffs 34 extend at least partially between the front waist edge 10 and the rear waist edge 12 of the absorbent article on opposite sides of the longitudinal axis 80 and are at least present in the crotch region 7. The barrier leg cuffs 34 may be joined at the proximal edge 64 with the chassis of the absorbent article by a bond 65 which may be made by gluing, fusion bonding, or combination of other suitable bonding processes. The bond 65 at the proximal edge 64 may be continuous or intermittent. The bond 65 closest to the raised section of the leg cuffs 34 delimits the proximal edge 64 of the standing up section of the leg cuffs 34.

The barrier leg cuffs 34 may be integral with the topsheet 24 or the backsheet 25 or may be a separate material joined to the absorbent article's chassis. The material of the barrier leg cuffs 34 may extend through the whole length of the diapers but may be "tack bonded" to the topsheet 24 towards the front waist edge 10 and rear waist edge 12 of the absorbent article so that in these sections the barrier leg cuff material remains flush with the topsheet 24.

Each barrier leg cuff 34 may comprise one, two or more elastic strands or strips of film 35 close to this free terminal edge 66 to provide a better seal.

In addition to the barrier leg cuffs 34, the absorbent article may comprise gasketing cuffs 32, which are joined to the chassis of the absorbent article, in particular to the topsheet 24 and/or the backsheet 25 and are placed externally relative to the barrier leg cuffs 34. The gasketing cuffs 32 may provide a better seal around the thighs of the wearer. Each gasketing leg cuff may comprise one or more elastic strings or elastic elements in the chassis of the absorbent article between the topsheet 24 and backsheet 25 in the area of the leg openings. All or a portion of the barrier leg and/or gasketing cuffs may be treated with a lotion or skin care composition. The barrier leg cuffs may be constructed in a number of different configurations, including those described in U.S. Pat. App. Publ. No. 2012/0277713.

In a form, the absorbent article may comprise front ears 46 and rear ears 40. The ears may be an integral part of the chassis, such as formed from the topsheet 24 and/or backsheet 25 as side panel. Alternatively, as represented on FIG. 5, the ears (46, 40) may be separate elements attached by gluing, heat embossing, and/or pressure bonding. The rear ears 40 may be stretchable to facilitate the attachment of the tabs 42 to the landing zone 44 and maintain the taped diapers in place around the wearer's waist. The rear ears 40 may also be elastic or extensible to provide a more comfortable and contouring fit by initially conformably fitting the absorbent article to the wearer and sustaining this fit throughout the time of wear well past when absorbent article has been loaded with exudates since the elasticized ears allow the sides of the absorbent article to expand and contract.

One function of the LMS 50 is to quickly acquire the fluid and distribute it to the absorbent core 28 in an efficient manner. The LMS 50 may comprise one or more layers, which may form a unitary layer or may remain as discrete layers which may be attached to each other. The LMS 50 may comprise two layers: a distribution layer 54 and an acquisition layer 52 disposed between the absorbent core and the topsheet, but the present disclosure is not limited to such a configuration.

The LMS 50 may comprise SAP as this may slow the acquisition and distribution of the fluid. In other forms, the LMS may be substantially free (e.g., 80%, 85%, 90%, 95%, or 99% free of) or completely free of SAP. The LMS may also comprise one or more of a variety of other suitable types of materials, such as opened-cell foam, air-laid fibers, or carded, resin bonded nonwoven materials, for example. Suitable example LMSs are described in WO 2000/59430 (Daley), WO 95/10996 (Richards), U.S. Pat. No. 5,700,254 (McDowall), and WO 02/067809 (Graef), for example.

The LMS 50 may comprise a distribution layer 54. The distribution layer 54 may comprise at least 50% or more by weight of cross-linked cellulose fibers, for example. The cross-linked cellulosic fibers may be crimped, twisted, or curled, or a combination thereof including crimped, twisted, and curled. This type of material is disclosed in U.S. Pat. Publ. No. 2008/0312622 A1 (Hundorf).

The LMS 50 may alternatively or additionally comprise an acquisition layer 52. The acquisition layer 52 may be disposed, for example, between the distribution layer 54 and the topsheet 24. The acquisition layer 52 may be or may comprise a non-woven material, such as an SMS or SMMS material, comprising a spunbonded, a melt-blown and a further spunbonded layer or alternatively a carded chemical-bonded nonwoven. The acquisition layer 52 may comprise air or wet-laid cellulosic, cross-linked cellulosic, or synthetic fibers, or blends thereof. The acquisition layer 52 may comprise a roll-stock web of synthetic fibers (which may be processed to increase void space, such as by solid state formation), or a combination of synthetic and cellulosic fibers, bonded together to form a highloft material. Alternatively, the acquisition layer 52 may comprise absorbent open cell foam. The nonwoven material may be latex bonded.

The LMS 50 of the absorbent article 20 may comprise channels that may generally enable better conformation of the absorbent article to the wearer's anatomy, leading to increased freedom-of-movement and reduced gapping. One or more of the channels of the LMS 50 may be configured to work in concert with various channels in the absorbent core 28, as discussed above. Furthermore, channels in the LMS 50 may also provide increased void space to hold and distribute urine, BM or other bodily exudates within the absorbent article, leading to reduced leakage and skin contact. Channels in the LMS 50 may also provide internal serviceable indicia, especially when highlighted via physical differences in texture, color, and/or pattern, to facilitate achieving the correct alignment of the absorbent article on a wearer. Thus, such physical differences may be, for example, visually and/or tactilely noticeable.

As stated previously, the laminates of the present invention may be utilized as a topsheet for a disposable absorbent article, examples of which include the sanitary napkin 1810 and diaper 20 discussed heretofore.

The webs/laminates of the present disclosure may be used as components of absorbent articles. More than one web/laminate may be used in a single absorbent article. In such a context, the webs/laminates may form at least a portion of: a topsheet; a topsheet and an acquisition layer; a topsheet and a distribution layer; an acquisition layer and a distribution layer; a topsheet, an acquisition layer, and a distribution layer; an outer cover; a backsheet; an outer cover and a backsheet, wherein a film (non-apertured layer) forms the backsheet and nonwoven web forms the outer cover; a leg cuff; an ear or side panel; a fastener; a waist band; or any other suitable portion of an absorbent article. The number of layers in a laminate may also be determined by the laminates' particular use.

In some forms, additional layers may be positioned between the topsheet and the absorbent core. For example, a secondary topsheet, acquisition layer, and/or distribution layer, each of which are known in the art, may be positioned between the topsheet and the absorbent core of the absorbent article. Similarly, additional layers may be positioned between an absorbent core and a backsheet.

Methods of Making Laminates and Disposable Absorbent Articles

The methods for making the laminates/webs of the present invention begin with obtaining the constituent layers of the laminate and/or material for the single web. For example, where the laminate comprises two layers, a first layer and a second layer should be obtained. It is possible to manufacture nonwoven layers as described heretofore. Alternatively, one or more of the nonwoven materials could be obtained from a nonwoven manufacturer. Suitable methods for making the constituent layers of the laminate are described herein and are known in the art. Similarly, films may be obtained from suitable suppliers. In some forms, where laminates are utilized, the laminate may be obtained from a manufacturer in the form of a roll. For example, a laminate comprising two layers of nonowoven may be provided by a manufacturer in the form of a roll of nonwoven laminate material. As another example, a laminate comprising a film layer and a nonwoven layer may be provided by a manufacturer in roll form.

Figure 7A:
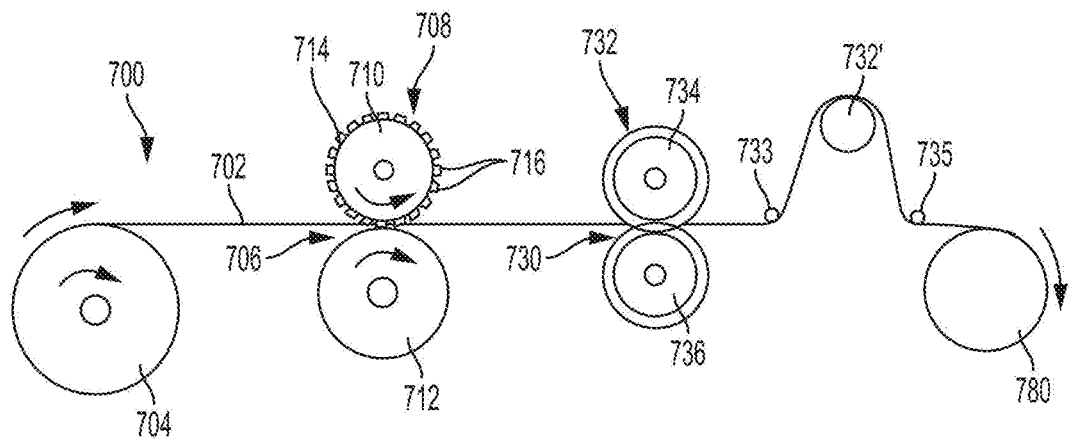
FIG. 7A is a schematic representation of an example process for producing the patterned apertured webs of the present disclosure in accordance with the present disclosure.

Referring to FIG. 7A, there is schematically illustrated at 700 one process for forming the laminate webs of the present disclosure. First, a precursor material 702 is supplied as the starting material. The precursor material 702 can be supplied as discrete webs, e.g. sheets, patches, etc. of material for batch processing. For commercial processing, however, the precursor material 702 may be supplied as roll stock, and, as such it can be considered as having a finite width and an infinite length. In this context, the length is measured in the machine direction (MD). Likewise, the width is measured in the cross machine direction (CD). The precursor material 702 may comprise the laminate 100 prior to the formation of apertures therein. In some forms of the present invention, the precursor material 702 may comprise the first layer 110 without the second layer 150 or vice versa.

The precursor material 702 may be unwound from a supply roll 704 and travel in a direction indicated by the arrow associated therewith as the supply roll 704 rotates in the direction indicated by the arrow associated therewith. The precursor material 702 passes through a nip 706 of a weakening roller (or overbonding) arrangement 708 formed by rollers 710 and 712, thereby forming a weakened precursor material. The weakened precursor material 702 has a pattern of overbonds, or densified and weakened areas, after passing through a nip 706. At least some of, or all of, these overbonds are used to form apertures in the precursor material 702. Therefore, the overbonds can correlate generally to the patterns of apertures created in the precursor material 702.

Figure 7B:
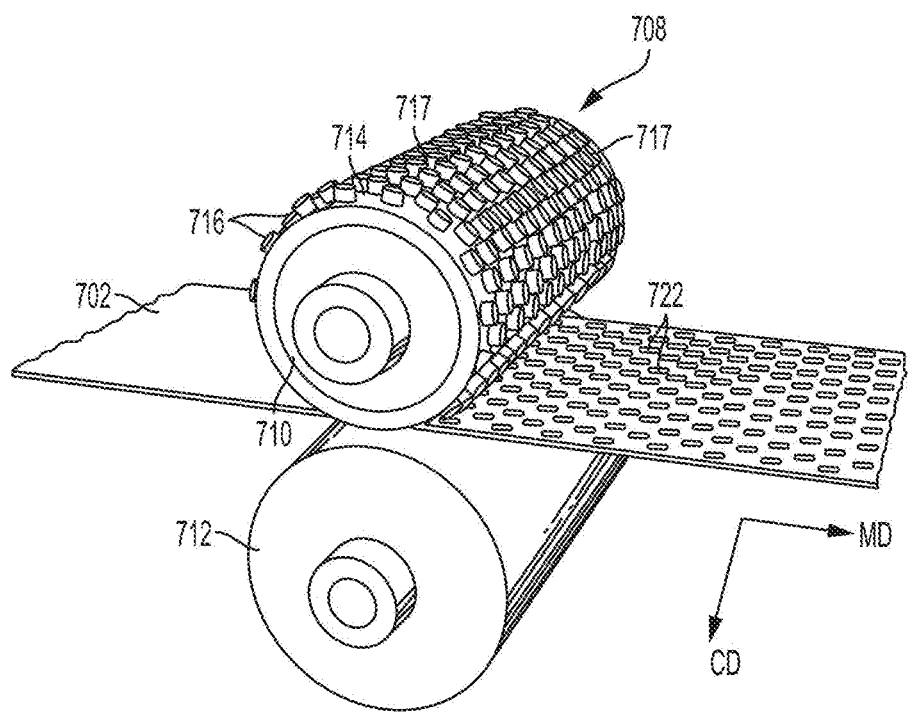
FIG. 7B is a perspective view of a web weakening arrangement of FIG. 7A in accordance with the present disclosure.

Referring to FIG. 7B, the precursor material weakening roller arrangement 708 may comprises a patterned calendar roller 710 and a smooth anvil roller 712. One or both of the patterned calendar roller 710 and the smooth anvil roller 712 may be heated and the pressure between the two rollers may be adjusted by known techniques to provide the desired temperature, if any, and pressure to concurrently weaken and melt-stabilize (i.e., overbond) the precursor material 702 at a plurality of locations 722. As will be discussed in further detail below, after the precursor material 702 passes through the weakening roller arrangement 708, the precursor material 702 may be stretched in the CD, or generally in the CD, by a cross directional tensioning force to at least partially, or fully, rupture the plurality of weakened, melt stabilized locations 722, thereby creating a plurality of at least partially formed apertures in the precursor material 702 coincident with the plurality of weakened, melt stabilized locations 722.

While melt stabilized locations 722 are shown across the entire width of the material 702, in some forms of the present invention, the melt stabilized locations 722 may be provided in zones on the material 722. Some examples of zones are provided with regard to FIGS. 39-43.

The patterned calendar roller 710 is configured to have a cylindrical surface 714, and a plurality of protuberances or pattern elements 716 which extend outwardly from the cylindrical surface 714. The pattern elements 716 are illustrated as a simplified example of a patterned calendar roller 710, but more detailed patterned calendar rollers that can be used to produce laminate webs of the present disclosure will be illustrated in subsequent figures. The protuberances 716 may be disposed in a predetermined pattern with each of the protuberances 716 being configured and disposed to precipitate a weakened, melt-stabilized location in the precursor material 702 to affect a predetermined pattern of weakened, melt-stabilized locations 722 in the precursor material 702. The protuberances 716 may have a one-to-one correspondence to the pattern of melt stabilized locations in the precursor material 702. As shown in FIG. 7B, the patterned calendar roller 710 may have a repeating pattern of the protuberances 716 which extend about the entire circumference of surface 714. Alternatively, the protuberances 716 may extend around a portion, or portions of the circumference of the surface 714. Also, a single patterned calendar roller may have a plurality of patterns in various zones (i.e., first zone, first pattern, second zone, second pattern).

Figure 8A:
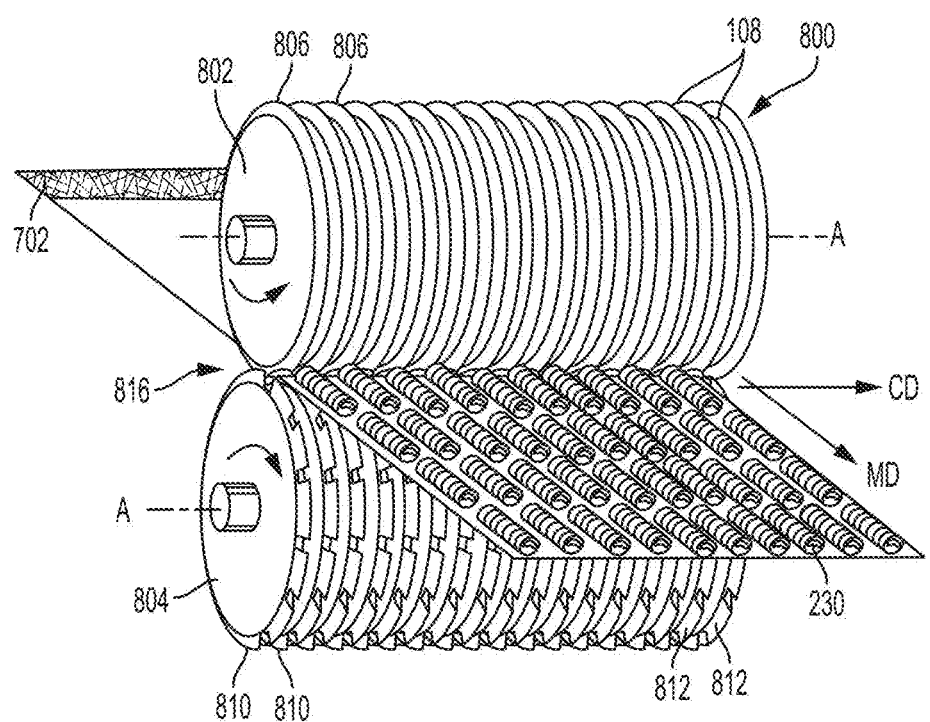
FIG. 8A is a perspective view showing an apparatus for producing tufts in the laminates of the present invention.
Figure 8B:
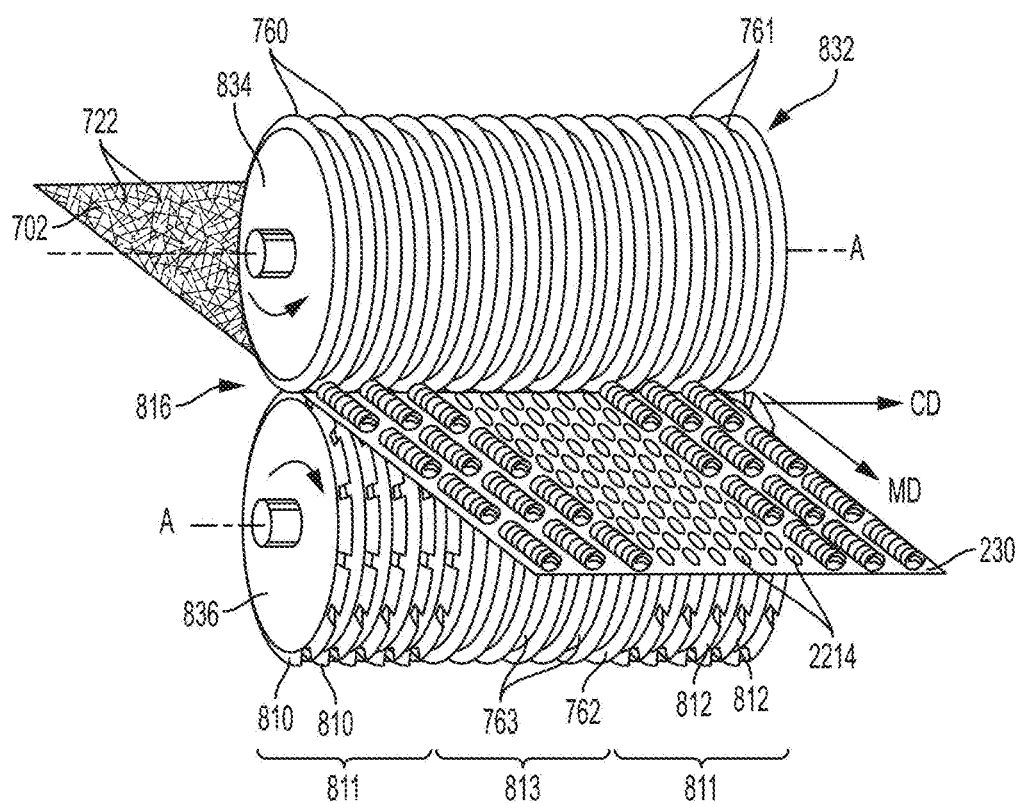
FIG. 8B is a perspective view showing an alternative apparatus for an incremental stretching system of the process of FIG. 7A in accordance with the present disclosure.
Figure 9:
FIG. 9 is a photograph of an example roller that can be used as roller 710 in the weakening arrangement of FIG. 7B in accordance with the present disclosure.
Figure 10A:
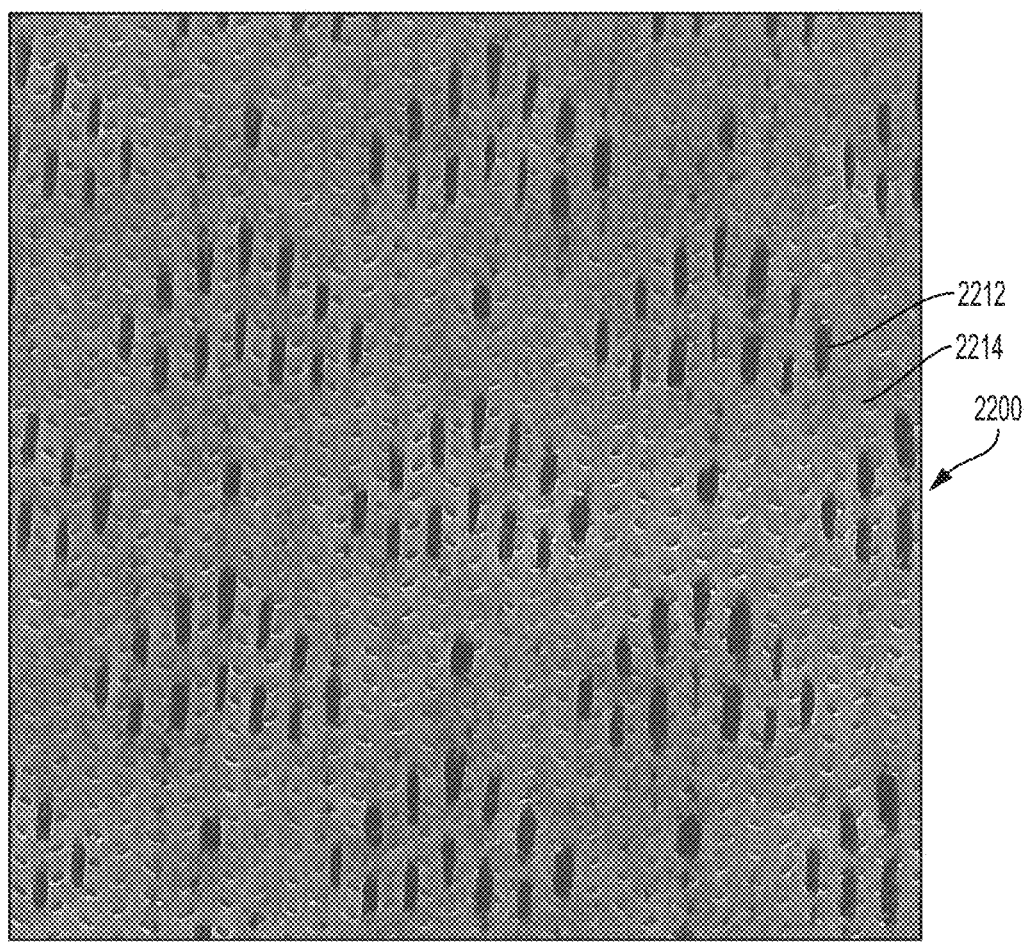
FIGS. 10A-10J are photographs of portions of example nonwoven laminates in accordance with the present disclosure.
Figure 10B:
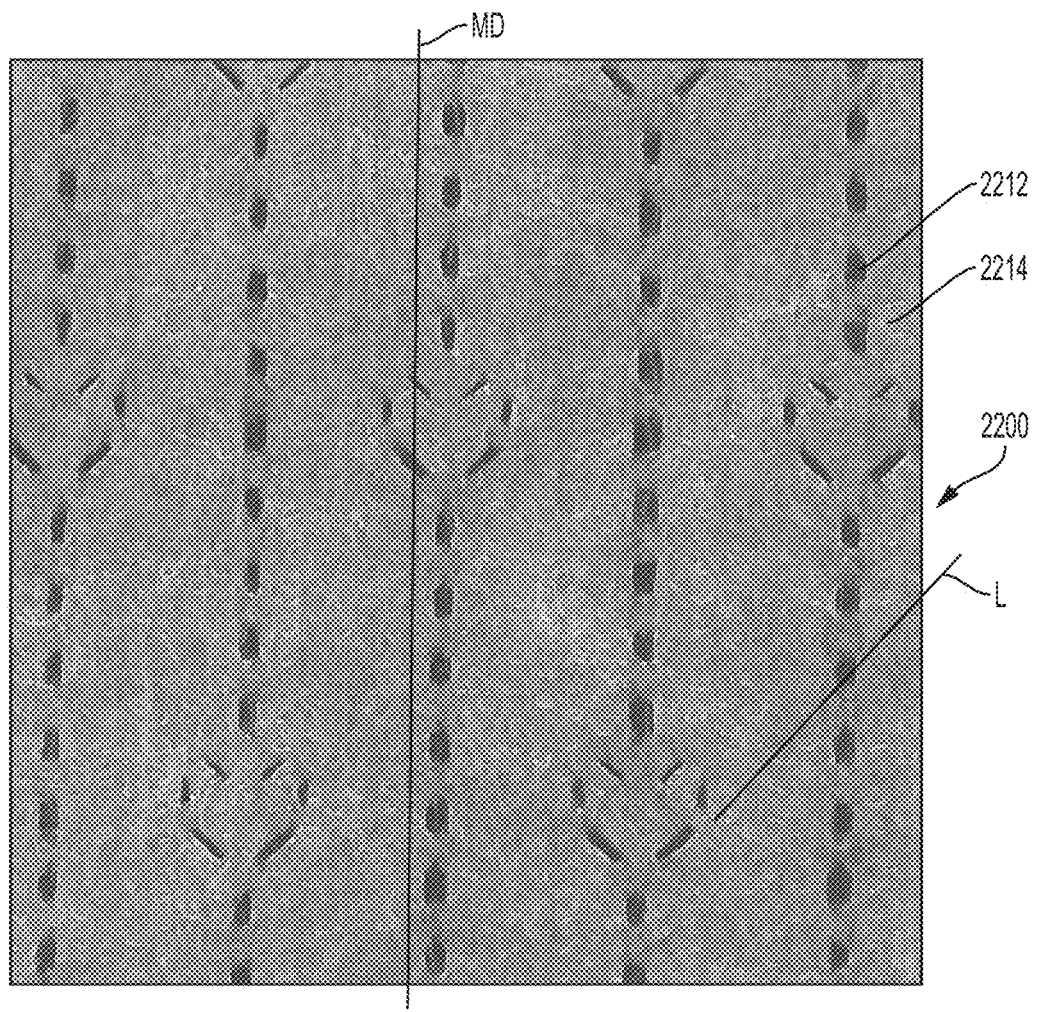
Figure 10C:
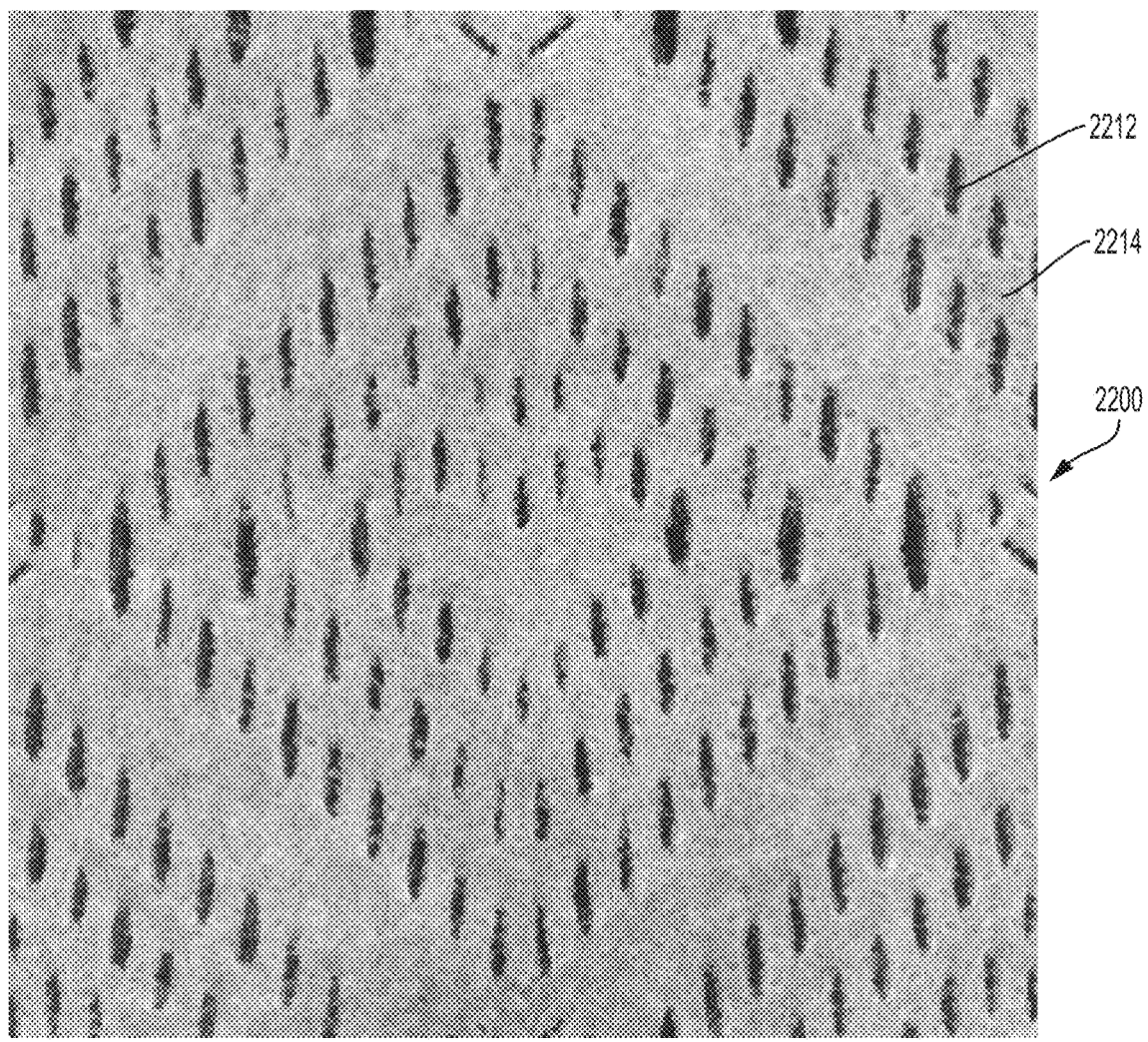
Figure 10D:
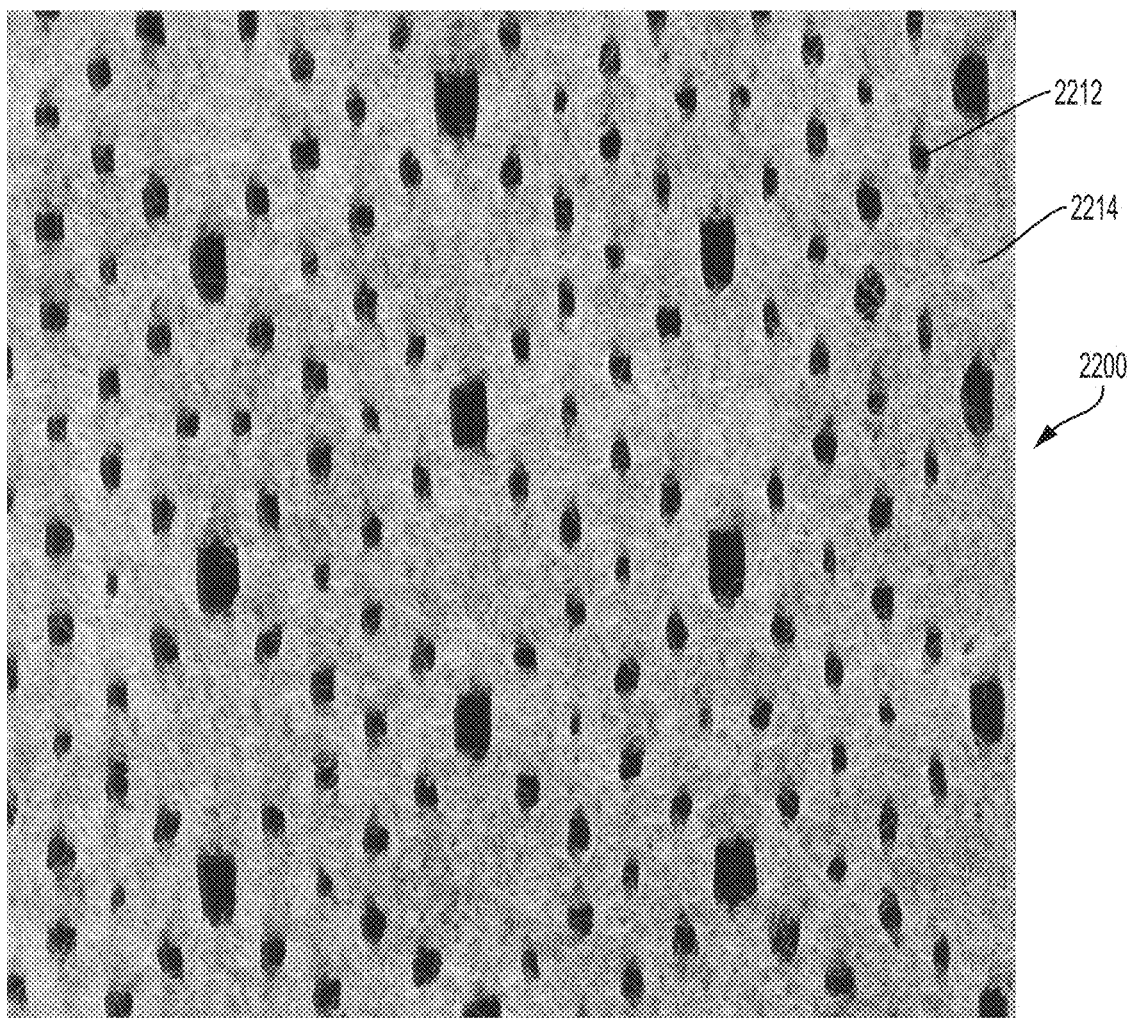
Figure 10E:
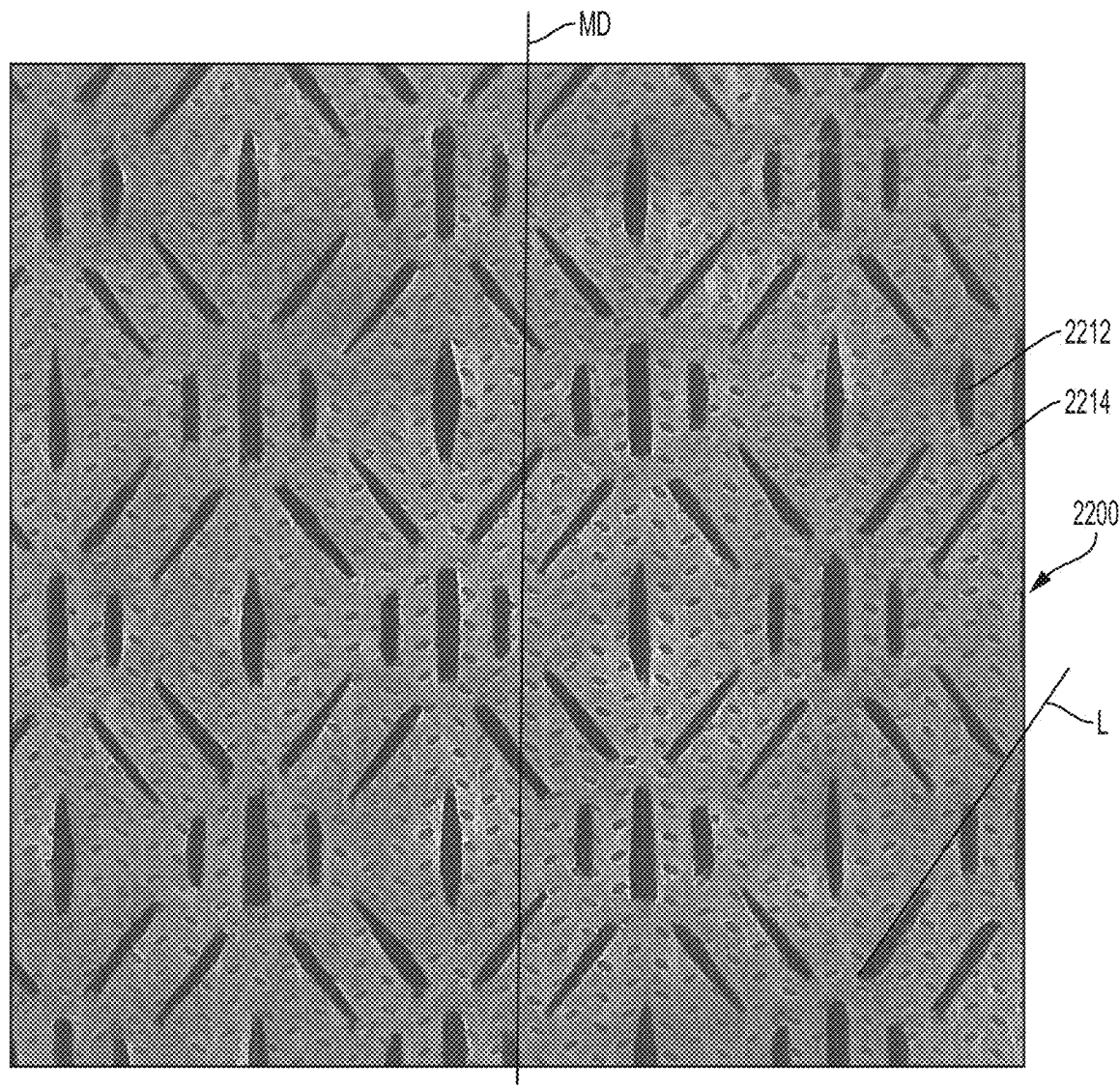
Figure 10F:
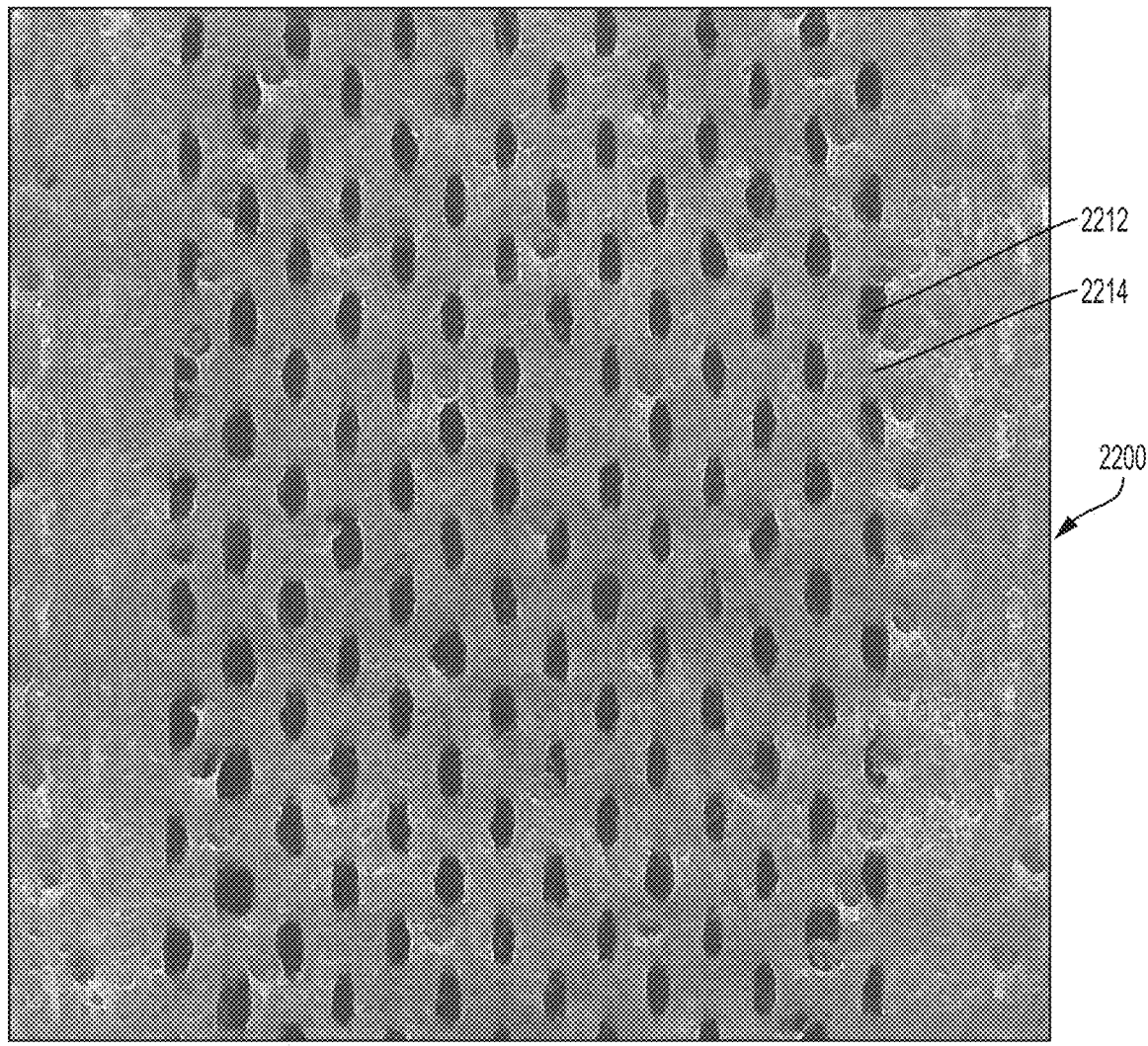
Figure 10G:
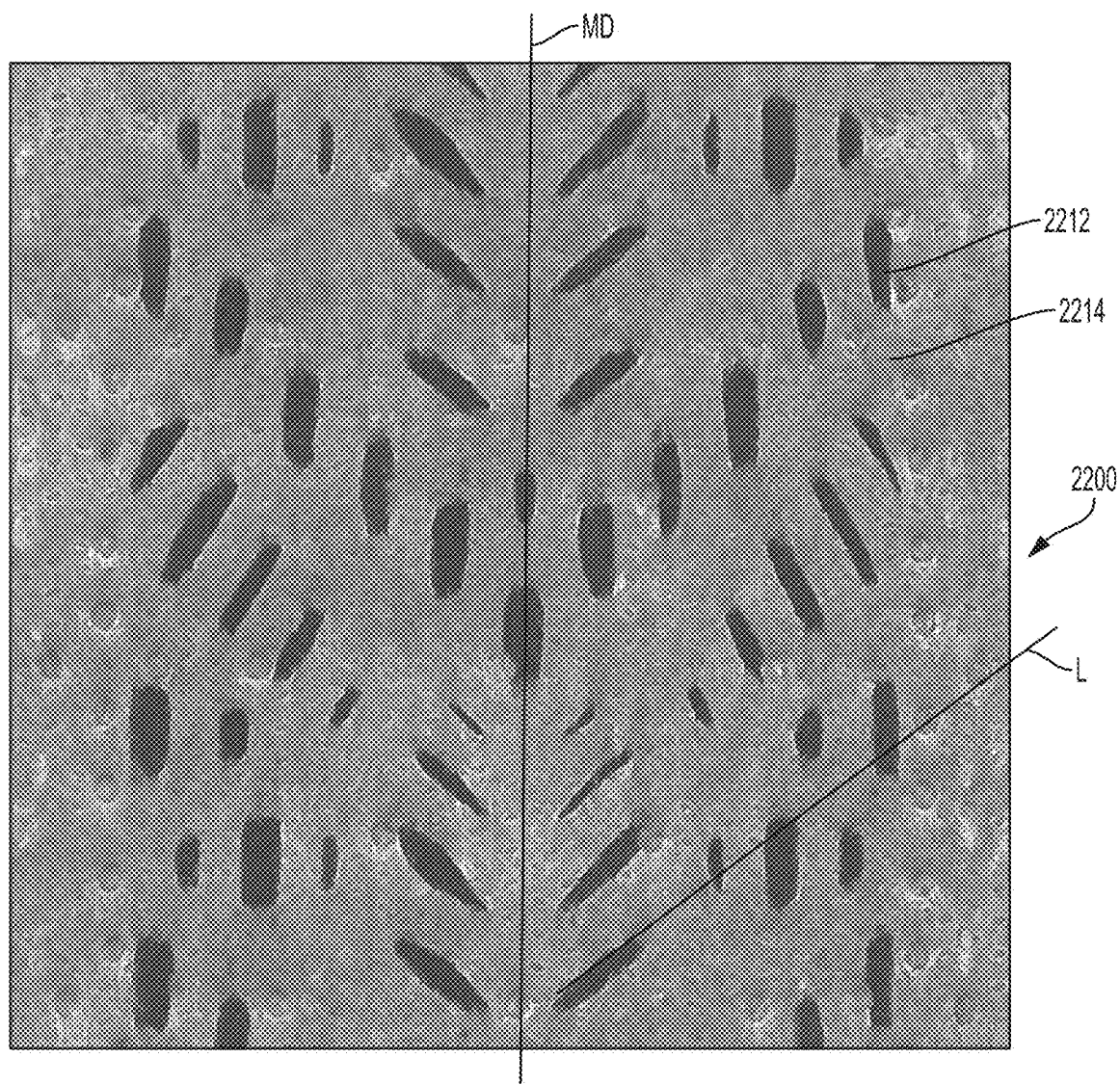
Figure 10H:
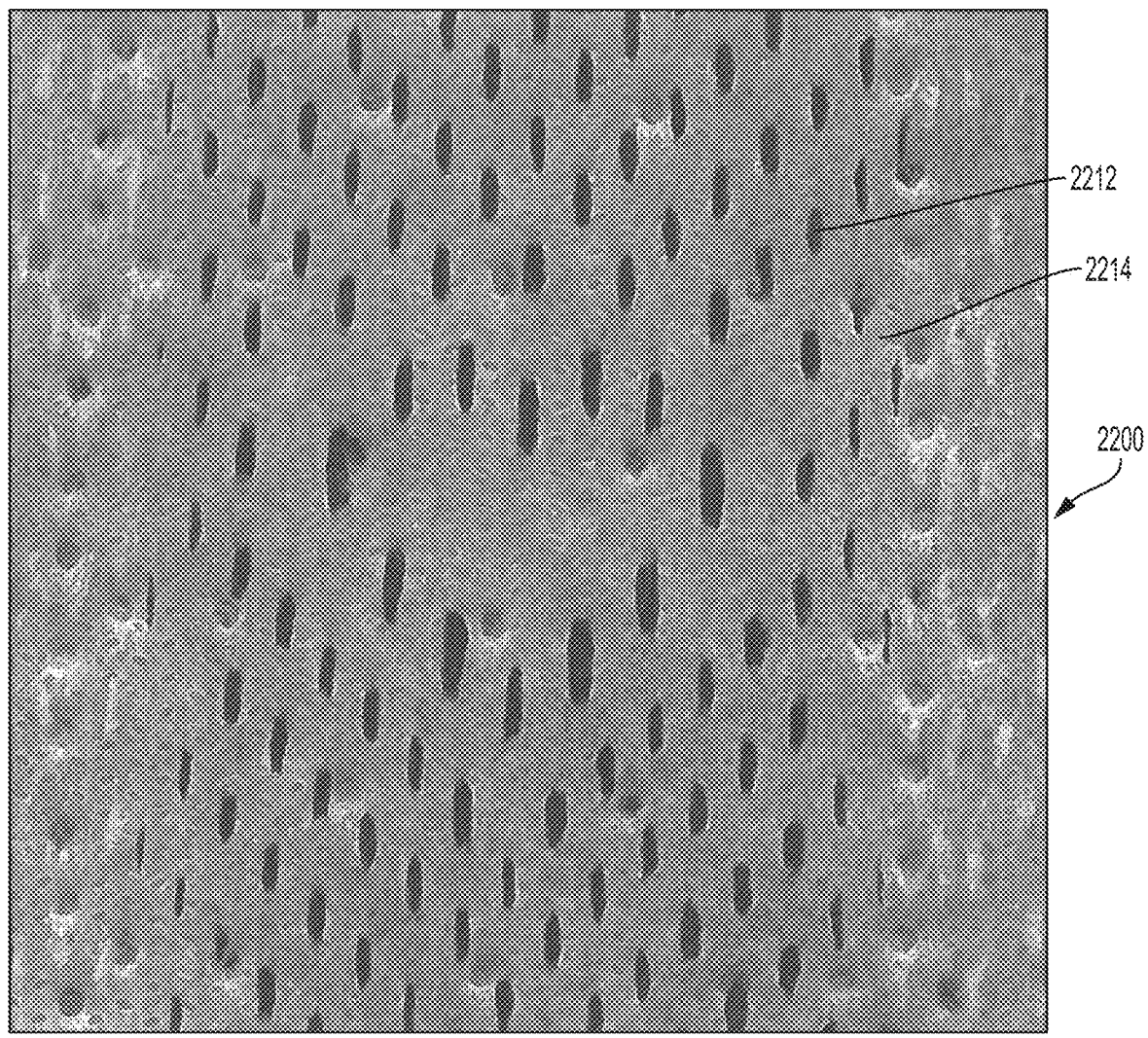
Figure 10I:
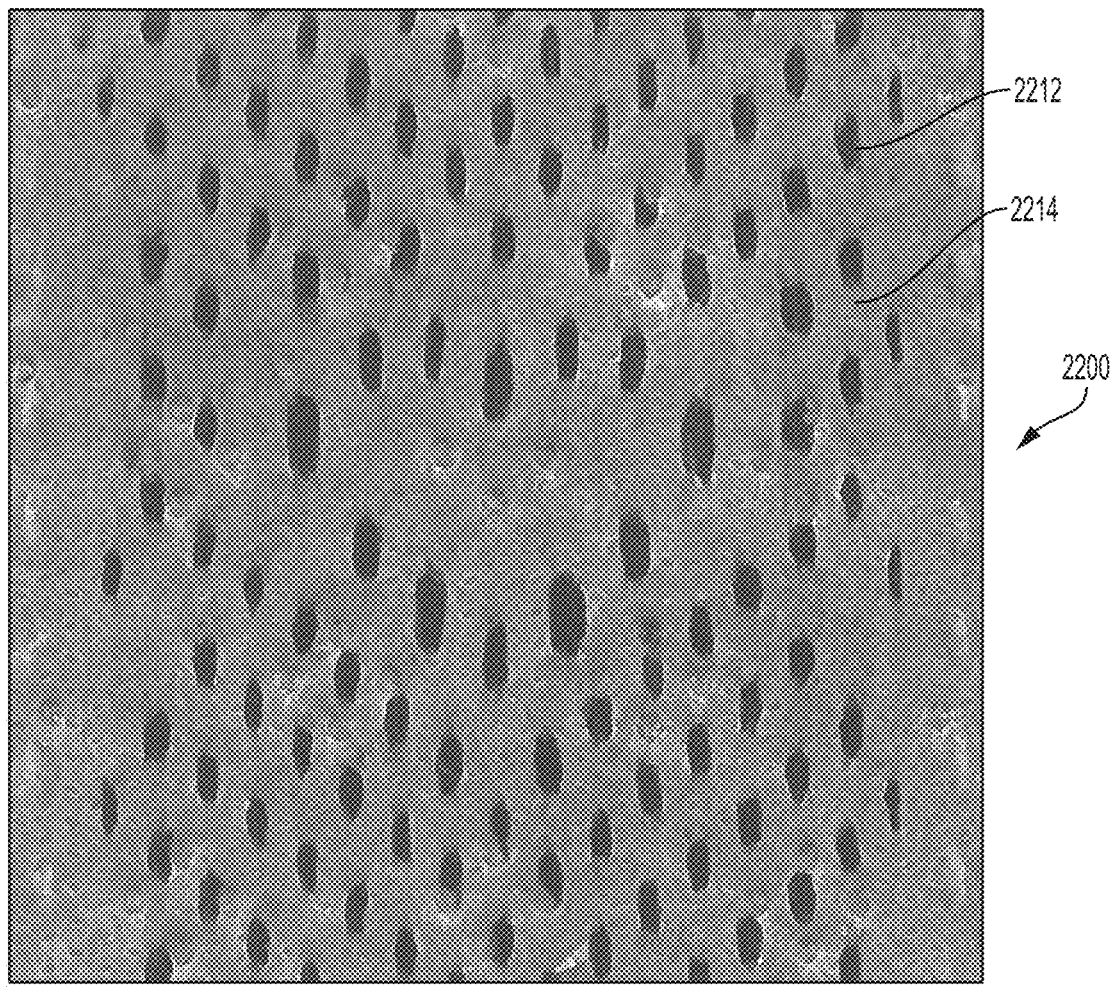
Figure 10J:
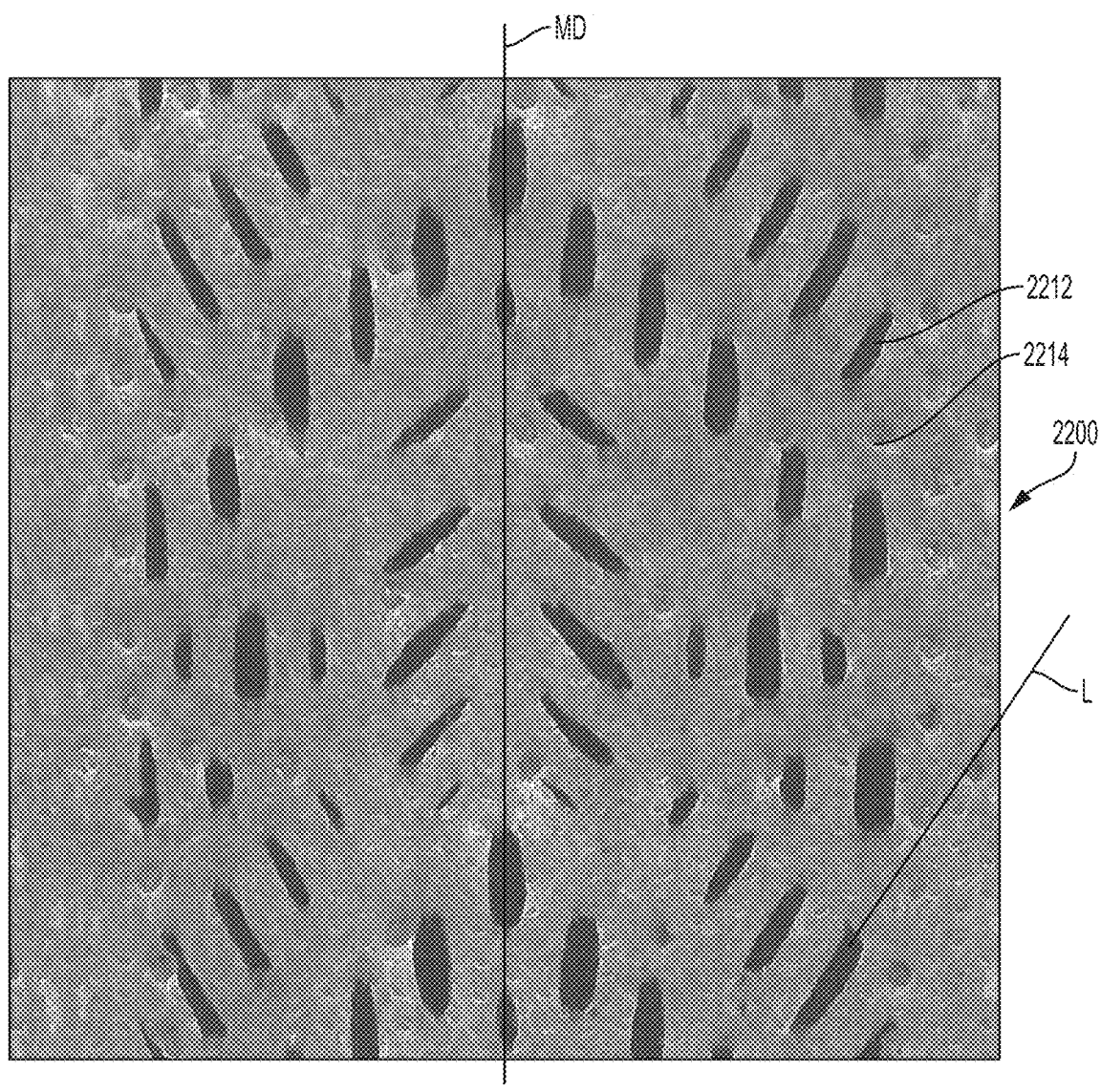
Figure 11:
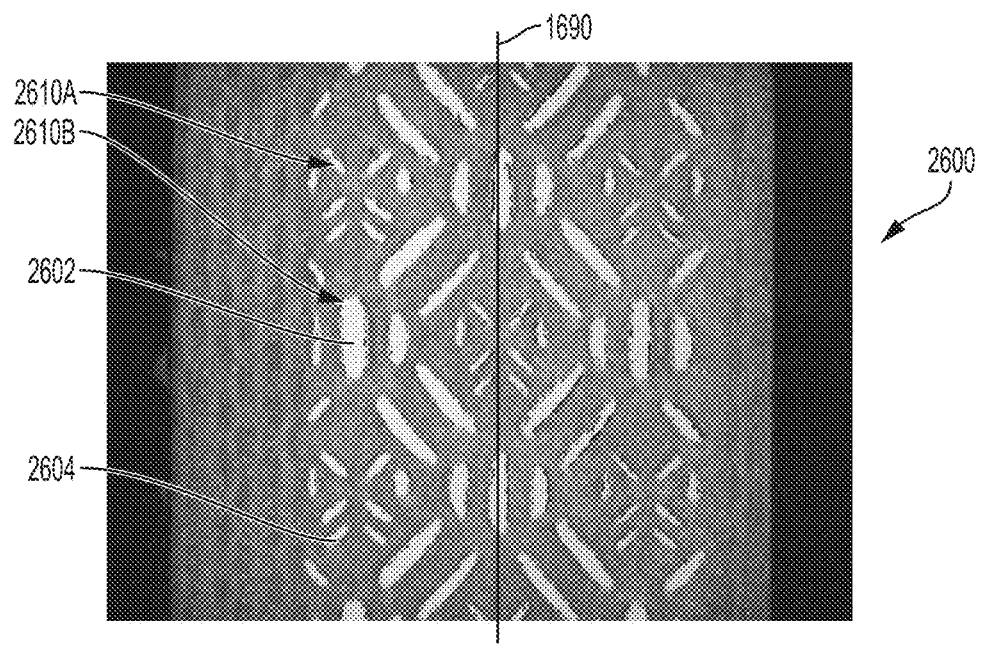
FIGS. 11-24 are photographs of nonwoven laminates constructed in accordance with the present invention.
Figure 12:
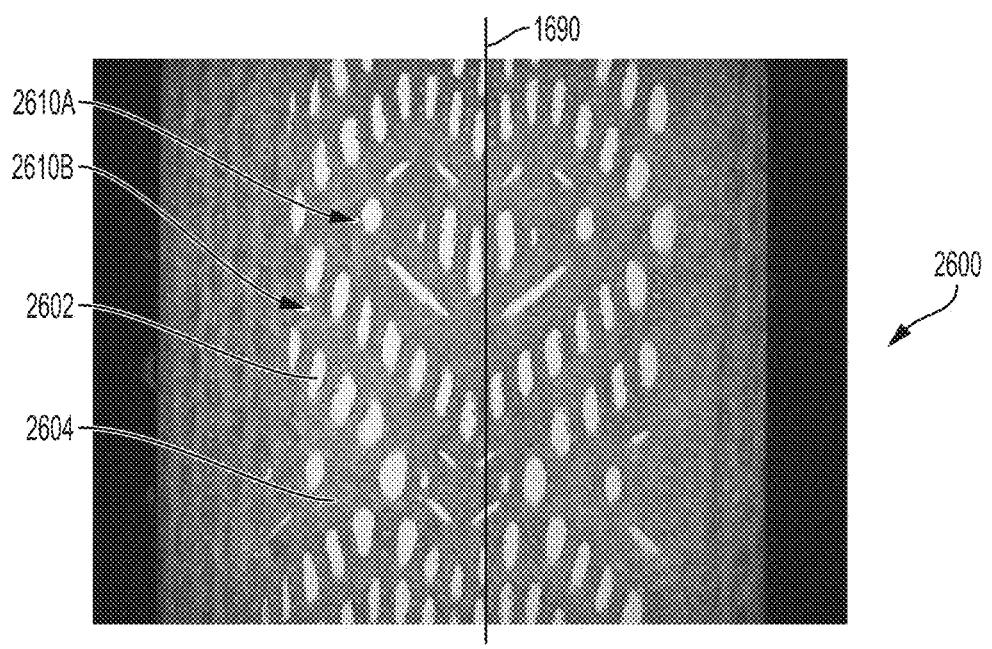
Figure 13:
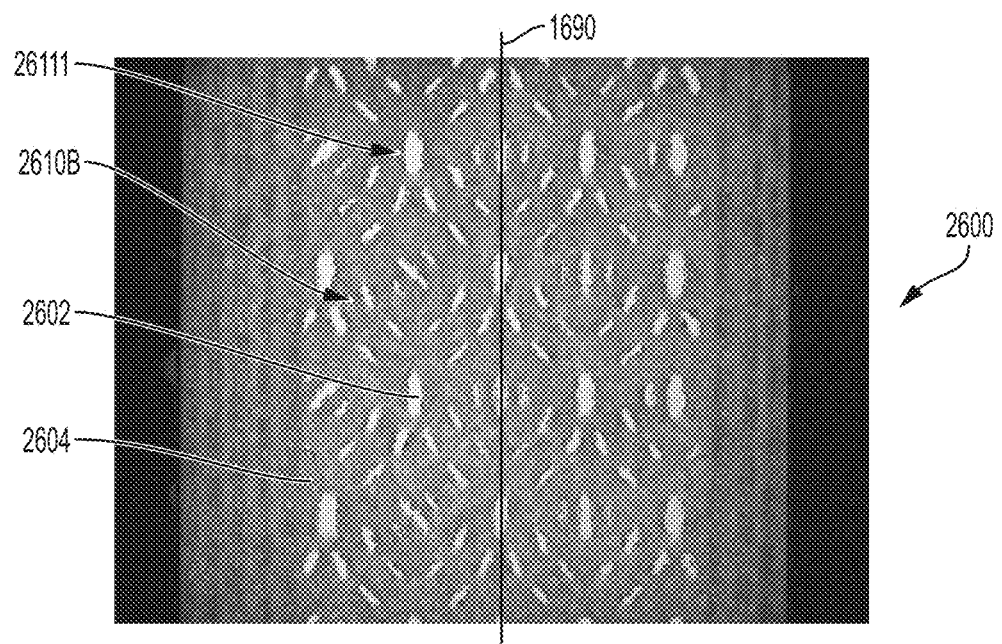
Figure 14:
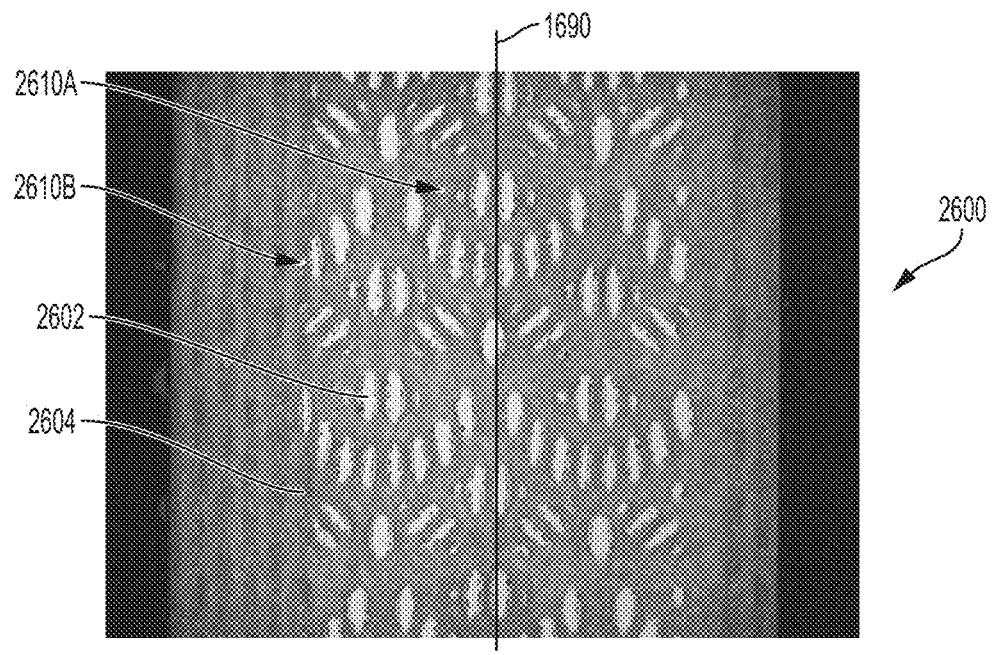
Figure 15:
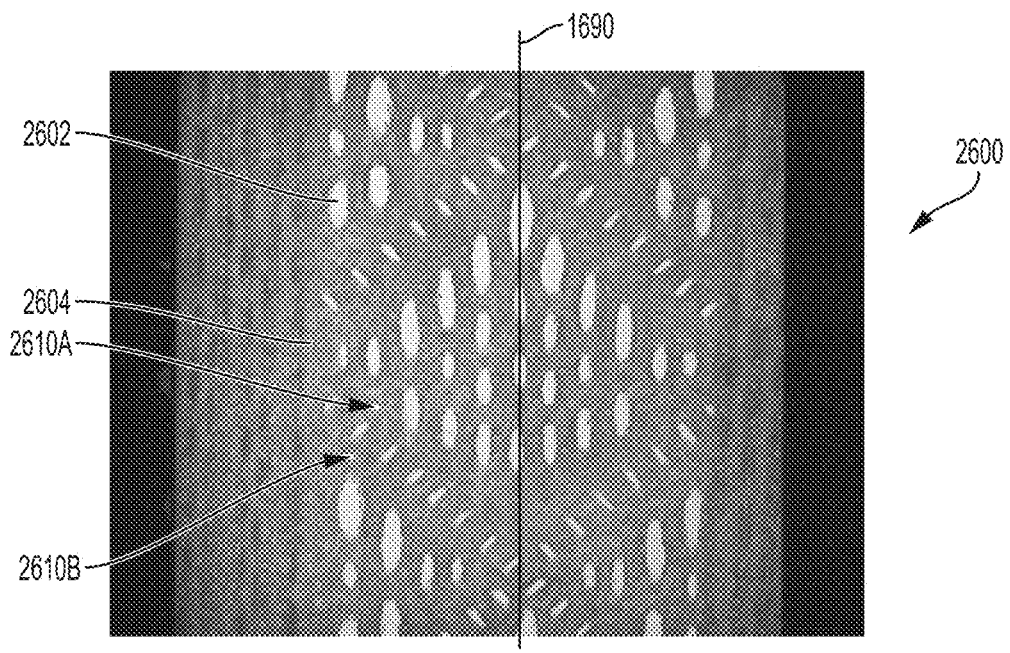
Figure 16:
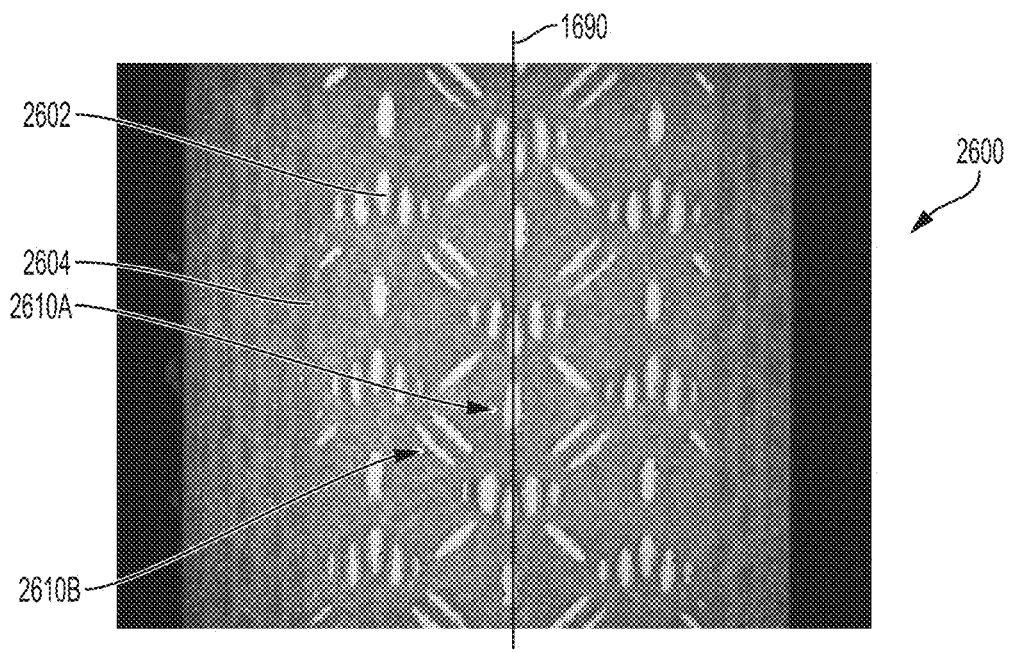
Figure 17:
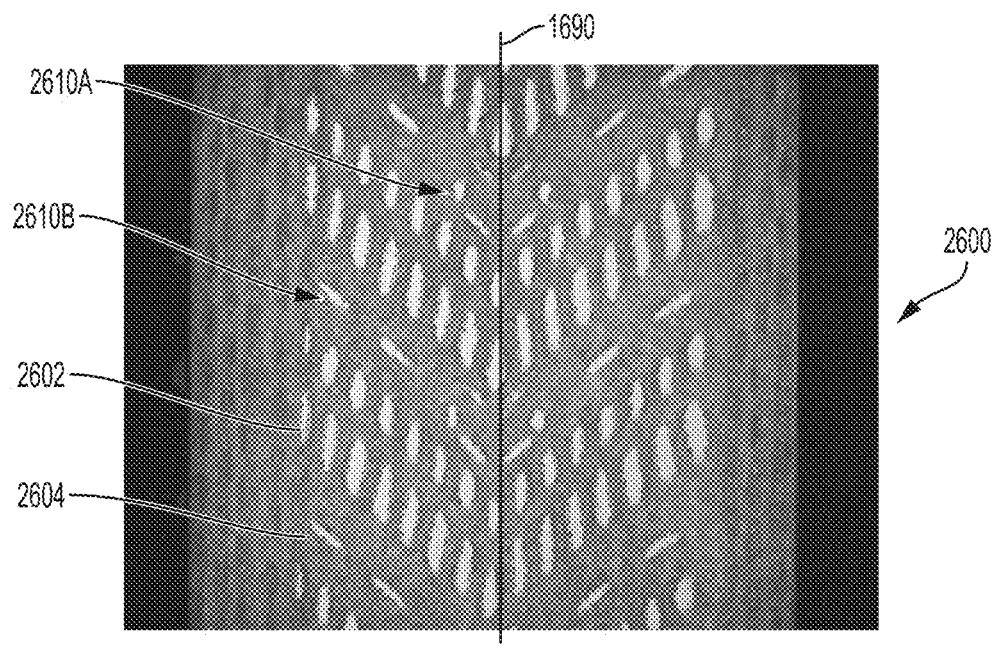
Figure 18:
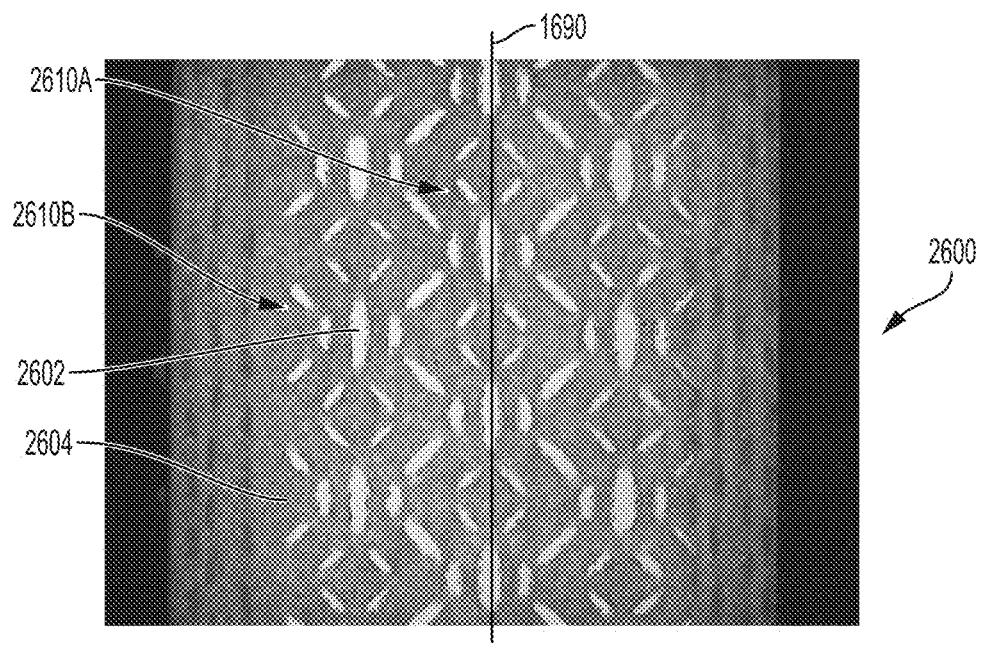
Figure 19:
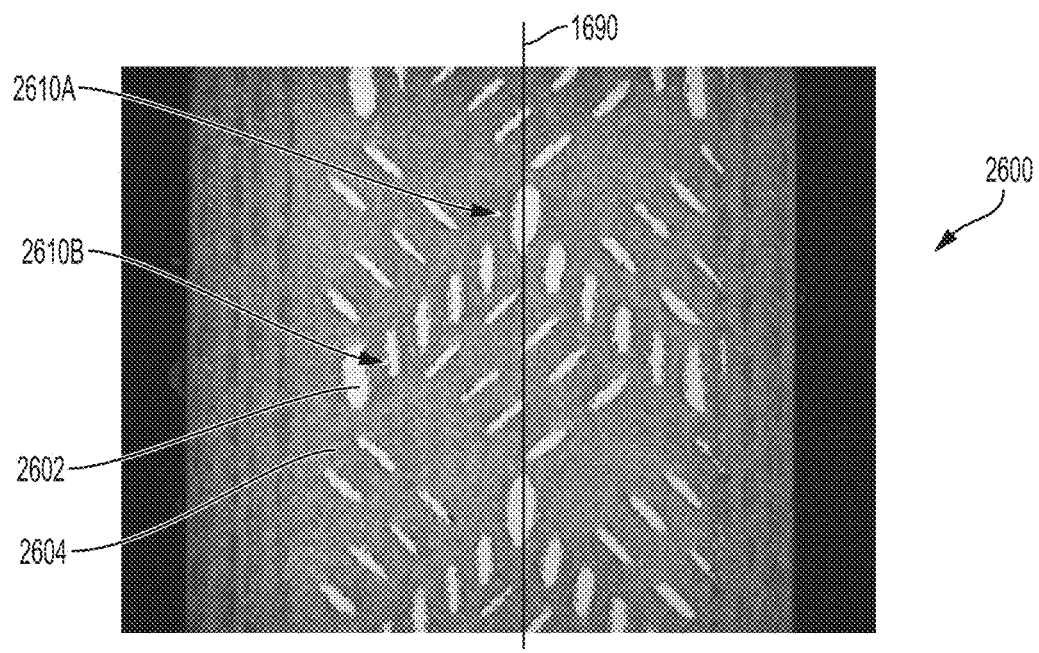
Figure 20:
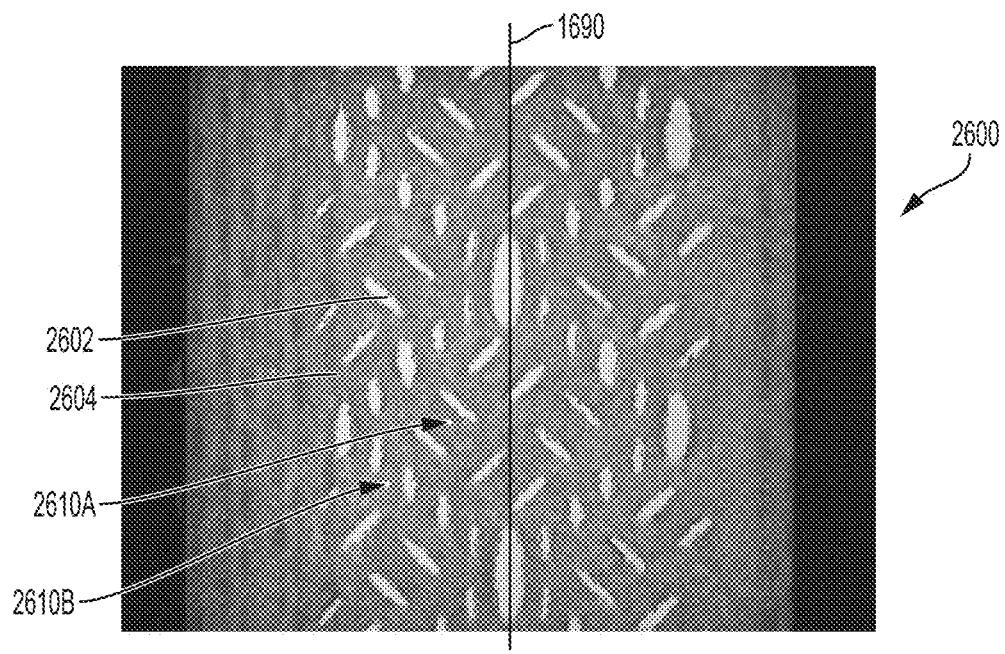
Figure 21:
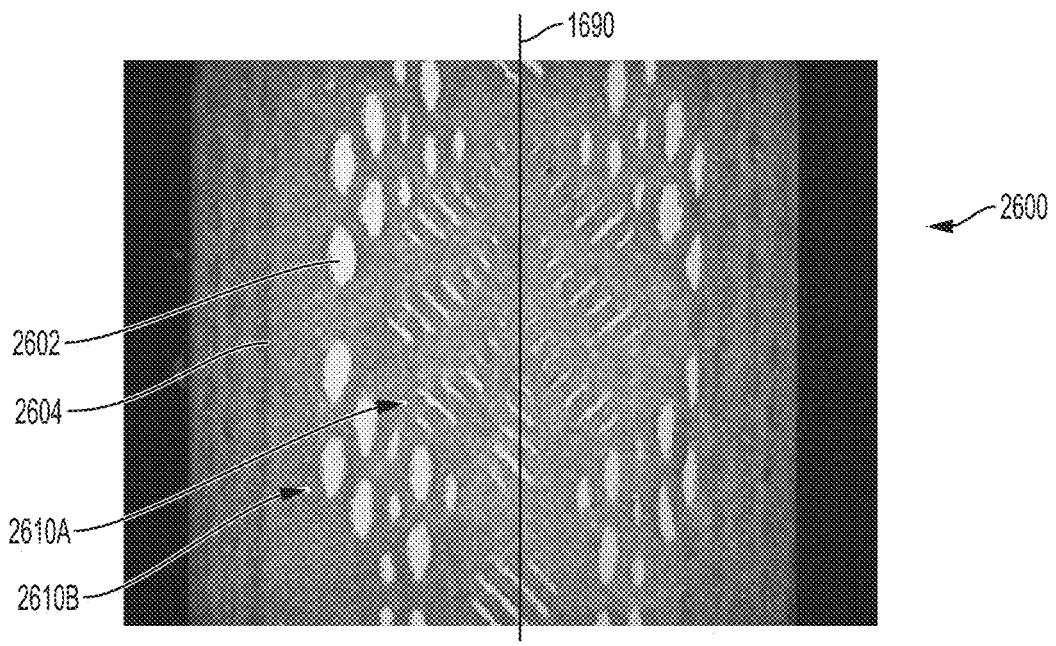
Figure 22:
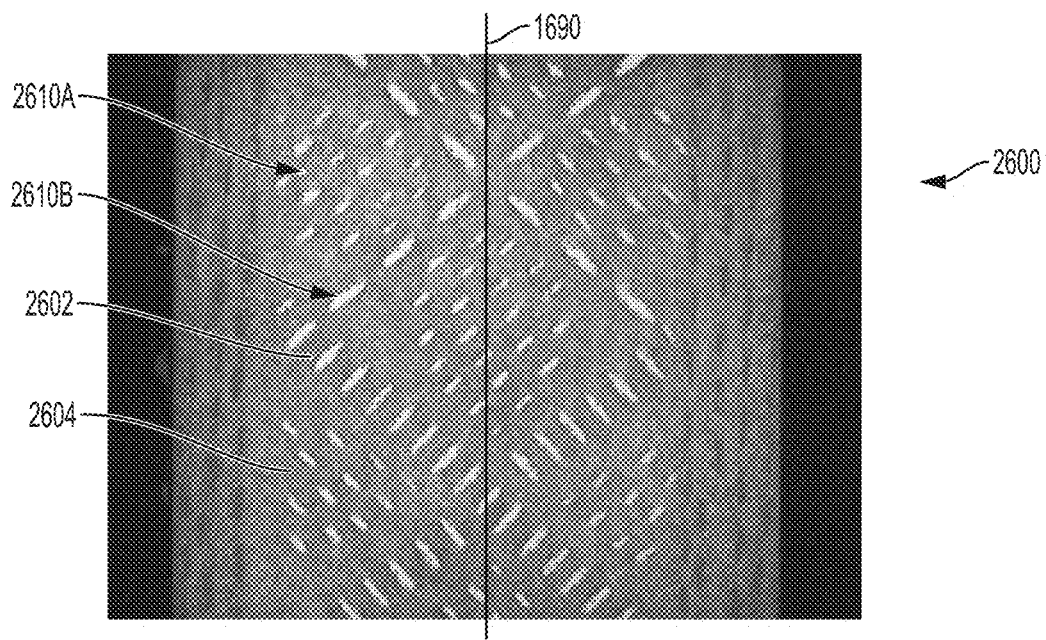
Figure 23:
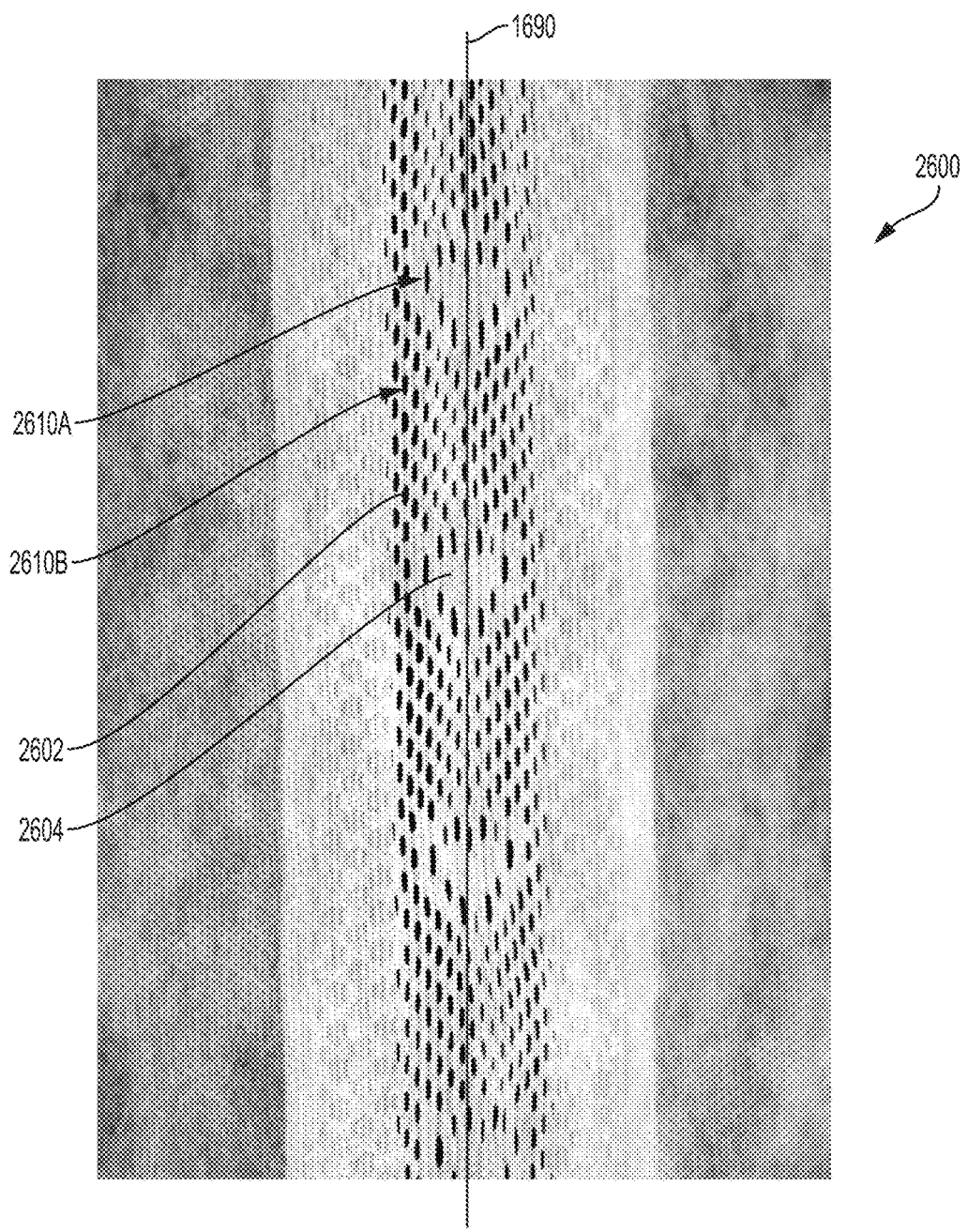
Figure 24:
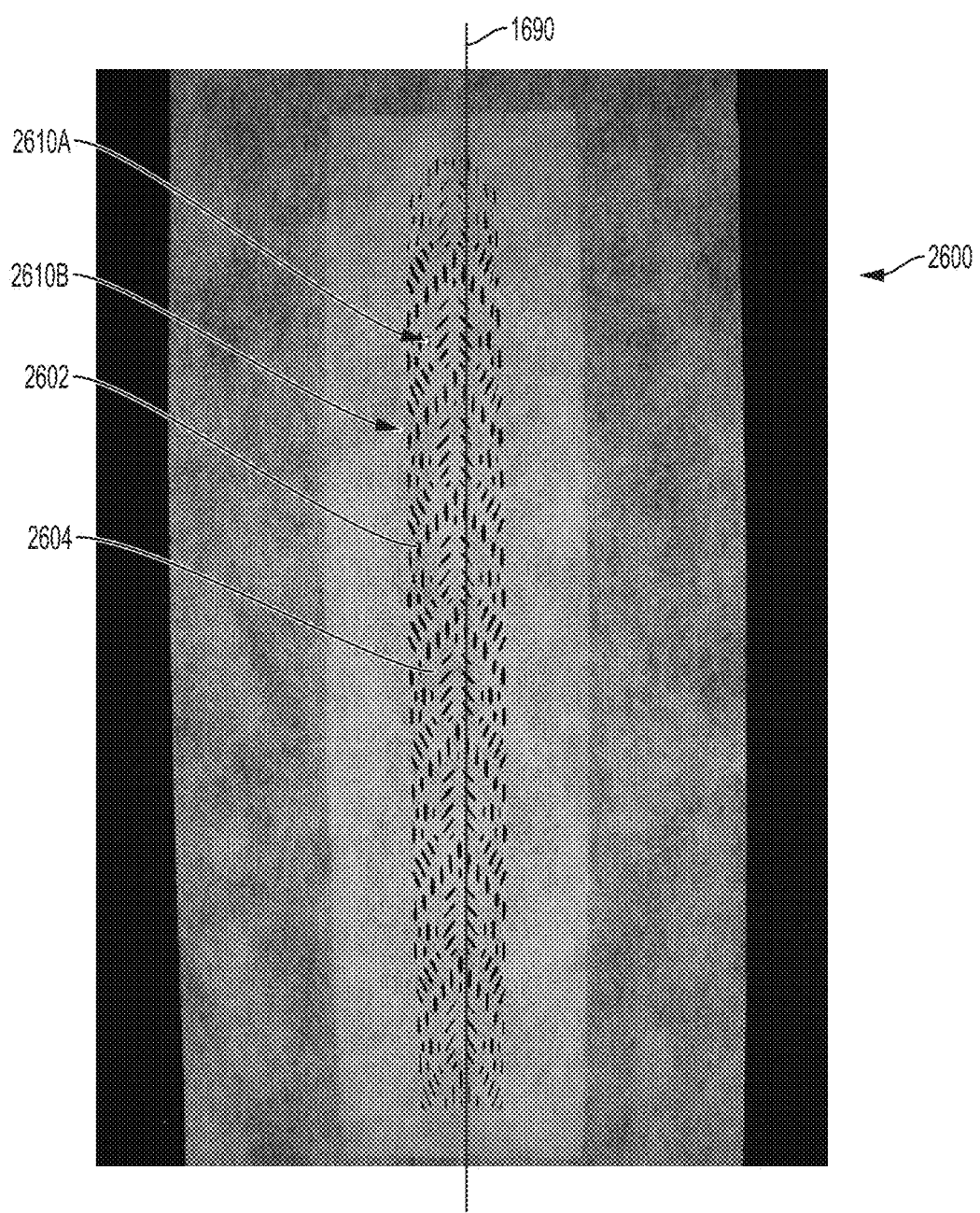

Some photographs of example rollers that may be used as patterned calendar roller 710 in the process 700 of FIG. 7A to produce the apertures in the laminates of the present disclosure are illustrated in FIG. 8A-8C. The pattern of protuberances 716 on the rollers in FIGS. 9A-9C would be formed in the precursor web 702, much like the melt-stabilized locations 722 of FIG. 7B. Exemplary patterned apertured webs produced from the rolls (similar to but not the same as the rolls in FIGS. 9A-9C) after cross-directional tensioning of the precursor material 702 are illustrated in FIGS. 10A-10J, respectively, with the apertures being indicated as element 2212 and the land areas (i.e., non-apertured areas) being indicated as element 2214. As seen in FIGS. 10A-10J, apertures 2212 and/or aperture arrays have been formed in the webs 702. The land areas 2214 correspond to areas in the precursor material 702 that have not been melt stabilized or overbonded. Stated another way, the land areas 2214 have not been contacted by a protuberance on the roller 710.

Referring back to FIG. 7B, the protuberances 716 may extend radially outwardly from surface 714 and have distal end surfaces 717. The anvil roller 712 may be a smooth surfaced, circular cylinder of steel, rubber or other material. The anvil roller 712 and the patterned calendar roller 710 may be switched in position (i.e., anvil on top) and achieve the same result.

From the weakening roller arrangement 708, the material 702 passes through a nip 730 formed by an incremental stretching system 732 employing opposed pressure applicators having three-dimensional surfaces which at least to a degree may be complementary to one another.

Figure 7C:
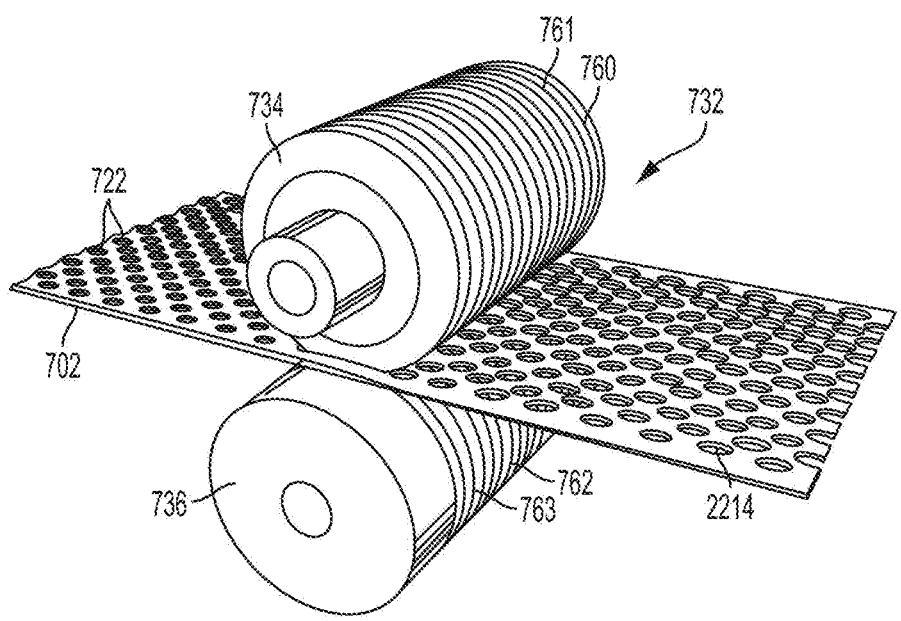
FIG. 7C is a perspective view of an incremental stretching system of the process of FIG. 7A in accordance with the present disclosure.

Referring now to FIG. 7C, there is shown a fragmentary enlarged view of the incremental stretching system 732 comprising two incremental stretching rollers 734 and 736. The incremental stretching roller 734 may comprise a plurality of teeth 760 and corresponding grooves 761 which may about the entire circumference of roller 734. The incremental stretching roller 736 may comprise a plurality of teeth 762 and a plurality of corresponding grooves 763. The teeth 760 on the roller 734 may intermesh with or engage the grooves 763 on the roller 736 while the teeth 762 on the roller 736 may intermesh with or engage the grooves 761 on the roller 734. As the precursor material 702 having weakened, melt-stabilized locations 722 passes through the incremental stretching system 732 the precursor material 702 is subjected to tensioning in the CD causing the material 702 to be extended (or activated) in the CD, or generally in the CD. Additionally the material 702 may be tensioned in the MD, or generally in the MD. The CD tensioning force placed on the material 702 is adjusted such that it causes the weakened, melt-stabilized locations 722 to at least partially, or fully, rupture thereby creating a plurality of partially formed, or formed apertures 704 coincident with the weakened melt-stabilized locations 722 in the material 702. However, the bonds of the material 702 (in the non-overbonded areas) are strong enough such that they do not rupture during tensioning, thereby maintaining the material 702 in a coherent condition even as the weakened, melt-stabilized locations rupture. However, it may be desirable to have some of the bonds rupture during tensioning.

Figure 7D:
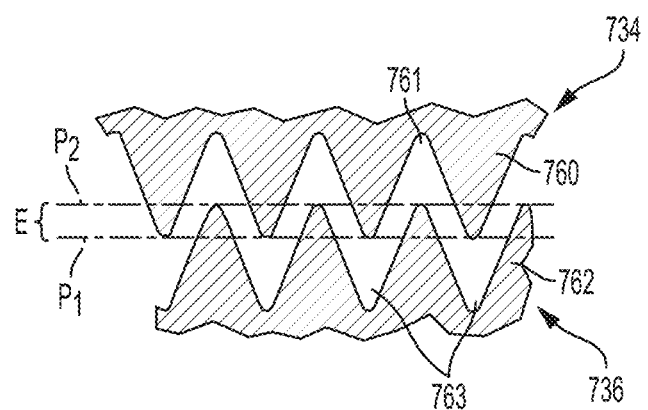
FIG. 7D is an enlarged view showing the details of teeth of the incremental stretching system of FIG. 7C in accordance with the present disclosure.

Referring to FIG. 7D, a more detailed view of the teeth 760 and 762 and the grooves 761 and 763 on the rollers 734 and 736 is illustrated. The term "pitch" refers to the distance between the apexes of adjacent teeth. The pitch may be between about 0.02 inches to about 0.30 inches (about 0.51 mm to about 7.62 mm) or may be between about 0.05 inches and about 0.15 inches (about 1.27 mm to about 3.81 mm), specifically reciting all 0.001 inch increments within the above-specified ranges and all ranges formed therein or thereby. The height (or depth) of the teeth is measured from the base of the tooth to the apex of the tooth, and may or may not be equal for all teeth. The height of the teeth may be between about 0.010 inches (about 0.254 mm) and about 0.90 inches (about 22.9 mm) or may be between about 0.025 inches (about 0.635 mm) and about 0.50 inches (about 12.7 mm), specifically reciting all 0.01 inch increments within the above-specified ranges and all ranges formed therein or thereby. The teeth 760 in one roll may be offset by about one-half of the pitch from the teeth 762 in the other roll, such that the teeth of one roll (e.g., teeth 760) mesh in the valley (e.g., groove 763) between teeth in the mating roll. The offset permits intermeshing of the two rolls when the rolls are "engaged" or in an intermeshing, operative position relative to one another. The teeth of the respective rolls may only be partially intermeshing in some instances. The degree to which the teeth on the opposing rolls intermesh is referred to herein as the "depth of engagement" or "DOE" of the teeth. The DOE may be constant or not constant. As shown in FIG. 7D, the DOE, indicated as "E", is the distance between a position designated by plane P1 where the apexes of the teeth on the respective rolls are in the same plane (0% engagement) to a position designated by plane P2 where the apexes of the teeth of one roll extend inward beyond the plane P1 toward the groove on the opposing roll. The optimum or effective DOE for particular laminate webs may be dependent upon the height and the pitch of the teeth and/or the structure of the material. Some example DOEs may in the range of about 0.01 inches to about 0.5 inches, about 0.03 inches to about 0.2 inches, about 0.04 inches to about 0.08 inches, about 0.05 inches, or about 0.06 inches, specifically reciting all 0.001 inch increments within the above-specified ranges and all ranges formed therein or thereby.

As the material 702 having the weakened, melt-stabilized locations 702 passes through the incremental web stretching apparatus 732, the material 702 is subjected to tensioning in the cross machine direction, or substantially in the cross machine direction, thereby causing the nonwoven web 702 to be extended in the cross machine direction. The tensioning force placed on the material 702 may be adjusted by varying the pitch, DOE, or teeth size, such that the incremental stretching is sufficient to cause the weakened, melt-stabilized locations 722 to at least partially, or fully rupture, thereby creating, or at least partially creating, a plurality of apertures 2212 coincident with the weakened, melt-stabilized locations 722 in the material 702.

Figure 7E:
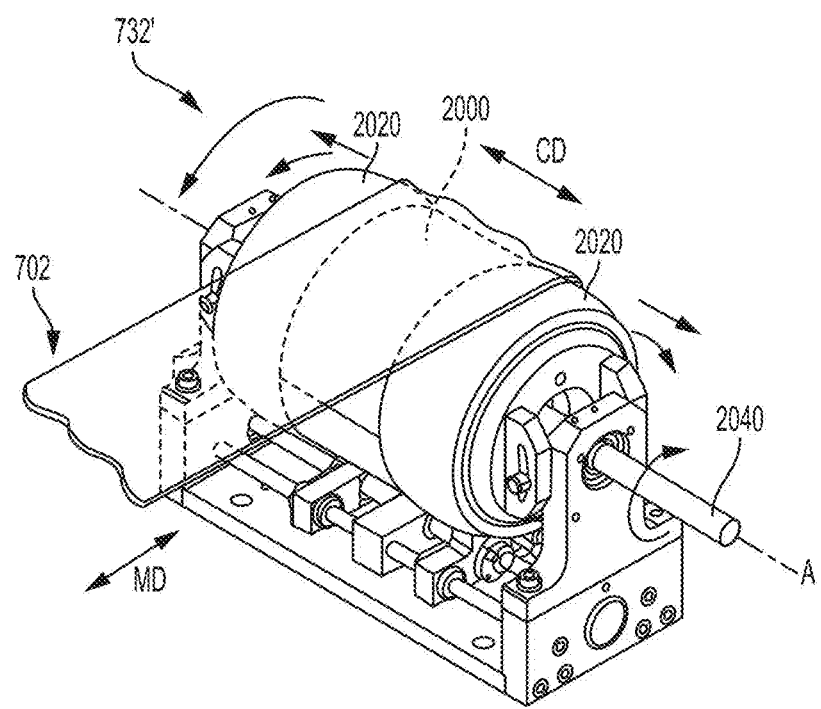
FIG. 7E is a perspective view of an example cross machine directional tensioning apparatus of the process of FIG. 7A in accordance with the present disclosure.

After the material 702 passes through the incremental web stretching apparatus 732, the web 702 may be advanced to and at least partially around a cross machine directional tensioning apparatus 732' (see e.g., FIGS. 7A and 7E). The cross machine directional tensioning apparatus 732' may be offset from the main processing line by running the web partially around two idlers 733 and 735 or stationary bars, for example. In other instances, the cross machine tensioning apparatus 732' may be positioned in line with the main processing line. The cross machine directional tensioning apparatus 732' may comprise a roll that comprises at least one outer longitudinal portion that expands along a longitudinal axis, A, of the roll, relative to a middle portion of the roll, to stretch and/or expand the material 702 in the cross machine direction. Instead of or in addition to expanding along the longitudinal axis, A, of the roll, the outer longitudinal portion may be angled relative to the longitudinal axis, A, of the roll in a direction away from the material 702 being advanced over the roll to stretch the material 702 in the cross machine direction or generally in the cross machine direction. In an instance, the roll may comprise two outer longitudinal portions that each may expand in opposite directions generally along the longitudinal axis, A, of the roll. The two outer portions may both be angled downwards in a direction away from the material 702 being advanced over the roll. This movement or positioning of the outer longitudinal portions of the roll allows for generally cross machine directional tensioning of the material 702, which causes the plurality of weakened locations 722 to rupture and/or be further defined or formed into apertures 2212.

The outer longitudinal portions of the roll may comprise vacuum, a low tack adhesive, a high coefficient of friction material or surface, such as rubber, and/or other mechanisms and/or materials to hold the material 702 to the outer lateral portions of the roll during movement of the outer longitudinal portion or portions relative to the middle portion of the roll. The vacuum, low tack adhesive, high coefficient of friction material or surface, and/or other mechanisms and/or materials may prevent, or at least inhibit, the held portions of the material 702 from slipping relative to the longitudinal axis, A, of the roll during stretching of the outer lateral portions of the material in the cross machine direction or generally in the cross machine direction.

FIG. 7E is a top perspective view of the example cross machine directional tensioning apparatus 732'. The cross machine directional tensioning apparatus 732' may comprise a roll comprising a middle portion 2000 and two outer longitudinal portions 2020 situated on either end of the middle portion 2000. The roll may rotate about its longitudinal axis, A, on a drive shaft 2040. The roll may rotate relative to the drive shaft 2040 or in unison with the drive shaft 2040, as will be recognized by those of skill in the art. The material 702 may be advanced over the entire cross machine directional width of the middle portion 2000 and at least portions of the cross machine directional widths of the outer longitudinal portions 2020. The material 702 may be advanced over at least about 5% up to about 80% of the circumference of the roll so that the cross machine directional stretching may be performed.

Figure 7F:
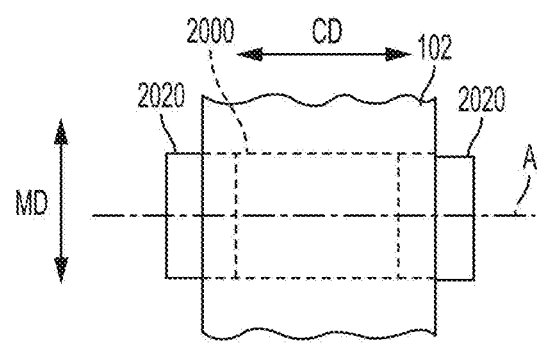
FIG. 7F is a schematic representation of a front view of an example cross machine directional tensioning apparatus with outer longitudinal portions in an unexpanded and non-angled position relative to a middle portion in accordance with the present disclosure.
Figure 7G:
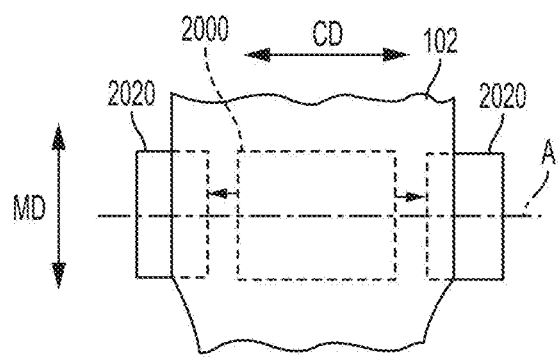
FIG. 7G is a schematic representation of a front view of the cross machine directional tensioning apparatus of FIG. 7F with the outer longitudinal portions in a longitudinally expanded position relative to the middle portion in accordance with the present disclosure.
Figure 7H:
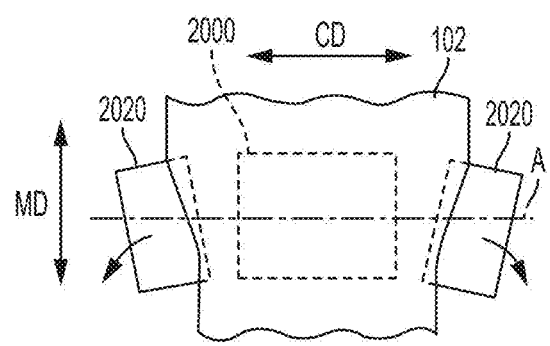
FIG. 7H is a schematic representation of a front view of the cross machine directional tensioning apparatus of FIG. 7F with the outer longitudinal portions in an angled and expanded position relative to the middle portion in accordance with the present disclosure.
Figure 7I:
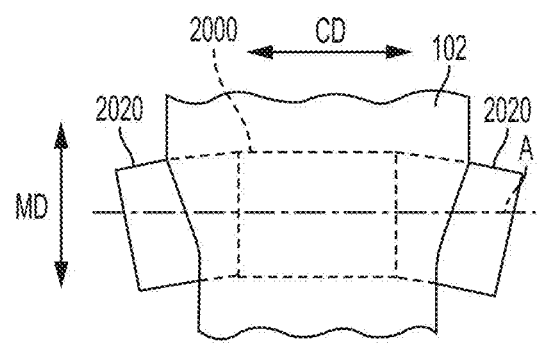
FIG. 7I is a schematic representation of a front view of a cross machine directional tensioning apparatus with outer longitudinal portions fixed in an angled position relative to a middle portion in accordance with the present disclosure.

FIG. 7F is a schematic representation of a front view of an example cross machine directional tensioning apparatus with outer longitudinal portions 2020 in an unexpanded or non-angled position relative to the middle portion 2000. FIG. 7G is a schematic representation of a front view of the cross machine directional tensioning apparatus of FIG. 7F with the outer longitudinal portions 2020 in a longitudinally expanded position relative to the middle portion 2000. FIG. 7H is a schematic representation of a front view of the cross machine directional tensioning apparatus of FIG. 7F with the outer longitudinal portions 2020 in an angled and expanded position relative to the middle portion 2000. In regard to 7H, the outer longitudinal portions 2020 may merely move or slide in a direction generally perpendicular to the machine direction of the material passing over the roll to apply the cross machine directional tensioning force to the material 702. FIG. 7I is a schematic representation of a front view of a cross machine directional tensioning apparatus with the outer longitudinal portions 2020 fixed in an angled position relative to the middle portion 2000 to apply the cross machine directional tensioning force to the material 702. In such a form, the middle portion 2000 and each of the outer longitudinal portions 2020 may comprise a separate roll.

Regardless of whether one or both of the outer longitudinal portions 2020 is moved, slid, rotated, fixed, and/or expanded relative to the middle portion 2000, this relative motion or positioning between the outer longitudinal portions 2020 and the middle portion 2000 stretches the materials 702 in a cross machine direction to further rupture or further define the weakened locations 2020 in the material 702 and create, or further form, a plurality the apertures 2212 the material 702. The cross machine directional tensioning force applied by the cross machine directional tensioning apparatus 732' may be, for example, 10-25 grams or 15 grams. In an instance, the cross machine directional tensioning apparatus may be similar to, or the same as, the incremental stretching apparatus 732 to apply the cross machine directional tensioning force. In still other instances, any suitable cross machine directional tensioning apparatus may be used to apply the cross machine directional tensioning force to the material 702.

If desired, the incremental stretching step or the cross machine directional stretching step described herein may be performed at elevated temperatures. For example, the material 102 and/or the rolls may be heated. Utilizing heat in the stretching step may serve to soften the material, and may aid in extending the fibers without breaking.

Referring again to 7A, the material 702 may be taken up on wind-up roll 780 and stored. Alternatively, the material 702 may be fed directly to a production line where it is used to form a portion of an absorbent article or other consumer product.

It is important to note that the overbonding step illustrated in FIGS. 7A and 7B could be performed by the material supplier and then the material may be shipped to a consumer product manufacturer to perform step 732. In fact, the overbonding step may be used in the nonwoven production process to form overbonds, which may be in addition to, or in lieu of, primary bonds formed in the nonwoven production process. Alternatively, the material supplier may fully perform the steps illustrated in FIG. 7A and then the material may be shipped to the consumer product manufacturer. The consumer product manufacturer may also perform all of the steps in FIG. 7A after obtaining a nonwoven material from a nonwoven material manufacturer.

One of ordinary skill in the art will recognize that it may be advantageous to submit the material 702 to multiple incremental stretching processes depending on various desired characteristics of the finished product. Both the first and any additional incremental stretching may either be done on-line or off-line. Furthermore, one of ordinary skill will recognize that the incremental stretching may be done either over the entire area of the material or only in certain regions of the material depending on the final desired characteristics.

The process 700 illustrated in FIG. 7A may comprise an additional step. Namely, subsequent to the incremental stretching the material 702 may be subjected to Z-direction stress to produce tufts and/or ridges. Depending on the orientations of tufts described heretofore, processing of laminates of the present invention can vary. Referring to FIG. 8A, there is shown an apparatus 800 and method for producing the laminates of the present invention. The apparatus 800 comprises a pair of intermeshing rolls 802 and 804, each rotating about an axis A—the axes A being parallel and in the same plane. Roll 802 comprises a plurality of ridges 806 and corresponding grooves 808 which extend unbroken about the entire circumference of roll 802.

Roll 804 is similar to roll 802, but rather than having ridges that extend unbroken about the entire circumference, roll 804 comprises a plurality of rows of circumferentially-extending ridges that have been modified to be rows of circumferentially-spaced teeth 810 that extend in spaced relationship about at least a portion of roll 804. The individual rows of teeth 810 of roll 804 are separated by corresponding grooves 812. In operation, rolls 802 and 804 intermesh such that the ridges 806 of roll 802 extend into the grooves 812 of roll 804 and the teeth 810 of roll 804 extend into the grooves 808 of roll 802. A nip 816 is formed between the counter-rotating intermeshing rolls 802 and 804. Both or either of rolls 802 and 804 can be heated by means known in the art such as by using hot oil filled rollers or electrically-heated rollers.

The apparatus 800 is shown in a configuration having one patterned roll, e.g., roll 804, and one non-patterned grooved roll 802. However, in certain embodiments it may be preferable to use two patterned rolls similar to roll 804 having either the same or differing patterns, in the same or different corresponding regions of the respective rolls. Such an apparatus can produce webs with tufts protruding from both sides of the nonwoven web.

Alternatively, the process 700 (shown in FIG. 7A) may comprise a pair of rolls utilized in the incremental stretching 732 system which accomplishes the incremental stretching to break open the melt stabilized areas and creates tufts. As shown in FIG. 8B, rolls 834 and 836 incremental stretching system 832 may replace the rolls 734 and 736 (shown in FIG. 7C).

Precursor web 702 has formed therein in predetermined regions a plurality of melt stabilized locations 722 prior to entering nip 816. Recall that the melt stabilized locations 722 may be provided in zones on the material 702. In the case of the incremental stretching system 832, the melt stabilized locations 722 may be provided in a central region 813.

Upon stretching in the CD in the portion of the apparatus 832 corresponding to the region 813, the melt stabilized locations 722 rupture to form apertures. As shown, the melt stabilized locations 722 may be limited to a central region of material 702.

The apparatus 832 comprises a pair of rolls 834 and 836, each rotating about parallel axes A. Roll 834 may be configured as described with regard to roll 734 (shown in FIG. 7C). Namely, roll 834 may comprise a plurality of circumferentially-extending ridges 760 separated by grooves 761. A second, intermeshing roll 836 comprises the central region 813 having essentially matching roll 834 and having ridges 762 separated by grooves 763. The intermeshing ridges 760, 762 and grooves 761, 763 of rolls 834 and 836 incrementally stretch precursor material 702 to form apertures 2212. In addition to region 813, roll 836 has two regions 811 comprising ridges having formed therein teeth 810, the toothed ridges separated by grooves 812. Ridges 760 of roll 834 intermesh with the grooves 812 of roll 836 to form the tufts as described herein. By combining both into one apparatus to form both apertures 2212 and tufts 230 in a laminate.

The materials of the present invention may be apertured as described in U.S. Pat. No. 5,628,097 entitled "Method for Selectively Aperturing a Nonwoven Web" which issued May 13th 1997 and U.S. Patent Publication 2003/0021951 entitled "High Elongation Apertured Nonwoven Web and Method of Making" which published Jan. 20, 2003. As described previously, the first nonwoven layer may be apertured independently from the second layer. Additional methods of aperturing may also be utilized. Some examples include rotary knife aperturing, hot pin aperturing, hydroentangling or needle punching. Additional aperture references include U.S. Patent Application Ser. No. 62/076,043, entitled "Patterned Apertured Webs and Methods For Making the Same," filed on Nov. 6, 2014. Additional references include U.S. Pat. Nos. 5,658,639; 5,916,661; 6,498,284; 7,917,985; and U.S. Patent Application Publication Nos. 2003/0021951; 2005/154362. The constituent layers of the laminate may be aperture independently of one another or may be aperture contemporaneously as a laminate. Still in other forms, the first layer may be aperture while the second layer is unapertured.

As disclosed above, a suitable aperturing process may manipulate material of the first layer 110 and the second layer 150 in the MD and/or CD direction (X and/or Y direction). This manipulation of constituent material is in-laminate manipulation. As noted previously, the manipulation of the material of the first layer and/or the second layer in the MD and/or CD may produce visible color differences from that of the first color and the second color, i.e. melt lip color and aperture color.

Processes for forming tufts in the materials of the present invention are further discussed in U.S. Pat. Nos. 7,410,683; 7,789,994; 7,838,099; 8,440,286; and 8,697,218.

The number, spacing, and dimensions of tufts can be varied to give varying texture to laminates of the present invention. For example, if tufts are sufficiently closely spaced the resultant laminate can have a terry cloth-like feel. Alternatively, tufts can be arranged in patterns such as lines or filled shapes to create portions of a laminate having greater texture, softness, bulk, absorbency or visual design appeal. For example, when tufts are arranged in a pattern of a line or lines, the tufts can have the appearance of stitching. Likewise, the size dimensions, such as the height, length and width of individual tufts can be varied.

Single tufts can be as long as about 3 cm in length and can be made alone or dispersed among tufts of various sizes. In some embodiments, the tufts may have a length ranging from about 1 mm to about 10 mm. In some embodiments, the tufts may have a length ranging from about 2 mm to about 8 mm; from about 3 mm to about 7 mm, or any ranges within the values recited or any numbers within the values recited.

Additionally, forms of the present invention are contemplated where a web/laminate of the present invention includes a plurality of tufts which are configured differently. For example, a laminate of the present invention may comprise a tufts 270 (shown in FIGS. 2A-2B) and/or a tuft 230 in a first area of the laminate and may comprise a tuft 270 (shown in FIG. 2C-2D) in a second area of the laminate without a corresponding tuft 230. Webs/laminates of the present invention may utilize any and all combinations of the tufts 230 and/or 270 described with regard to FIGS. 2A-2D) in accordance with the foregoing embodiments, e.g. first area with first set of tufts, second area with second set of tufts, third area with third set of tufts, and so on, wherein each of the first, second and third sets of tufts are different. Additional examples include variation in spacing between tufts in addition to or independent of variations in the tufts themselves.

The out-of-plane features disclosed herein with regard to FIGS. 2A-2D, may be provided in arrays or a plurality thereof. Such arrays of out-of-plane features or plurality of arrays of out-of-plane features may comprise a pattern or a plurality of patterns which form graphics and/or other depictions, hereafter, "structural indicia." Additional forms are contemplated where the out-of-plane features described herein may be utilized in any combination.

As disclosed previously, the disclosed tufts may be formed as a result of the manipulation of constituent material of the first layer and the second layer in the positive Z-direction. Note that manipulation of constituent fibers in the negative Z-direction is also contemplated either independently from or in conjunction with manipulation in the positive Z-direction. Additionally, while tufts are disclosed, continuous ridges which extend the entire length or a large portion thereof of the laminate are also contemplated. As disclosed previously, the Z-direction manipulation of the constituent fibers of the first layer and the second layer can produce visible differences between the out-of-plane features versus the first color and the second color, i.e. core feature color and non-core feature color.

As stated previously, the first layer and the second layer, as described herein, may be provided as discrete layers. For example, embodiments are contemplated where the first layer is derived from a first supply roll having a first specific fiber makeup while the second layer is derived from a second supply roll having a second specific fiber makeup. In some embodiments, the fiber makeup between the first supply roll and the second supply roll can be different as described herein.

Referring back to FIGS. 3A and 3B, with regard to the formation of absorbent articles, the above laminate may be utilized as a topsheet. The topsheet may be joined to a backsheet 316 as described herein. The backsheet 316 may comprise printing as described herein. An absorbent core 318 as described herein, may be disposed between the laminate and the backsheet 316. The topsheet may be joined to the backsheet 316 about a periphery of the absorbent article.

As previously disclosed, additional layers may be provided between the topsheet and the backsheet, e.g. secondary topsheets, acquisition layers, distribution layers, dusting layers, etc. For those forms which include an additional layer, the additional layer may be joined to the topsheet, e.g. the laminate, prior to joining the topsheet to the backsheet. In some forms, the additional layer may comprise printing as disclosed herein. In some forms, the additional layer may be fusion bonded to the laminate. As stated previously, the fusion bonding process manipulates constituent fibers of the first layer and the second layer of the laminate in the negative Z-direction. And, with the appropriate ΔE*, as noted previously, this manipulation of the constituent fibers of the first layer and second layer in the negative Z-direction, can produce a color, i.e. bond site color, which is different than the first color and the second color.

Absorbent articles can be manufactured on converting lines which are known in the art. Printing on nonwoven and/or film layers is also well known in the art. For those forms of the invention which comprise printing, the printing step may be done online during the converting process or offline. Offline printing generally occurs prior to the conversion of the constituent layer of the absorbent article being assembled in the form of the absorbent article.

The printing step may comprise providing a first colorant via printing ink, pigment associated with a liquid impermeable polymeric film; a first nonwoven layer, and a second nonwoven layer via a process that is offline from the converting manufacturing line. The printing step may additionally comprise providing a second colorant via printing ink, pigment associated with a liquid impermeable polymeric film, the first nonwoven layer, and the second nonwoven layer.

Applying a third colorant to one of the liquid impermeable polymeric film, the first nonwoven layer, and the second nonwoven layer on the converting manufacturing line As disclosed herein, the apertures, tufts, and/or bonds may be provided in arrays forming patterns. Such arrays may be coordinated with one another as described herein.

Joining of Layers

The layers of a laminate and/or absorbent article may be bonded together using any bonding methods known to those of skill in the art, such as adhesive bonding, patterned adhesive coating, ultrasonic bonding, thermal bonding, mechanical bonding, or any combination of these bonding methods. Alternatively, the various layers may be bonded together only at the perimeter of the apertures, through bonding the layers or overbonding the layers as disclosed previously. Additional bonding methods were disclosed with regard to the bond sites. The webs of the present invention may be similarly joined to any adjacent layers of an absorbent article as described above.

Aperture Arrays and Patterns

As previously noted, for those forms of the webs/laminates of the present invention where apertures are present, the apertures may be arranged in patterns forming designs, shapes, etc.—apertured indicia.

The apertures in the webs and/or at least one or more layers of a laminate, as described herein, may be grouped in spaced arrays of apertures (see e.g., FIGS. 10A-10J). An aperture array includes two or more apertures having much closer spacing between the apertures than the distance between the aperture arrays. The distance between the array and other apertures is at least about 1.5, at least about 2 times, or at least about 3 times the maximum distance between apertures in the array. Four examples of laminate 2200 comprising patterned apertures are illustrated in FIGS. 10A-10J. As illustrated, the laminate 2200 may take on a number of configurations. The apertures are labeled 2212 and the land areas (non-apertured areas) are labeled 2214. A number of additional example aperture pattern configurations are illustrated in subsequent figures.

The aperture arrays may form a regular or recognizable shape, such as a heart shape, polygon, ellipse, arrow, chevron, and/or other shapes known in the pattern art. The apertures arrays may differ in one portion of the laminate compared to another portion of the laminate. In an absorbent article context, the aperture arrays may differ in one region of the absorbent article compared to another region of the absorbent article. Additionally, the aperture arrays may be coordinated in regions of the absorbent article where the aperture arrays are present. The aperture arrays may be concave, convex, or may include concavities and convexities. The aperture arrays may be organized into "macro-arrays" having a higher order structure. For example, referring to FIGS. 11-24, a laminate 2600 is illustrated with aperture arrays 2602 that may be separated by a continuous, inter-connected land area pattern 2604. In such an instance, the land area pattern 2604 may function as a fluid distribution pathway and the aperture arrays 2602 may function as fluid "drains" thereby promoting fluid access to the underlying absorbent material or absorbent core. The shape of the aperture arrays may enhance the ability of the arrays to manage fluid, such as bodily exudates (i.e., urine, runny BM, menses). For example, aperture arrays including a concavity facing a fluid insult location in an absorbent article may function as fluid collection "traps" as the fluid may travel along the "land area" in the concavity to a point where the concavity ends. At this location, the fluid may enter the apertures in the direction of the fluid path or those on either side of the concavity if the fluid turns in either lateral direction. Example aperture array shapes having a concavity include heart shapes, star shapes, some polygons, crescents, and chevrons, to name a few examples.

In some forms apertures, or arrays thereof, in a laminate 2600, may form one or more continuous or semi-continuous patterns 2606, resulting in discrete "macro" land areas 2608. In such an instance, the discrete macro land areas 2608 may function as fluid deposition regions. Fluid moving from the discrete macro land areas 2608 in any direction may be absorbed into the apertures of the continuous or semi-continuous pattern 2606.

In some forms, the apertures, or aperture arrays thereof, in a laminate 2600 may form linear patterns 2610 alternating with continuous or semi-continuous land areas 2612. The laminate may include unidirectional or multi-directional (and intersecting) aperture or aperture array patterns. Linear aperture or array patterns may be oriented parallel to the longitudinal or lateral axis, or at an angle between 0 and 90 degrees, specifically reciting all 0.5 degree increments within the specified range and all ranges formed therein, from either the longitudinal or lateral axis. Linear apertures or aperture array patterns may function to restrict fluid movement along the laminate to a greater degree in one direction compared to another direction. Apertures for non-woven webs may be similarly configured.

A laminate 2600 may comprise an array of apertures comprising a plurality of patterns 2610A and 2610B with continuous or semi-continuous land areas. As shown, a first pattern 2610A may comprise apertures which are oriented in a direction which is generally parallel to a machine direction 1675 (shown in FIG. 25) as well as apertures which are oriented at multiple angles with respect to the machine direction. Similarly, a second pattern 2610B may comprise apertures which are oriented at multiple angles with respect to the machine direction 1675 as well as apertures which are generally parallel to the machine direction 1675. As shown, the apertures of the first pattern 2610A and/or the second pattern 2610B may be of different lengths, different angles with respect to the machine direction 1675, and/or different Effective Aperture AREAs.

Additionally, at least one or a plurality of apertures in the first pattern 2610A may be substantially enclosed by the second pattern 2610B. For example, the second pattern may form a quilt like pattern, e.g. diamond shaped boundaries or any other suitable shape, with the first pattern disposed within the second pattern thereby forming a unit. The combination of the first pattern and the second pattern may repeat so that there are a plurality of units. Additionally, the first pattern within the second pattern may be different from one unit to the next. Additional patterns may be utilized. The apertures angled with respect to the machine direction 1675 are believed to aid in fluid acquisition/distribution. For example, fluid moving along the laminate 2600 in the machine direction 1675 may be diverted, in part, because of the angled apertures.

Figure 25:
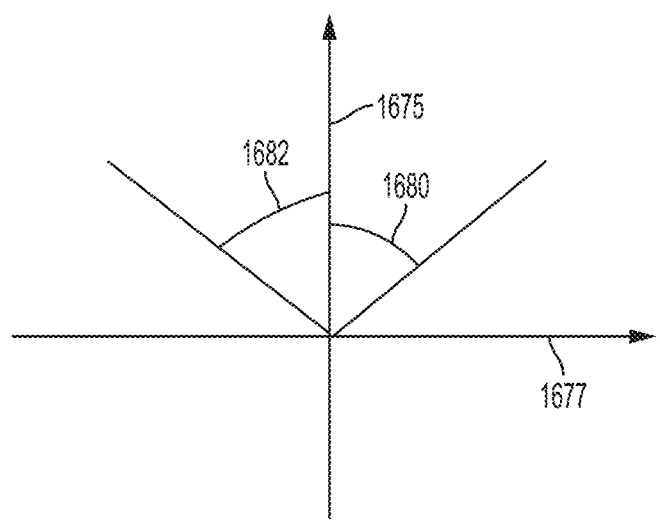
FIG. 25 is a depiction of a coordinate system for the nonwoven laminates of the present invention.

Referring to additionally to FIG. 25, as noted previously, the first pattern 2610A and/or the second pattern 2610B may comprise a plurality of apertures of which at least a portion are angled with respect to the machine direction 1675 at a first angle 1680 and another portion are angled with respect to the machine direction 1675 at a second angle 1682. The first angle 1680 and the second angle 1682 may be different from one another. In some forms, the second angle 1682 may be the mirror image of the first angle 1680. For example, the first angle may be about 30 degrees from an axis parallel to the machine direction 1675 while a second angle is −30 degrees from the axis parallel to the machine direction 1675. Similarly, the first pattern 2610A and/or the second pattern 2610B may comprise a plurality of apertures which are oriented generally parallel to the machine direction 1675. As mentioned previously, apertures which are oriented generally parallel to the machine direction 1675 generally have a lower aspect ratio and larger Effective Aperture AREA (described hereafter) as opposed to those apertures which are angled with respect to the machine direction 1675. It is believed that those apertures with increased Effective Aperture AREA allow for quicker fluid acquisitions time. While any suitable angle may be utilized, as discussed hereafter, once the first angle 1680 and the second angle 1682 are increased beyond 45 degrees from the machine direction 1675, the forces of the cross-direction 1677 stretching act more along the long axis of the aperture than perpendicular thereto. So, apertures which are angled more than 45 degrees with respect to the machine direction 1675 typically comprise less Effective Aperture AREA than those which are angled to a lesser extent with respect to the machine direction 1675.

As stated previously, the angled apertures are believed to provide additional fluid handling benefits for the laminate 2600 for example a decrease in fluid run-off. In some forms, greater than about 10 percent of the apertures are angled with respect to the machine direction 1675. Additional forms are contemplated where greater than about 20 percent, greater than about 30 percent, greater than about 40 percent, greater than about 50 percent, greater than about 60 percent, greater than about 70 percent, greater than about 80 percent and/or less than 100 percent, less than about 95 percent, less than about 90 percent, less than about 85 percent of the apertures are angled with respect to the machine direction 1675 including any number or any ranges encompassed by the foregoing values.

Referring back to FIGS. 11-24, the population density of angled apertures may be greater nearer a centerline 1690 of the laminate 2600. For example, spacing between adjacent apertures near the centerline 1690 may be a first distance while spacing between adjacent apertures further away from the centerline 1690 may be a second distance. The first distance may be less than the second distance. As an example, spacing between adjacent apertures can be about 1 mm. As such, the first distance may be about 1 mm while the second distance may be about 3 mm or greater. Additional forms are contemplated where the distance between adjacent apertures increases with increasing distance from the centerline.

Additionally, in some instances, apertures nearer the centerline 1690 may be angled at the first angle 1680 while apertures further from the centerline 1690 are positioned at the second angle 1682. The first angle 1680 may be greater than the second angle 1682 with respect to the centerline 1690. For, example, the apertures further from the centerline 1690 may be oriented such that they are generally parallel to the centerline 1690 while the apertures positioned closer to the centerline 1690 are angled with respect to the centerline 1690. In some forms, the angle at which apertures are positioned relative to the centerline 1690 may decrease as the distance from the centerline 1690 increases. For example, a first aperture adjacent the centerline 1690 may be oriented at a first angle of 30 degrees with respect to the centerline 1690, while a second aperture 1 mm from the centerline 1690 may be oriented at 20 degrees from the centerline. The apertures positioned furthest away from the centerline 1690 may be generally parallel to the centerline 1690. Additional configurations are contemplated where apertures near the centerline 1690 are angled to a lesser extent than those further from the centerline 1690. In some embodiments, the apertures near the centerline 1690 may be generally parallel to the centerline 1690 while the apertures further from the centerline 1690 are angled with respect to the machine direction 1675.

As stated previously the lengths of the apertures may vary as well. In conjunction with being angled as disclosed above or independently therefrom, in some embodiments, the apertures adjacent the centerline 1690 may be longer than those which are further away from the centerline 1690. Similarly, the size of the apertures may vary. Variances in aperture size (Effective Aperture AREA) may be employed in conjunction with the variation of aperture angle and/or the variation in aperture length, or variances in aperture size may be employed independently of the variation of aperture angle and/or variation in aperture length. For those embodiments where aperture size may vary, larger apertures may be positioned adjacent the centerline 1690 while apertures having a smaller Effective Aperture AREA are positioned further away from the centerline 1690. For example, apertures adjacent the centerline 1690 may have an Effective Aperture AREA of 15 square millimeters while apertures further away from the centerline may have less Effective Aperture AREA, e.g. 1.0 square mm. Any of the values/ranges of Effective Aperture AREA provided herein may be utilized for configuring the Effective Aperture AREA variance described above.

As mentioned previously, the angle of orientation of the aperture can impact the fluid handling capabilities of the laminate 2600. Moreover, length of the aperture, width of the aperture, Effective Aperture AREA, spacing between apertures, as well as aperture density can similarly impact fluid handling. However, many of length of apertures, width of apertures, angle of orientation, spacing and density can have competing/negative impacts on the other variables. As stated previously, apertures which are at a greater angle to the machine direction 1675 tend to open less and therefore have less Effective Aperture AREA than apertures which are either parallel to the machine direction 1675 or which have a smaller angle with respect to the machine direction 1675. Similarly, angled apertures which are too closely spaced together tend to open less and therefore have less Effective Aperture AREA. As such, spacing between adjacent angled apertures may be increased over that which is between apertures which are generally oriented parallel to the machine direction 1675.

Bond Arrays and Patterns

The bonding may be done in a pattern of bonds or in arrays of bonds. The pattern may be a regular, uniform pattern or an irregular, non-uniform pattern. The bonding patterns may comprise a substantially continuous bond pattern or may be formed of discrete bonding points. The discrete bonding points may form a pattern. The pattern of bonding points may be homogeneous or non-homogeneous. A bond pattern in one region of a laminate may differ from a bond pattern in another region of the laminate. For example, the bond pattern may be different in the machine direction or the cross-machine direction of the laminate. An absorbent article including the laminate may have a different bond pattern in the front region vs. the back region, the center region vs. side regions, or the crotch region vs. waist regions of the absorbent article, for example. If adhesive is used in the bonding process, the adhesive may be tinted, pigmented, and/or patterned to create a pattern as discussed hereafter.

Substrates, layers and/or elements of a laminate and/or disposable absorbent articles may be bonded together. Some specific examples of bonding can occur between multiple nonwoven layers of a topsheet. In another example, a topsheet (including one or more layers) may be bonded to a subjacent layer (layer between the topsheet and an absorbent core)—including secondary topsheets, acquisition layers or the like. In yet another example, the topsheet (including one or more layers) may be bonded to the absorbent core. In each of the above examples, the constituent layers of the topsheet may be bonded together in a separate step and then subsequently fusion bonded to another component.

As noted previously, the bonding may comprise a pattern or a plurality of patterns which form graphics and/or other depictions, hereafter "bond indicia". Some examples of bond indicia are shown in FIGS. 26-29. In another example, substrates, layers and/or elements of a laminate and/or disposable absorbent articles may be adhesively bonded together.

Any suitable method may be utilized to form bonds between layers/substrates described herein. Some suitable examples are ultrasonic, heated rolls, and the like. In a specific example, substrates, layers and/or elements of a disposable absorbent articles may be bonded together via fusion bonding, ultrasonic bonding, or the like. In another example, substrates, layers and/or elements of disposable absorbent articles may be adhesively bonded together.

The mechanical bonding methods, e.g. fusion bond, ultrasonic, etc. can cause localized areas of the web to thin and become film like—in the case of nonwovens. These thinner areas can have different opacity characteristics with respect to the constituent material around the bond. As such, visual/color effects can be achieved. For example, the thinner areas may appear as a different color than the constituent material around the bond.

Bonding of the layers of an absorbent article is critical to the performance of said article. Bonding is important for the integrity of the product and of the layers to ensure sustained performance and durability throughout wear. Bonding can ensure connectivity between desired layers of the product to aid in fluid transfer between the layers. This is especially critical in nonwoven topsheet laminates with a hydrophobic nonwoven upper layer to ensure fluid access to the hydrophilic nonwoven lower layer. Fusion bonding has additional advantages over adhesive in that it lowers raw material cost, eliminates line hygiene issues, and allows bonding of layers between which the use of adhesive would not be feasible.

In order to ensure the integrity of the product, the total area of the bonding (calculated as a percent area of the outer perimeter of bonding region) may range from 5% to 25%, 10% to 20%, 12% to 18%. The size of each individual fusion bond nub may range from 0.5 sqmm to 5 sqmm, 1 sqmm to 3 sqmm. The spacing between bond nubs can range from 1 mm to 5 cm, 1.6 mm to 3 cm. However, the spacing of bonds can impact the loft of the laminate which in turn can impact the soft feel of the laminate. Bond spacing with regard to laminates in sanitary pads is discussed hereafter.

In some forms, the bonds, as stated previously, may be configured in patterns so as to create bond indicia. But apart from forming bond indicia, the bonds can help secure the layers of the absorbent article together. Additionally, in some forms, the bonds may be utilized to secure the laminate to subjacent layers of a disposable absorbent article, e.g. a secondary topsheet, absorbent core, etc.

As shown in FIGS. 26-29, bond patterns 3000A, 3000B, 3000C, and 3000D of the present invention may comprise a plurality of bond sites 3002. The bond sites may be any suitable shape. As shown, the bond sites are approximately circular; however, elliptical, diamond, heart, star, clover (3 leaf, 4 leaf), bowtie, combinations thereof, and the like are contemplated. In some forms, the constituent bond sites 3002 of a bond pattern may comprise combinations of shapes.

As shown, the bond pattern 3000A may comprise a plurality of arrays of bond sites, e.g. 3010, 3020, 3030, and 3040. The first array 3010 may be a continuous series of bond sites 3002 which enclose the second array 3020, the third array 3030, and the fourth array 3040. As shown, the second array 3020 may be discontinuous and disposed between the first array 3010 and the third array 3030. The third array 3030, much like the first array 3010 may be continuous and may enclose the fourth array 3040. The fourth array 3040 may be discontinuous and be disposed in a target area on the absorbent article. The target area signifies the location of the article which is likely to receive the fluid insult from the wearer assuming the absorbent product is donned properly.

Where the bond sites 3002 between the first array 3010 (forming the scalloped edge) and the third array 3030 are spaced between about 10 mm to about 12 mm, with a plurality of bond sites which make up the second array disposed therebetween, a soft feeling laminate may be achieved. For those forms of the present invention comprising boundary arrays, e.g. first array 3010 and the third array 3030, spacing between adjacent bonds (spacing between bond sites in different but adjacent arrays) can be about 8 mm. The soft feeling can be increased if a plurality of tufts/ridges are disposed between the first array 3010 and the second array 3030.

Additionally, adjacent bond sites in the first array 3010 may not provide a soft feel if center to center spacing of the bond sites is less than about 4 mm. In contrast, spacing bond sites at center-to-center distances of greater than 4.8 mm could risk losing the visual appeal of the bond site. For example, where a sanitary pad comprises printing viewable from the wearer-facing surface, said printing may overpower the visual existence of the bond sites when adjacent bond sites of an array, e.g. first array 3010 are spaced apart by greater than about 4.8 mm.

With the discontinuous fourth array 3040, fluid insults can be provided with adequate access to the laminate. Additionally, with the continuous third array 3030, fluid insults are encouraged to stay within the target area as opposed to meandering to outer edges of the article.

Figure 26:
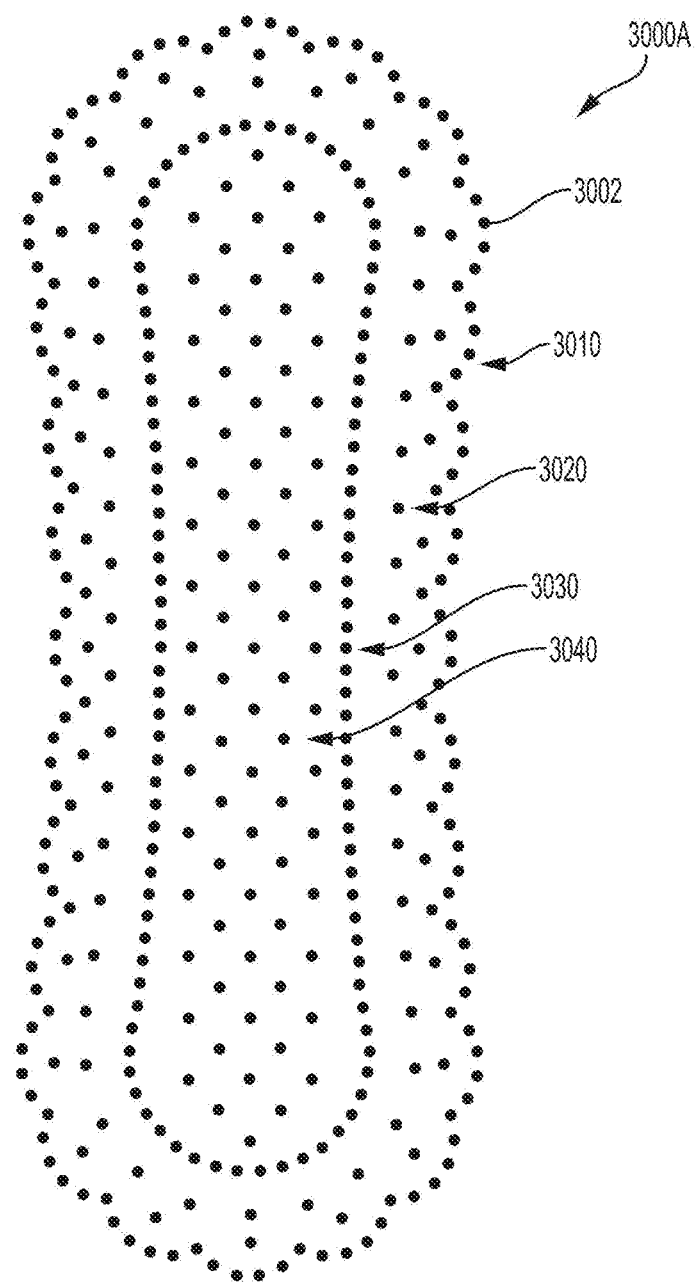
FIGS. 26-29 represent a schematic illustration of bond patterns for laminates of the present invention.

As shown in FIG. 26, the bond pattern 3000B may comprise a plurality of arrays of bond sites. For example, a first array 3010B may be continuous and comprise bond sites which are arranged in the shape of hearts, clouds, etc. A second array 3020B is disposed within the first array 3010B and disposed about a third array 3030B. The third array 3030B is continuous and surrounds the fourth array 3040B. Much like the arrays of the bond pattern 3000A, the arrays of the bond pattern 3000B can provide fluid handling benefits.

Figure 27:
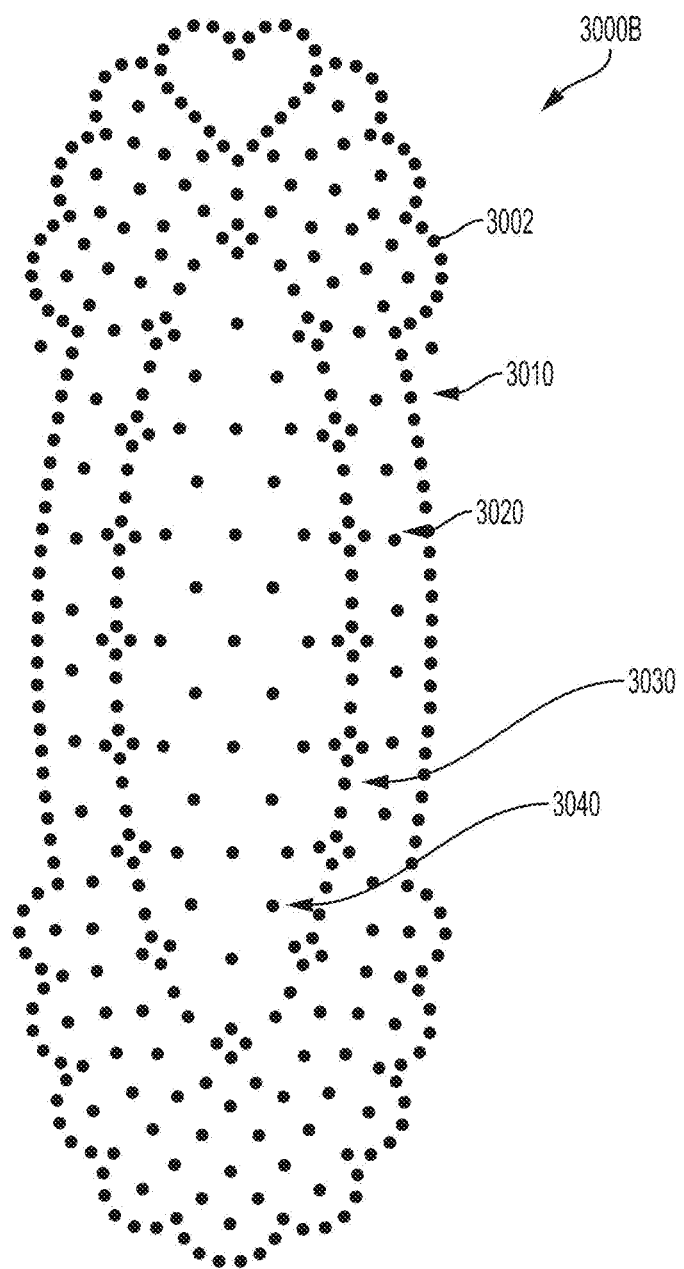

As shown in FIG. 27, a bond pattern 3000C may comprise a plurality of arrays of bond sites. However, in contrast with the previous bond patterns, a first array 3010C may be discontinuous about the entire periphery of a pad. As shown, the first array 3010C comprises a plurality of continuous segments of bond sites each of which is disconnected from one another. A second array 3020C may be disposed inboard of the first plurality 3010C and may also comprise a plurality of continuous segments which are discontinuous. A third array 3030C may comprise continuous bond sites and enclose a fourth array 3040C. The fourth array 3040C comprises a plurality of discontinuous bond sites. Much like the bond patterns discussed previously, the bond pattern 3000C may provide fluid handling benefits.

Figure 28:
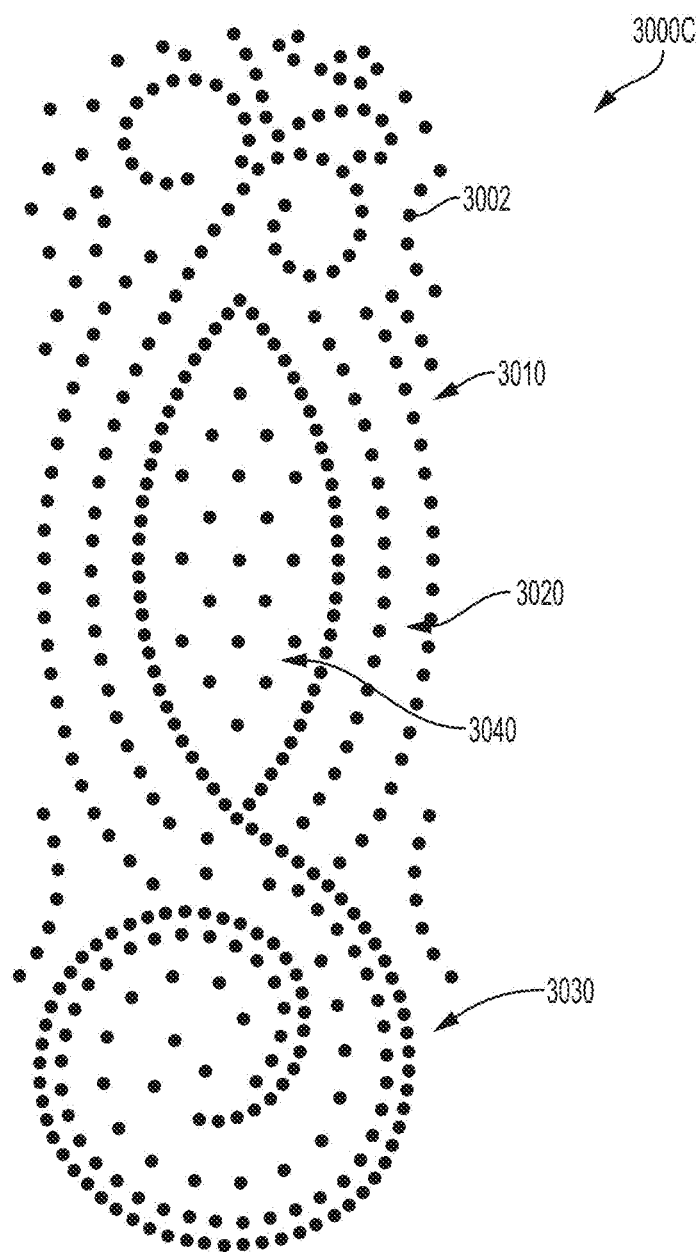
Figure 29:
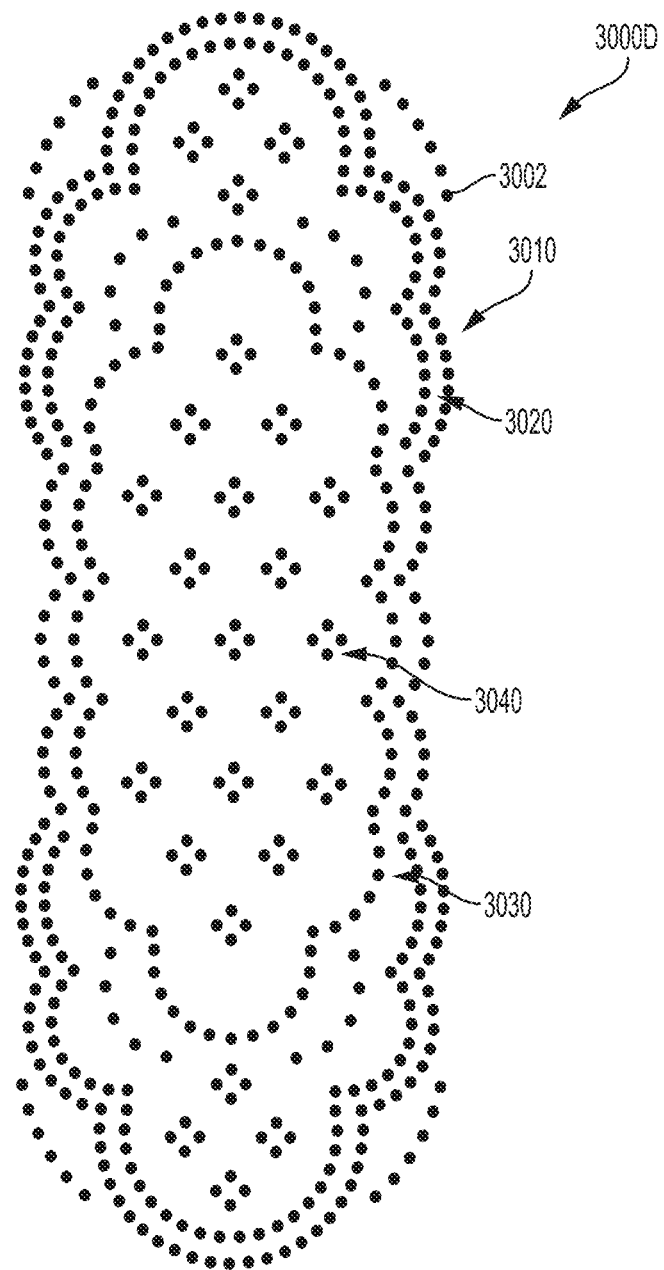

As shown in FIG. 28, a bond pattern 3000D may comprise a plurality of arrays of bond sites. For example, a first array 3010D may comprise a plurality of bond sites which are arranged in a continuous fashion and may enclosed a second array 3020D, a third array 3030D and a fourth array 3040D of bond sites. The second array 3020D may comprise a plurality of bond sites which form continuous elements as well as a plurality of bond sites which form discontinuous elements. These continuous elements may be disposed at a first end and second end of the absorbent article. The third array 3030D of plurality of bond sites may be continuous and may enclosed the fourth array 3040D. The fourth array 3040D may comprise a plurality of bond sites which form a plurality of elements. Each of the elements may be continuous but discontinuous with respect to the other elements. For example, each element may comprise a plurality of bond sites, e.g. 4. The bond sites would be considered continuous for each respective element, but the bond sites from element to element would be discontinuous.

Patterned Adhesive

In some forms, adhesive may be used to join the layers of an absorbent article together including the webs/laminates of the present invention. The adhesive may comprise a pigment, a tint, or a dye. The colored adhesive, in a form of the present invention, may be positioned between the adjunct layers of the article, e.g. the first layer and second layer of a laminate. In some forms, more than one colored adhesive may be used in the article. The colored adhesive may also be situated in any suitable location. For example, if the laminate has more than two layers, adhesive may be disposed on the surface of or intermediate any of the layers. The colored adhesive may also be deposited in zones of the laminate and/or in patterns throughout the laminate. The colored adhesive may be different or the same in different zones of the laminate. The colored adhesive may be positioned intermediate the layers of the laminate or positioned on any other surfaces of the laminate. Additional layers may also be provided in a laminate having one or more colored adhesives. As stated previously, adhesive and particularly colored adhesive may be applied such that the adhesive forms a pattern or a plurality of patterns which form graphics and/or other depictions, referred to as "adhesive indicia." Adhesive indicia, in some forms, may also be created via the use of clear adhesive. The application of clear adhesive, in some instances can change the opacity of materials which are being adhesively joined.

In an instance, a colored adhesive may be positioned between two low basis weight materials (e.g., 15 gsm or less, 10 gsm or less) forming a laminate, so that the colored adhesive may be visible from either side of the laminate. In a topsheet context, this can provide a high basis weight topsheet to achieve improved softness, while still retaining the benefit of seeing the colored adhesive from either side of the laminate.

As stated previously, the adhesive utilized to bond/join layers and/or elements of disposable absorbent articles using the laminate of the present invention may comprise adhesive indicia. Accordingly, the laminates and/or absorbent articles of the present disclosure, or portions thereof, may comprise one or more patterned adhesives applied thereto or printed thereon. The patterned adhesives may be present within the laminates or under the laminates such that at least a portion of the patterned adhesives can be viewable through the laminates, e.g. through apertures and/or land areas. Patterned adhesives are adhesives that are applied to one or more layers of the laminates, or between layers of the same, in particular patterns to provide the absorbent articles, or portions thereof, with certain patterns, visible patterns, and/or certain textures. The patterned adhesives may be printed on or otherwise applied to any suitable layer of the laminates or applied above or beneath them. Methods for applying patterned adhesives to layers or substrates by adhesive printing are disclosed, for example, in U.S. Pat. No. 8,186,296, to Brown et al., issued on May 29, 2012, and in U.S. Pat. Appl. Publ. No. 2014/0148774, published on May 29, 2014, to Brown et al. Other methods of applying patterned adhesives to substrates known to those of skill in the art are also within the scope of the present disclosure.

A patterned adhesive may have the same color or a different color as at least one layer of a laminate or absorbent article. In some instances, the patterned adhesive may have the same or a different color as both or all layers of a laminate. In some instances, aperture patterns in at least one layer of the absorbent article may coordinate with patterned adhesive to visually create a three-dimensional appearance. The apertured patterns may be the same or different than patterns of the patterned adhesive.

In an instance, a laminate may comprise a first layer comprising a plurality of apertures and a plurality of land areas and a second layer comprising a plurality of apertures and a plurality of land areas. A patterned pigmented substance, such as ink or a patterned adhesive, may be positioned at least partially intermediate the first layer and the second layer. The plurality of apertures of the first layer may be at least partially aligned with the plurality of apertures of the second layer. The patterned pigmented or colored substance may be at least partially viewable through the aligned portions of the apertures in the first and second layers.

Figure 95:
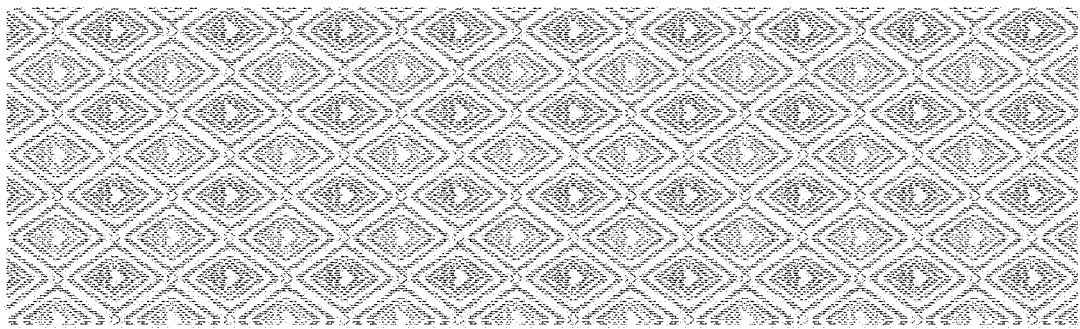
FIGS. 93-99 are illustrations showing overbonds, patterned adhesive and combination of overbonds and patterned adhesive, respectively.
Figure 94:
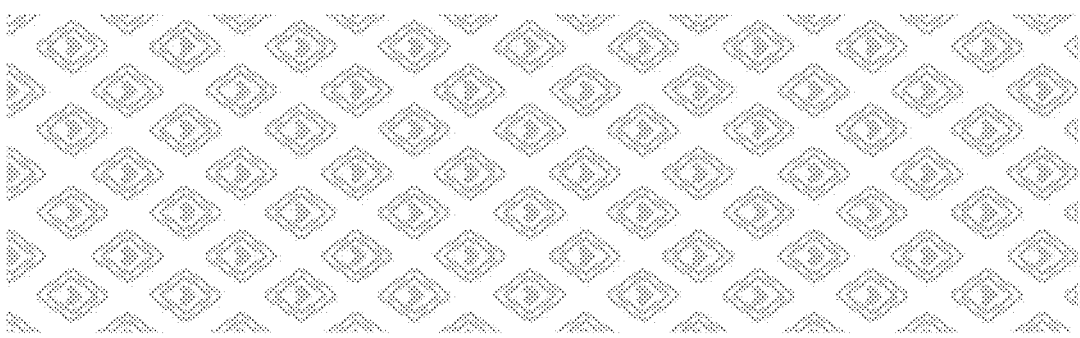
Figure 93:
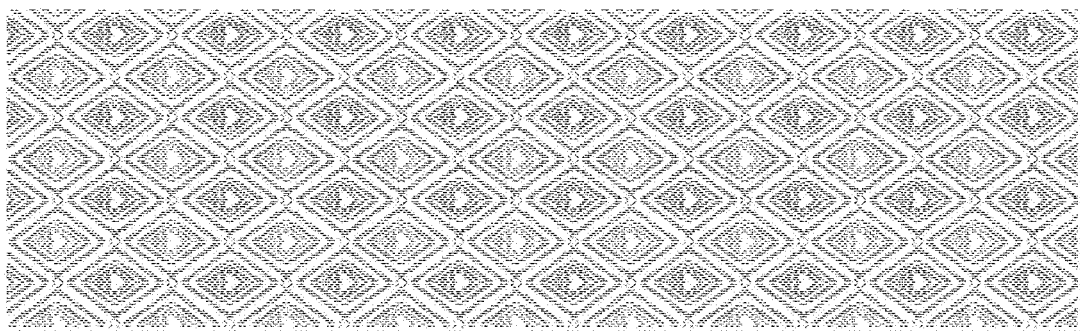
Figure 98:
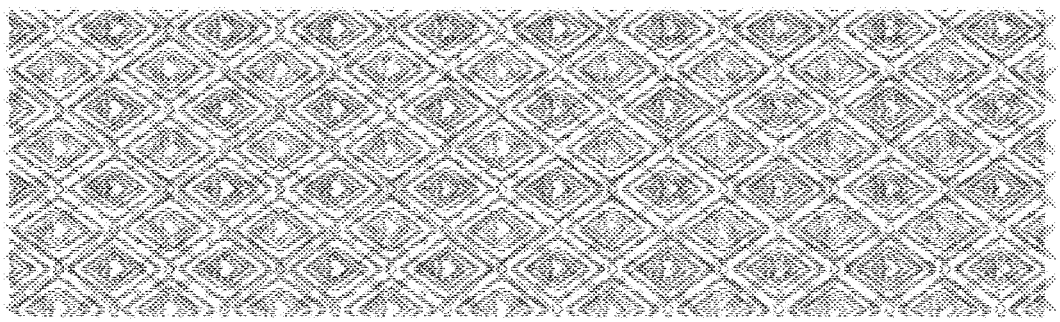
Figure 97:
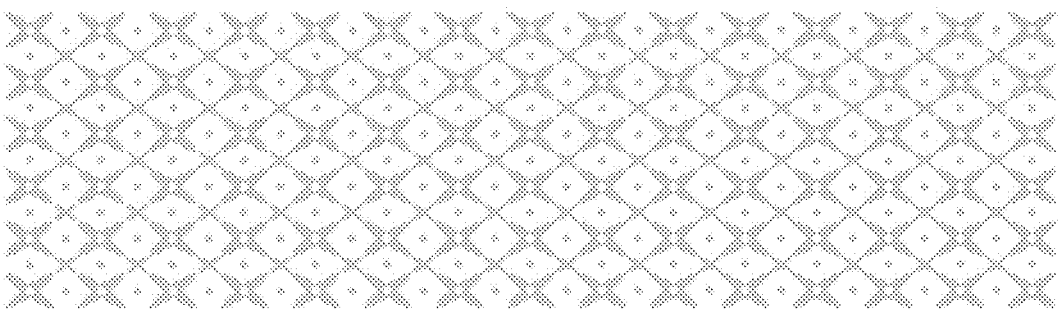
Figure 96:
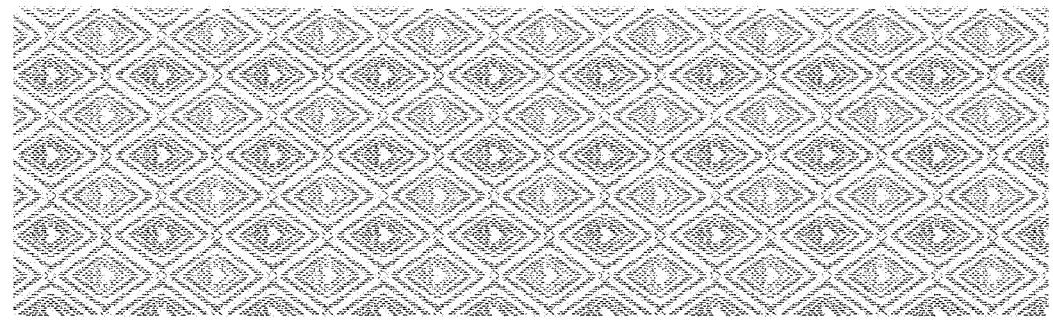

Regarding FIGS. 93-95, a plurality of overbonds are shown on a web arranged in a plurality of arrays which will eventually—when processed as described herein—produce apertured indicia. In FIG. 94 adhesive indicia on a web is depicted. As noted previously, the adhesive may comprise a color or may be clear in some forms. Regarding FIG. 95, a combination of the overbonds of FIG. 93 and the adhesive indicia of FIG. 95 are shown. Note that given the arrangement of the overbonds of FIG. 93, the resulting apertured indicia would appear similar (coordinated) with the adhesive indicia shown in FIG. 94. In such forms, it may be beneficial to register the apertured indicia with the adhesive indicia to produce the desired visual effect. Adhesive indicia and apertured indicia which may not require registration are depicted in FIGS. 96-98. A similar effect is depicted in FIG. 99.

Figure 99:
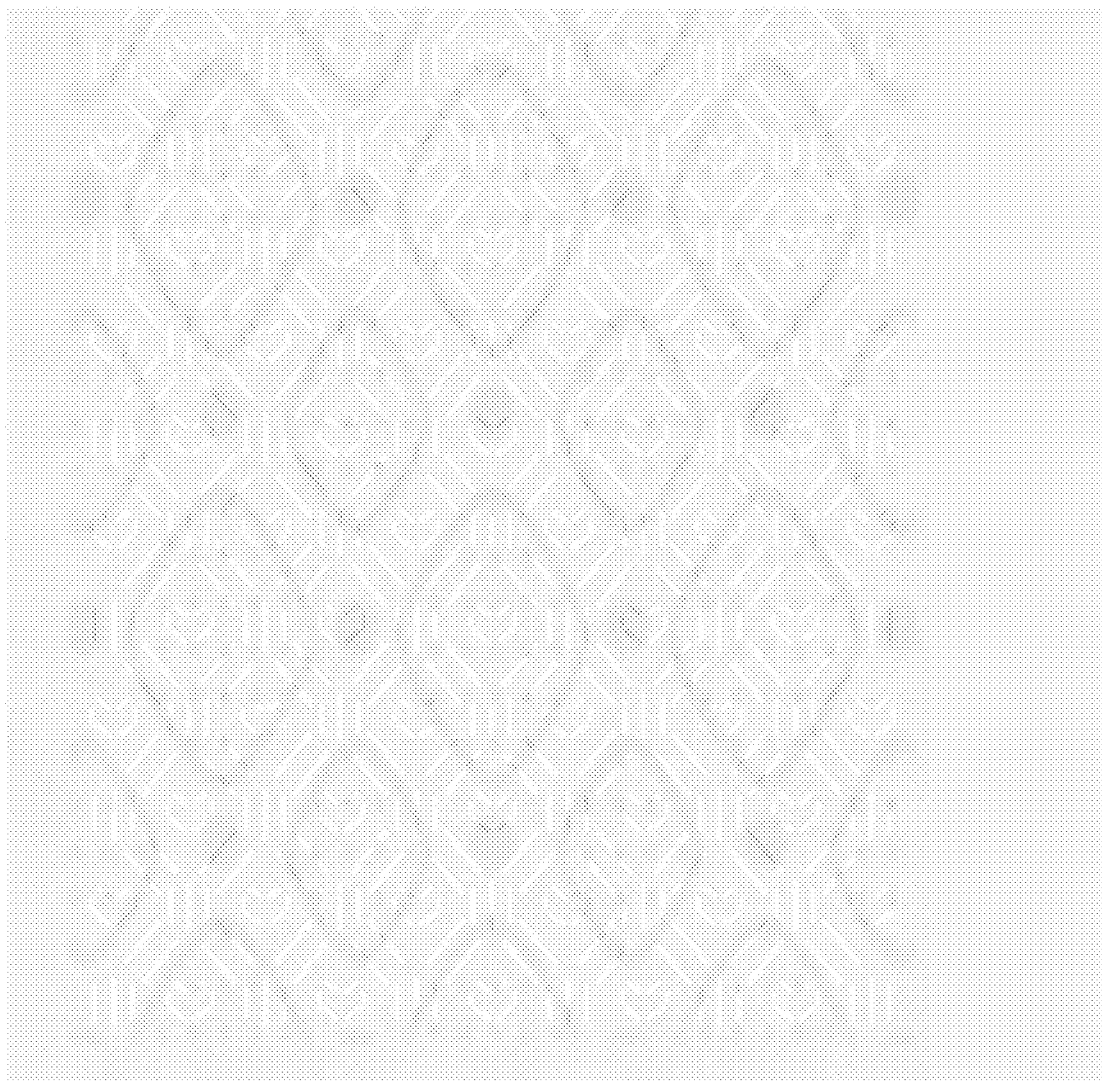

Regarding FIG. 99, a combination of apertured indicia and adhesive indicia is shown on a web. The apertured indicia and the adhesive indicia are not registered. As such, portions of the adhesive indicia are visible through only a portion of the apertures. The effect can highlight portions of the adhesive indicia which are visible through the apertures. The remainder of the adhesive indicia may still be visible through the web which comprises the apertured indicia.

Printing

Either in addition to or in lieu of the various layers being colored, one or more of the layers of the laminates and/or absorbent articles of the present disclosure may include printing, e.g., with ink or a pigmented or colored pattern. Multiple colors of ink may be utilized and/or the ink may be applied to the laminates/absorbent articles of the present invention in gradients. Namely, a printed color may increase in intensity. Gradient effects may be applied to a single printed color or to multiple printed colors.

The ink may be deposited via any printing process known in the art including, but not limited to, flexographic printing and digital inkjet printing. The printing may comprise a pattern or a plurality of patterns which form graphics and/or other depictions, hereafter, "printed indicia." The printing may be on an external surface of a first layer of the laminate, between the first and second layers of the laminate, or may be on a surface beneath the second layer of the laminate. The printing may also be situated in any suitable location if the laminate has more than two layers (e.g., on the surface of any of the layers). The printing may also be deposited in zones of the laminate and/or in patterns throughout the laminate. The printing may be different or the same in different zones of the laminate. If the printing will be covered by one of the layers, e.g. the covering layer, it may have a relatively low opacity to enhance the visual appearance of the printing. The density of the printing (e.g., clarity and contrast) may be enhanced by including small-denier fibers in the printed layer including, but not limited to, melt-blown fibers, microfibers, and nanofibers. The printing may be on the first layer, the second layer, and/or may be on a separate layer positioned at least partially intermediate the first and second layers. In an instance, the printing may indicate the proper orientation of an absorbent article on a wearer (e.g., front/rear). It will be understood that printing may be used with any of the various forms and configurations of the laminates disclosed herein. In some forms, more than one type or color, for example, of printing may be used in a single nonwoven web. Additional layers may also be provided in a laminate having one or more printed patterns.

Coordinated Arrays and/or Patterns

Heretofore, bond indicia, adhesive indicia, structural indicia, and printed indicia have been introduced. Additionally, for those forms where the laminates of the present invention comprise patterned apertures, the array of apertures may comprise a pattern or a plurality of patterns which form graphics and/or other depictions, hereafter, "apertured indicia." The apertured indicia may coordinate with at least one of printed indicia, bond indicia, adhesive indicia, and/or structural indicia. For example, in the absorbent article context, located beneath the laminate or within the laminate adhesive indicia may be present which coordinate with the apertured indicia. In an instance, the laminate may be used a topsheet, an outer cover, an ear, or other portion of an absorbent article.

The aperture pattern in a laminate may coordinate with features under it and/or around it, such as bond sites, material edges, channels, and/or discolored or colored materials. In some specific executions, the laminate may be used to accentuate or block/hide these features. The aperture patterns of a laminate may also be used to indicate the correct front vs. rear, left vs. right orientation of an absorbent article or other consumer product.

Apertured indicia may be coordinated with printed indicia elsewhere on the product and/or packaging. For example, a disposable absorbent article of the present invention may comprise apertured indicia which provides the appearance of a snowflake. The article may additionally comprise printed indicia elsewhere on the article itself and/or its packaging, wherein the printed indicia provides the appearance of a snowflake. In such embodiments, the feminine article may comprise a release liner which includes a printed snowflake pattern and/or be placed in a package comprising a printed snowflake pattern.

Embodiments are contemplated where the apertured indicia is coordinated with adhesive indicia, bond indicia, and/or structural indicia. Embodiments are contemplated where at least two of the following are coordinated on an absorbent article: apertured indicia, adhesive indicia, printed indicia, bond indicia, structural indicia. Similar embodiments are contemplated with regard to the packaging for the disposable absorbent articles described herein (including release liners and/or secondary packaging). Additionally, the aforementioned indicia may be coordinated across the absorbent article, its packaging, and/or its secondary packaging (including release liners) or any combination thereof.

In some specific forms, while a portion of the top sheet may include apertured indicia, other portions of the topsheet may include printed indicia which is coordinated with the apertured indicia. In other forms, a sub-layer, e.g. acquisition layer, secondary topsheet, and/or absorbent core may comprise printed indicia which is coordinated with the apertured indicia of the topsheet. Still in other forms, the backsheet may comprise printed indicia which is coordinated with the apertured indicia of the topsheet. Additional forms are contemplated where a portion of the topsheet includes apertured indicia, the backsheet includes printed indicia coordinated with the apertured indicia, packaging of the feminine article includes printed indicia coordinated with the apertured indicia, a non-apertured portion of the topsheet includes printed indicia which is coordinated with the apertured indicia and/or a sub-layer, e.g. acquisition layer, secondary topsheet, and/or absorbent core comprise printed indicia which is coordinated with the apertured indicia. Similar embodiments are contemplated with adhesive indicia, structural indicia, bond indicia, and/or any combinations thereof.

In other specific forms, the topsheet may comprise apertured indicia and first printed indicia. The first printed indicia may coordinate with second printed indicia on secondary packaging while apertured indicia may coordinate with printed indicia on primary packaging for the absorbent article.

Indicia is visually coordinated when one or more elements of the indicia have two or more visual characteristics that are either matched or are caused to match. As used herein, the term "match" or "matched" is used to describe the way or degree to which apertured indicia, printed indicia, bond indicia, adhesive indicia, and/or structural indicia, or characteristics thereof visually fit together or are caused to fit together. For example, apertured indicia and printed indicia are considered matched if some aspects of the apertured indicia are identical to similar aspects of the printed indicia. In one form of match, for example, apertured indicia and printed indicia that resemble each other are said to match. The same can be true for any combination of the heretofore mentioned indicia. As used herein, the term "coordinate" or "coordination" is used to describe how indicia of the overall absorbent article and/or its packaging visually belong together. Components or elements are considered to be coordinated if they match, or are caused to match. As used herein, the term "caused to match" is used to describe how any combination of aforementioned indicia are made to appear matched to one another by using coordinating indicia (any combination of the above) which has a coordinating feature which ties the aforementioned indicia together. For example, if apertured indicia and printed indicia each have a visual characteristic different from one another and coordinating indicia has visual characteristics which match each of the apertured indicia and printed indicia, the coordinating feature causes the apertured indicia and printed indicia to be matched to one another.

Additionally, patterns comprising multiple features may be coordinated. As an example, a first array of apertures may be grouped with adjacent bond sites to form a pattern unit. This pattern unit may be repeating. For example, a first pattern unit may be disposed adjacent a first end of an absorbent article while a second pattern unit is disposed adjacent a second end of an absorbent article. As another example, the first pattern unit may be disposed adjacent a first end of an absorbent article while the second pattern unit is disposed adjacent a transverse axis of the absorbent article. Still another example may comprise additional pattern units which may be disposed in any suitable location on an absorbent article. Pattern units may comprise any combination of features. For example a pattern unit may comprise apertures, bonds, print, structures, or combinations thereof.

Some examples of coordinated indicia include theme related indicia. In some embodiments, indicia described herein may be coordinated where at least two of the indicia, e.g. apertured and printed include at least one of items generally thought of as lucky, e.g. balloons, rainbows, pots of gold, moons (printed indicia may include blue moon), clovers, horseshoes, stars, hearts, and the like or combinations thereof. Other examples of coordinated indicia include numbers, letters, combinations of numbers and letters; winter themes including snowflakes and/or the like; spring themes including flowers, bees, birds, butterflies, trees, sun, geometric shapes, squares, rectangles, triangles, oval, circles; curves including uni-radial arcs, multi-radial arcs, spirals, truncated sinusoidal waves.

An aperture pattern in a web/laminate may form a recognizable visual element, such as a heart or a water droplet, for example. An aperture pattern that forms one or more water droplet shapes in a laminate used as a topsheet or an outer cover of an absorbent article may be used to aid communication of absorbency and/or wetness. Such a feature may be combined with a wetness indicator of an absorbent article.

Various commonly understood shapes may be created in a laminate. These shapes may be shapes that have commonly understood proper orientations, such as hearts, for example. An example is the use of one or more hearts on an outer cover or topsheet of a front waist region and/or a back waist region of a diaper. The caregiver would understand to place the diaper on the wearer with the point of the heart facing toward the wearer's feet because of the common knowledge of the orientation of hearts.

In one instance, a web/laminate may comprise a first non-apertured layer comprising a pattern having a color and a second nonwoven layer comprising a pattern of apertures. The pattern on the first non-apertured layer may be printed on the layer, for example, and may form graphics or other indicia. At least 50% to 100% of the pattern on the first non-apertured layer may be aligned with the pattern of apertures to draw attention to the apertures. The alignment, or partial alignment, of the pattern of apertures on the first layer with the pattern having a color of the second layer may make aid in aligning the product on a wearer if the laminate is provided on an absorbent article. In other examples, a laminate may comprise a first nonwoven layer and a second nonwoven layer which are co-apertured as described herein. In such configurations, the first nonwoven layer may be fused to the second nonwoven layer about a periphery of each of the apertures formed in the laminate. In such configurations, the first nonwoven layer may have a different color than the second nonwoven layer. In yet another example, a first nonwoven layer may be apertured and may be joined to a second nonwoven layer which is not apertured. In such configurations, the first nonwoven layer and the second nonwoven layer may comprise different colors.

Additionally, where the web/laminate is utilized as a topsheet, a secondary topsheet—disposed between the topsheet and an absorbent core—may comprise printing/printed indicia. Such printing may be of a different color than that of the first color and/or the second color. And, such printing is visible through the topsheet such that the wearer can view the printing prior to donning the absorbent article.

The apertured indicia, printed indicia, adhesive indicia, bond indicia when used on a topsheet and/or backsheet of a disposable absorbent article, may be utilized to ensure proper alignment of the absorbent article. For example, any one of apertured indicia, printed indicia, adhesive indicia, bond indicia, and/or combinations thereof, may be utilized to highlight proper alignment. In one specific example, printed indicia may be utilized to communicate to a wearer the proper orientation of a feminine hygiene pad. Proper orientation of the feminine hygiene pad can reduce the likelihood of leakage.

Additionally, the apertured indicia, printed indicia, adhesive indicia, bond indicia when used on a topsheet and/or backsheet of a disposable absorbent article may be utilized to highlight features of the absorbent article which would otherwise not be noticeable by simple visual inspection of the article. For example, absorbent cores of disposable absorbent articles are generally disposed between the topsheet and the backsheet. In many instances, upon visual inspection, a wearer may not be able to discern the boundaries of the absorbent core which are typically inboard of the periphery of the absorbent article. In such instances, at least one of apertured indicia, printed indicia, adhesive indicia, bond indicia or any combination thereof, may be utilized to communicate the boundaries of the absorbent core. This may provide some reassurance to the wearer regarding the "zone" of absorbency. Still in other configurations, at least one of apertured indicia, printed indicia, adhesive indicia, bond indicia or any combination thereof, may be utilized to communicate a particular area of the absorbent core. For example, an absorbent article may comprise an absorbent core having variable absorbing capacity. In such instances, at least one of the apertured indicia, printed indicia, adhesive indicia, bond indicia or any combination thereof, may be utilized to highlight an area of the core having higher absorbing capacity than other areas. Conversely, apertured indicia, printed indicia, adhesive indicia, bond indicia or any combination thereof, may be utilized to highlight those portions of the absorbent core which have lower capacity than another portion of the absorbent core. Still other executions are contemplated where a first array of apertured indicia, printed indicia, adhesive indicia, bond indicia or any combination thereof is utilized to communicate to the wearer a portion of the absorbent core having higher absorbing capacity than other portions while a second array of apertured indicia, printed indicia, adhesive indicia, bond indicia or any combination thereof are used to communicate to the wearer regarding other portions of the absorbent core having lower absorbing capacity. In such executions, the first array and the second array may or may not be coordinated.

Zones

The webs/laminates of the present invention may be employed in a zonal fashion. For example, a first zone may comprise a first aperture pattern while a second zone comprises a second aperture pattern. When utilized as topsheets in disposable absorbent articles, the different aperture patterns can be configured to receive certain bodily exudates or inhibit or encourage their flow in any desired direction. For example, a first pattern may be better configured to receive and/or direct the flow of urine, while a second pattern may be better configured to receive and/or direct the flow of runny BM/menses. In other instances where the webs/laminates are used as a topsheet of an absorbent article, a first web/laminate having a first pattern may be configured to receive heavy gushes of bodily exudates while a second web/laminate having a second different pattern may be configured to restrict lateral bodily exudate flow in any desired direction. The first pattern may be situated in, for instance, the middle of the absorbent article or in the crotch region, while the second pattern may be situated in the front and rear waist regions or outer perimeter topsheet regions of the absorbent article.

The zones in a web/laminate may be positioned in the machine direction, the cross direction, concentric, or combinations thereof. If a product, such as an absorbent article, has two different zones in the machine direction, the zones may have the same or a similar cross-direction width (e.g., +/−2 mm) for ease in processing. One or more of the zones may have curved or straight boundaries or partial boundaries.

Any suitable zones, including more than two, of different or the same webs/laminates are envisioned within the scope of the present disclosure. The various zones may be in the topsheet as mentioned above, but may also be present on an outer cover or a cuff for example. In some instances, the same or a different pattern of zones of laminates may be used on the wearer-facing surface (e.g., topsheet) and the garment-facing surface (e.g., outer cover).

In some forms, a topsheet or other portion of an absorbent article may have two or more zones. As noted above, in some forms, a first zone of the laminate may have a different aperture pattern than a second zone. The first zone and the second zone may have different functionalities owing to the different aperture patterns. A functionality of the first zone may be to provide liquid bodily exudate distribution (fluid moving on the laminate), while the functionality of the second zone may be to provide liquid bodily exudate acquisition (fluid penetrating the laminate). Benefits of such a zoned web/laminate can be better use of an absorbent core and more efficient liquid bodily exudate distribution within the absorbent core. This is especially important if an air-felt free core is used in that typical air-felt free cores somewhat struggle with liquid bodily exudate distribution once the liquid bodily exudate is received therein.

In an example, an absorbent article may comprise a web/laminate that forms a first portion and a second, different portion thereof. Aperture patterns in each portion of the web/laminate may be the same, substantially similar, or different. In another instance, an absorbent article may comprise a web/laminate that comprises a first portion of an absorbent article, and wherein a second portion of the absorbent article has graphics, printing, patterned adhesives, or other indicia that forms a pattern that is similar to, substantially similar to, coordinates with, or is different than an aperture pattern in the web/laminate.

In some forms, a web/laminate may have a plurality of zones. A first zone may have at least some apertures having a first angle (central longitudinal axis of aperture vs. MD), first size, and/or first shape, while a second zone (or third or fourth zone etc.) may have apertures having a second, different angle (central longitudinal axis of aperture vs. MD), second, different size, and/or second, different shape.

Figure 30:
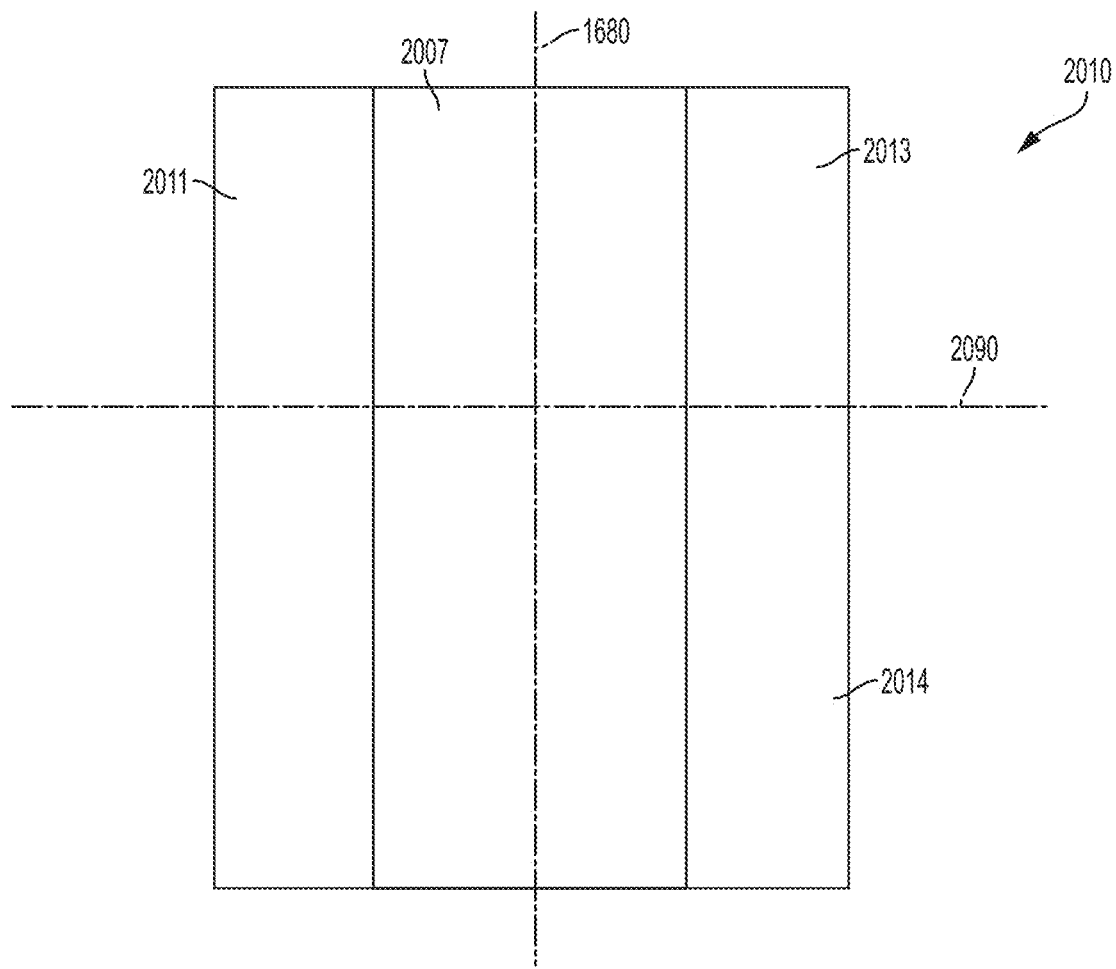
FIGS. 30-34 are schematic illustrations of disposable absorbent articles comprising a plurality of zones in accordance with the present invention.

As stated previously, the webs/laminates of the present invention may be utilized in a number of different components of absorbent articles. Referring to FIG. 30, in one specific example, the webs/laminate of the present invention may comprise a plurality of zones. As shown, a topsheet 2014 of a disposable absorbent article 2010, may comprise a first zone 2007, a second zone 2011 and a third zone 2013. Absorbent articles may comprise more zones or less zones as described hereafter. The zones described herein may be equally utilized with regard to the backsheet, absorbent core, acquisition layers, distribution layers, etc.

The first zone 2007 may comprise an array of apertures as described herein. As shown the first zone 2007 may have a width parallel to a lateral axis 2090 which does not extend the full width of the topsheet 2014. Instead, the second zone 2011 and the third zone 2013 may be placed on either side of the first zone 2007. In some forms, the second zone 2011 and the third zone 2013 may comprise a first array of out-of-plane features and a second array of out-of-plane features, respectively. For these forms, the array of apertures in the first zone 2007 may form apertured indicia which may be coordinated with the array of out-of-plane features in the second zone 2011 and/or the array of out-of-plane features in the third zone 2013. In a specific execution, the first zone 2007 comprises an array of apertures, the second and third zones 2011 and 2013, respectively, comprise an array of out-of-plane features, wherein the array of out-of-plane features in both the second zone 2011 and the third zone 2013 comprise tufts and/or ridges oriented in the Z-direction or negative Z-direction.

Still in other embodiments, the first zone 2007 may comprise an array of out-of-plane features while the second zone 2011 and the third zone 2013 comprise a first array of apertures and a second array of apertures, respectively. In such embodiments, the array of out-of-plane features may be coordinated with the array of apertures in the second zone 2011 and the third zone 2013.

In some forms, the first zone 2007 may comprise the array of apertures as well as an array of fusion bonds. The fusion bonds, as mentioned previously, may be configured to provide bond indicia. In some forms, bond indicia may be coordinated with the apertured indicia in the first zone 2007. In other embodiments, bond indicia may be present, in addition to the first zone 2007, in the second zone 2011 and/or third zone 2013. In such forms, the bond indicia may be coordinated with the apertured indicia in the first zone 2007 or may be un-coordinated with respect to the apertured indicia. Adhesive indicia, printed indicia may similarly be provided in the first zone 2007, the second zone 2011, and/or the third zone 2013. In such forms, the adhesive indicia, printed indicia may be coordinated with the apertured indicia or may be un-coordinated with the apertured indicia. In a specific execution, the first zone 2007 comprises an array of apertures forming apertured indicia and an array of fusion bonds forming bond indicia. The second zone 2011 and the third zone 2013 may each comprise an array of out-of-plane features, wherein the array of out-of-plane features comprise tufts 1770 oriented in the Z-direction. In such executions, the apertured indicia may be coordinated with bond indicia. In other executions, bond indicia may not be coordinated with apertured indicia.

In some forms, the first zone 2007, the second zone 2011 and/or the third zone 2013 may comprise a plurality of indicia selected from printed indicia, apertured indicia, adhesive indicia, structural indicia, and bond indicia. In such embodiments, any combination of the plurality of indicia may be coordinated with indicia within its respective zone and/or with regard to one of the other or both zones.

While heretofore, zones have been disclosed primarily in the context of laminates, laminates without apertures and laminates without patterned apertures may similarly comprise variable zones. Webs of the present invention may be similarly configured. For example, the first zone 2007 may comprise printed indicia while the second zone 2011 and the third zone 2013 comprise structural indicia. The printed indicia and the structural indicia may be coordinated. In other examples, the first zone 2007 may comprise adhesive indicia while the second and the third zones 2011 and 2013, respectively, comprise structural indicia. The adhesive indicia may be coordinated with the structural indicia. In yet another example, the first zone 2007 may comprise bond indicia while the second zone 2011 and third zone 2013 comprise structural indicia. The bond indicia may be coordinated with the structural indicia. Still in other forms, the first zone 2007 may comprise apertured indicia and printed indicia while the second zone 2011 and the third zone 2013 comprise structural indicia. The structural indicia may be coordinated with the apertured indicia which in turn may be coordinated with the printed indicia.

The first zone 2007 may comprise a majority of the apertures of the article onto which the web/laminate is utilized. In some forms, a substantial number of the apertures of an article may be comprised by the first zone 2007. In some forms, substantially all of the apertures of the article may be comprised by the first zone 2007. In some forms, the first zone 2007 may extend to and comprise apertures which are positioned most proximal to the second zone 2011 and third zone 2013. Lines 4407 and 4409 (shown in FIG. 35A) tangent to a periphery of these apertures and generally parallel to a longitudinal axis, may define the first zone 2007, second zone 2011, and third zone 2013.

In some additional forms, as shown in the examples in FIGS. 59-85, and as noted previously, the backsheet of the absorbent articles may comprise printing. Printing on the backsheet may be coordinated with the printing visible from the wearer-facing surface of the absorbent article. Printing on the backsheet may also be coordinated with the apertured indicia, structural indicia, bond indicia, adhesive indicia, and/or printed indicia. And, as noted previously, the backsheet may also comprise a color excluding conventional white either in addition to the printing or independent therefrom.

Other suitable configurations of zones are described with regard to FIGS. 31-34. FIGS. 31-34 may represent a portion of a wearer-facing surface of an absorbent article, such as a diaper, an adult incontinence product, and/or a sanitary napkin.

Figure 31:
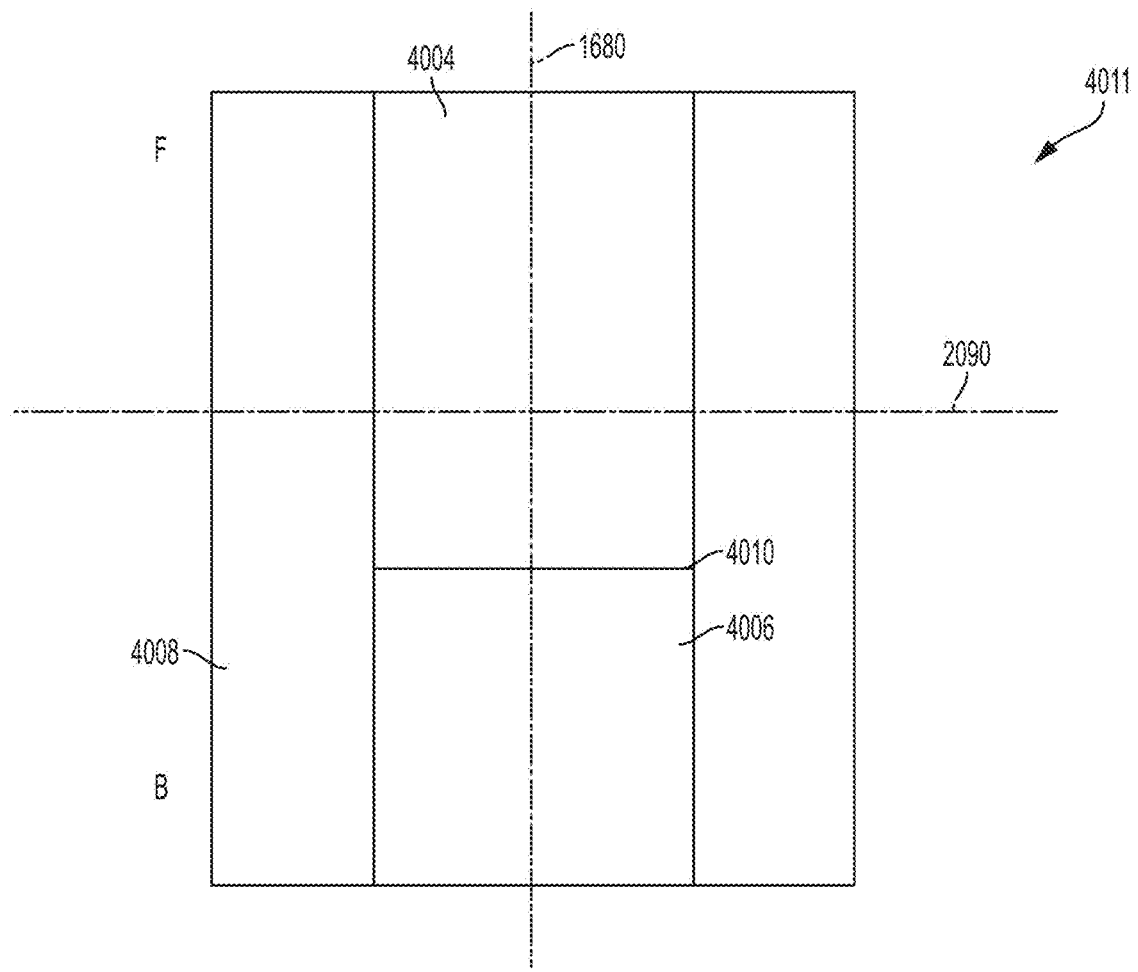

FIG. 31 illustrates an example of an absorbent article having three zones. The front portion, F, may be positioned in a front portion of an absorbent article or a back portion of an absorbent article. The back portion, B, may be positioned in a front portion of an absorbent article or a back portion of an absorbent article. A first zone 4004 and a second zone 4006 may be positioned intermediate two portions of the third zone 4008. The zones 4004, 4006, and 4008 may be provided as separate pieces of material that are partially overlapped and joined or bonded together or may be provided as one piece of material. In an instance, the first zone 4004 and the second zone 4006 may be provided as one piece of material or as two pieces of material that partially overlapped and joined or bonded together.

The first zone 4004 may comprise a plurality of out-of-plane features as described above with reference to FIGS. 2A-2D. The out-of-plane features may extend upwardly out of the page or downwardly into the page. The second zone 4006 may comprise a plurality of out-of-plane features as described above with reference to FIGS. 2A-2D. The out-of-plane features may extend upwardly out of the page or downwardly into the page. The second zone 4006 may have a different or the same pattern, shape, size, and/or orientation of the out-of-plane features compared to the pattern, shape, size, and/or orientation of the first zone 4004. The third zone 4008 may comprise a pattern of apertures, wherein at least two apertures of the pattern of apertures have different sizes, shapes, and/or orientations. The pattern of apertures may be any of the various patterns described herein or other suitable patterns. A substantially-laterally extending separation element, 4010, may extend between the intersection of the first zone 4004 and the second zone 4006.

In another instance, still referring to FIG. 31, the first zone 4004 may comprise a pattern of apertures, wherein at least two apertures of the pattern of apertures have different sizes, shapes, and/or orientations. The pattern of apertures may be any of the various patterns described herein or other suitable patterns. The second zone 4006 may comprise a pattern of apertures, wherein at least two apertures of the pattern of apertures have different sizes, shapes, and/or orientations. The pattern of apertures may be any of the various patterns described herein or other suitable patterns. The second zone 4006 may have a different or the same pattern of apertures as the first zone 4004. The third zone 4008 may comprise a plurality of out-of-plane features as described above with reference to FIGS. 2A-2D. The out-of-plane features may extend upwardly out of the page or downwardly into the page. A substantially-laterally extending separation element, 4010, may extend between the intersection of the first zone 4004 and the second zone 4006.

Figure 32:
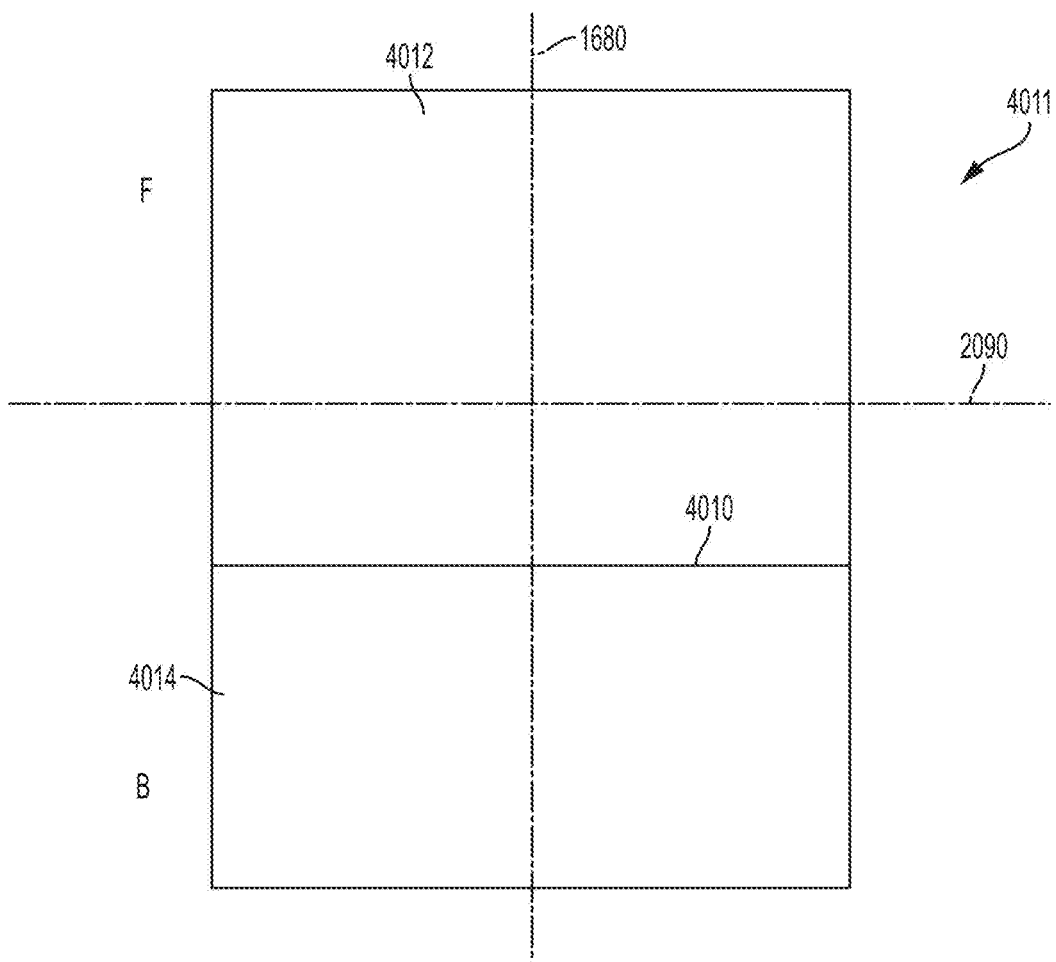

FIG. 32 illustrates an example of an absorbent article having a first zone 4012 and a second zone 4014. The front portion, F, may be positioned in a front portion of an absorbent article or a back portion of an absorbent article. The back portion, B, may be positioned in a front portion of an absorbent article or a back portion of an absorbent article. The zones 4012 and 4014 may be provided as two separate pieces of material that are partially overlapped and joined or bonded together or may be provided as one piece of material. The first zone 4012 may comprise a pattern of apertures, wherein at least two apertures of the pattern of apertures have different sizes, shapes, and/or orientations. The pattern of apertures may be any of the various patterns described herein or other suitable patterns. The second zone 4014 may comprise a plurality of out-of-plane features as described above with reference to FIGS. 2A-2D. The out-of-plane features may extend upwardly out of the page or downwardly into the page. A substantially-laterally extending separation element, 4010, may extend between the intersection of the first zone 4012 and the second zone 4014.

In another instance, still referring to FIG. 32, the second zone 4014 may comprise a pattern of apertures, wherein at least two apertures of the pattern of apertures have different sizes, shapes, and/or orientations. The pattern of apertures may be any of the various patterns described herein or other suitable patterns. The first zone 4012 may comprise a plurality of out-of-plane features as described above with reference to FIGS. 2A-2D. The out-of-plane features may extend upwardly out of the page or downwardly into the page. A substantially-laterally extending separation element, 4010, may extend between the intersection of the first zone 4012 and the second zone 4014.

Figure 33:
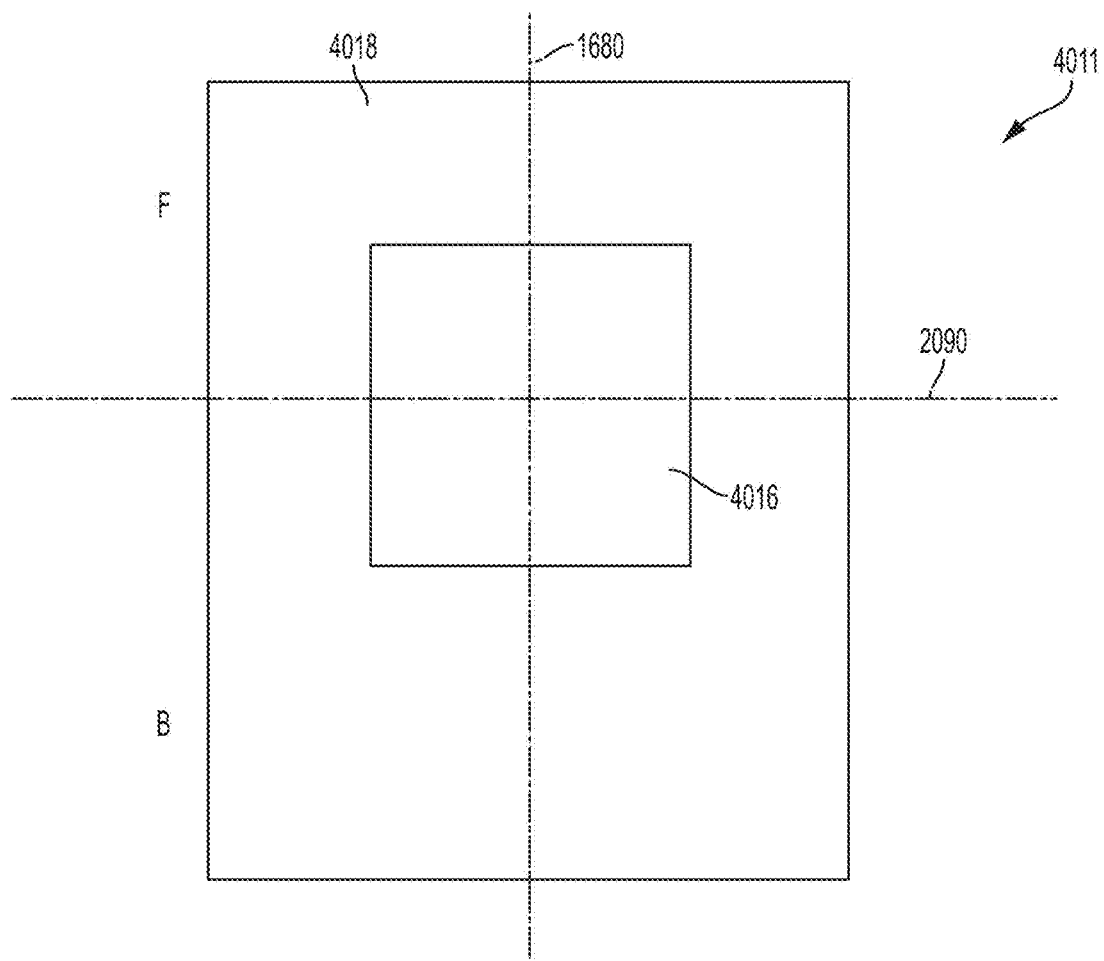

FIG. 33 illustrates an example of a substrate having a first zone 4016 and a second zone 4018. The front portion, F, may be positioned in a front portion of an absorbent article or a back portion of an absorbent article. The back portion, B, may be positioned in a front portion of an absorbent article or a back portion of an absorbent article. The zones 4016 and 4018 may be provided as two separate pieces of material that are partially overlapped and joined or bonded together or may be provided as one piece of material. The second zone 4018 may at least partially, or fully, surround the first zone 4016.

Still referring to FIG. 33, the first zone 4016 may comprise a plurality of out-of-plane features as described above with reference to FIGS. 2A-2D. The out-of-plane features may extend upwardly out of the page or downwardly into the page. The second zone 4018 may comprise a plurality of out-of-plane features as described above with reference to FIGS. 2A-9B. The out-of-plane features may extend upwardly out of the page or downwardly into the page. The second zone 4018 may have a different or the same pattern, shape, size, and/or orientation of the out-of-plane features compared to the pattern, shape, size, and/or orientation of the first zone 4016.

In another instance, still referring to FIG. 33, the first zone 4016 may comprise a pattern of apertures, wherein at least two apertures of the pattern of apertures have different sizes, shapes, and/or orientations. The pattern of apertures may be any of the various patterns described herein or other suitable patterns. The second zone 4018 may comprise a plurality of out-of-plane features as described above with reference to FIGS. 2A-2D. The out-of-plane features may extend upwardly out of the page or downwardly into the page.

In yet another instance, still referring to FIG. 33, the second zone 4018 may comprise a pattern of apertures, wherein at least two apertures of the pattern of apertures have different sizes, shapes, and/or orientations. The pattern of apertures may be any of the various patterns described herein or other suitable patterns. The first zone 4016 may comprise a plurality of out-of-plane features as described above with reference to FIGS. 2A-2D. The out-of-plane features may extend upwardly out of the page or downwardly into the page.

In another instance, still referring to FIG. 33, the first zone 4016 may comprise a pattern of apertures, wherein at least two apertures of the pattern of apertures have different sizes, shapes, and/or orientations. The pattern of apertures may be any of the various patterns described herein or other suitable patterns. The second zone 4018 may comprise a pattern of apertures, wherein at least two apertures of the pattern of apertures have different sizes, shapes, and/or orientations. The pattern of apertures may be any of the various patterns described herein or other suitable patterns. The patterns of apertures of the first zone 4016 and the second zone 4018 may be different or the same.

Figure 34:
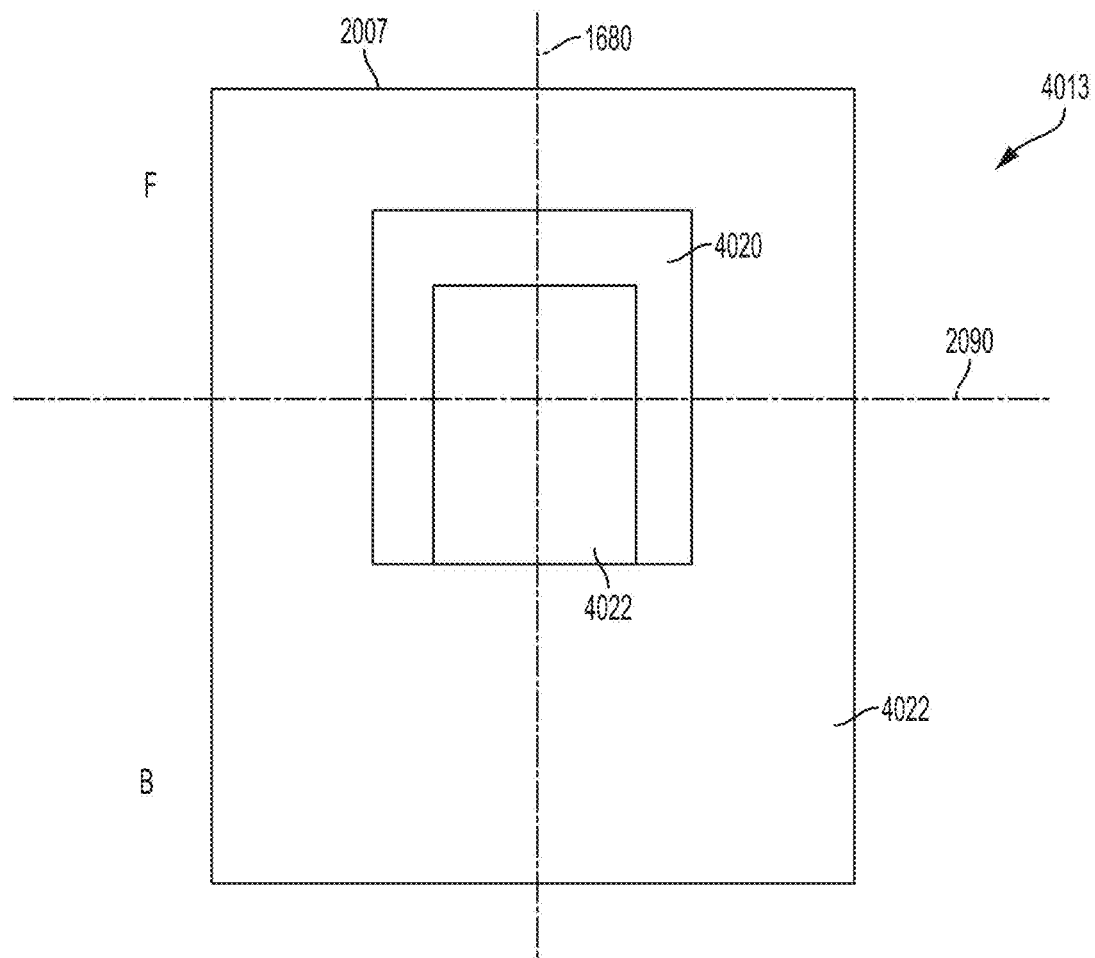

FIG. 34 illustrates an example of an absorbent article having a first zone 4020 and a second zone 4022. The front portion, F, may be positioned in a front portion of an absorbent article or a back portion of an absorbent article. The back portion, B, may be positioned in a front portion of an absorbent article or a back portion of an absorbent article. The zones 4020 and 4022 may be provided as two separate pieces of material that are partially overlapped and joined or bonded together or may be provided as one piece of material. The second zone 4022 may at least partially, or fully, surround the first zone 4020.

Still referring to FIG. 34, the first zone 4020 may comprise a pattern of apertures, wherein at least two apertures of the pattern of apertures have different sizes, shapes, and/or orientations. The pattern of apertures may be any of the various patterns described herein or other suitable patterns. The second zone 4022 may comprise a pattern of apertures, wherein at least two apertures of the pattern of apertures have different sizes, shapes, and/or orientations. The pattern of apertures may be any of the various patterns described herein or other suitable patterns. The patterns of apertures of the first zone 4020 and the second zone 4022 may be different or the same.

Still referring to FIG. 34, the first zone 4020 may comprise a pattern of apertures, wherein at least two apertures of the pattern of apertures have different sizes, shapes, and/or orientations. The pattern of apertures may be any of the various patterns described herein or other suitable patterns. The second zone 4022 may comprise a plurality of out-of-plane features as described above with reference to FIGS. 2A-2D. The out-of-plane features may extend upwardly out of the page or downwardly into the page Still referring to FIG. 34, the second zone 4022 may comprise a pattern of apertures, wherein at least two apertures of the pattern of apertures have different sizes, shapes, and/or orientations. The pattern of apertures may be any of the various patterns described herein or other suitable patterns. The first zone 4020 may comprise a plurality of out-of-plane features, for example as described above with reference to FIGS. 2A-2D. The out-of-plane features may extend upwardly out of the page or downwardly into the page. Additional out-of-plane features described herein are contemplated for provision in the first zone 4020.

The first zone 4020 may comprise a plurality of out-of-plane features as described above with reference to FIGS. 2A-2D. The out-of-plane features may extend upwardly out of the page or downwardly into the page. The second zone 4022 may comprise a plurality of out-of-plane features as described above with reference to FIGS. 2A-2D. The out-of-plane features may extend upwardly out of the page or downwardly into the page. The second zone 4022 may have a different or the same pattern, shape, size, and/or orientation of the out-of-plane features compared to the pattern, shape, size, and/or orientation of the first zone 4020.

Visual Texture

Apertures, aperture arrays, three-dimensional elements, tufts, printing, patterned adhesives, or any combinations of these "texture elements" may impart a variable visually observed texture in a laminate. Variations in observable textures have been extensively studied in the psychological and neurological sciences. Some small texture elements are much more readily ("instantly") detected by the human visual perception system than others. Most texture patterns having similar "second order" (iso-dipole) statistics cannot be discriminated in a brief "flash" observation. However, exceptions to this (i.e., iso-dipole texture elements that are easily discriminated) have been defined and are known in the literature as "textons". Webs/laminates including texture elements forming texton shapes provide a way to create easily recognizable "zones" on a laminate or in an absorbent article, signaling regions having different functions, and/or providing strong cues as to correct product orientation on a wearer (e.g., front/back). Forms of the webs/laminates of the present disclosure may include texture elements forming texton shapes, including quasi-collinearity, corner features, and closure of local features. A reference is Julesz, B., et al, *Visual Discrimination of Textures with Identical Third-Order Statistics*, Biological Cybernetics vol. 31, 1978, pp. 137-140).

Effective Open Area

The webs/lamiantes of the present invention may have an Effective Open Area between about 5% to about 50%, about 5% to about 40%, about 8% to about 35%, about 10% to about 30%, about 10% to about 25%, about 3% to about 15%, or about 8% to about 15%, specifically including all 0.1% increments within the specified ranges and all ranges formed therein or thereby. All Effective Open Area percents are determined using the Aperture Test described herein. Webs/laminates having a higher Effective Open Area may have utility as a topsheet or acquisition layer or system in an absorbent article (more functional to absorbent bodily exudates), while webs/laminates having a lower Effective Open Area may have utility as an outer cover of an absorbent article (more decorative or for breathability purposes). In some forms of the present invention, for hydrophilic webs—where a body contacting surface is hydrophilic—the percentage open area can generally be less. For hydrophobic webs—where a body contacting surface is hydrophobic—the percentage open area may be increased to ensure good acquisition rates. As an example, for a hydrophobic topsheet, the percentage open area can be from about 5% to about 50%. As another example, for a hydrophilic topsheet, the percentage can be from about 1% to about 50%.

Effective Aperture Area

The webs and laminates of the present invention may have apertures having an Effective Aperture AREA in the range of about 0.1 mm$^2$ to about 15 mm$^2$, 0.3 mm$^2$ to about 14 mm$^2$, 0.4 mm$^2$ to about 12 mm$^2$, 0.3 mm$^2$ to about 10 mm$^2$, 0.5 mm$^2$ to about 8 mm$^2$, 1.0 mm$^2$ to about 8 mm$^2$, or about 1.0 mm$^2$ to about 5 mm$^2$, specifically including all 0.05 mm increments within the specified ranges and all ranges formed therein or thereby. All Effective Aperture Areas are determined using the Aperture Test described herein. A plurality of the apertures in a web/laminate may be different in Effective Aperture Areas. The Relative Standard Deviation ("RSD") of the Effective Aperture Areas may be at least about 20 percent, at least about 30 percent, at least about 50 percent or at least about 55 percent, or at least about 60 percent.

Interaperture Distance and Average Interaperture Distance

The webs/laminates of the present invention may have apertures that have an Average Interaperture Distance of less than about 3.5 mm, less than about 3 mm, less than about 2.5 mm, less than about 2 mm, less than about 1.5 mm, less than about 1 mm, in the range of about 1 mm to about 6 mm, in the range of about 1 mm to about 5 mm, in the range from about 1 mm to about 4 mm, in the range from about 1 mm to about 3.5 mm, in the range of about 1 mm to about 3 mm, in the range of about 1 mm to about 2.5 mm, in the range of about 2 mm to about 4 mm, in the range of about 3.5 mm to about 10 mm, or in the range of about 0.08 mm to about 11 mm, specifically reciting all 0.1 mm increments within the above-specified ranges and all ranges formed therein or thereby, according to the Interaperture Distance Test herein.

The webs/laminates may have Interaperture Distances, calculated according to the Interaperture Distance Test herein. The Interaperture Distances may have a distribution having a mean and a median. The mean may be greater than, different than, or less than the median. The difference between the mean and the median may be in the range of about 1% to about 25%, about 4% to about 25%, about 5% to about 20%, about 8% to about 20%, about 4% to about 15%, or about 1% to about 8%, for example, specifically reciting all 0.1% increments within the above specified ranges and all ranges formed therein or thereby. A first zone of an apertured web may have Interaperture Distances. The Interaperture Distances of a first zone may have a first distribution having a first mean and a first median. The first mean may be greater than, different than, or less than the first median by the ranges set forth above in this paragraph. A second zone of the apertured web may have Interaperture Distances. The Interaperture Distances of the second zone may have a second distribution having a second mean and a second median. The second mean may be greater than, less than, or different than the second median by the ranges set forth above in this paragraph. A third zone of the webs/laminate may have Interaperture Distances. The Interaperture Distances of the third zone may have a third distribution having a third mean and a third median. The third mean may be greater than, different than, or less than the third median by the ranges set forth above in this paragraph. The first, second, and third means may be the same or different. The first, second, and third medians may be the same or different. The first, second, and third zones may be in a topsheet, a topsheet layer, an acquisition layer, an outercover, an outercover layer, or any other component of an absorbent article or other consumer products.

In other instances, a first portion of an absorbent article or other consumer product may have a first web/laminate that has Interaperture Distances, according to the Interaperture Distance Test herein. The Interaperture Distances of the first portion have a first distribution. A second portion of an absorbent article or other consumer product may have a second web/laminate that has Interaperture Distances, according to the Interaperture Distance Test herein. The Interaperture Distances of the second portion have a second distribution. A third portion of an absorbent article or other consumer product may have a third web/laminate that has Interaperture Distances, according to the Interaperture Distance Test herein. The Interaperture Distances of the third portion have a third distribution. The first, second, and third distributions may be the same or different. The first distribution may have a first mean and a first median. The first mean may be greater than, less than, or different than the first median in the range of about 1% to about 25%, about 4% to about 25%, about 5% to about 20%, about 8% to about 20%, about 4% to about 15%, or about 1% to about 8%, for example, specifically reciting all 0.1% increments within the above-specified ranges and all ranges formed therein or thereby. The second distribution may have a second mean and a second median. The second mean may be greater than, different than, or less than the second median by the ranges set forth above in this paragraph. The third distribution may have a second mean and a second median. The second mean may be greater than, different than, or less than the second median by the ranges set forth above in this paragraph. The first, second, and third means may be the same or different. The first, second, and third medians may be the same or different. The Relative Standard Deviation (RSD) of the Interaperture Distances may be at least 25%, at least about 35%, at least about 40%, at least about 50%, or at least about 55%. The Maximum Interaperture Distance in a given web/laminate or pattern may be at least about 5 mm, at least about 8 mm, at least about 10 mm, or at least about 11 mm.

Average Absolute Feret Angle and Absolute Feret Angle

Webs/laminates may have one or more apertures having an Absolute Feret Angle, according to the Absolute Feret Angle Test, of at least about 2 degrees, 5 degrees, 15 degrees, at least about 18 degrees, at least about 20 degrees, at least about 22 degrees, at least about 25 degrees, at least about 30 degrees, at least about 35 degrees, at least about 40 degrees, at least about 45 degrees, at least about 50 degrees, at least about 55 degrees, at least about 60 degrees, or in the range of about 2 degrees to about 80 degrees, in the range of about 5 degrees to about 75 degrees, in the range of about 10 degrees to about 70 degrees, or in the range of about 15 degrees to about 65 degrees, specifically reciting all 0.1 degrees increments within the above-specified ranges and all ranges formed therein or thereby.

Webs/laminates may have a plurality of apertures having an Average Absolute Feret Angle, according to the Average Absolute Feret Angle Test, of at least about 2 degrees, 5 degrees, 15 degrees, at least about 18 degrees, at least about 20 degrees, at least about 22 degrees, at least about 25 degrees, at least about 30 degrees, at least about 35 degrees, at least about 40 degrees, at least about 45 degrees, at least about 50 degrees, at least about 55 degrees, at least about 60 degrees, or in the range of about 2 degrees to about 80 degrees, in the range of about 5 degrees to about 75 degrees, in the range of about 10 degrees to about 70 degrees, or in the range of about 15 degrees to about 65 degrees, specifically reciting all 0.1 degrees increments within the above-specified ranges and all ranges formed therein or thereby. These apertures may all be within a single repeat unit of the web/laminate.

At least two, at least 3, at least 4, at least 5, at least 6, at least 7, at least 8, at least 9, or at least 10 of the apertures in web/laminate, or a repeat unit of web/laminate, may each have a different Absolute Feret Angle, according to the Absolute Feret Angle Test herein. In other instances, some of the apertures may have Absolute Feret Angles that are the same, while other of the apertures may have Absolute Feret Angles that are different. In addition to having different Absolute Feret Angles, the at least two, at least 3, at least 4, at least 5, at least 6, at least 7, at least 8, at least 9, or at least 10 apertures may have different sizes and/or shapes. At least some of the At least two, at least 3, at least 4, at least 5, at least 6, at least 7, at least 8, at least 9, or at least 10 apertures may also have the same size and/or shape, while having different Absolute Feret Angles.

Apertures oriented at feret angles greater than zero relative to the machine direction may have a higher aspect ratio than apertures that are aligned in the machine direction or vice versa. Apertured webs having elongated apertures oriented at different feret angles may provide liquid bodily exudate handling benefits when the web/laminate is used as a topsheet in an absorbent article. For example, fluid run-off may be reduced in the front or back of the absorbent article when the apertures are not all aligned in the machine direction, but instead are oriented at an angle relative to the machine direction (e.g., about 30 degrees, about 45 degrees, or even about 90 degrees) as the apertures can more readily acquire the liquid bodily exudates. Therefore, it may be desirable to have the central longitudinal axes of the elongated apertures oriented at multiple different feret angles in order to most effectively acquire liquid bodily exudates running along the surface of the web/laminate and prevent, or at least inhibit, run-off and soiling of garments.

In some forms of the present invention, a web/laminate may comprise a plurality of apertures wherein a first portion of the apertures have an Absolute Feret angle of less than about 20 degrees and wherein a second portion of the apertures have an Absolute Feret angle of greater than about 20 degrees. In some forms, the first portion may comprise about 50% of the plurality of apertures. In some forms, the first portion may comprise about 40% of the plurality of apertures. In some forms, a first plurality of apertures may comprise more apertures than a second plurality of apertures by a ratio of about 3 to 1 or about 5 to 1. In some forms, the first plurality of apertures may be disposed about the second plurality of apertures.

In some examples, a pattern of overbonds, each of which is oriented solely in the machine direction, or substantially in the machine direction (i.e., +/−5 degrees or less from the machine direction), may be used to create a web/laminate with apertures having central longitudinal axes that are not all oriented in the machine direction or, stated another way, that are angled more than 5 degrees with respect to the machine direction. The nonwoven web 2200 of FIGS. 10B, 10E, 10G, and 10J may have some apertures 2212 having a central longitudinal axis, L, having an angle with respect to the machine direction. The angle may be from about 5 degrees to about 70 degrees with respect to the machine direction, specifically reciting all 0.5 degree increments within the specified range and all ranges formed therein. Some of the apertures 2212 in the nonwoven laminate 2200 may also have a central longitudinal axis, L1, that extends parallel to, or substantially parallel to (e.g., +/− less than 5 degrees), the machine direction. The cross directional stretching step or steps described herein may be used to create the apertures and to orient the central longitudinal axes, L, of at least some of the apertures in a direction not parallel to, or substantially parallel to, the machine direction. At least some of the apertures in a web/laminate having their central longitudinal axes not parallel to, or substantially parallel to, the machine direction may have a first plurality of apertures having central longitudinal axes extending in a first direction with respect to the machine direction and a second plurality of apertures having central longitudinal axes extending at a second, different direction relative to the machine direction. The first and second directions may be 30 degrees and −30 degrees, respectively, 10 degrees and 20 degrees respectively, or −20 degrees and 30 degrees respectively, to provide a few examples. Those of skill in the art will recognize that angles relative to the machined are also within the scope of the present disclosure.

The apertures in a web or laminate having apertures generally parallel to the machine direction and produced by machine direction overbonds may be more open (i.e., have a lower aspect ratio) than they would have been if the overbonds had been oriented at an angle (5 degrees or more) with respect to the machine direction. Overbonds oriented at an angle with respect to the machine direction typically produce apertures having higher aspect ratios post cross directional stretching that are less open.

Additional suitable overbond patterns are disclosed in U.S. Application Ser. No. 62/177,405 filed on Mar. 13, 2015, with regard to FIGS. 55-116 which show schematic representations of a variety of overbond patterns. Those of skill in the art will recognize that other suitable overbond patterns are also within the scope of the present disclosure, along with variations of the illustrated patterns. Additional overbond patterns are disclosed with regard to FIGS. 91 and 92.

Figure 91:
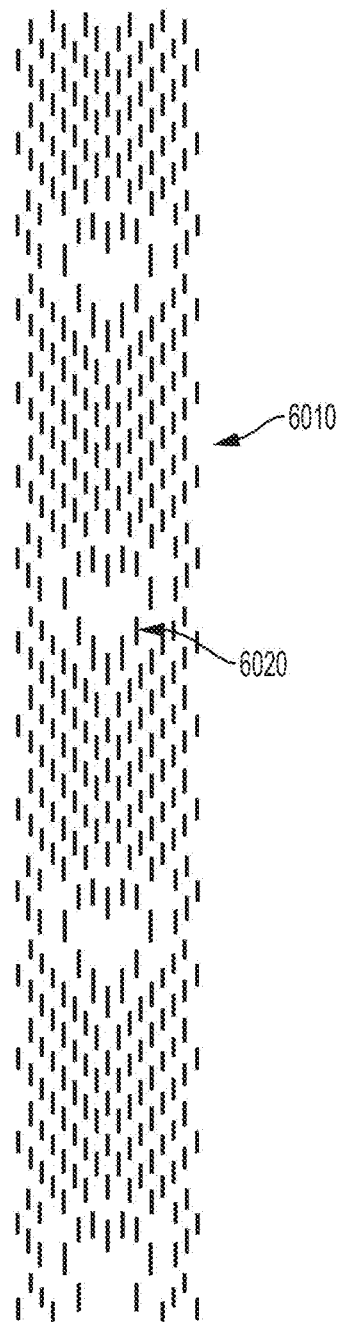
FIGS. 91 and 92 represent a schematic illustrations exemplary overbond patterns having at least some overbonds with central longitudinal axes that are substantially parallel to a machine direction in accordance with the present disclosure.

As shown in FIG. 91, a suitable overbond pattern for use with the crimped fiber spunbond nonwoven webs/nonwoven laminates of the present invention may comprise an array of overbonds disposed in several groups. For example, a first plurality of overbond sites 6010 may surround a second plurality of overbond sites 6020. Generally, the second plurality of overbond sites 6020 may be arranged to form (subsequent to processing) apertured indicia. As shown, hearts.

Figure 92:
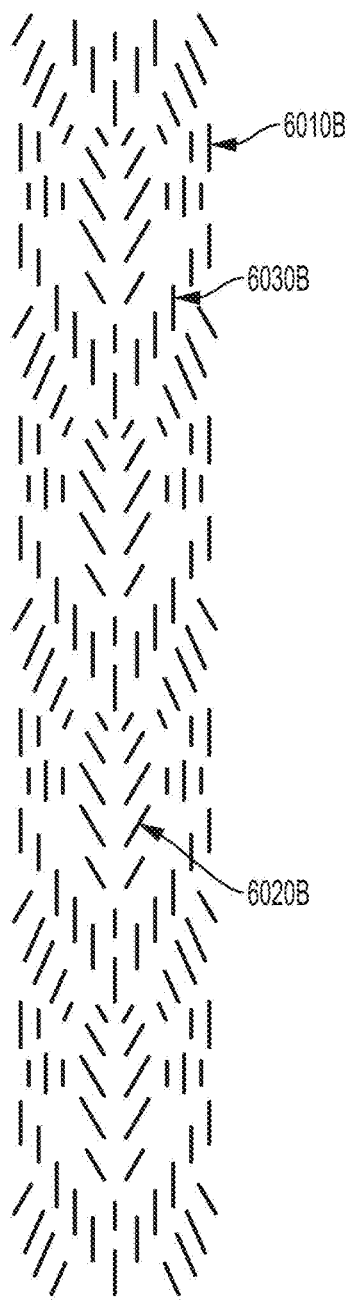

As shown in FIG. 92, another suitable overbond pattern for use with the nonwoven webs of the present invention may comprise a first plurality of overbond sites 6010B, a second plurality of overbond sites 6020B, and a third plurality of overbond sites 6030B. As shown, the first plurality of overbond sites 6010B may, at least in part, surround the second plurality of overbond sites 6020B. Much like the overbond pattern of FIG. 91, the overbond sites 6010B are shown generally parallel to a longitudinal axis (not shown). The resulting apertures will generally be aligned with respect to the longitudinal axis. Additionally, the third plurality of overbond sites 6030B is angled with respect to the longitudinal axis at a first angle. The second plurality of overbond sites 6020B is angled with respect to the longitudinal axis at a second angle. In the form shown, the first angle and the second angle are different. The first and the second angle may be any of the ranges described heretofore with regard to the angles of the apertures.

Similarly, additional suitable aperture patterns for webs/laminates of the present invention are disclosed in U.S. Application Ser. No. 62/177,405 filed on Mar. 13, 2015, with regard to FIGS. 117-162 which show schematic representations of a variety of overbond patterns. In these Figures, the white areas represent non-apertured areas (land areas) and the black areas represent apertured areas. Those of skill in the art will recognize that other suitable patterns of nonwoven laminates are also within the scope of the present disclosure, along with variations of the illustrated patterns.

Additionally, in some forms of the present invention, the webs/laminates of the present invention may be produced and subsequently provided to a disposable absorbent article converting line. However, in some forms, a manufacturer may obtain a web which comprises apertures as described herein. In some forms, a manufacturer may obtain a web which comprises out-of-plane deformations as described herein. In some forms, a manufacturer may obtain a web which comprises overbonds as described herein. Similarly, a manufacturer may obtain a supply roll which comprises a laminate comprising a web and another web as described herein.

Overbonds are typically a melt-stabilized area in a material, e.g. nonwoven, which has a stabilized film-like form. In some examples, webs/laminates of the present disclosure, a pattern of overbonds, each of which is oriented solely in the machine direction, or substantially in the machine direction (i.e., +/−5 degrees or less from the machine direction), may be used to create a laminate with apertures having central longitudinal axes that are not all oriented in the machine direction or, stated another way, that are angled more than 5 degrees with respect to the machine direction. The laminate 2200 of FIGS. 10A-10J may have some apertures 2212 having a central longitudinal axis, L, having an angle with respect to the machine direction. The angle may be from about 5 degrees to about 70 degrees with respect to the machine direction, specifically reciting all 0.5 degree increments within the specified range and all ranges formed therein. Some of the apertures 2212 in the laminate 2200 may also have a central longitudinal axis, L1, that extends parallel to, or substantially parallel to (e.g., +/− less than 5 degrees), the machine direction. The cross directional stretching step or steps described herein may be used to create the apertures and to orient the central longitudinal axes, L, of at least some of the apertures in a direction not parallel to, or substantially parallel to, the machine direction. At least some of the apertures in a laminate or web having their central longitudinal axes not parallel to, or substantially parallel to, the machine direction may have a first plurality of apertures having central longitudinal axes extending in a first direction with respect to the machine direction and a second plurality of apertures having central longitudinal axes extending at a second, different direction relative to the machine direction. The first and second directions may be 30 degrees and −30 degrees, respectively, 10 degrees and 20 degrees respectively, or −20 degrees and 30 degrees respectively, to provide a few examples. Those of skill in the art will recognize that angles relative to the machined are also within the scope of the present disclosure.

Aperture Aspect Ratio and Area

The apertures of the apertured webs of the present disclosure may have an aspect ratio of greater than one, for example, greater than two, greater than 3, greater than 5, or greater than 10, but typically less than 15. The aperture patterns in the apertured web may comprise apertures having more than one aspect ratio, such as two or more distinct populations or having a substantially continuous distribution of aspect ratios having a slope greater than zero. Additionally, the aperture patterns of the apertured webs may comprise apertures with more than two effective aperture area, either as two or more distinct populations or as a distribution of aperture areas having a slope greater than zero. The Relative Standard Deviation (RSD) of the aperture aspect ratios may be at least about 15%, at least about 25%, at least about 30%, or at least about 40%, or at least about 45%.

Packages

Absorbent articles comprising the webs/laminates of the present disclosure may be placed into packages. The packages may comprise polymeric films and/or other materials. Graphics or indicia relating to properties of the absorbent articles may be formed on, positioned on, and/or placed on outer portions of the packages. Each package may comprise one or more absorbent articles. The absorbent articles may be packed under compression so as to reduce the size or height of the packages while still providing an adequate amount of absorbent articles per package.

Accordingly, packages of the absorbent articles according to the present disclosure may have an in-bag stack height of less than about 80 mm, less than about 78 mm, or less than about 76 mm, according to the In-Bag Stack Height Test described herein. Alternatively, packages of the absorbent articles of the present disclosure may have an in-bag stack height of from about 72 mm to about 80 mm or from about 74 mm to about 78 mm, specifically reciting all 0.5 mm increments within the specified ranges and all ranges formed therein or thereby, according to the In-Back Stack Height Test described herein. Further details regarding in-back stack height are disclosed in U.S. Pat. No. 8,585,666, to Weisman et al., issued on Nov. 19, 2013.

EXAMPLES

Figure 35A:
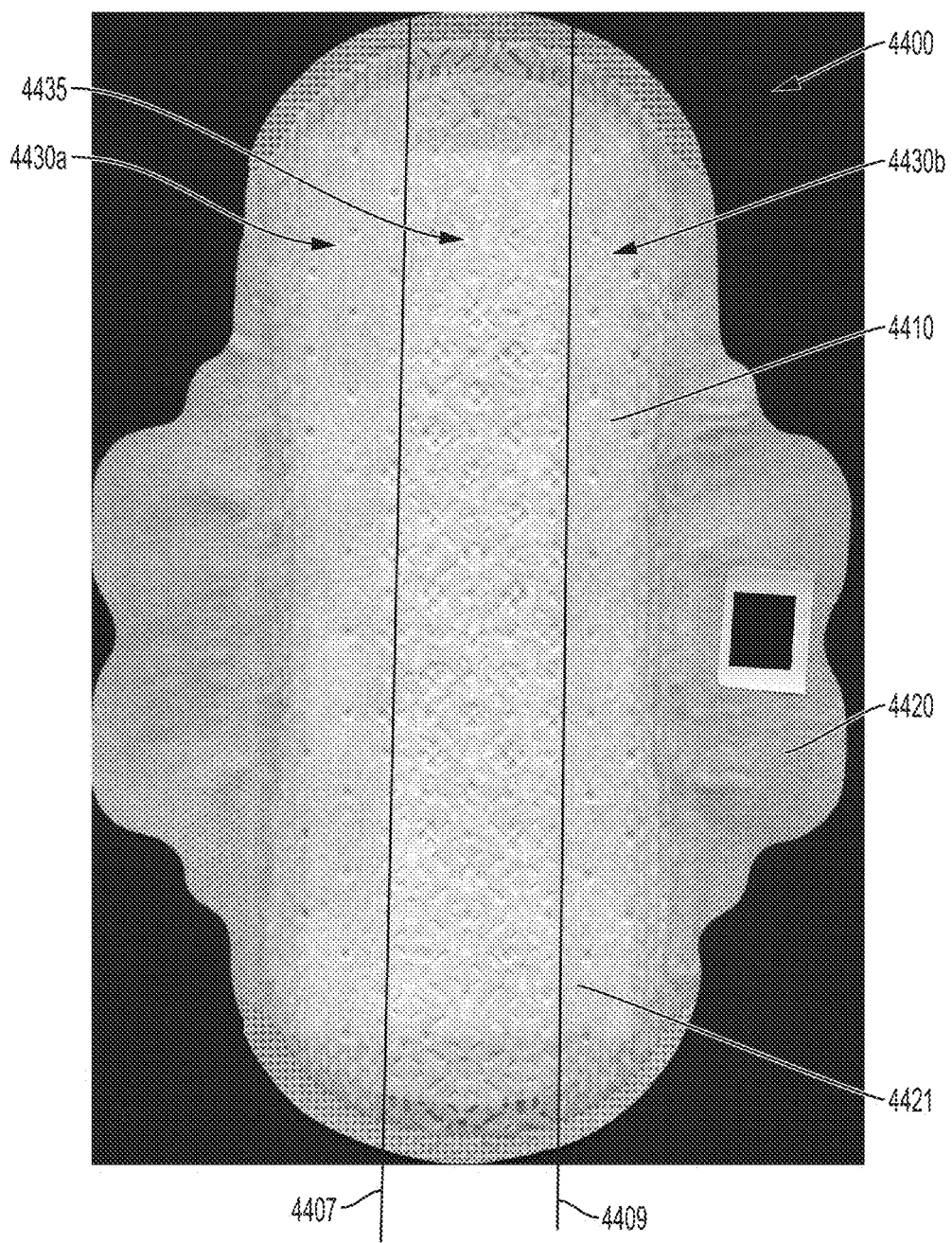
FIG. 35A is a photograph of an exemplary sanitary pad constructed in accordance with the present invention.
Figure 35B:
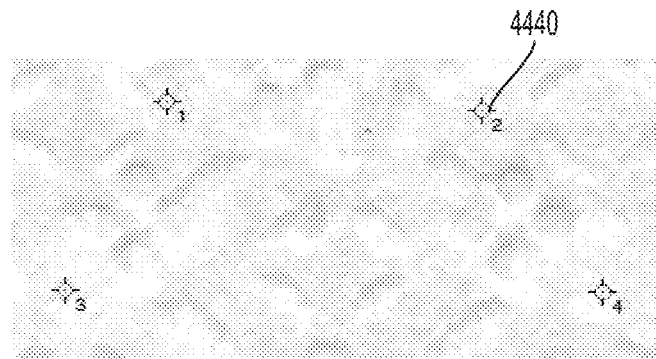
FIGS. 35B-35H are photographs showing various portions of the sanitary pad of FIG. 44A.
Figure 35C:
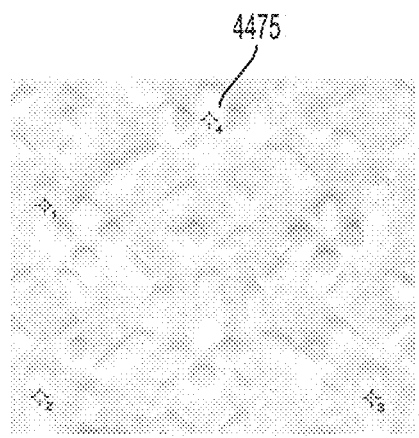
Figure 35D:
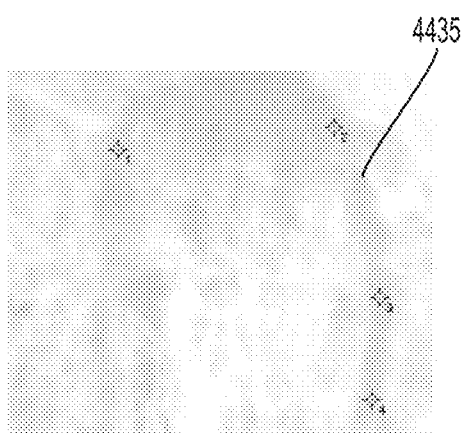
Figure 35E:
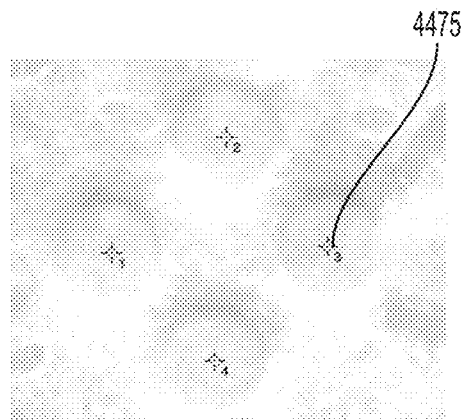
Figure 35F:
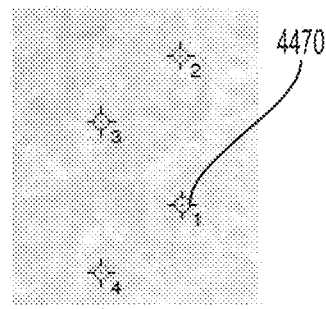
Figure 35G:
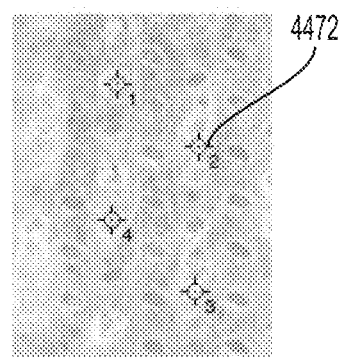
Figure 35H:
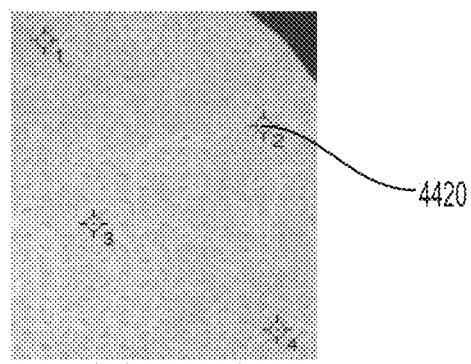

Below are provided many examples of laminates and disposable absorbent articles constructed in accordance with the present invention. Referring to FIGS. 35A-35G, each of the tested laminates comprised two nonwoven layers and were incorporated into a sanitary pad 4400. Each of these laminates were tested for color variances in accordance with the L*, a*, b*, methodology provided below. Each of the color measurements were taken at several locations on the sanitary pad 4400. Color measurements were taken on a topsheet 4410 in land areas 4440 (as depicted FIG. 35B), in apertures 4425 (as depicted in FIG. 35C), in melt lip 4435 (as depicted in FIG. 35D), in fusion bond sites 4475 (as depicted in FIG. 35E), in tufts 4470 above an absorbent core 4420 (as depicted in FIG. 35F), tufts 4472 (outboard of the absorbent core 4420 depicted in FIG. 35G), and wings 4420 (depicted in FIG. 35H). Note that the absorbent core 4421 depicted in FIG. 35A is positioned beneath the topsheet 4410.

Regarding the L*, a*, b* values provided herein, delta E* or "ΔE*" is determined by the equation provided below.

$$\Delta E = \sqrt{(L1-L2)^2 + (a1-a2)^2 + (b1-b2)^2}$$

Each of the examples below, i.e. 1-24, utilize two nonwoven layers laminated together. L*, a*, b* values were measured for each of the individual nonwoven layers against a white background. The L, a, b values for each of the individual nonwoven layers are provided in Table 1. Note that for each of the nonwoven layers there are two facets measured. Specifically, L*, a*, b* was measured in the area of the fibers—fiber area. And, L*, a*, b* was measured at calendar bonded areas—calendar bond area. The fibers of an individual nonwoven layer of the samples were bonded together via calendar bonding. Each nonwoven layer comprised about 18 percent calendar bonding. Each of the nonwoven layers comprised bi-component fibers with a core sheath configuration where the core was colored as provided in Table 1, and the sheath did not comprise $TiO_2$ for colorant. In contrast to the foregoing, the orchid colored nonwoven layer comprised polypropylene/polypropylene side-by-side configured fibers with color disposed in both components of the fiber.

TABLE 1

| Color - Location | L* | a* | b* |
|---|---|---|---|
| White - fiber area | 99 | −1 | −3 |
| White - calendar bond area | 97 | −1 | −3 |
| Light purple - fiber area | 87 | 3 | −10 |

TABLE 1-continued

| Color - Location | L* | a* | b* |
|---|---|---|---|
| Light purple - calendar bonded area | 89 | 1 | −7 |
| Peach - fiber area | 96 | 4 | 5 |
| Peach - calendar bonded area | 90 | 3 | 6 |
| Blue - fiber area | 83 | −11 | −28 |
| Blue - calendar bonded area | 87 | −8 | −19 |
| Mint green - fiber area | 97 | −11 | 3 |
| Mint green - calendar bonded area | 97 | −7 | 4 |
| Orchid - fiber area | 69 | 48 | −29 |
| Orchid - calendar bonded area | 65 | 51 | −31 |
| Light blue - fiber area | 96 | −5 | −7 |
| Light blue - calendar bonded area | 95 | −6 | −8 |
| Purple - fiber area | 56 | 8 | −18 |
| Purple - calendar bonded area | 63 | 5 | −14 |

Example 1

Referring back to FIG. 35A, the sanitary pad 4400 was created utilizing a white nonwoven upper layer with a basis weight of 25 gsm and a lower nonwoven layer of light purple having a basis weight of 20 gsm. The layers were laminated and used as the topsheet 4410 of the sanitary pad 4400. Averages of measured L*, a*, b* values for the sanitary pad 4400 is provided below in Table 2A.

TABLE 2A

| Location | L* | a* | b* |
|---|---|---|---|
| Land | 94 | 2 | −8 |
| Aperture | 96 | 1 | −5 |
| Melt Lip | 87 | 4 | −8 |
| Fusion bond site | 92 | 3 | −8 |
| Tuft inboard of absorbent core | 90 | 3 | −10 |
| Tuft outboard of absorbent core | 85 | −1 | −9 |
| Wings | 79 | −3 | −7 |

Of particular interest is a first zone 4435, a second zone 4430a, and a third zone 4430b. As shown, a plurality of apertures is disposed in the first zone 4435. And, as discussed previously, in the formation of apertures, stretching of the laminate may occur in the MD and/or CD direction. For the sanitary pad 4400 shown, the stretching in the CD direction appears to have made the first zone 4435 physically lighter in color shade than the second zone 4430a and third zone 4430b. The lighter shade can provide a perception of loft as well as highlight the apertures which can provide a perception of functionality.

It is believed that the incremental stretching de-densifies the laminate material. It is believed that processing breaks up bond sites separates fibers, and pushes fibers out of plane thereby increasing loft. The de-densified area is believed to have a lower basis weight than the non-de-densified areas. Additionally, it is believed that in processing (particularly the stretching process as described herein) land areas are thinned and apertures allow a light colored, e.g. white secondary topsheet to be seen therethrough. With regard to the pads described herein, the apertures can be provided in the first zone 4435. As such, the first zone 4435 may be less dense than the second and third zones 4430a and 4430b. The de-densified first zone 4435 then can appear lighter than the second and third zones 4430a and 4430b. This de-densification of the laminate material in the first zone 4435 can also enhance the perception of loft/softness within the first zone 4435.

Table 2B shows the average L*, a*, b* values measured for the first zone 4435 and second and third zones 4430a and 4430b, respectively with a 101×101 pixels averaged per measurement.

TABLE 2B

| Location | L* | a* | b* |
|---|---|---|---|
| First Zone | 86 | 1 | −6 |
| Second and Third Zones | 81 | 1 | −6 |

Example 2

Figure 36:
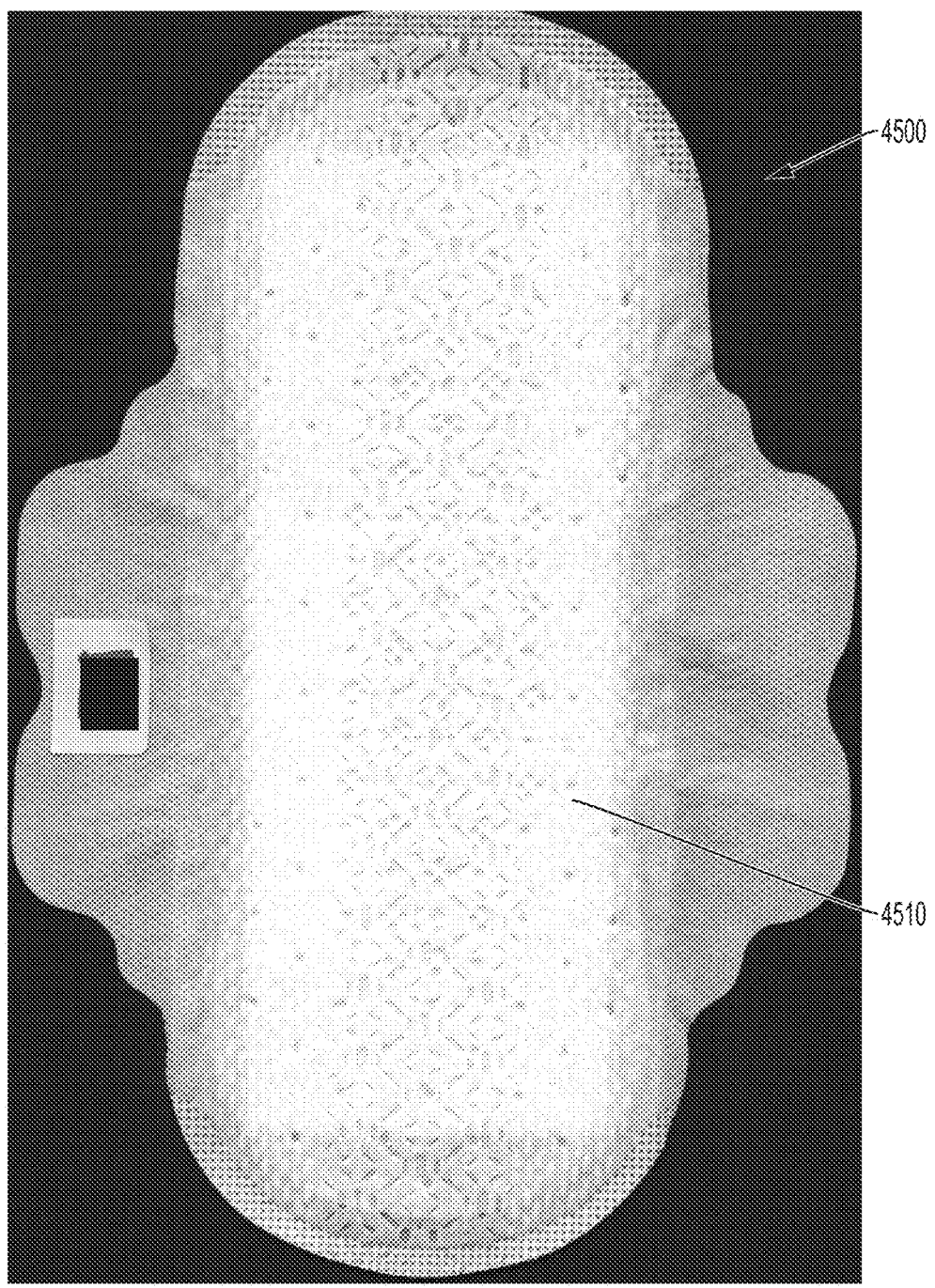
FIG. 36 is a photograph of an exemplary sanitary pad constructed in accordance with the present invention.

Referring to FIG. 36, a sanitary pad 4500 was created utilizing two white nonwoven layers as a topsheet 4510 of the sanitary pad 4500. Averages of measured L*, a*, b* values for the sanitary pad 4500 are provided below in Table 3. Each of the L*, a*, b* values measured were taken at locations similar to those described in FIGS. 35B-35H.

TABLE 3

| Location | L* | a* | b* |
|---|---|---|---|
| Land | 100 | 0 | −2 |
| Aperture | 98 | 0 | −3 |
| Melt Lip | n/a | n/a | n/a |
| Fusion bond site | 97 | 0 | −2 |
| Tuft inboard of absorbent core | 99 | −1 | −5 |
| Tuft outboard of absorbent core | 90 | −2 | −7 |
| Wings | 80 | −3 | −7 |

Note that the melt lip of Example 2 was not able to be captured by the person measuring the color variances of the features of the sanitary pad 4500.

Example 3

Figure 37:
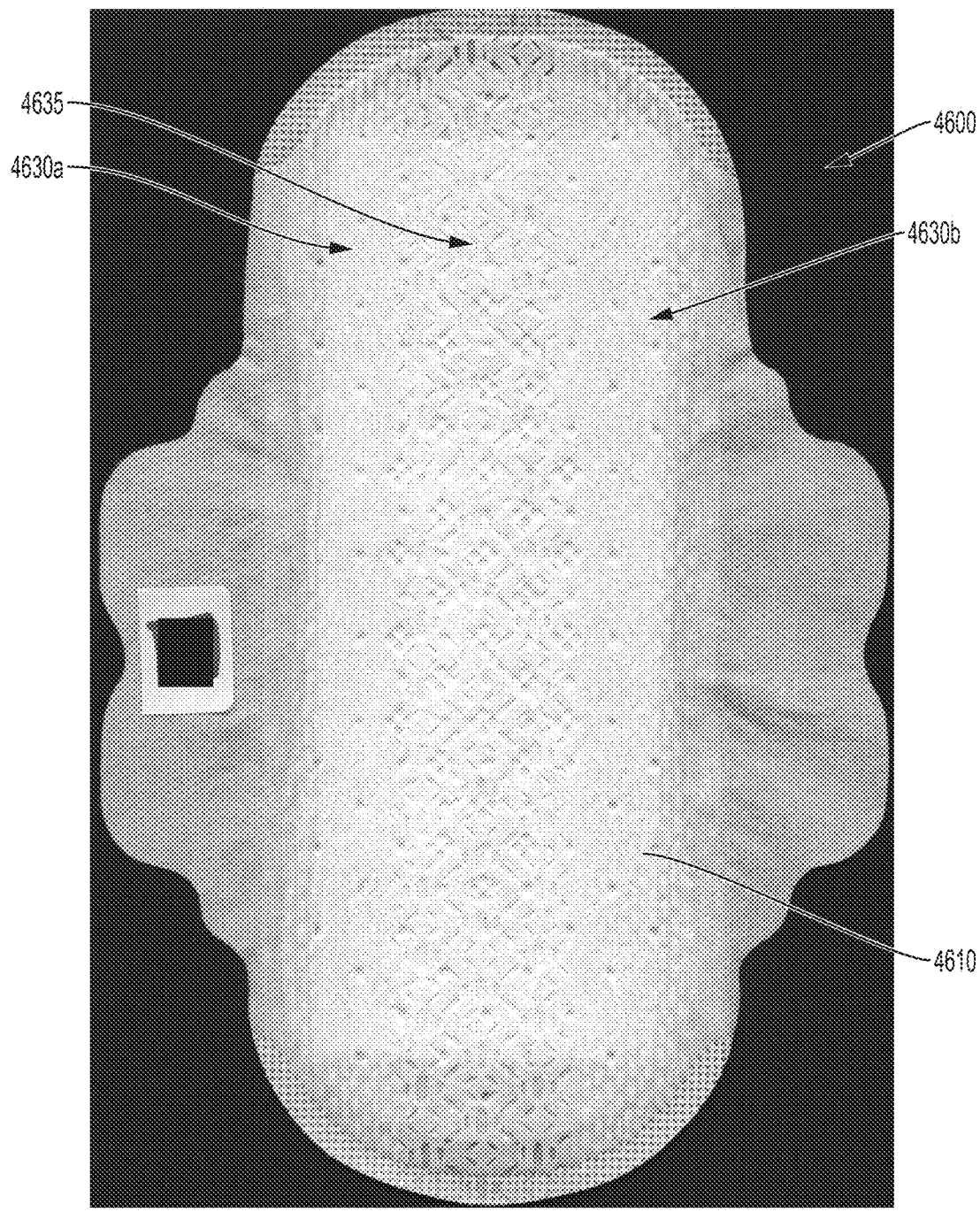
FIG. 37 is a photograph of an exemplary sanitary pad constructed in accordance with the present invention.

Referring to FIG. 37, a sanitary pad 4600 was created utilizing a white nonwoven layer as an upper layer and a peach colored layer (25 gsm) as a lower layer of a laminate. The laminate was utilized as a topsheet 4610 of the sanitary pad 4600. Averages of the measured L*, a*, b* values for the sanitary pad 4600 are provided below in Table 4A. Each of the L*, a*, b* values measured on the sanitary pad 4600 were taken at locations similar to those described in FIGS. 35B-35H.

TABLE 4A

| Location | L* | a* | b* |
|---|---|---|---|
| Land | 98 | 4 | 3 |
| Aperture | 98 | 1 | 0 |
| Melt Lip | 94 | 5 | 6 |
| Fusion bond site | 99 | 2 | 2 |

TABLE 4A-continued

| Location | L* | a* | b* |
|---|---|---|---|
| Tuft inboard of absorbent core | 97 | 7 | 6 |
| Tuft outboard of absorbent core | 94 | 3 | 0 |
| Wings | 81 | −3 | −7 |

Similar to the lightening effect discussed with regard to FIG. 35A, a similar lightening effect in a first zone 4635 may occur with respect to a second zone 4630a and a third zone 4630b. Table 4B shows the average L*, a*, b* values measured for the first zone 4635 and second and third zones 4630a and 4630b, respectively with a 101×101 pixels averaged per measurement.

TABLE 4B

| Location | L* | a* | b* |
|---|---|---|---|
| First Zone | 92 | 2 | 3 |
| Second and Third Zones | 89 | 3 | 4 |

Example 4

Figure 38A:
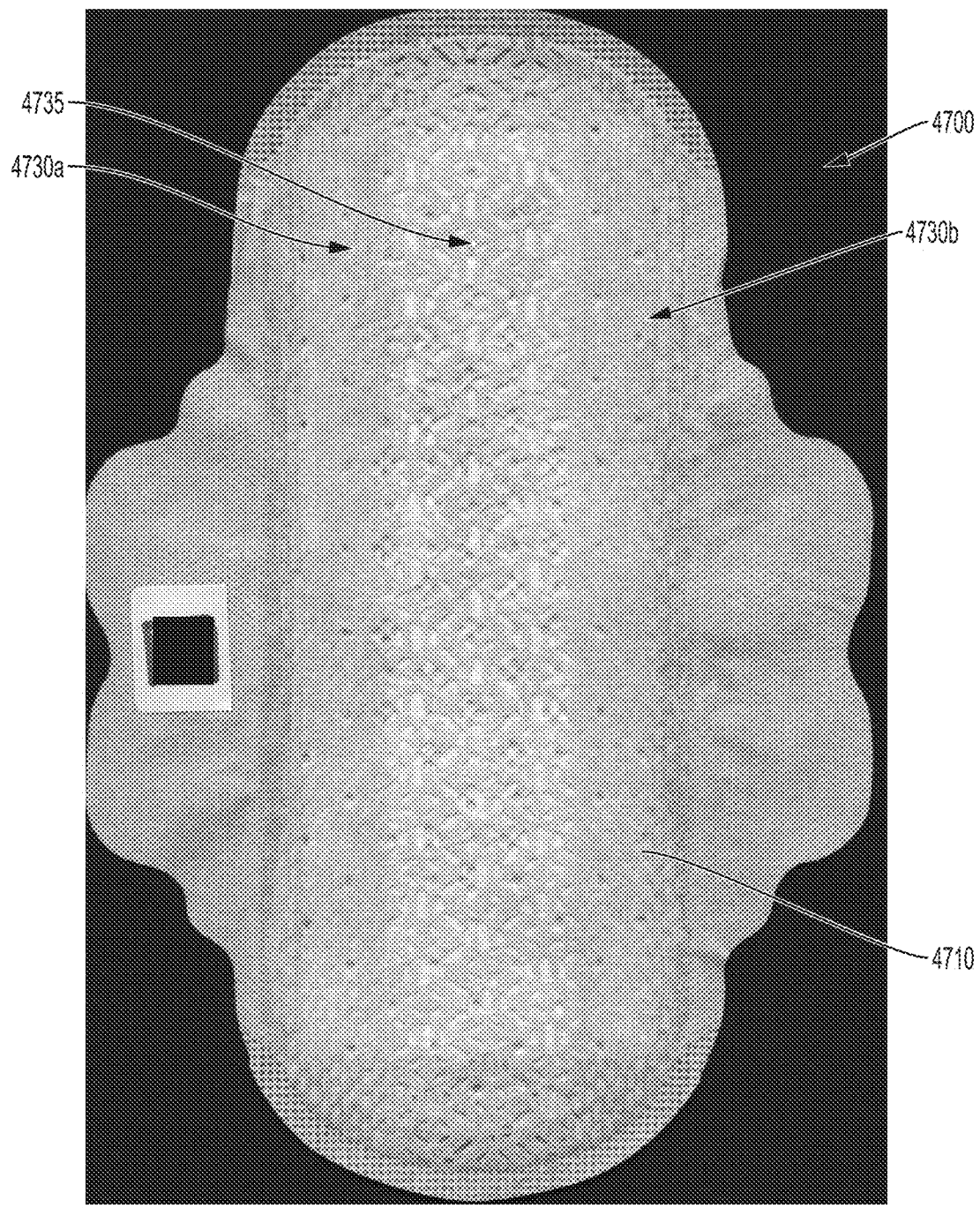
FIG. 38 is a photograph of an exemplary sanitary pad constructed in accordance with the present invention.
Figure 38B:
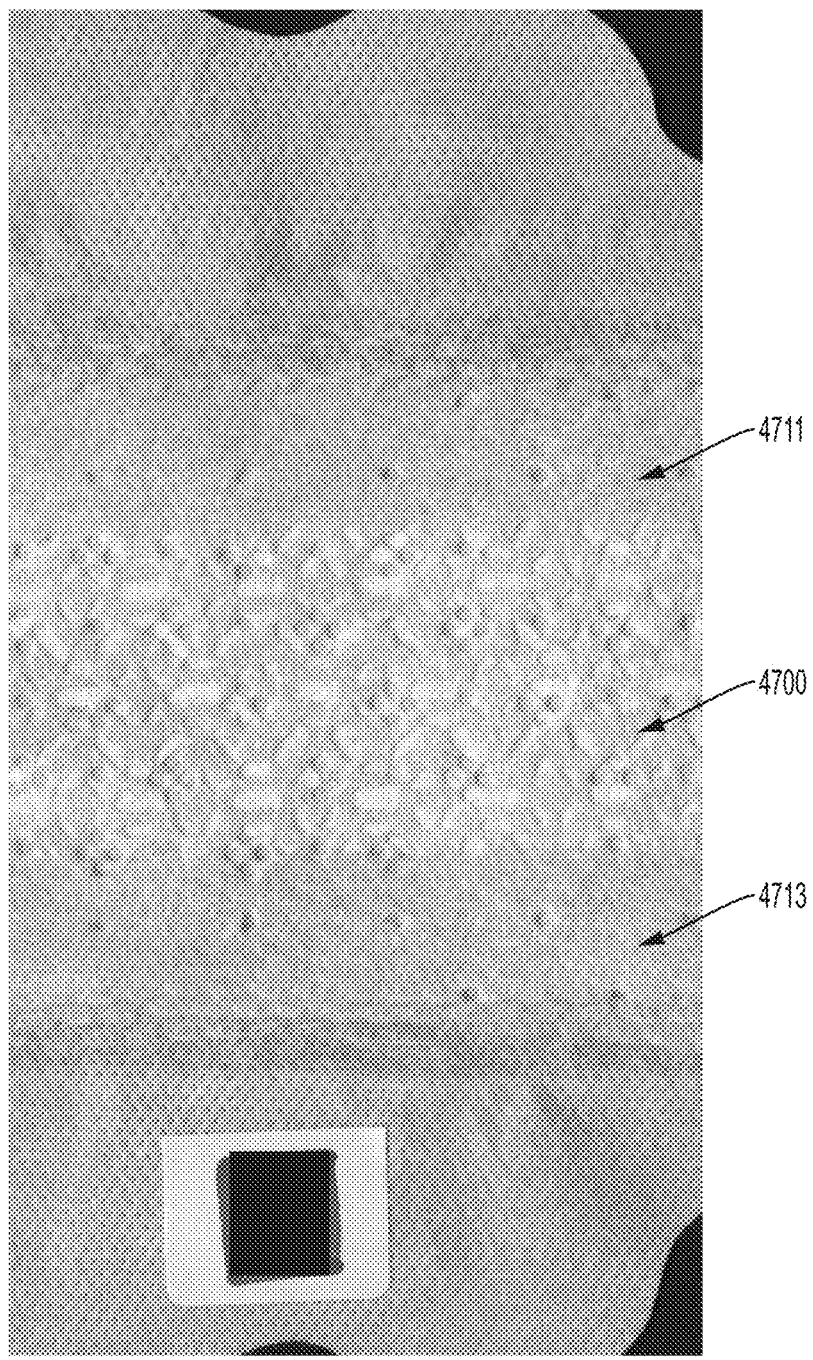

Referring to FIGS. 38A and 38B, a sanitary pad 4700 was created utilizing a white nonwoven layer as an upper layer and a blue colored layer (25 gsm) as a lower layer of a laminate. The laminate was utilized as a topsheet 4710 of the sanitary pad 4700. Averages of the measured L*, a*, b* values for the sanitary pad 4700 are provided below in Table 5A. Each of the L*, a*, b* values measured on the sanitary pad 4700 were taken at locations similar to those described in FIGS. 35B-35H.

TABLE 5A

| Location | L* | a* | b* |
|---|---|---|---|
| Land | 87 | −7 | −25 |
| Aperture | 95 | −2 | −9 |
| Melt Lip | 80 | −11 | −34 |
| Fusion bond site | 85 | −8 | −22 |
| Tuft inboard of absorbent core | 83 | −7 | −25 |
| Tuft outboard of absorbent core | 80 | −6 | −19 |
| Wings | 81 | −3 | −7 |

Similar to the lightening effect discussed with regard to FIG. 35A, a similar lightening effect in a first zone 4735 may occur with respect to a second zone 4730a and a third zone 4730b. Table 5B shows the average L*, a*, b* values measured for the first zone 4735 and second and third zones 4730a and 4730b, respectively with a 101×101 pixels averaged per measurement.

TABLE 5B

| Location | L* | a* | b* |
|---|---|---|---|
| First Zone | 81 | −5 | −18 |
| Second and Third Zones | 76 | −5 | −20 |

Example 5

Figure 39:
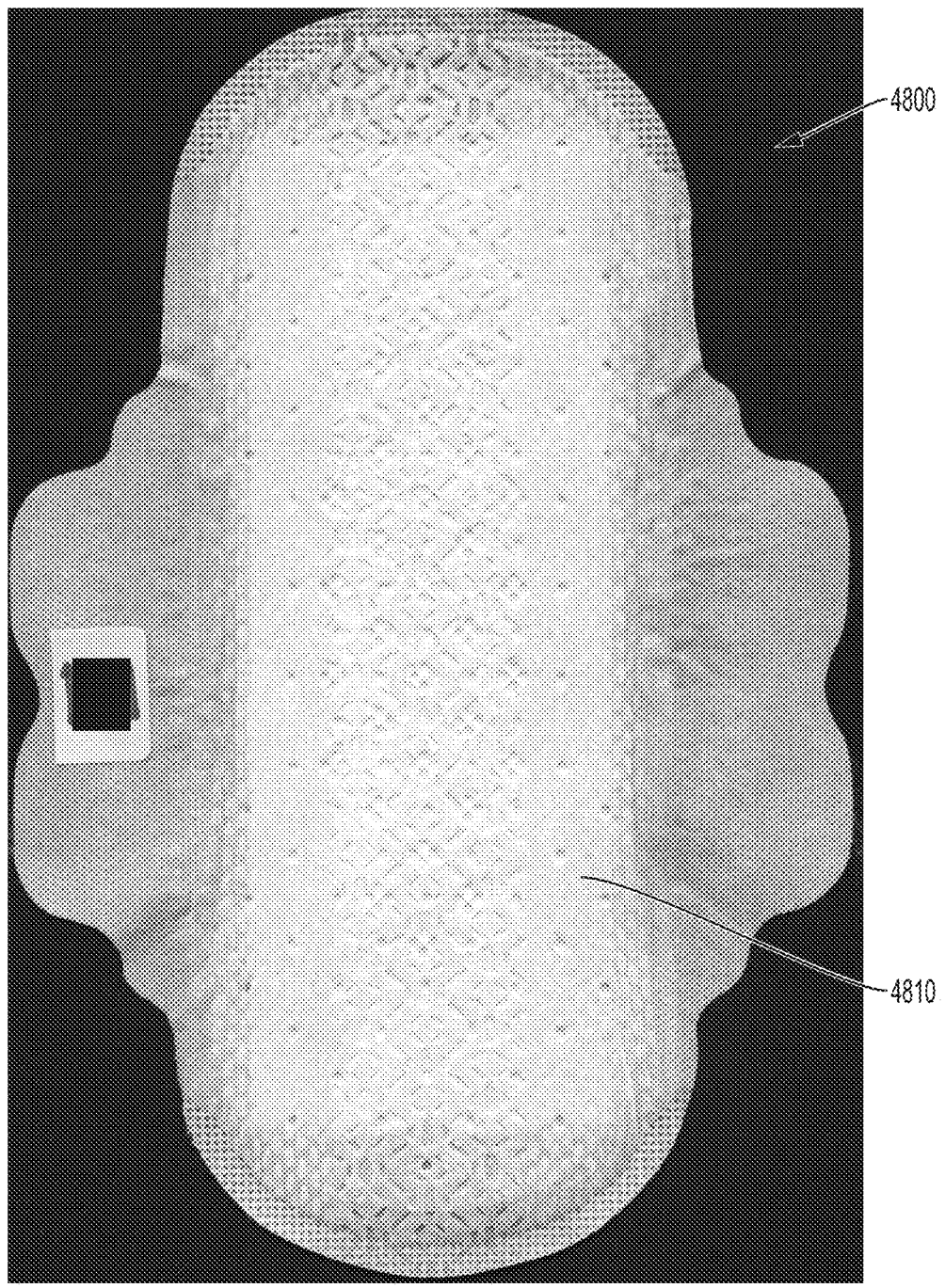
FIG. 39 is a photograph of an exemplary sanitary pad constructed in accordance with the present invention.

Referring to FIG. 39, a sanitary pad 4800 was created utilizing a white nonwoven layer as an upper layer and a mint green colored layer (22 gsm) as a lower layer of a laminate. The laminate was utilized as a topsheet 4810 of the sanitary pad 4800. Averages of the measured L*, a*, b* values for the sanitary pad 4800 are provided below in Table 6. Each of the L*, a*, b* values measured on the sanitary pad 4800 were taken at locations similar to those described in FIGS. 35B-35H.

TABLE 6

| Location | L* | a* | b* |
|---|---|---|---|
| Land | 99 | −9 | 2 |
| Aperture | 99 | −3 | 0 |
| Melt Lip | 97 | −12 | 5 |
| Fusion bond site | 98 | −7 | 2 |
| Tuft inboard of absorbent core | 97 | −15 | 5 |
| Tuft outboard of absorbent core | 94 | −11 | 0 |
| Wings | 80 | −3 | −7 |

Example 6

Figure 40:
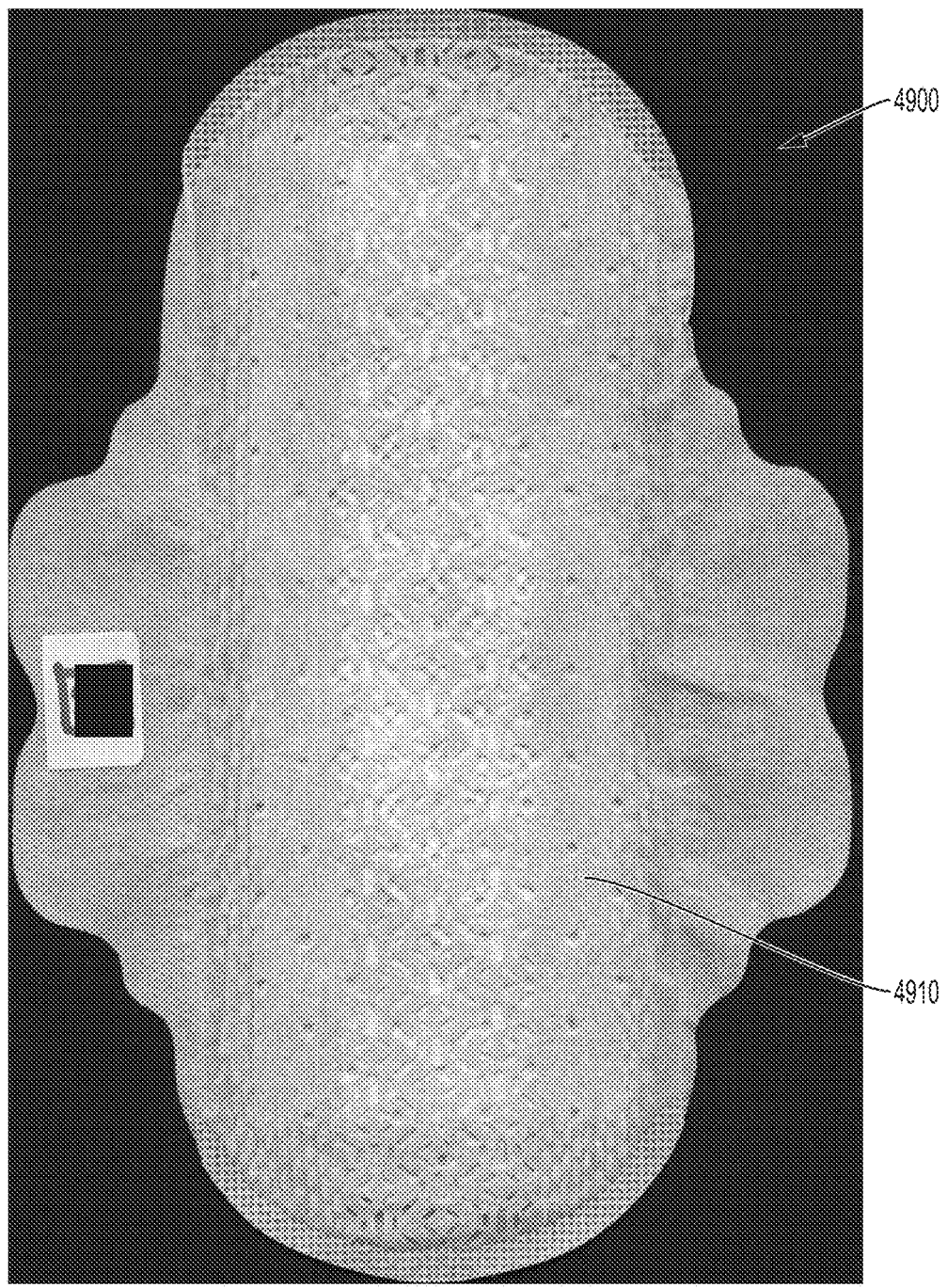
FIG. 40 is a photograph of an exemplary sanitary pad constructed in accordance with the present invention.

Referring to FIG. 40, a sanitary pad 4900 was created utilizing a white nonwoven layer as an upper layer and an orchid colored layer (25 gsm) as a lower layer of a laminate. The laminate was utilized as a topsheet 4910 of the sanitary pad 4900. Averages of the measured L*, a*, b* values for the sanitary pad 4900 are provided below in Table 7. Each of the L*, a*, b* values measured on the sanitary pad 4900 were taken at locations similar to those described in FIGS. 35B-35H.

TABLE 7

| Location | L* | a* | b* |
|---|---|---|---|
| Land | 87 | 20 | −14 |
| Aperture | 95 | 6 | −6 |
| Melt Lip | 83 | 30 | −20 |
| Fusion bond site | 85 | 24 | −16 |
| Tuft inboard of absorbent core | 83 | 25 | −16 |
| Tuft outboard of absorbent core | 83 | 20 | −17 |
| Wings | 79 | −3 | −7 |

Some additional sample laminates were created and measured for L*, a*, b* without incorporation into a disposable absorbent article. L*, a*, b* values were measured for each of the laminates against a white background. Details are provided below.

Example 7

Figure 41:
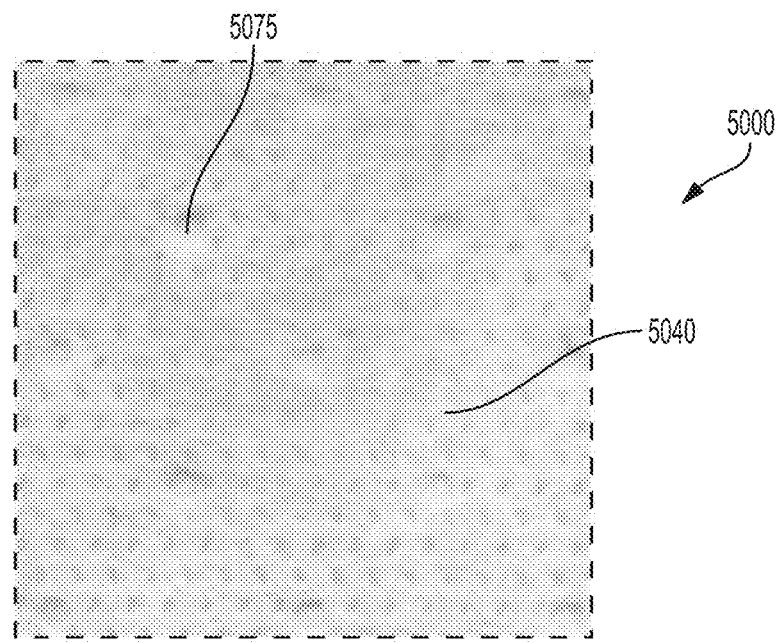
FIGS. 41-58 are photographs of portions of exemplary nonwoven laminates constructed in accordance with the present invention.

Referring to FIG. 41, a laminate 5000 was created utilizing a white nonwoven layer as an upper layer and a blue colored layer (25 gsm) as a lower layer of the laminate. Averages of the measured L*, a*, b* values for the laminate 5000 are provided below in Table 8. Bond sites 5075 and the land areas 5040 of the laminate 5000 were measured over a white background.

TABLE 8

| Location | L* | a* | b* |
| --- | --- | --- | --- |
| Fusion bond site | 89 | −8 | −17 |
| Land Area | 90 | −7 | −20 |

The ΔE* between the bond site and the land area was 2.94.

Example 8

Figure 42:
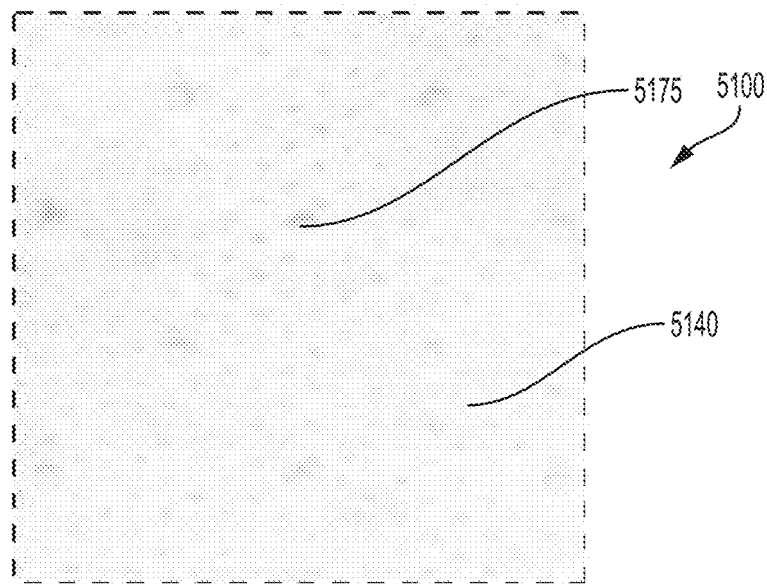

Referring to FIG. 42, a laminate 5100 was created utilizing a white nonwoven layer as an upper layer and a light blue colored layer (25 gsm) as a lower layer of the laminate. Averages of the measured L*, a*, b* values for the laminate 5100 are provided below in Table 9. The bond sites 5175 and the land areas 5140 of the laminate 5100 were measured over a white background.

TABLE 9

| Location | L* | a* | b* |
| --- | --- | --- | --- |
| Fusion bond site | 96 | −5 | −8 |
| Land Area | 98 | −4 | −7 |

The ΔE* between the bond site and the land area was 2.06.

Example 9

Figure 43:
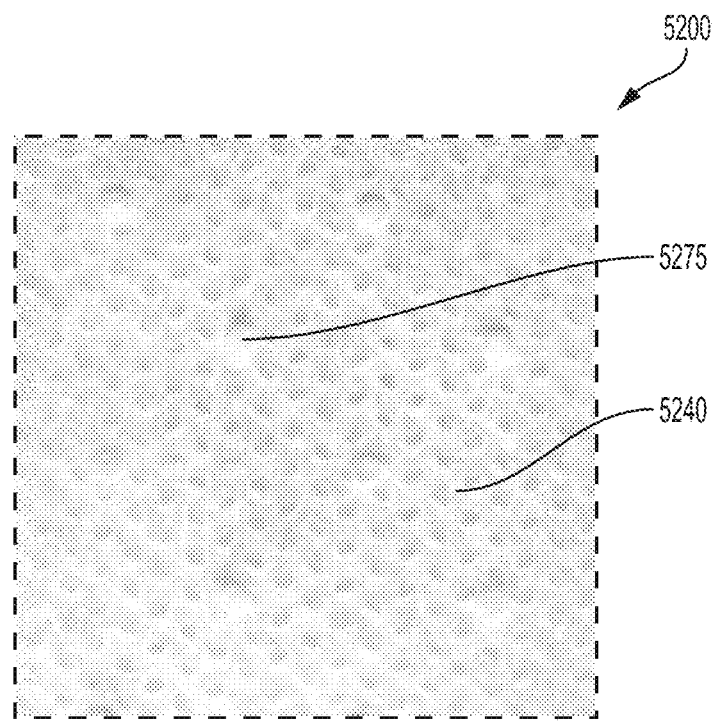

Referring to FIG. 43, a laminate 5200 was created utilizing a white nonwoven layer as an upper layer and a light purple colored layer (20 gsm) as a lower layer of the laminate. Averages of the measured L*, a*, b* values for the laminate 5200 are provided below in Table 10. Bond sites 5275 and the land areas 5240 of the laminate 5200 were measured over a white background.

TABLE 10

| Location | L* | a* | b* |
| --- | --- | --- | --- |
| Fusion bond site | 89 | 2 | −8 |
| Land Area | 90 | 2 | −9 |

The ΔE* between the bond site and the land area was 1.18.

Example 10

Figure 44:
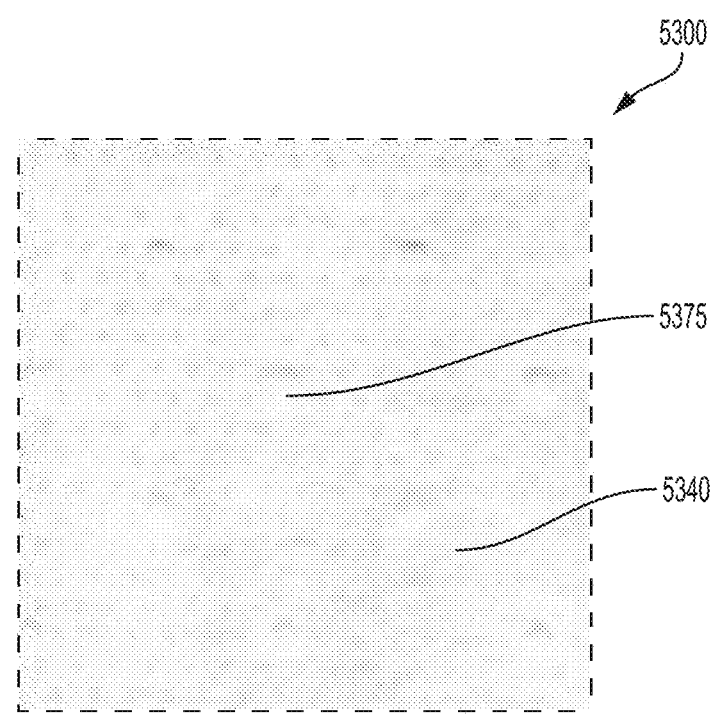

Referring to FIG. 44, a laminate 5300 was created utilizing a white nonwoven layer as an upper layer and a mint green colored layer (22 gsm) as a lower layer of the laminate. Averages of the measured L*, a*, b* values for the laminate 5300 are provided below in Table 11. Bond sites 5375 and the land areas 5340 of the laminate 5300 were measured over a white background.

TABLE 11

| Location | L* | a* | b* |
| --- | --- | --- | --- |
| Fusion bond site | 97 | −11 | 3 |
| Land Area | 98 | −12 | 3 |

The ΔE* between the bond site and the land area was 0.85.

Example 11

Figure 45:
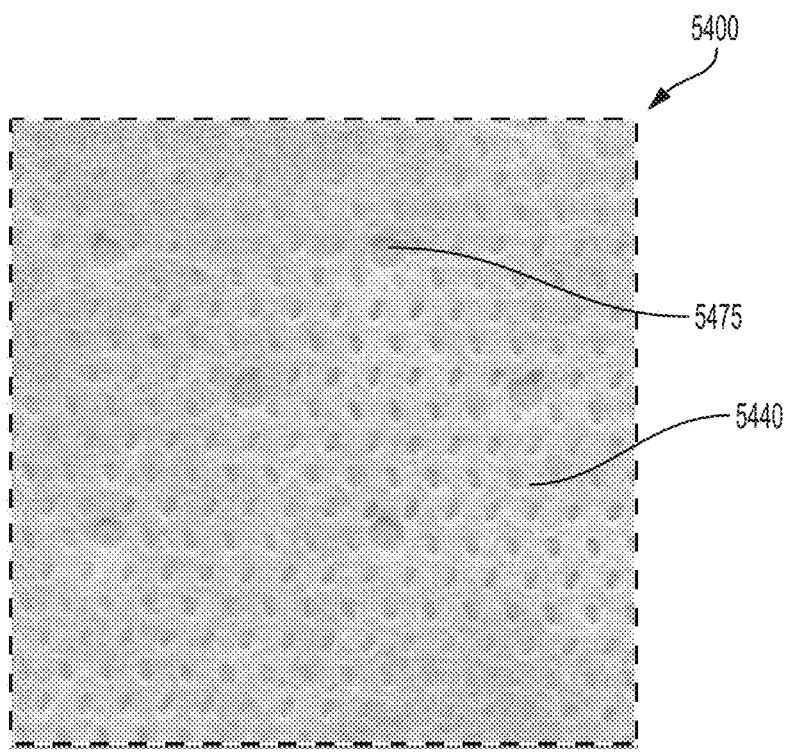

Referring to FIG. 45, a laminate 5400 was created utilizing a white nonwoven layer as an upper layer and an orchid colored layer (25 gsm) as a lower layer of the laminate. Averages of the measured L*, a*, b* values for the laminate 5400 are provided below in Table 12. Bond sites 5475 and the land areas 5440 of the laminate 5400 were measured over a white background.

TABLE 12

| Location | L* | a* | b* |
| --- | --- | --- | --- |
| Fusion bond site | 77 | 30 | −20 |
| Land Area | 80 | 24 | −16 |

The ΔE* between the bond site and the land area was 8.52.

Example 12

Figure 46:
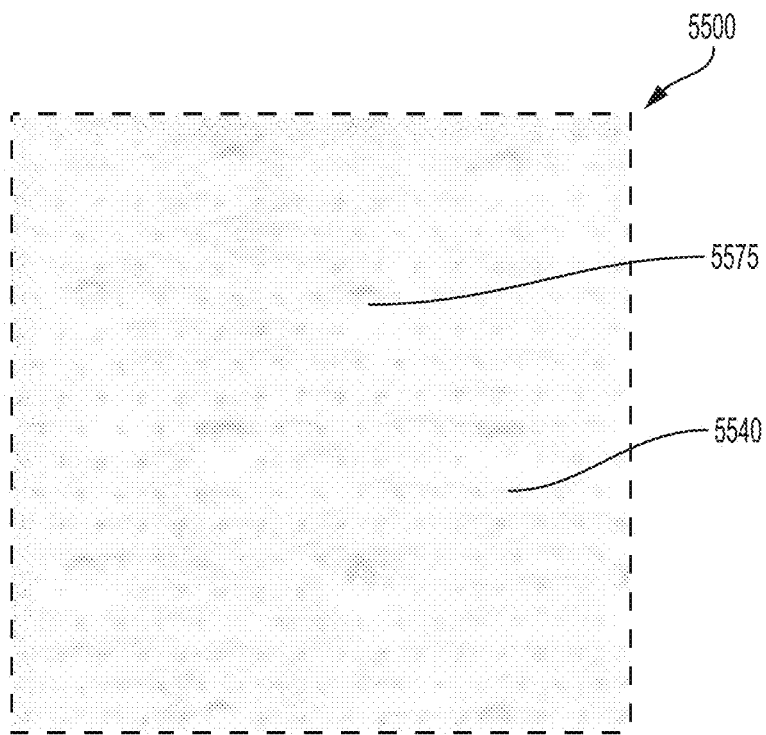

Referring to FIG. 46, a laminate 5500 was created utilizing a white nonwoven layer as an upper layer and a peach colored layer (25 gsm) as a lower layer of the laminate. Averages of the measured L*, a*, b* values for the laminate 5500 are provided below in Table 13. Bond sites 5575 and the land areas 5540 of the laminate 5500 were measured over a white background.

TABLE 13

| Location | L* | a* | b* |
| --- | --- | --- | --- |
| Fusion bond site | 96 | 4 | 4 |
| Land Area | 97 | 4 | 4 |

The ΔE* between the bond site and the land area was 1.13.

Example 13

Figure 47:
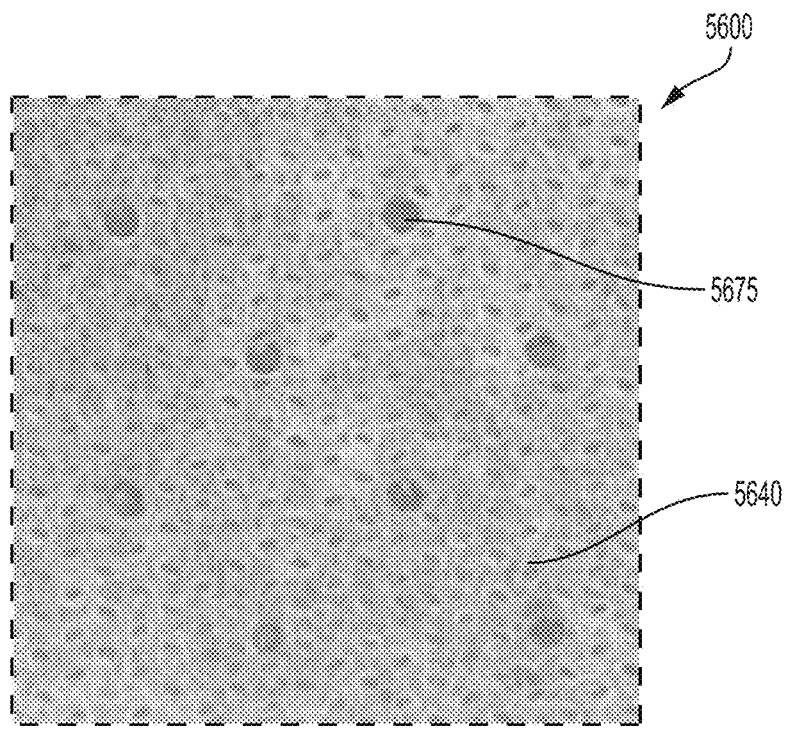

Referring to FIG. 47, a laminate 5600 was created utilizing a white nonwoven layer as an upper layer and a purple colored layer as a lower layer of the laminate. Averages of the measured L*, a*, b* values for the laminate 5600 are provided below in Table 14. Bond sites 5675 and the land areas 5640 of the laminate 5600 were measured over a white background.

TABLE 14

| Location | L* | a* | b* |
| --- | --- | --- | --- |
| Fusion bond site | 60 | 7 | −18 |
| Land Area | 75 | 1 | −10 |

The ΔE* between the bond site and the land area was 17.89.

Example 14

Figure 48:
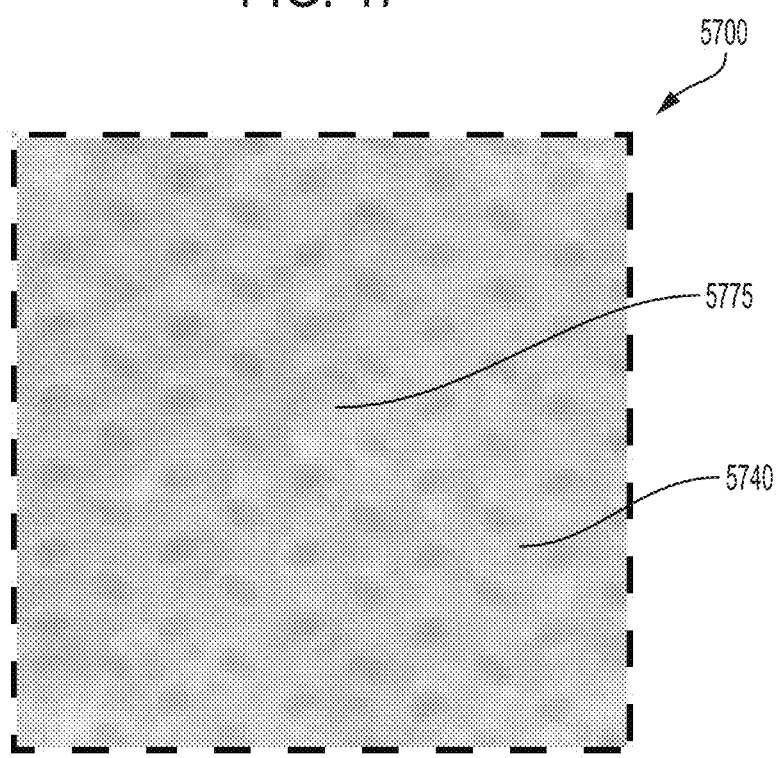

Referring to FIG. 48, a laminate 5700 was created utilizing a light blue nonwoven layer as an upper layer and a blue colored layer as a lower layer of the laminate. Averages of the measured L*, a*, b* values for the laminate 5700 are provided below in Table 15. Bond sites 5775 and the land areas 5740 of the laminate 5700 were measured over a white background.

TABLE 15

| Location | L* | a* | b* |
|---|---|---|---|
| Fusion bond site | 84 | −10 | −23 |
| Land Area | 83 | −10 | −26 |

The ΔE* between the bond site and the land area was 3.14.

Example 15

Figure 49:
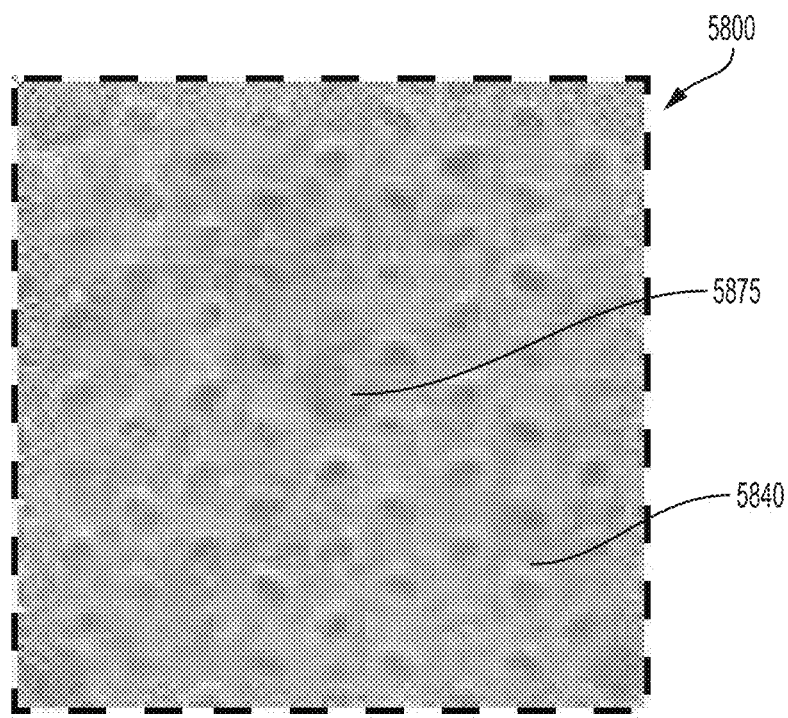

Referring to FIG. 49, a laminate 5800 was created utilizing a mint green nonwoven layer as an upper layer and an orchid colored layer as a lower layer of the laminate. Averages of the measured L*, a*, b* values for the laminate 5800 are provided below in Table 16. Bond sites 5875 and the land areas 5840 of the laminate 5800 were measured over a white background.

TABLE 16

| Location | L* | a* | b* |
|---|---|---|---|
| Fusion bond site | 66 | 41 | −25 |
| Land Area | 70 | 25 | −16 |

The ΔE* between the bond site and the land area was 19.29.

Example 16

Figure 50:
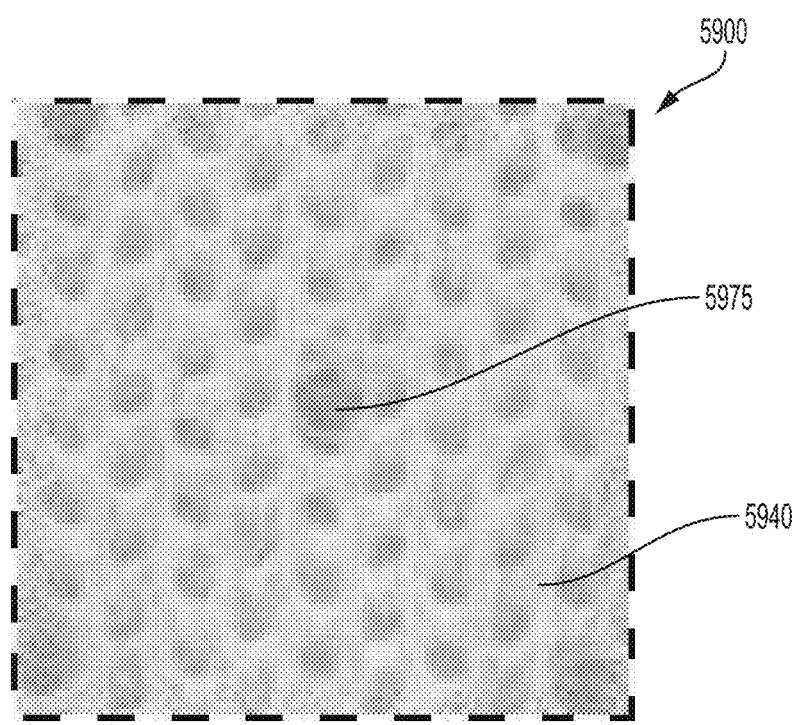

Referring to FIG. 50, a laminate 5900 was created utilizing a peach nonwoven layer as an upper layer and an orchid colored layer as a lower layer of the laminate. Averages of the measured L*, a*, b* values for the laminate 5900 are provided below in Table 17. Bond sites 5975 and the land areas 5940 of the laminate 5900 were measured over a white background.

TABLE 17

| Location | L* | a* | b* |
|---|---|---|---|
| Fusion bond site | 70 | 40 | −19 |
| Land Area | 80 | 21 | −5 |

The ΔE* between the bond site and the land area was 25.10.

Example 17

Figure 51:
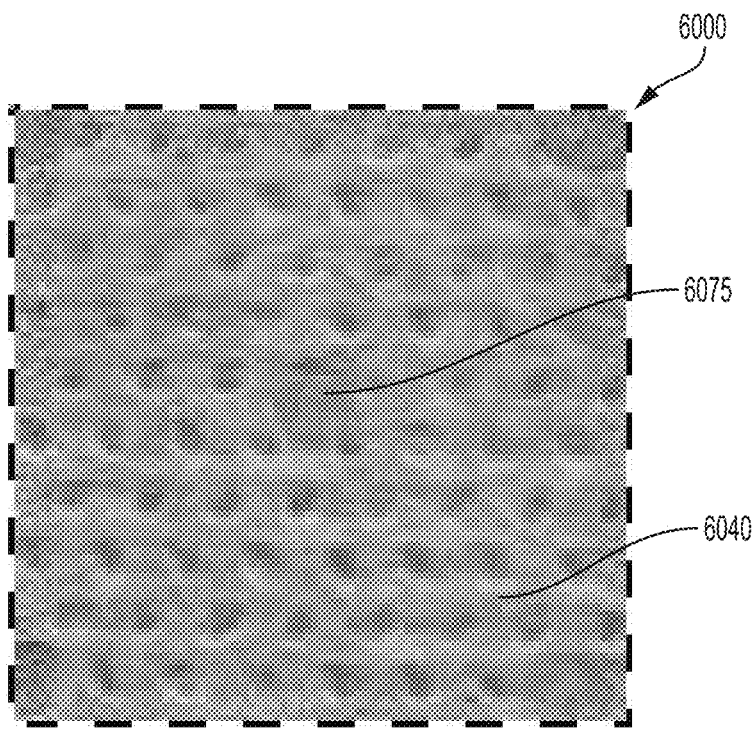

Referring to FIG. 51, a laminate 6000 was created utilizing a light purple nonwoven layer as an upper layer and a purple colored layer as a lower layer of the laminate. Averages of the measured L*, a*, b* values for the laminate 6000 are provided below in Table 18. Bond sites 6075 and the land areas 6040 of the laminate 6000 were measured over a white background.

TABLE 18

| Location | L* | a* | b* |
|---|---|---|---|
| Fusion bond site | 58 | 8 | −19 |
| Land Area | 63 | 5 | −15 |

The ΔE* between the bond site and the land area was 6.88.

Example 18

Figure 52:
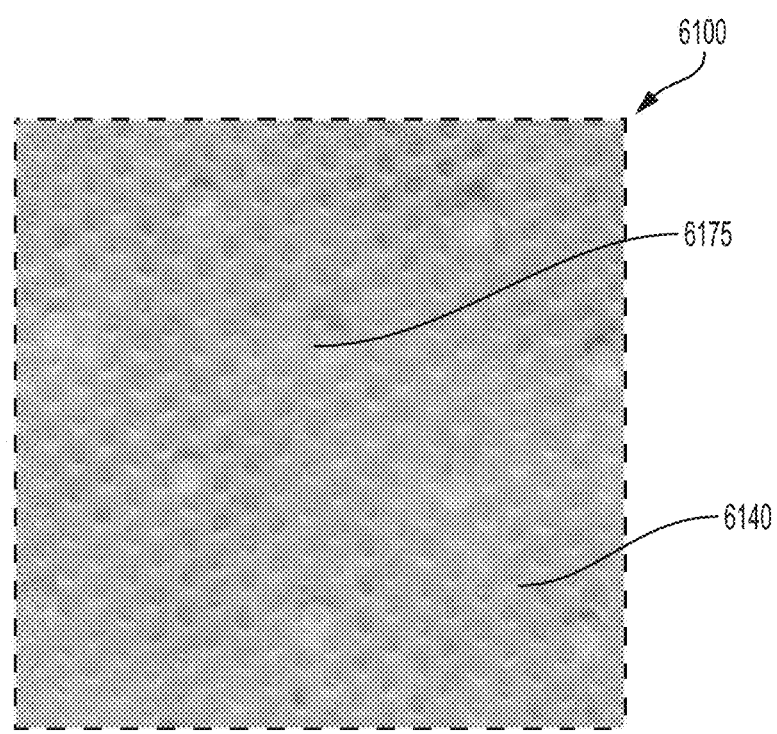

Referring to FIG. 52, a laminate 6100 was created utilizing a blue nonwoven layer as an upper layer and a blue colored layer as a lower layer of the laminate. Averages of the measured L*, a*, b* values for the laminate 6100 are provided below in Table 19. Bond sites 6175 and the land areas 6140 of the laminate 6100 were measured over a white background.

TABLE 19

| Location | L* | a* | b* |
|---|---|---|---|
| Fusion bond site | 79 | −11 | −31 |
| Land Area | 77 | −12 | −38 |

The ΔE* between the bond site and the land area was 6.86.

Example 19

Figure 53:
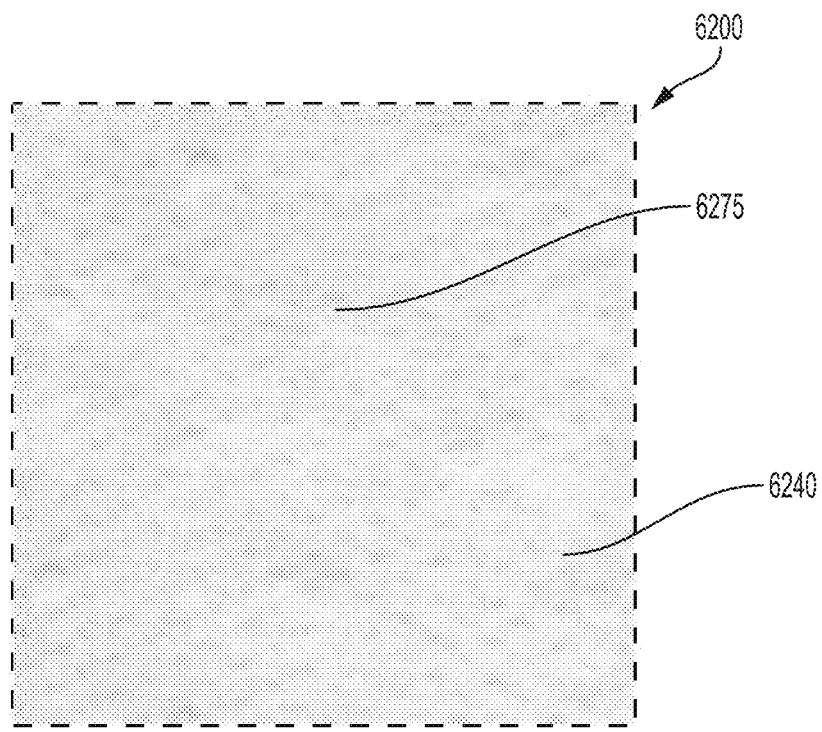

Referring to FIG. 53, a laminate 6200 was created utilizing a light blue nonwoven layer as an upper layer and a light blue colored layer as a lower layer of the laminate. Averages of the measured L*, a*, b* values for the laminate 6200 are provided below in Table 20. Bond sites 6275 and the land areas 6240 of the laminate 6200 were measured over a white background.

TABLE 20

| Location | L* | a* | b* |
|---|---|---|---|
| Fusion bond site | 92 | −7 | −10 |
| Land Area | 93 | −7 | −11 |

The ΔE* between the bond site and the land area was 0.47.

Example 20

Figure 54:
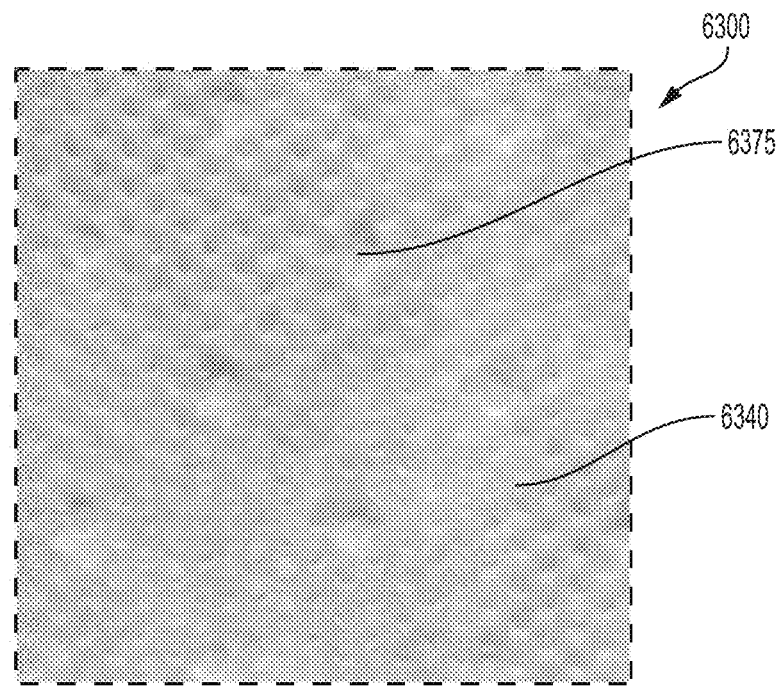

Referring to FIG. 54, a laminate 6300 was created utilizing a light purple nonwoven layer as an upper layer and a light purple colored layer as a lower layer of the laminate. Averages of the measured L*, a*, b* values for the laminate 6300 are provided below in Table 21. Bond sites 6375 and the land areas 6340 of the laminate 6300 were measured over a white background.

TABLE 21

| Location | L* | a* | b* |
|---|---|---|---|
| Fusion bond site | 80 | 4 | −13 |
| Land Area | 79 | 4 | −14 |

The ΔE* between the bond site and the land area was 1.88.

Example 21

Figure 55:
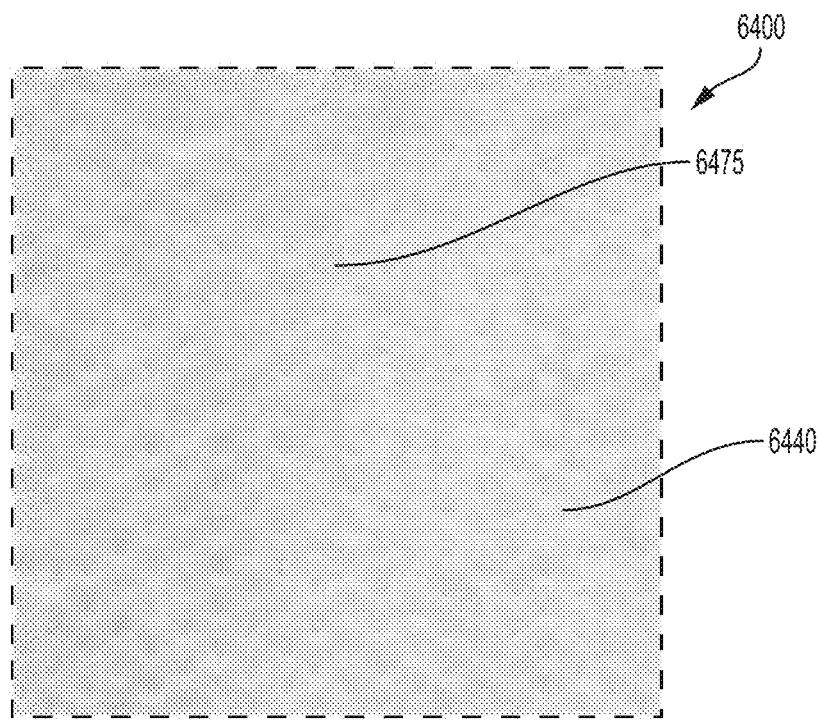

Referring to FIG. 55, a laminate 6400 was created utilizing a mint green nonwoven layer as an upper layer and a mint green colored layer as a lower layer of the laminate. Averages of the measured L*, a*, b* values for the laminate 6400 are provided below in Table 22. Bond sites 6475 and the land areas 6440 of the laminate 6400 were measured over a white background.

TABLE 22

| Location | L* | a* | b* |
| --- | --- | --- | --- |
| Fusion bond site | 94 | −21 | 9 |
| Land Area | 93 | −23 | 10 |

The ΔE* between the bond site and the land area was 2.82.

Example 22

Figure 56:
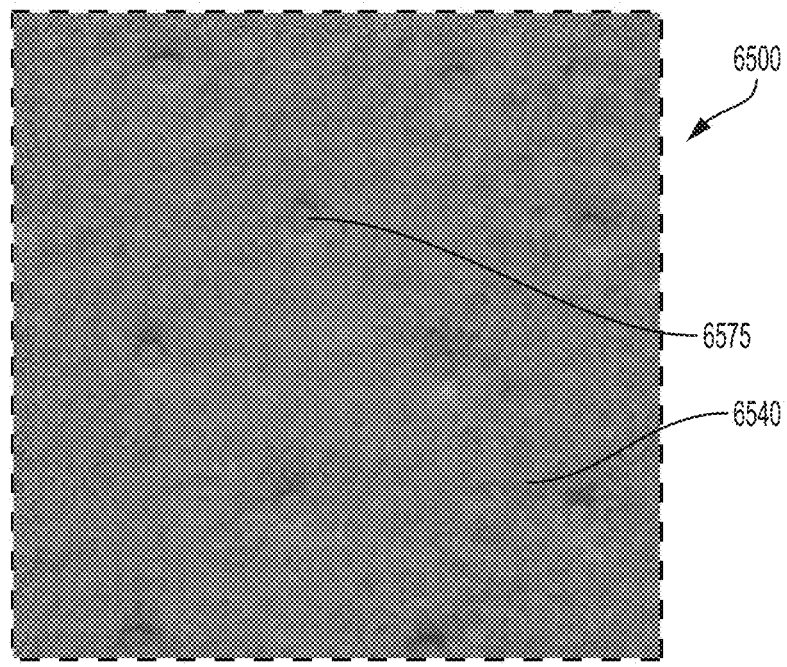

Referring to FIG. 56, a laminate 6500 was created utilizing an orchid nonwoven layer as an upper layer and an orchid colored layer as a lower layer of the laminate. Averages of the measured L*, a*, b* values for the laminate 6500 are provided below in Table 23. Bond sites 6575 and the land areas 6540 of the laminate 6500 were measured over a white background.

TABLE 23

| Location | L* | a* | b* |
| --- | --- | --- | --- |
| Fusion bond site | 60 | 53 | −29 |
| Land Area | 61 | 53 | −30 |

The ΔE* between the bond site and the land area was 0.67.

Example 23

Figure 57:
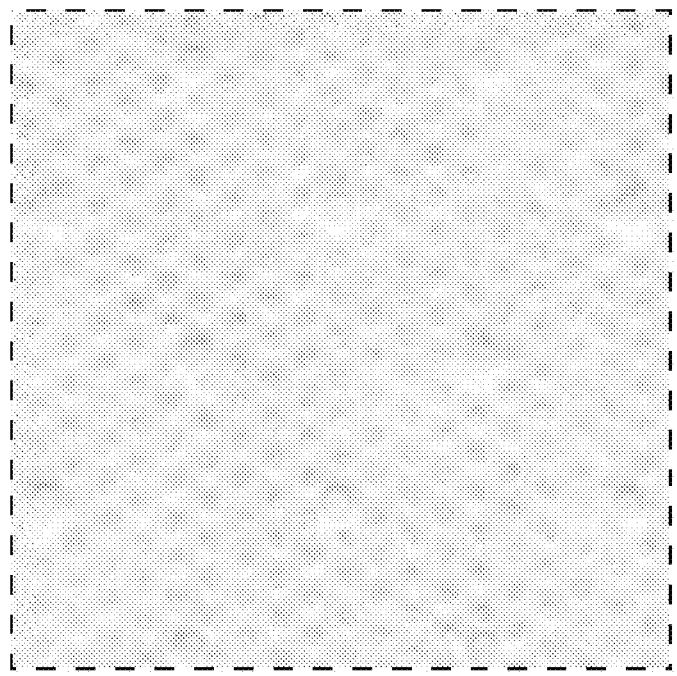

Referring to FIG. 57, a laminate 6600 was created utilizing peach colored nonwoven layer as an upper layer and a peach colored layer as a lower layer of the laminate. Averages of the measured L*, a*, b* values for the laminate 6600 are provided below in Table 24. Bond sites 6675 and the land areas 6640 of the laminate 6600 were measured over a white background.

TABLE 24

| Location | L* | a* | b* |
| --- | --- | --- | --- |
| Fusion bond site | 92 | 9 | 10 |
| Land Area | 93 | 9 | 10 |

The ΔE* between the bond site and the land area was 1.37.

Example 24

Figure 58:
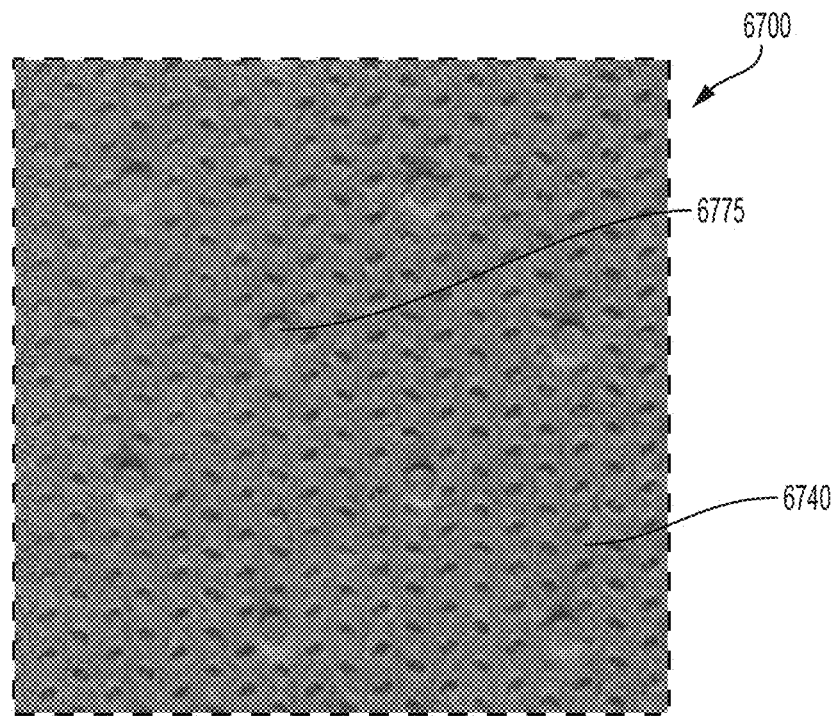

Referring to FIG. 58, a laminate 6700 was created utilizing purple colored nonwoven layer as an upper layer and a purple colored layer as a lower layer of the laminate. Averages of the measured L*, a*, b* values for the laminate 6700 are provided below in Table 25. Bond sites 6775 and the land areas 6740 of the laminate 6700 were measured over a white background.

TABLE 25

| Location | L* | a* | b* |
| --- | --- | --- | --- |
| Fusion bond site | 50 | 7 | −17 |
| Land Area | 49 | 8 | −17 |

The ΔE* between the bond site and the land area was 1.76.

Example 25

Figure 89:
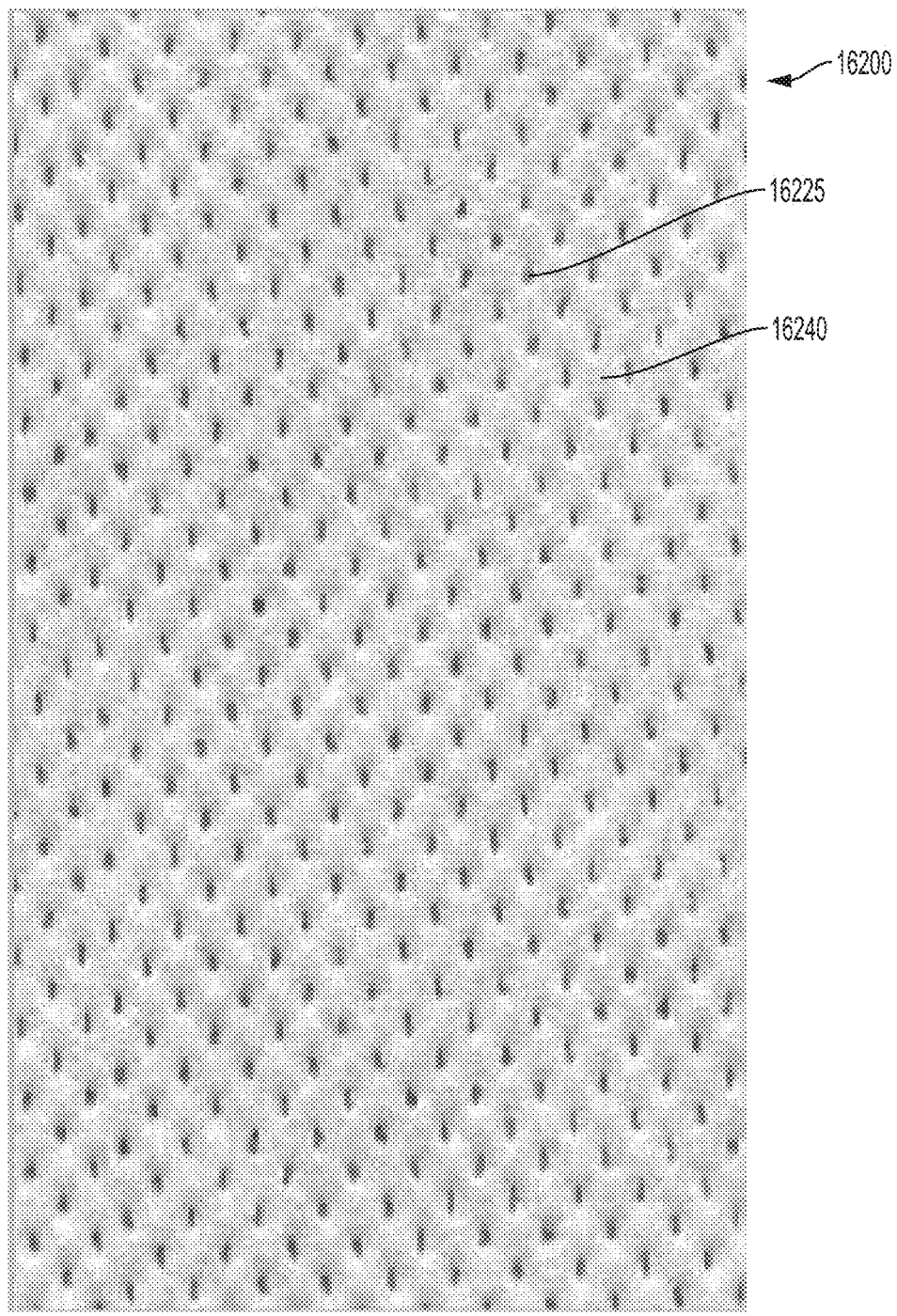
FIGS. 89 and 90 are photographs showing portions of exemplary nonwoven laminates constructed in accordance with the present invention.
Figure 90:
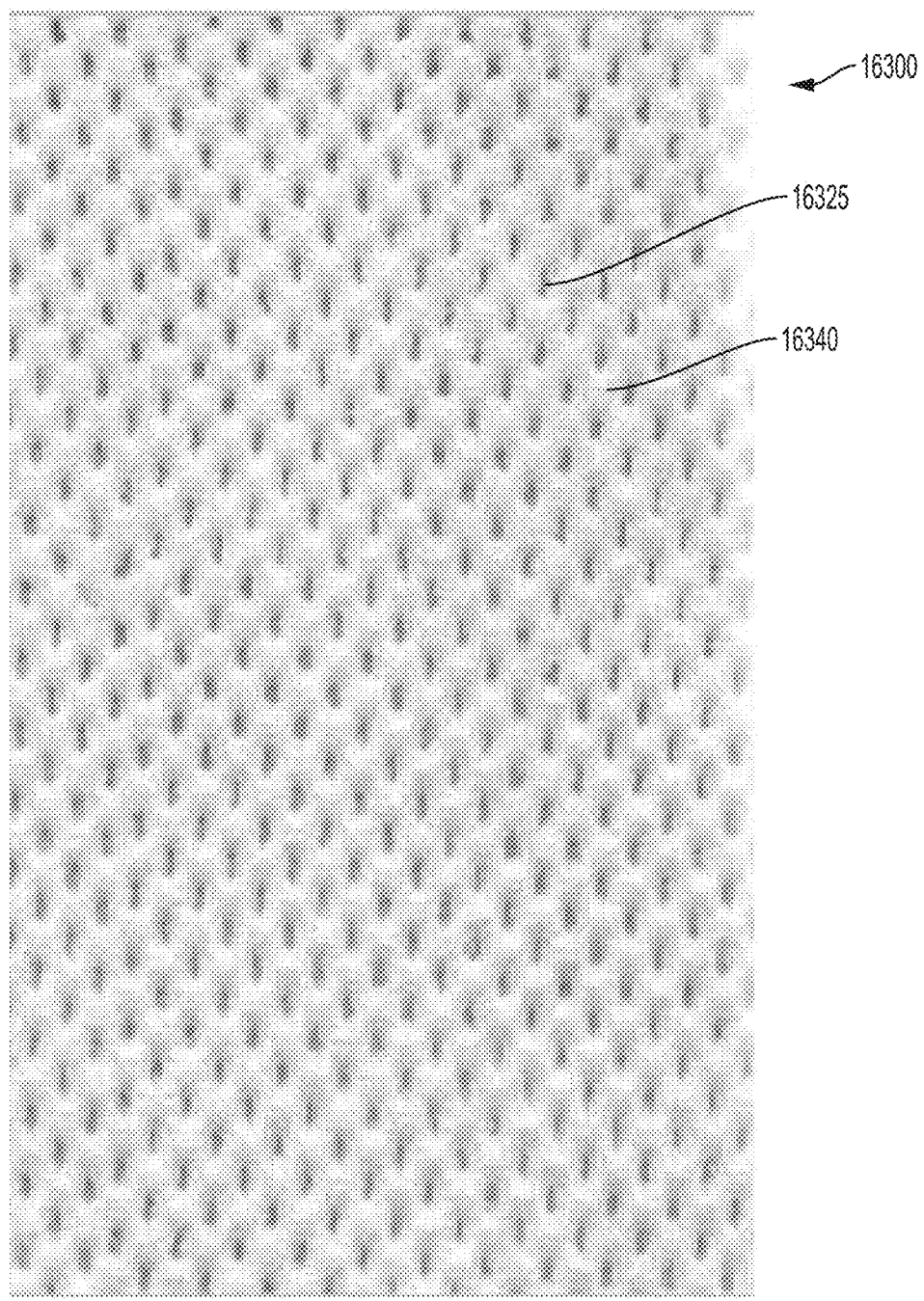

Referring to FIGS. 89 and 90, laminates 16200 and 16300 are shown, respectively. Each of the laminates comprised an upper layer nonwoven which was a 28 gsm bi-component comprising 3 gsm fine fiber. Additionally, the same nonwoven lower layer was used—see Table 1 (Orchid color). For the laminate 16200, the upper layer comprised a plurality of apertures 16225 creating an open area of about 9.7%. Note the second layer was not apertured. The laminate 16300 comprised a plurality of apertures 16325 in the upper layer and no apertures in the second layer. The open area of the upper layer was about 20.5%.

As shown, despite the same materials for the laminates 16200 and 16300 being used, differing colors in the respective land areas 16240 and 16340 are present as well as differing colors viewable through the apertures 16325 and 16225. The measured ΔE* between land area colors was about 9.0, and the ΔE* between aperture colors was about 42.67.

Without wishing to be bound by theory, it is believed that for apertures having a length over 5 mm, the above color effect may be minimal. However, for those apertures having a length under 5 mm, a color effect may be produced. For example, with decreasing length, it is believed that ΔL* similarly may decrease.

Additional examples of sanitary pads are provided herein with regard to FIGS. 59-85. Each of the sanitary pads described herein may comprise arrays of fusion bonds, arrays of apertures, arrays of tufts/ridges, adhesive patterns, printing on layers showing on a wearer-facing surface, printing on layers showing on a garment-facing surface, or combinations thereof. The fusion bonds may be arranged to provide bond indicia. Similarly the apertures may be arranged to provide apertured indicia. And, the tufts/ridges may be arranged to provide structural indicia. As noted herein, the bond indicia, apertured indicia, structural indicia, and/or printing may be coordinated in any of the sanitary pads described herein. Additionally, the sanitary pads herein may comprise printed indicia which may also be coordinated with the bond indicia, apertured indicia, and/or structural indicia. The printed indicia may be provided on a wearer-facing surface of the sanitary pad and/or on the garment-facing surface of the sanitary pad.

Each of the sanitary pads of the present invention comprise a topsheet, a backsheet, and an absorbent core disposed between the topsheet and the backsheet. Additional materials and/or layers of material may be provided between the topsheet and the backsheet as described herein. The sanitary pads of the present invention may comprise zones as described herein.

Figure 59:
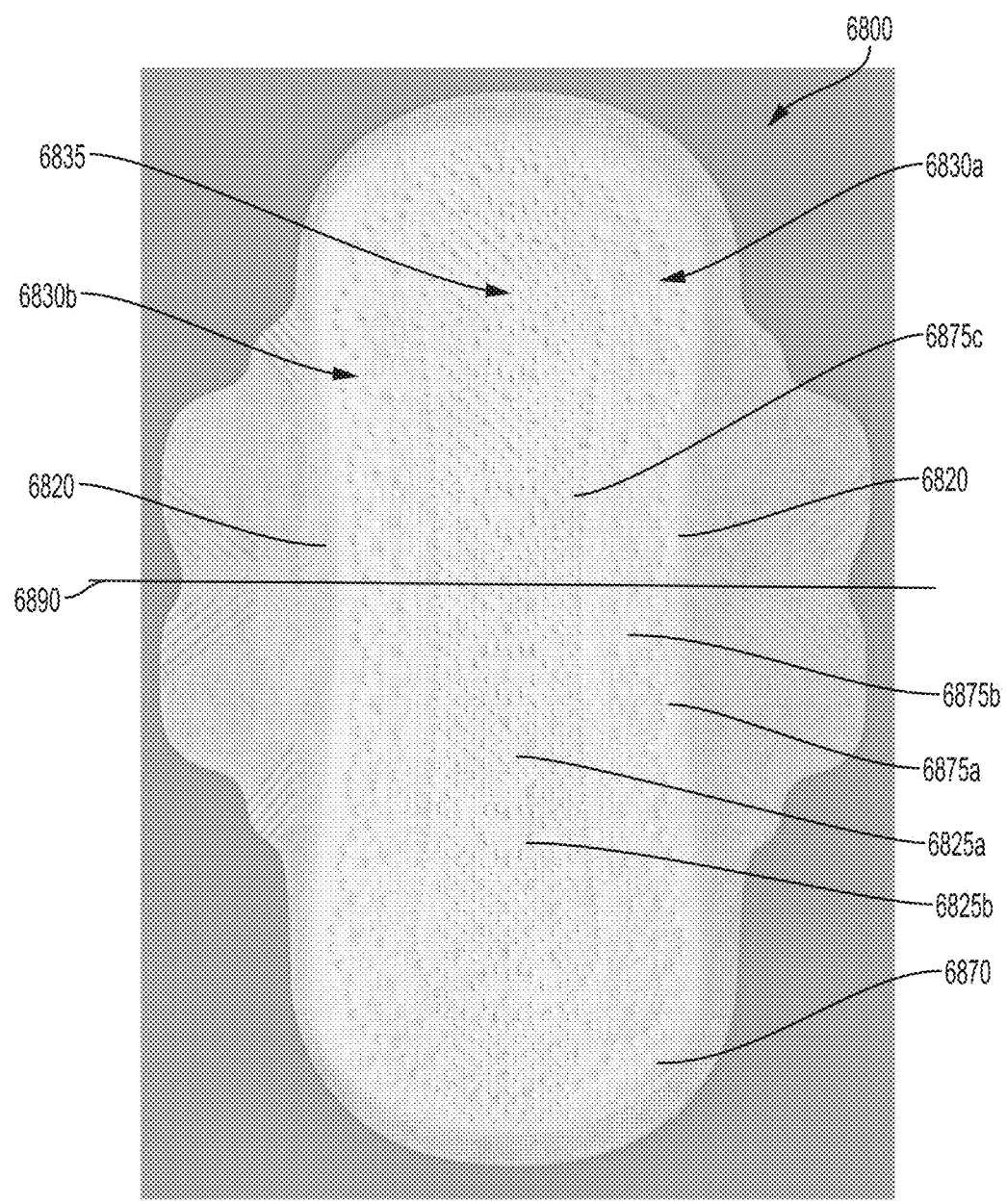
FIGS. 59-85 are schematic illustrations of sanitary napkins constructed in accordance with the present invention.

As shown in FIG. 59, a sanitary pad 6800 may comprise a plurality of apertures 6825a and 6825b and a plurality of tufts 6870. The sanitary pad 6800 may comprise a plurality of zones arranged in a generally longitudinal fashion. A first zone 6835 may be disposed between a second zone 6830a and a third zone 6830b. The plurality of apertures 6825a and 6825b may be predominantly disposed within the first zone 6835. Similarly, the plurality of tufts 6870 may predominantly be disposed in the second zone 6830a and the third zone 6830b.

The sanitary pad 6800 may further comprise a plurality of fusion bonds arranged as described with regard to FIG. 26. As shown, a first array of fusion bonds 6875a may be arranged in the form of a plurality of scallops. Such curvature of the fusion bond sites can mask straight edges of sanitary pad 6800 similar to the convex arcs discussed with regard to FIGS. 60 and 61. The scalloping of the fusion bonds 6875a can mask straight edges of the article and provide a perception of curvature and a more shape fitting pad. For example, where array of tufts 6870 are disposed in rectilinearly, the curvature of the scalloped fusion bond pattern can mask straight edges of the tuft 6870 array. Similarly, the scalloped fusion bond pattern can mask straight edges associated with the array of apertures 6825a and 6825b. Similarly, topsheets comprising a colored lower layer typically reveal the rectilinear nature of the colored lower layer. The scalloped fusion bond pattern 6875a can mask the straight edges of the colored lower layer as well.

Additionally, the scalloped arrangement of the fusion bonds 6875a can provide a perception of curvature to the tufts 6870 and/or arrays of apertures 6825a and 6825b. The first plurality of fusion bonds 6875a may be arranged in the form of scallops and extend the majority of the full length of the pad 6800.

A second array of fusion bonds 6875b can be disposed in between the first array 6875a and a third array 6875c of fusion bonds. The third array of fusion bonds 6875c can surround, at least in part, the arrays of apertures 6875a, 6875b. As shown, the second plurality of fusion bonds 6875b forms a boundary of sorts separating the intermediate zone 6835 from the outer zones 6830a and 6830b.

The scalloped edges can indicate softness to a user. And because the tufts are predominantly disposed within a region between the first array of fusion bonds 6875a and the third array of fusion bonds 6875c, the second zone 6830a and third zone 6830b may be softer than the first zone 6835. As such, the fusion bond pattern may help signal to the user of the sanitary pad 6800, the presence of softer lateral zones.

The arrays of apertures 6825a and 6825b can be generally disposed in the intermediate zone 6835. The first array of apertures 6825a may form a plurality of lines which are angled with respect to a lateral axis 6890 of the pad 6800. The first array of apertures 6825a collectively, generally form chevron shaped apertured indicia.

The second array of apertures 6825b may collectively form separate apertured indicia, e.g. a heart. As shown, the second array of apertures 6825b forms a repeating pattern of hearts. Any shape may be provided via the first and/or second arrays 6825a and 6825b of apertures and that shape may be repeated. Alternatively, additional arrays of apertures may be provided which produce apertured indicia which is different. For example, on a disposable absorbent article, a first array of apertures may provide apertured indicia in the shape of a heart. A second array of apertures may provide apertued indicia in the shape of a star. The first and second array of apertures may repeat in a pattern. Or, in some forms, a third array of apertures may provide apertured indicia in the shape of a flower. Additional arrays of apertures may be provided for additional depictions/apertured indicia.

Figure 60:
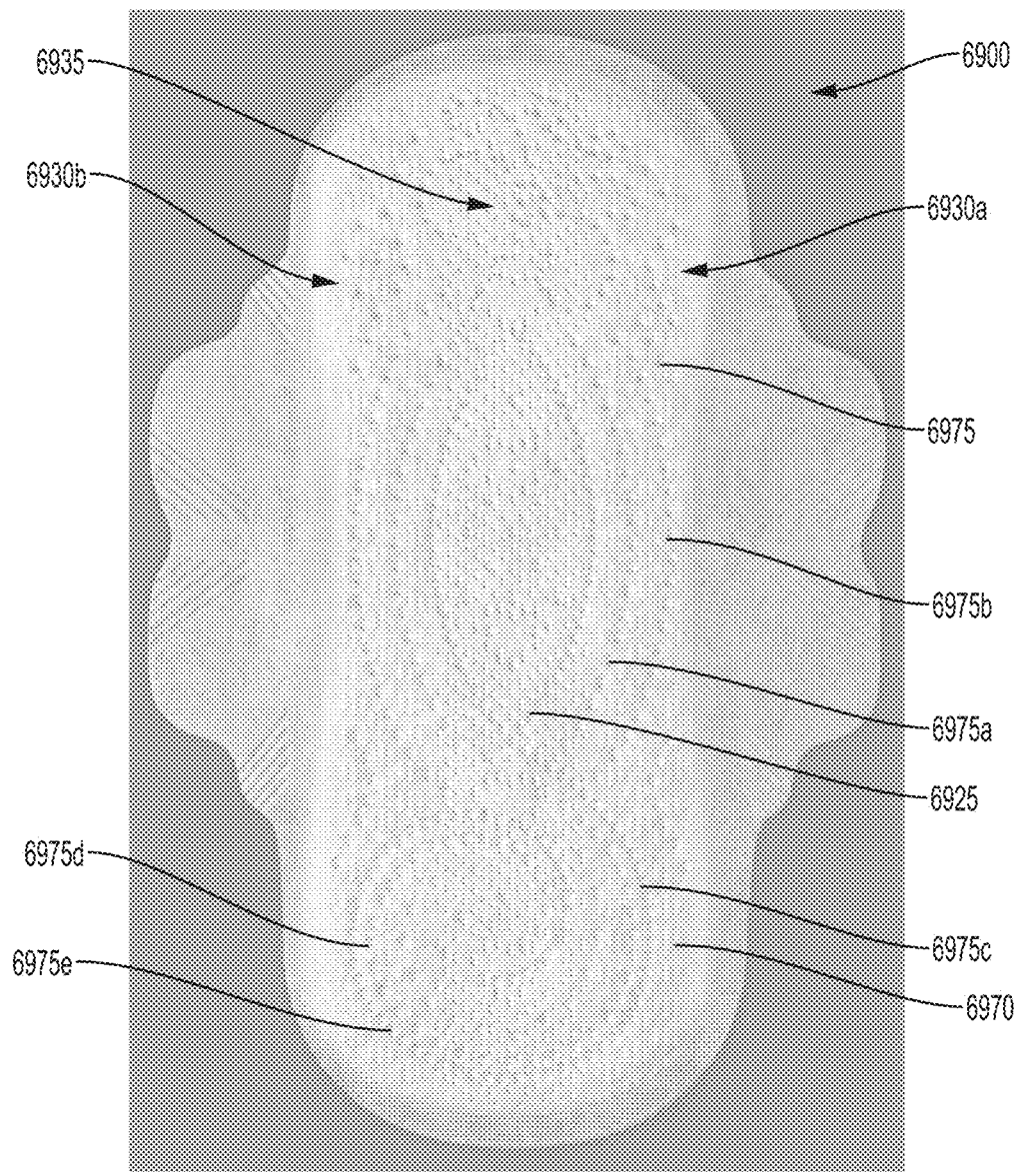
Figure 61:
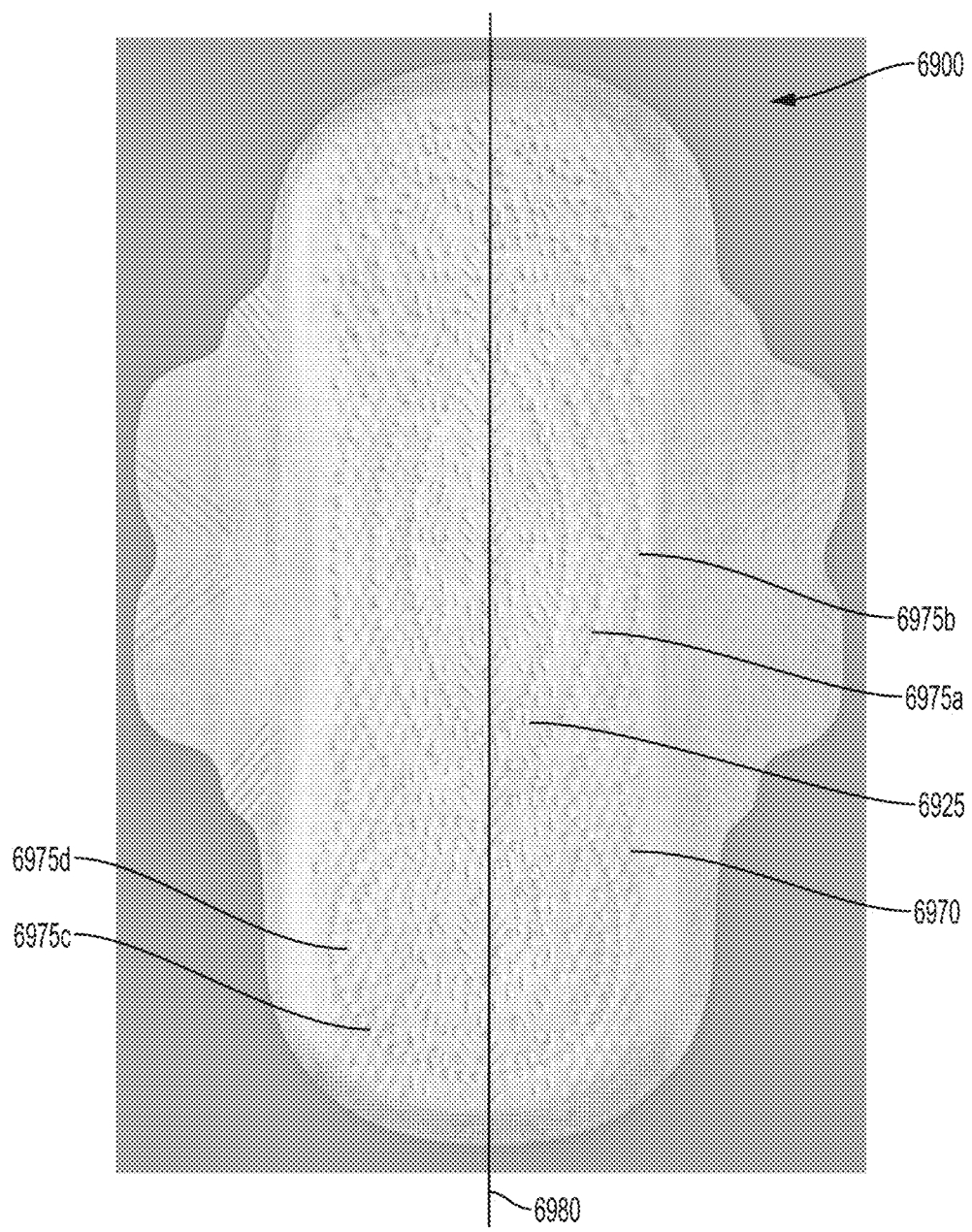

Regarding FIGS. 60 and 61, sanitary pad 6900 is shown. In some forms, sanitary pad 6900 may comprise arrays of bonds 6975a and 6975b extending generally longitudinally along the sides of the sanitary pad 6900. The arrays of bonds 6975a and 6975b are provided in the form of a pair of convex arcs which are positioned on either side of a central portion of the sanitary pad 6900. As shown, the convex arc may be disposed primarily in outer zones 6930a and 6930b. A portion of the fusion bonds which make up the convex arcs may be disposed in an intermediate zone 6935.

The curvature of the array of fusion bonds 6975 can provide a perception to the consumer of a more shape fitting pad. Namely, the convex arcs 6975a and 6975b can provide a perception of curvature to the overall sanitary pad 6900 masking straight edges of the pad 6900. Similarly, arrays of tufts 6970 may appear to be provided on the sanitary pad 6900 in a curved fashion because of the influence of the convex arcs 6975a and 6975b of the array of fusion bonds.

Additionally, as shown, a third array of fusion bonds 6975c is provided which generally exists similarly may extend the length of the pad 6900 or a large portion thereof. The third array 6975c may comprise fusion bonds which are disposed in the outer zones 6930a, 6930b as well as in the intermediate zone 6935.

As shown, the sanitary pad 6900 may comprise a colored nonwoven layer which can help highlight the features of the sanitary pad 6900. Specifically, the tufts 6970, fusion bonds, and apertures 6925 can be highlighted.

Alternatively, the plurality of apertures 6925 may be arranged as shown in FIG. 60. The plurality of apertures 6925 may comprise multiple arrays. For example, a first array may comprise a plurality of apertures angled at a first angle with respect to a longitudinal axis 6980. A second array may comprise a plurality of apertures angled at a second angle with respect to the longitudinal axis 6980. The first and second angles can be different. Additionally, the plurality of apertures 6925 may comprise a third array including a plurality of apertures angled at a third angle with respect to the longitudinal axis 6980. The third angle may be different than the first angle and/or the second angle. Additional arrays of apertures at additional angles are contemplated. The additional angles may be different than the first, second, and/or third angles.

Figure 62:
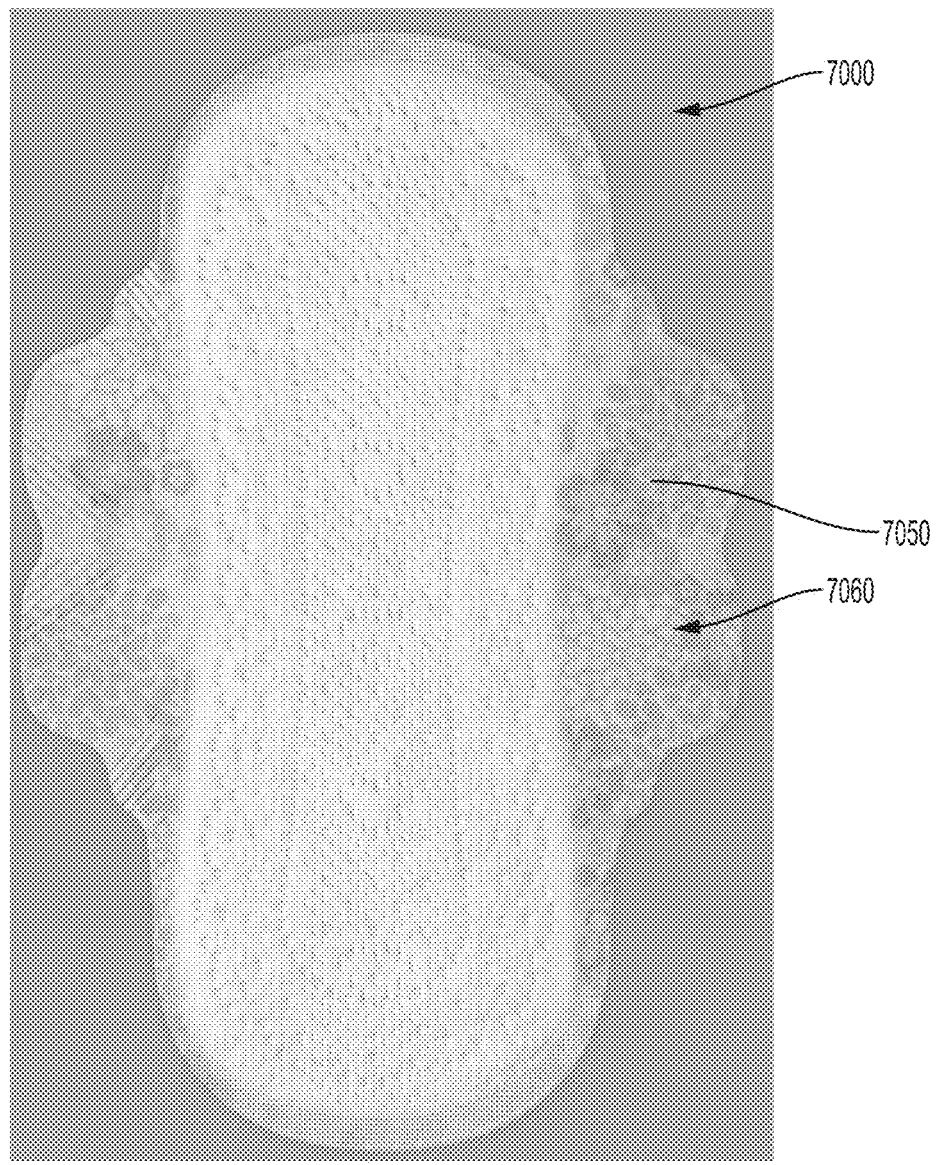

Regarding FIG. 62, a sanitary pad 7000 is shown. The sanitary pad 7000 may comprise a plurality of zones as disclosed previously. For example, the sanitary pad 7000 may comprise a first zone comprising a plurality of apertures, a second zone comprising a plurality of tufts, and a third zone comprising a plurality of tufts as described herein.

Additionally, as shown, the backsheet of the sanitary pad 7000 may comprise printing 7050 which is visible when viewing the pad 7000 from the wearer-facing surface 7060, i.e. topsheet, and the garment-facing surface, i.e. the backsheet. And, as stated previously, the printing on the backsheet may coordinate with the apertured indicia, adhesive indicia, structural indicia, bond indicia, and/or printed indicia elsewhere on the pad 7000. The sanitary pad 7000 may comprise a topsheet which comprises a colored layer.

Figure 63:
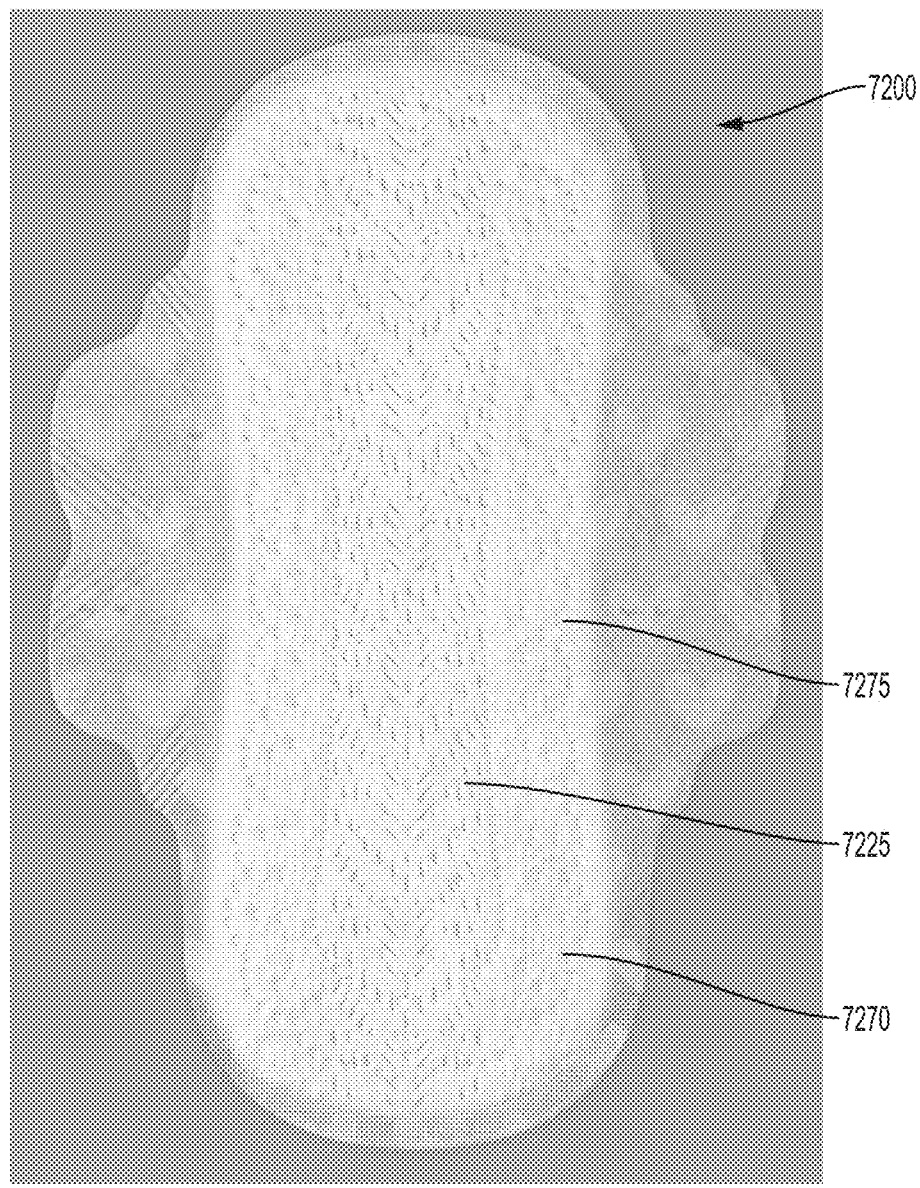

FIG. 63 depicts another sanitary pad 7200 constructed in accordance with the present invention. The pad 7200 may comprise a plurality of tufts 7270 and a plurality of fusion bonds 7275. The plurality of tufts 7270 and plurality of fusion bonds 7275 may be configured similar to the tufts and fusion bonds in FIG. 68. Additionally, pad 7200 may comprise printing on its backsheet in accordance to that described regarding FIG. 62. Apertures 7225 may be configured similar to that described with regard to FIG. 61.

Figure 64:
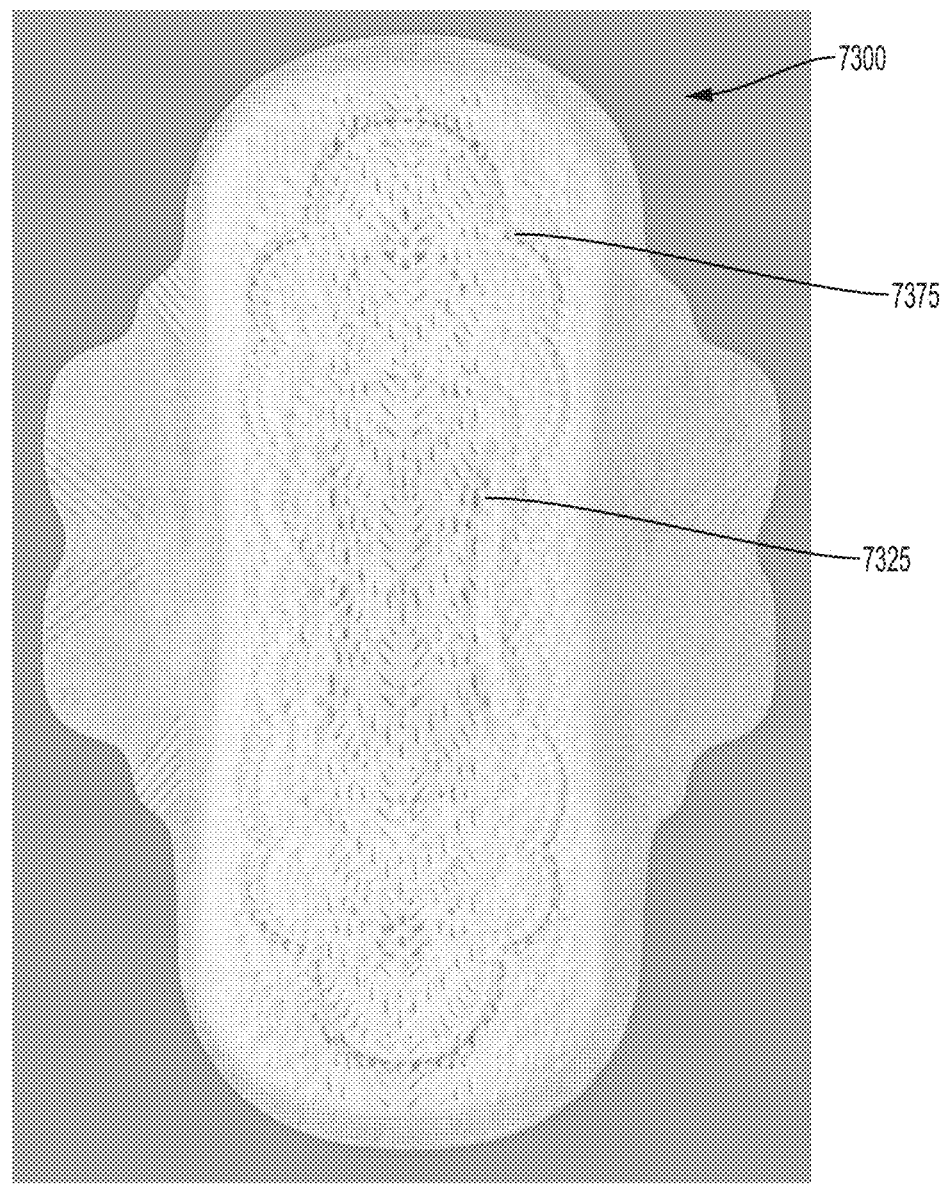

FIG. 64 depicts a sanitary pad 7300 constructed in accordance with the present invention. The sanitary pad 7300 may comprise the fusion bonds, tufts, and apertures similar to that described herein. For example, the sanitary pad 7300 comprises arrays of apertures, arrays of fusion bonds, and arrays of tufts. Each of these arrays can be arranged as described heretofore. Additionally, the sanitary pad 7300 comprises printing beneath the topsheet. As shown, a portion of the printing is visible through the apertures 7325 highlighting at least a portion of the apertures. Additionally, the sanitary pad 7300 comprises a plurality of fusion bonds 7375 which are registered with the underlying print. As shown, a color different is exhibited between the underlying print in the fusion bonds 7375 and the underlying print which is not registered with the fusion bonds 7375. Additional examples are provided herein.

Also, as shown, the printing 7350 may be curvilinear. The curvilinear nature of the printing 7350 may provide a perception of curvature of tufts, apertures, and/or fusion bonds. The curvature of the printing may help with masking straight edges of the sanitary pad. The curvilinear printing may be utilized in conjunction with the scalloped/curvilinear arrays of fusion bonds, scalloped/curvilinear arrays of tufts, and/or scalloped/curvilinear arrays of apertures.

Figure 65:
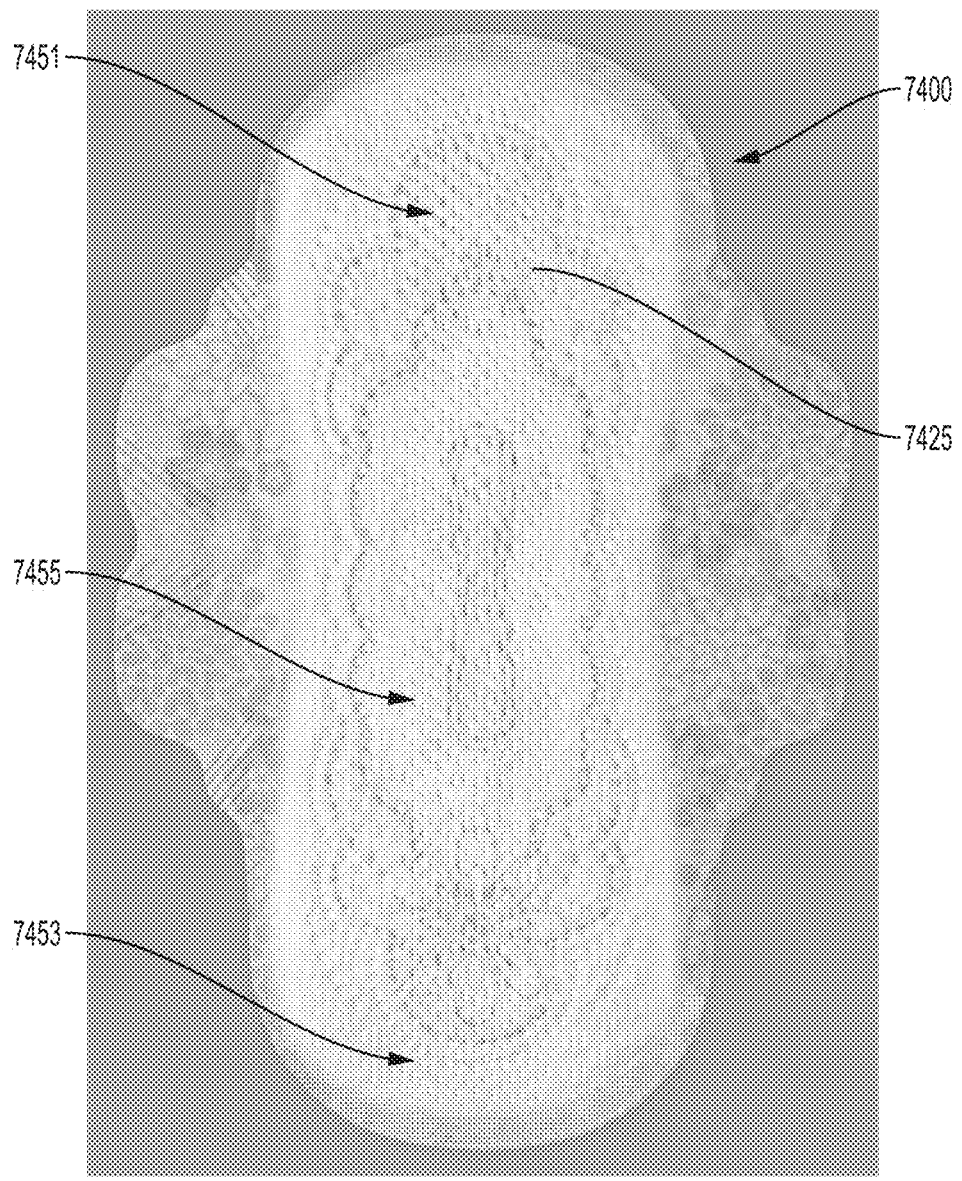

Regarding FIG. 65, a sanitary pad 7400 is shown. The sanitary pad 7400 may comprise a plurality of apertures, a plurality of tufts, a plurality of fusion bonds as described herein. Additionally, pad 7400 may comprise printing on a printed layer subjacent to the topsheet of the sanitary pad.

As shown, the pad 7400 may comprise a first end portion 7451, a second end portion 7453 and an intermediate portion 7455 disposed between the first end portion 7451 and the second end portion 7453. The first end portion 7451, intermediate portion 7455, and second end portion 7453 generally make up about a third of the length of the pad 7400 each.

As shown, in the first end portion 7451 and the second end portion 7453, the printing may comprise a plurality of colors a portion of which are registered with the apertures 7425 such that two different colors are viewable through the apertures 7425. Additionally, the printing on the printed layer 7451 is viewable through the topsheet. Such a configuration of printing and apertures can provide the pad 7400 with different colors for the same color print. Namely, the printing visible through the aperture appears darker than the printing which can be seen through the topsheet.

Figure 66A:
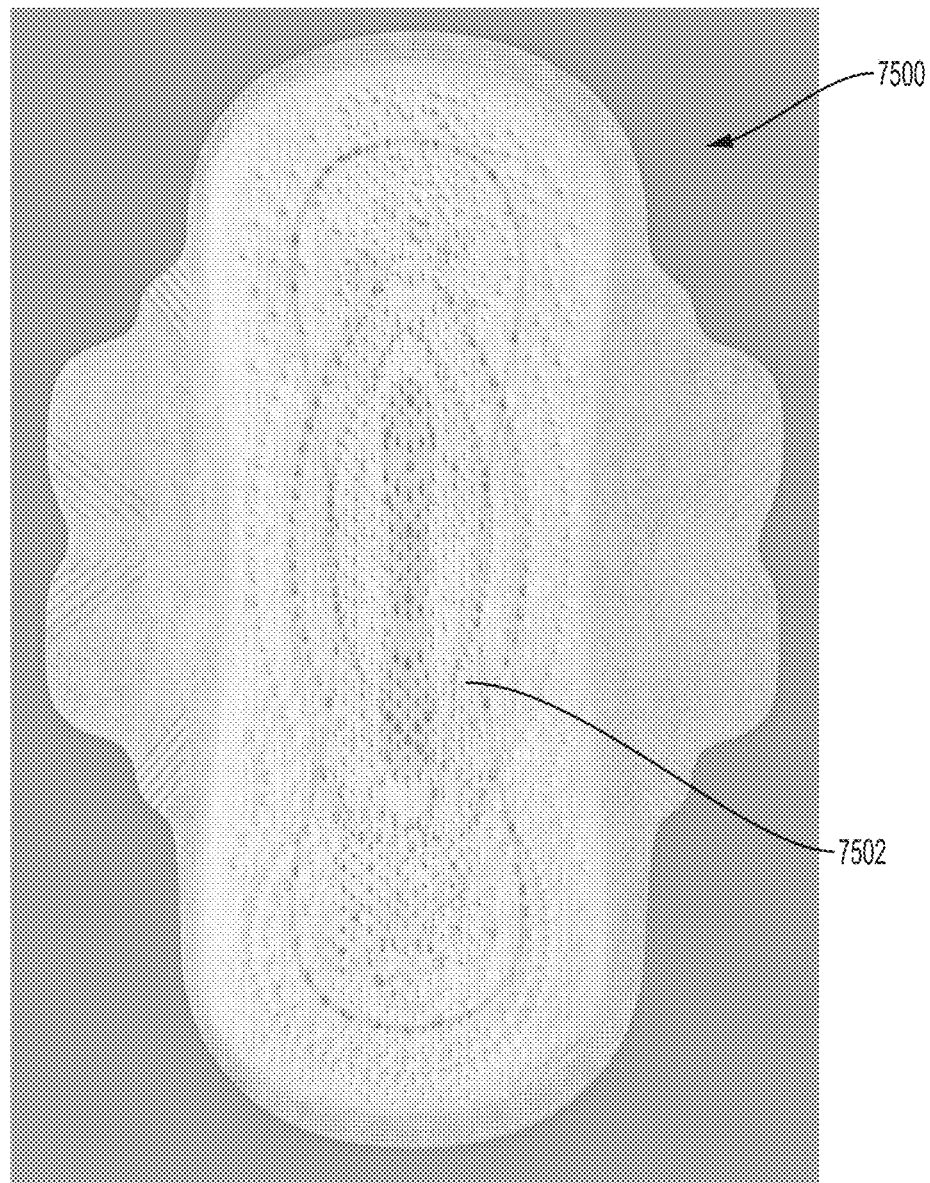
Figure 66B:
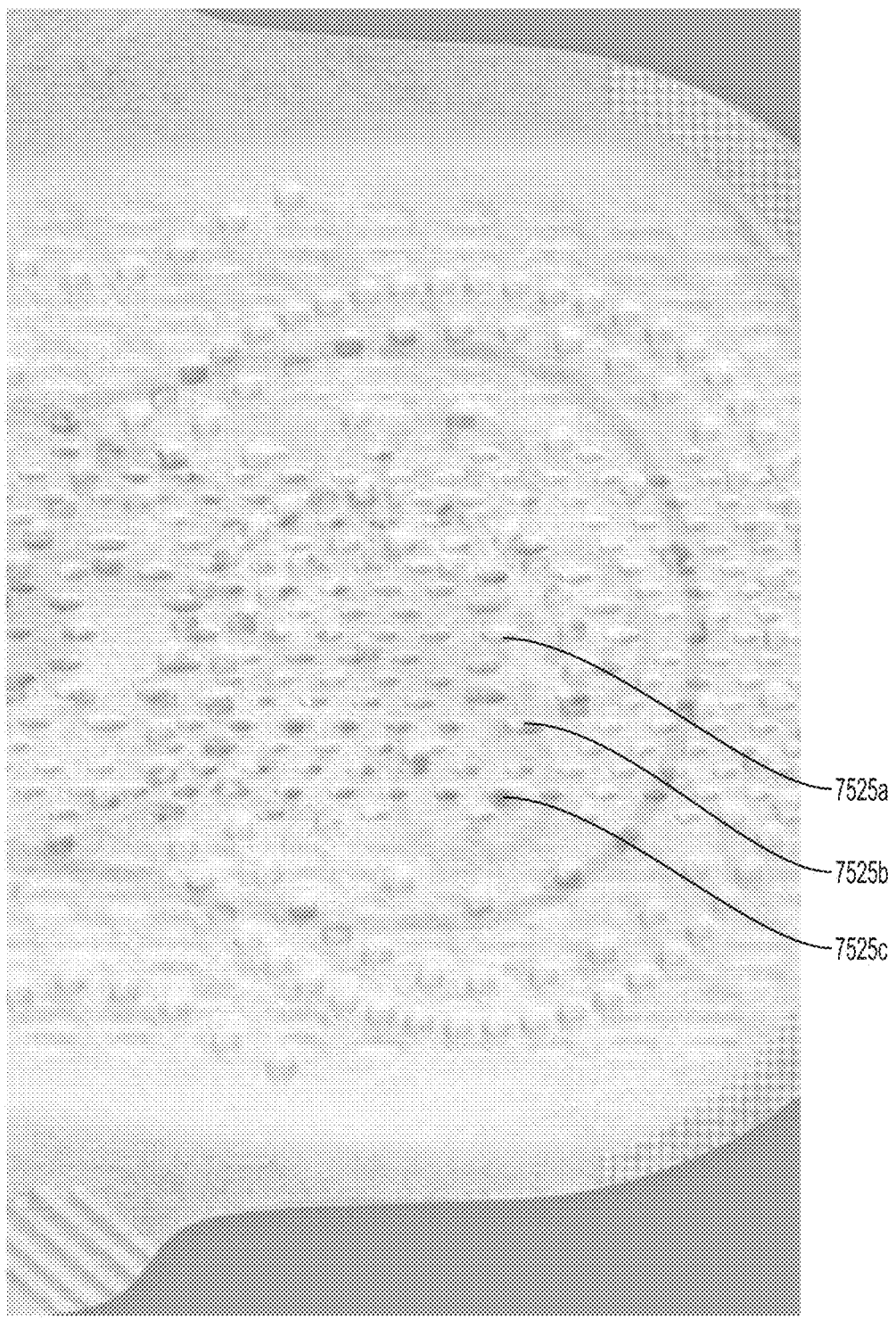

Another sanitary pad 7500 constructed in accordance with the present invention is shown in FIGS. 66A and 66B. Sanitary pad 7500 comprises printing arranged as provided herein. Namely, only a portion of the printing is visible through the apertures. Similarly, the fusion bonds, apertures, and tufts may be arranged as described heretofore. The printing specifically for sanitary pad 7500 creates a boundary area 7502 which generally coincides with the first zone as disclosed heretofore. A plurality of the fusion bond sites of sanitary pad 750 are registered with the print which effectively highlights the fusion bond sites.

As show in FIG. 66B, the sanitary pad 7500 may comprise a plurality of apertures. A first plurality of apertures 7325c may be 100 percent registered with the print underneath the topsheet of the sanitary pad 7500 causing the aperture color to effectively be the print color. A second plurality of apertures 7325b may be only partially registered with the print causing the aperture color to be, in part, the print color, and in part, the color of the underlying structure, e.g. conventional white. A third plurality of apertures 7325a may not be registered at all with the print such that the aperture color is that of the underlying structure, e.g. conventional white.

Such an arrangement of apertures can be beneficial though. It is believed that larger diameter size apertures, while helpful for draining fluid from the topsheet, can appear harsh to some users of sanitary pads. Indeed a difficult balance is required for these users. While one could potentially try to hide the existence of the apertures to avoid this pitfall, an appearance where apertures are not readily visible can communicate a lack of functionality to many users. However, where only a portion of the printing underneath the topsheet is visible through the apertures 7325b, the apertures 7325b may appear smaller than the apertures 7325c which are fully highlighted. An additional benefit is that the printing visible through the aperture appears darker than the printing which is viewable through the topsheet. As such, a multi-tone color scheme can be provided with only the provision of a single ink/pigment. Accordingly, multi-tones could be available for multiple colors of ink/pigment.

As noted previously, a laminate/web of the present invention may have apertures having an Effective Aperture AREA in the range of about 0.1 $mm^2$ to about 15 $mm^2$, 0.3 $mm^2$ to about 14 $mm^2$, 0.4 $mm^2$ to about 12 $mm^2$, 0.3 $mm^2$ to about 10 $mm^2$, 0.5 $mm^2$ to about 8 $mm^2$, 1.0 $mm^2$ to about 8 $mm^2$, or 1.0 $mm^2$ to about 5.0 $mm^2$, specifically including all 0.05 mm increments within the specified ranges and all ranges formed therein or thereby. Printing that appears through the apertures may occupy from about 5 percent to about 90 percent of the Effective Aperture AREA of at least a plurality of apertures of the sanitary pads. In some forms, a plurality of apertures may comprise printing which is occupies less than 25 percent of the Effective Aperture Area. In some forms, a plurality of apertures may comprise printing which occupies greater than about 25 percent to about 80 percent of the Effective Aperture Area. In some forms, a plurality of apertures may comprise printing which occupies greater than about 50 percent to about 90 percent of the Effective Aperture Area. In some forms an absorbent article of the present invention may comprise, a first plurality of apertures each of which comprises printing which occupies 100 percent of the Effective Aperture Area of the first plurality of apertures; a second plurality of apertures each of which comprises printing which occupies between about 75 percent to about 90 percent of the Effective Aperture Area of the second plurality of apertures; a third plurality of apertures each of which comprises printing which occupies between about 40 percent to about 75 percent of the Effective Aperture Area of the third plurality of apertures; a fourth plurality of apertures each of which comprises printing which occupies between about 5 percent to about 40 percent of the Effective Aperture Area of the third plurality of apertures; and/or fourth plurality of apertures each of which comprising no printing visible through the aperture. Forms are contemplated where apertures either comprise printing which occupies only a portion of a plurality of apertures or no printing.

Additionally, in some forms, a portion of the plurality of apertures 7325 may appear completely filled with print, while another portion of the plurality of apertures 7325 is less than completely filled. In some forms, a first plurality of apertures each of which comprises printing which occupies 100 percent of the Effective Aperture Area may comprise less than about 75 percent of the plurality of apertures 7325. In some forms, the first plurality of apertures may comprise less than about 50 percent of the plurality of apertures. In some forms, the first plurality of apertures may comprise greater than about 1 percent of the plurality of apertures.

Figure 67:
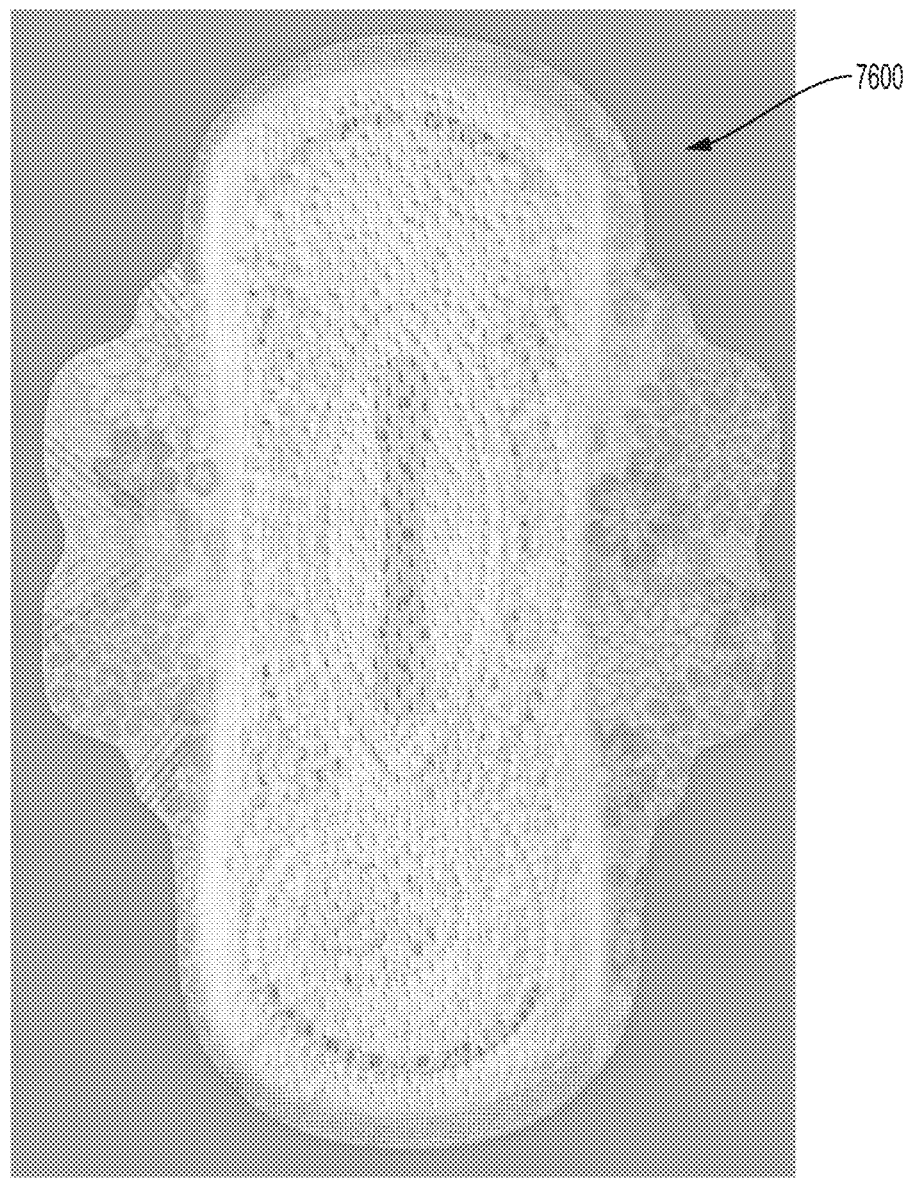

A sanitary pad 7600 is shown in FIG. 67. Sanitary pad 7600 comprises a colored laminate as a topsheet wherein at least one of the layers comprises a color, e.g. pink. While some of the fusion bonds are registered with the printing, a substantial number are not registered. However, where the printing and the colored layer are generally close to being the same color, emphasis may be removed from items which are not registered. Exact color match is not required. For example a pink shade and a red print signal may be sufficiently close.

Figure 68:
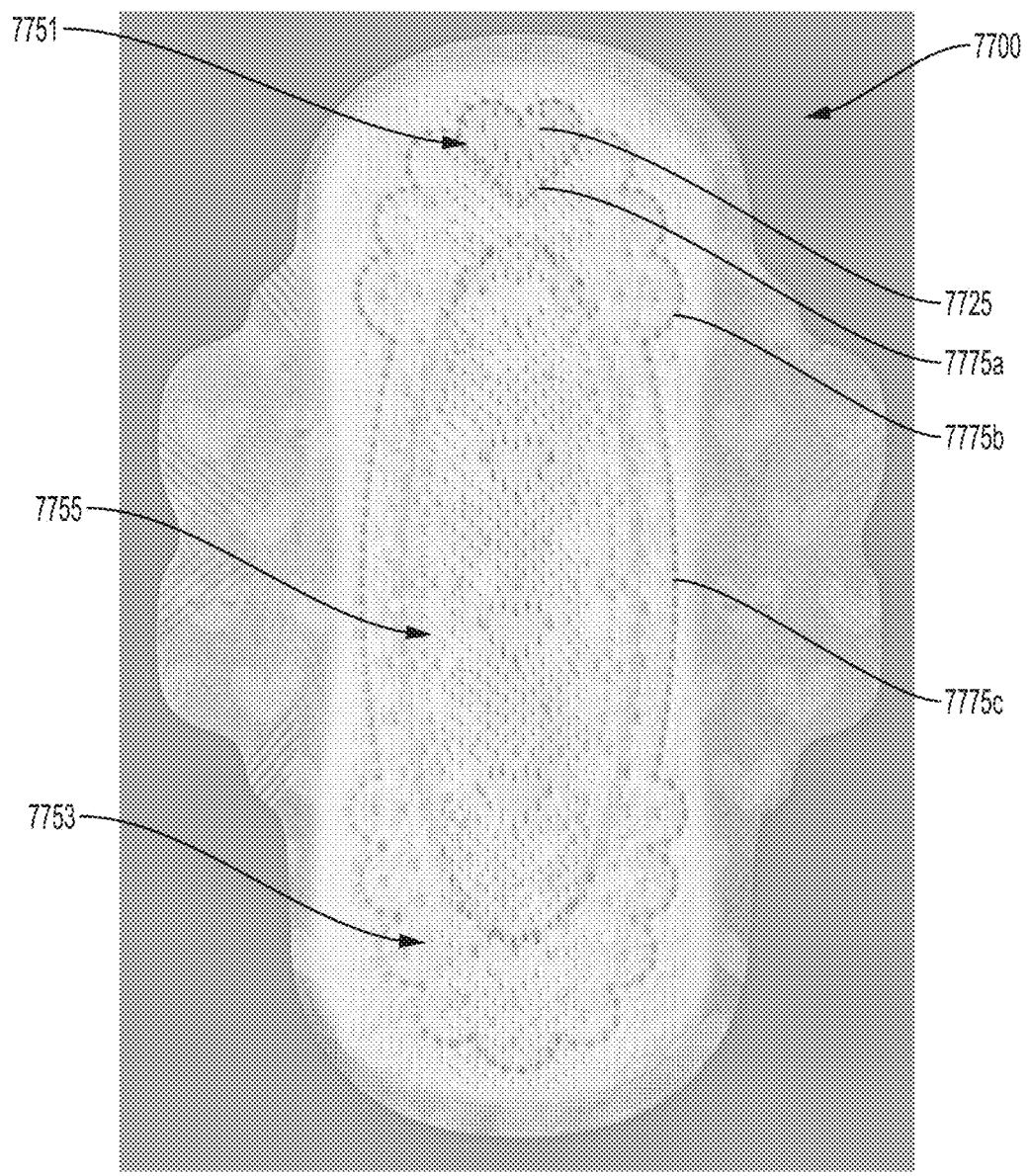

Another sanitary pad 7700 constructed in accordance with the present invention is shown in FIG. 68. Pad 7700 may comprise the printing arranged as provided herein, as well as the arrays of fusion bonds, arrays of apertures, and/or arrays of tufts as provided herein. The pad 7700 may comprise a first end portion 7751, a second end portion 7753, and an intermediate portion 7755 disposed between the first end portion 7751 and the second end portion 7753. The first end portion 7751, the second end portion 7753, and intermediate portion 7755 generally make up about a third of the length of the pad 7700 each.

As shown, the scalloped arrays of fusion bonds 7775b may be arranged at opposite ends of the pad 7700. The scallped arrays of fusion bonds 7775b may be primarily disposed in the first end portion 7751 and/or the second end portion 7753. Another fusion bond array 7775c may be primarily disposed in the intermediate portion 7755. The fusion bond array 7775c may form convex arcs the benefits of which were previously discussed.

Previously, the scalloped array of fusion bonds extended for a large portion of the length of their respective pads. Additionally, as shown, fusion bond array 7775a may form bond indicia which is coordinated with apertured indicia created by an array of apertures 7725. Forms are contemplated where apertured indicia, bond indicia, structural indicia, adhesive indicia, and/or printed indicia are combined to form a single pattern. For example, as shown, a fusion bond site may be included with apertures 7725 to form apertured indicia, e.g. a heart. The printing for pad 7700 may be derived from a printed secondary topsheet or another printed layer disposed between the topsheet and the absorbent core of the pad 7700.

Figure 69:
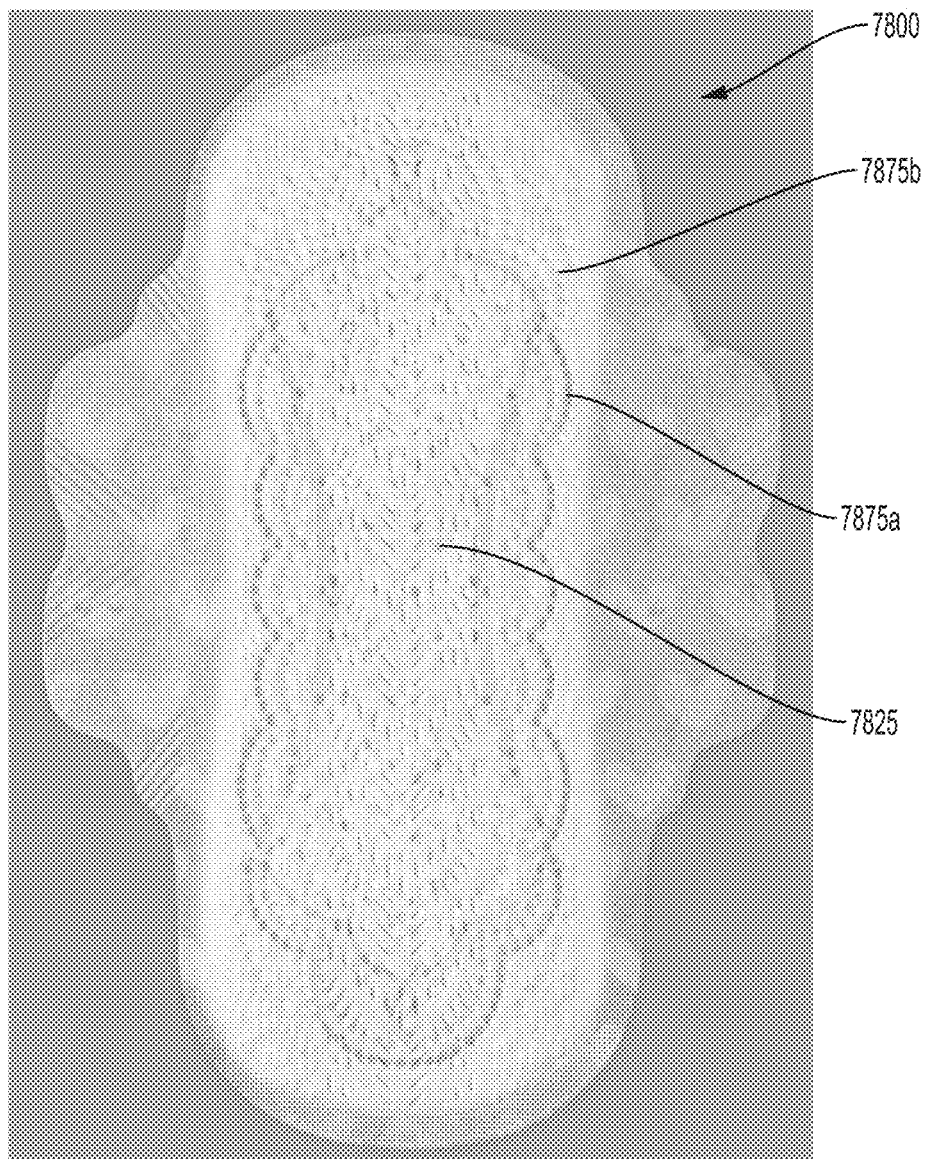

Another sanitary pad 7800 constructed in accordance with the present invention is shown in FIG. 69. Pad 7800 may comprise the printing arranged as provided herein, as well as the arrays of fusion bonds, arrays of apertures, and/or arrays of tufts as provided herein. As shown, multiple colors may be utilized in printing. And such printing may be arranged such that only a portion of the printing shows through a plurality of apertures 7825. In such forms, a plurality of apertures may comprise a first color which is visible therethrough while a second plurality of apertures comprise a second color which is visible therethrough. The first color and the second color may be different.

Also, as shown, a plurality of fusion bonds 7875a may be registered with the printing such that a first plurality of fusion bonds provide a first color and a second plurality of fusion bonds provide a second color, wherein the first color and the second color may be different. Additionally, such configurations allow the highlighting of specific portions of the pad 7800. For example, the first plurality of fusion bonds 7875a are registered with printing such that they appear in contrast to the overall color perceived by the user. A second plurality of fusion bonds 7875b, while still perceptible, are not highlighted.

Registration techniques for ensuring overlap between printing and fusion bonds and/or printing and apertures (to some extent) are provided with regard to FIGS. 86-88C.

Figure 70:
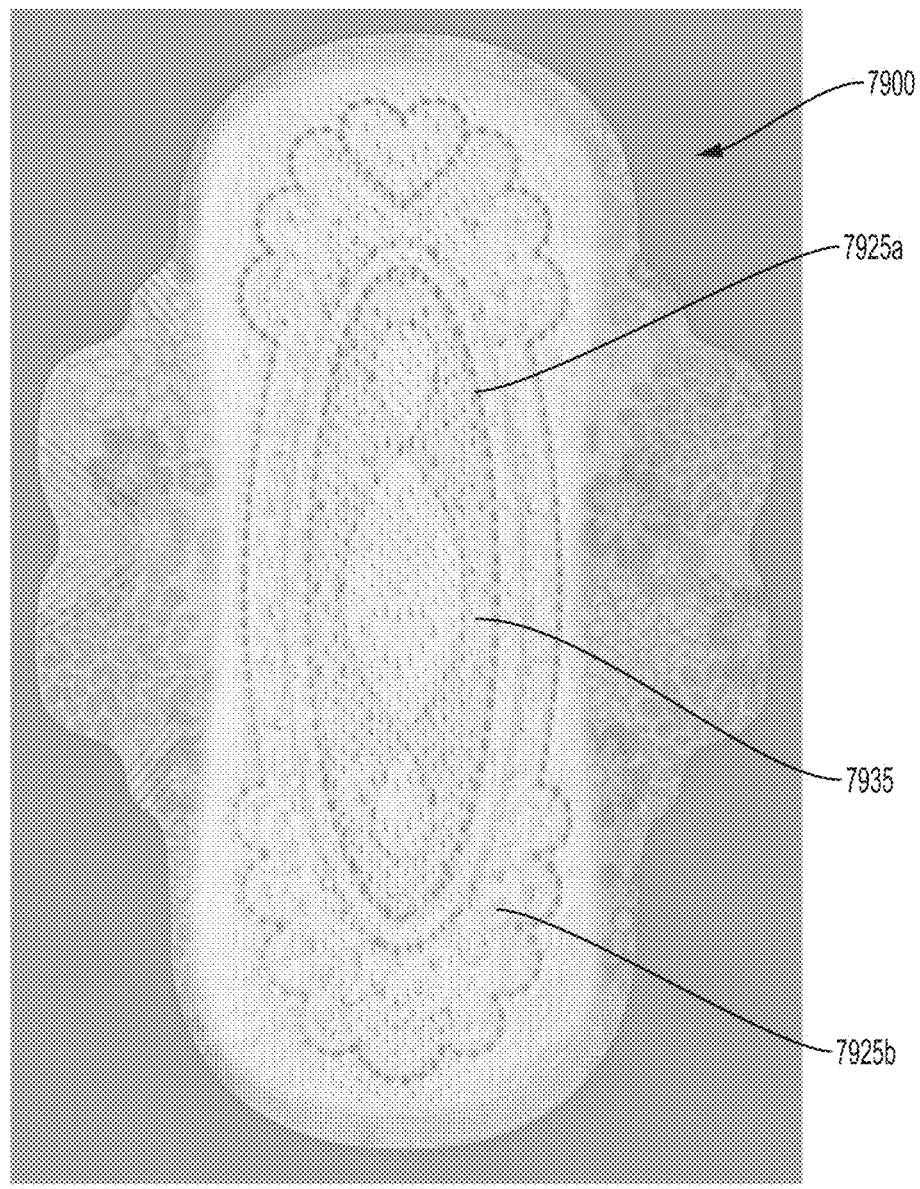
Figure 71:
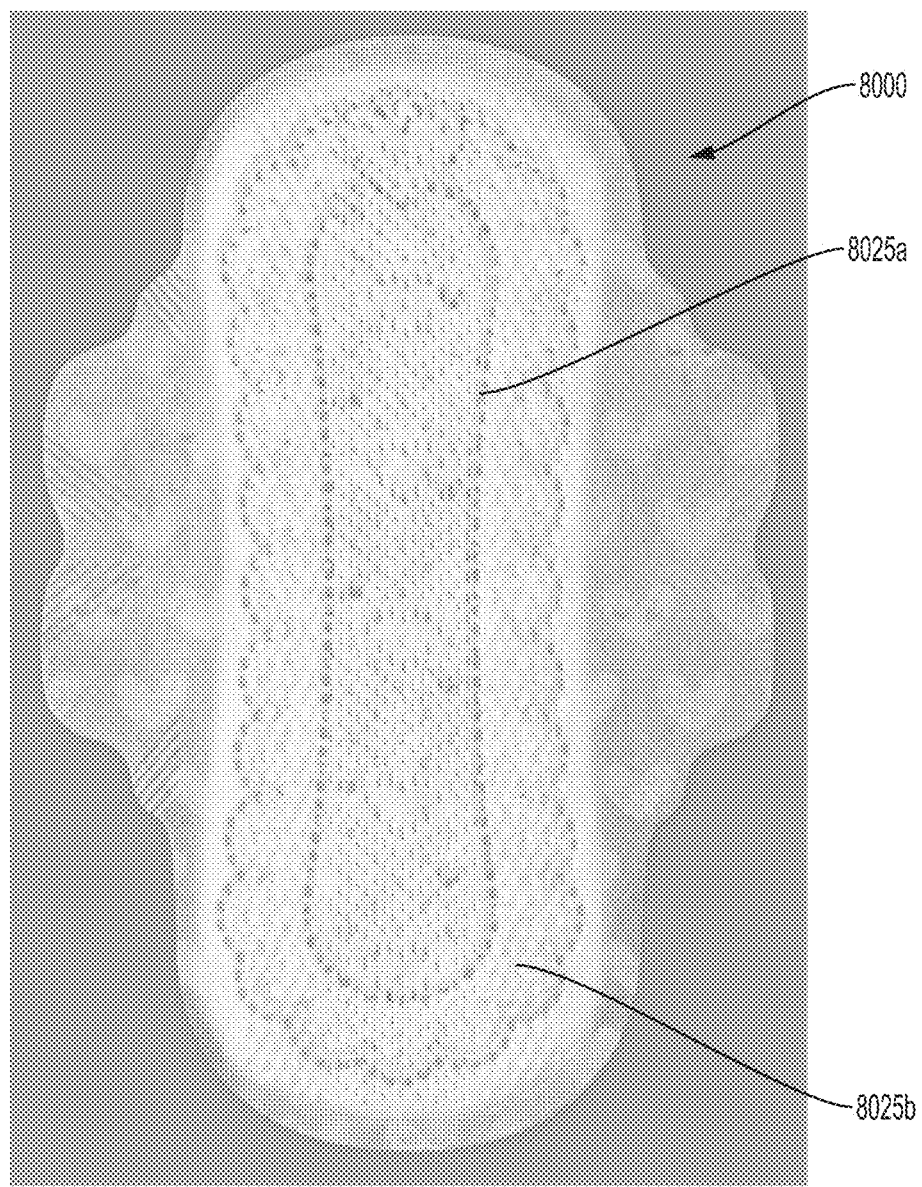

Pads 7900 and 8000 may provide additional examples of sanitary pads constructed in accordance with the present invention. These pads 7900 and 8000 are depicted in FIGS. 70 and 71, respectively. Each may comprise the plurality of fusion bonds, plurality of apertures, plurality of tufts, and printing as described herein. As discussed above, the fusion bonds may be registered with printing such that at least some fusion bonds are highlighted with respect to others. As shown, a plurality of fusion bonds 7925a and 8025a may be highlighted with respect to a second plurality of fusion bonds 7925b and 8025b. The first plurality of fusion bonds 7925a and 8025a may highlight a target area for each of their respective pads. The target area can be a location on the pad which is expected to be the primary point of contact for liquid insults.

Regarding pad 7900, a first zone 7935 is highlighted, in part, because of the boundary of fusion bonds as noted above. The boundary is even more pronounced because a large portion of the fusion bonds 7975a are registered with the printing. However, a larger amount of printing is provided in the first zone 7935. As noted previously, in some forms of the present invention, the first zone 7935 may comprise a substantial portion of the apertures of the sanitary pads herein. The level of printing is decreased outside of the fusion bonds 7975a.

Figure 72:
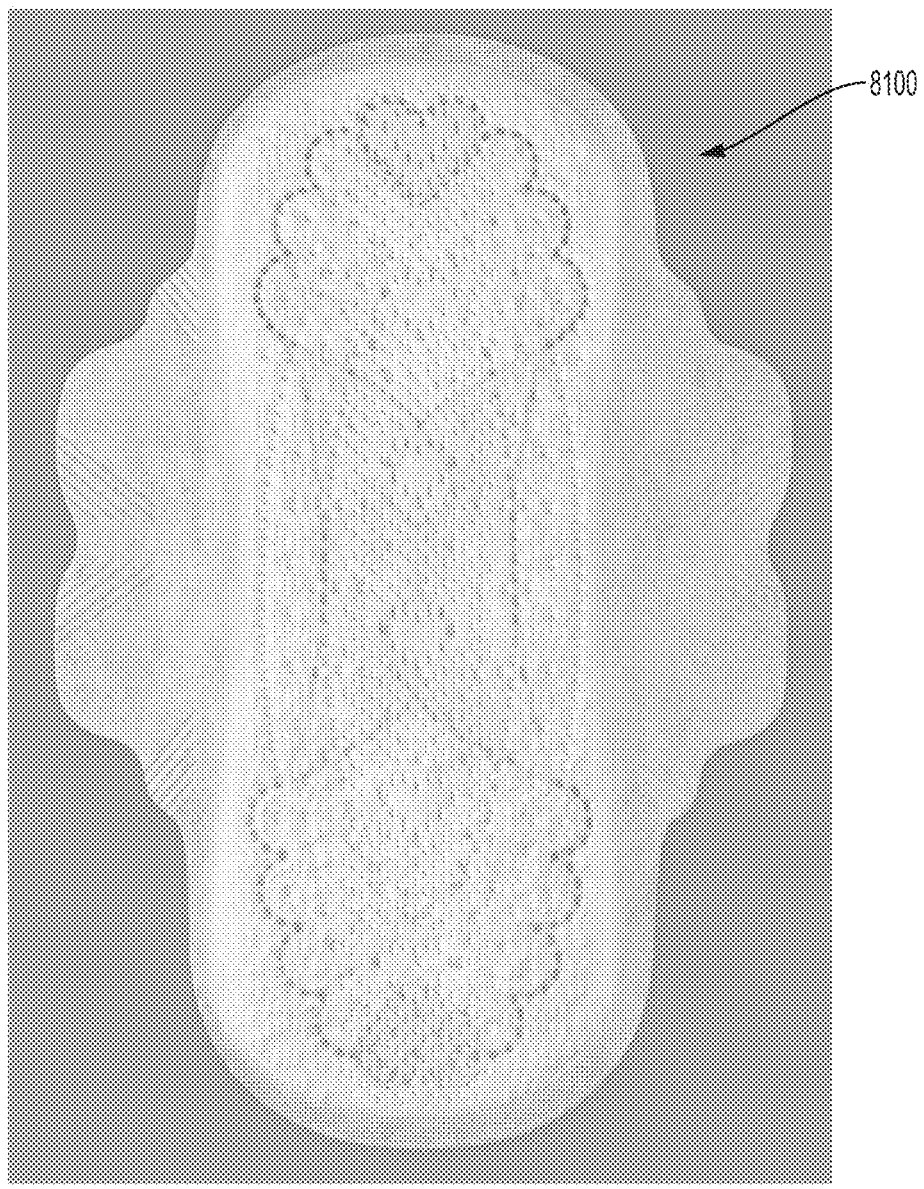

Regarding FIG. 72, a pad 8100 is shown. The pad 8100 may comprise a plurality of apertures, plurality of tufts, and plurality of fusion bonds arranged as described herein. Additionally, the pad 8100 may comprise printing as shown. As shown, registration between a plurality of fusion bond sites and the printing may occur. And where multiple colors are utilized in the printing, multiple color variants are potentially available via the manipulations disclosed herein.

Figure 73A:
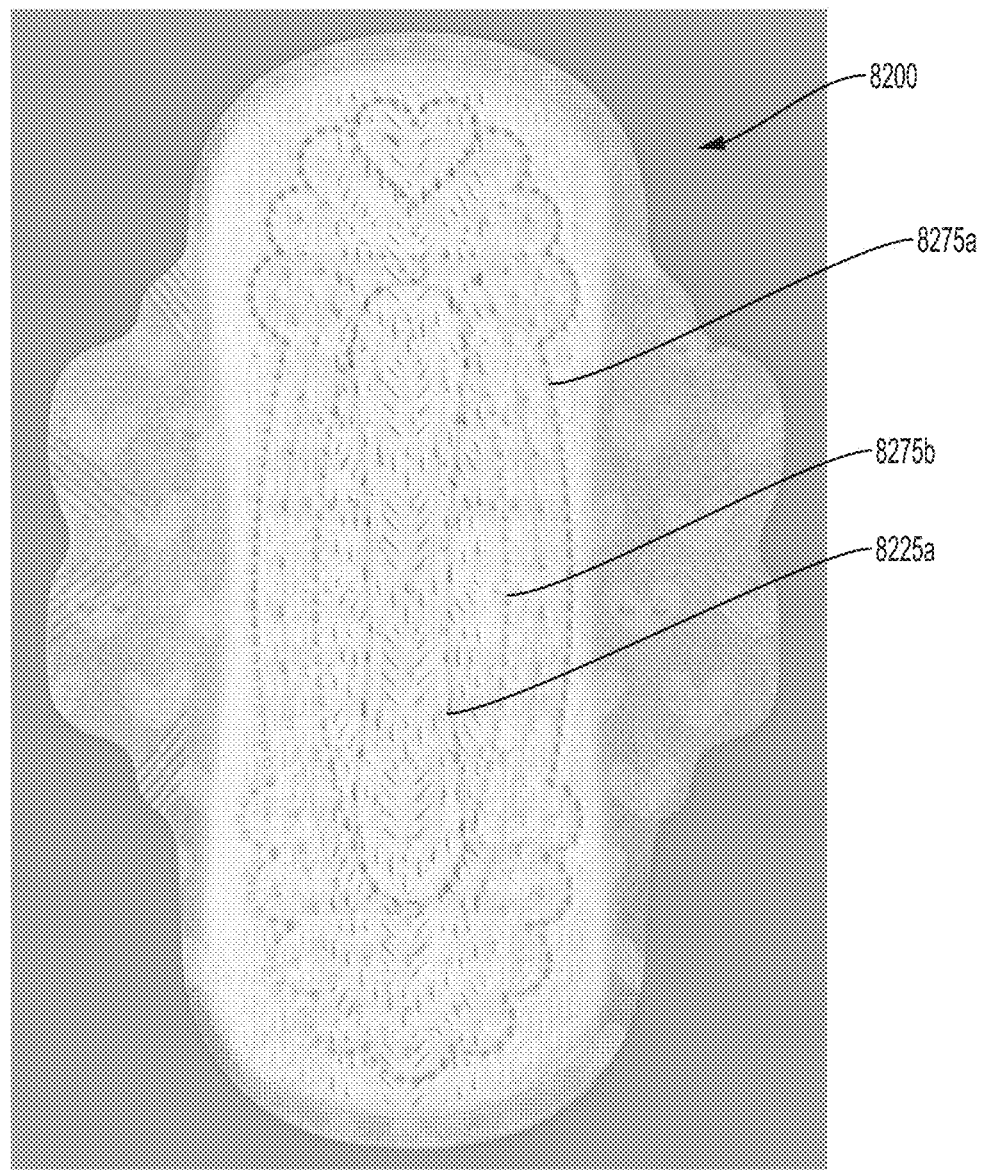
Figure 73B:
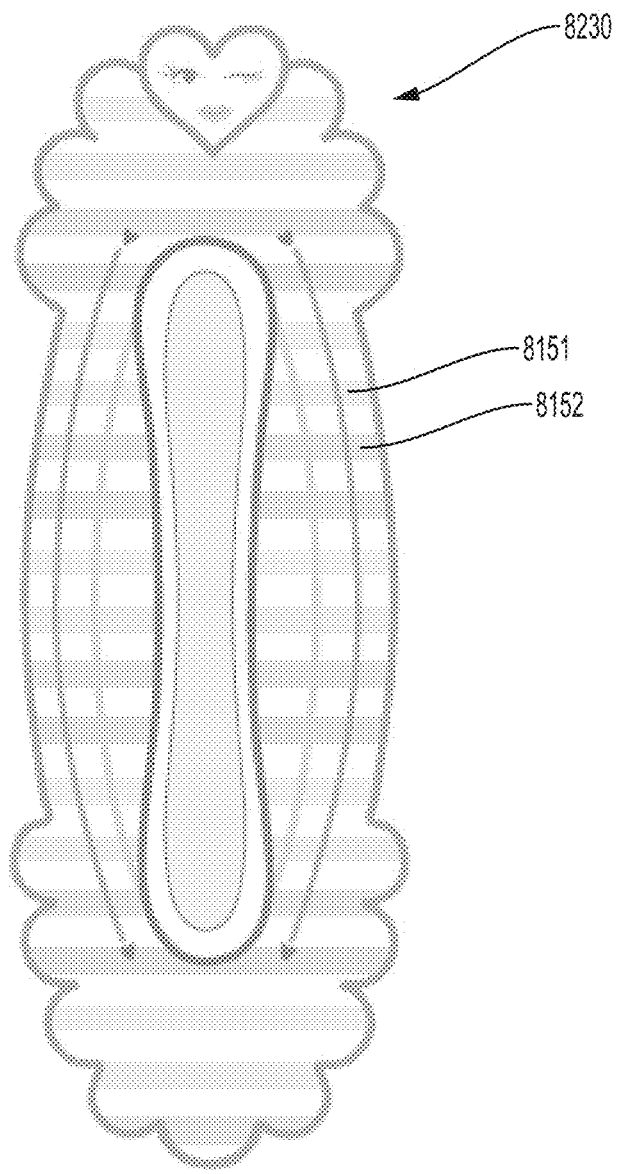

Regarding FIG. 73A, a sanitary pad 8200 is shown. The pad 8200 may comprise a plurality of fusion bonds, plurality of apertures, and a plurality of tufts as provided herein. Additionally, the pad 8200 may comprise printing. Printing may be provided to the pad 8200 as provided herein. As shown, printing 8250 (shown in FIG. 73B) may be provided via a printed layer 8230. Printed layer 8230 may comprise a plurality of printed stripes 8251 and 8252. The printed stripes 8251 may comprise a first color, and the printed stripes 8252 may comprise a second color. The first color and the second color may be different. Additionally, as shown, the first color may be provided in form of a gradient from light to dark or dark to light from one end to the center of the pad. In this manner, printing which appears through laterally spaced apart apertures may appear the same color, while printing which appears through apertures which are longitudinally spaced apart may appear as different colors.

As shown, the plurality of fusion bonds may comprise a first boundary 8275a and a second boundary 8275b. As shown, a portion of the fusion bonds of the first boundary 8275a may be registered with regard to the printing, and a portion of the fusion bonds of the second boundary 8275b may be registered with respect to the printing. In some forms, the printing may comprise a gradient of color which begins with a light hue toward the center of the pad 8200 and darkens as the print extends laterally outward. In this manner, the first boundary 8275a may be more pronounced than the second boundary. The opposite effect could be achieved by reversing the gradient of color.

Still in other forms, registration of the fusion bonds of the first boundary 8275a and the fusion bonds of the second boundary 8275b may be controlled such that more of the fusion bonds of the first boundary 8275a are registered with the printing than are the fusion bonds of the second boundary 8275b or vice versa. Additionally, a third boundary 8225a may be provided via registration of at least a portion of the plurality of apertures with the printing. Similar to the above, the intensity of the boundary 8225a may be controlled via the amount of registration provided between the apertures and the printing. As shown, the plurality of printed stripes may have variable lengths. At least some of the printed stripes extend to the first boundary 8275a.

Figure 74:
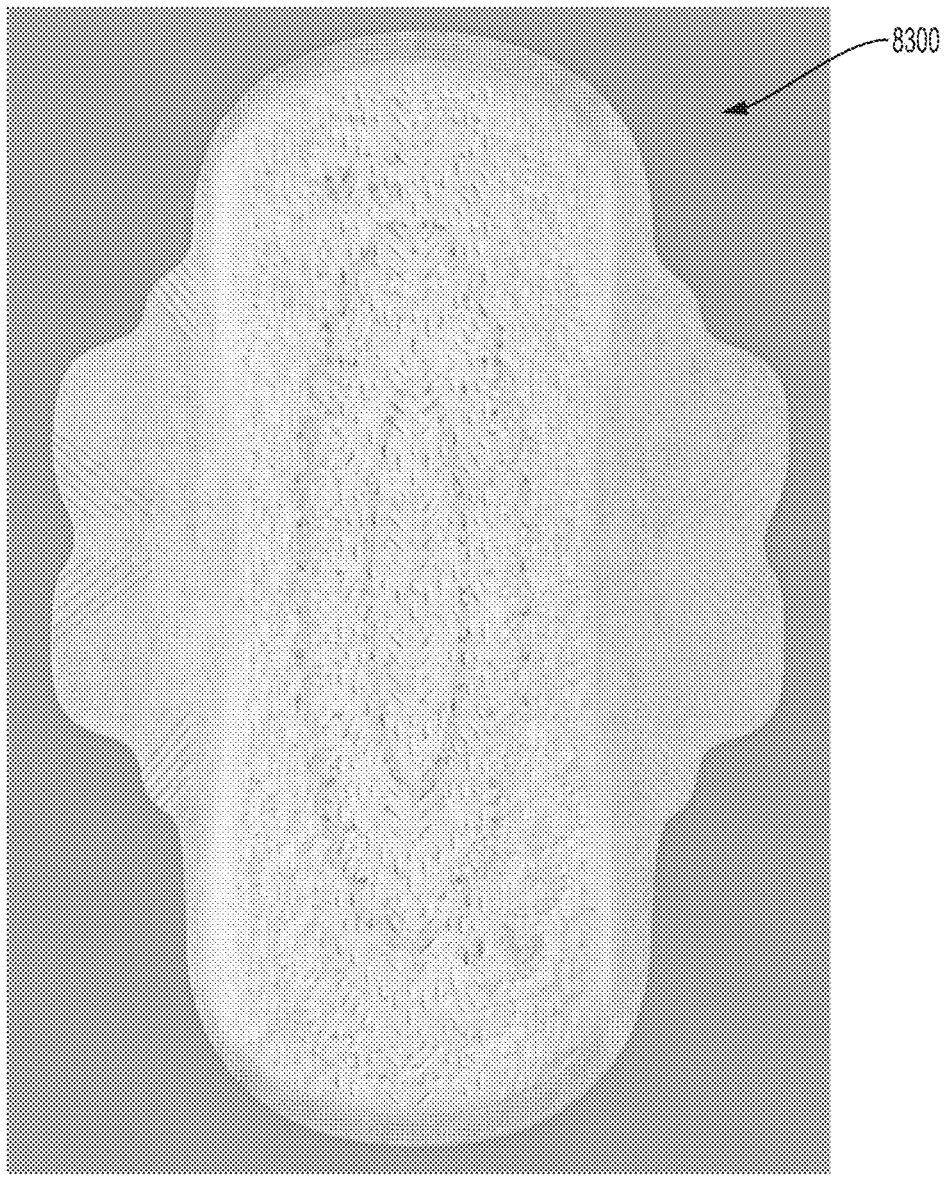
Figure 76:
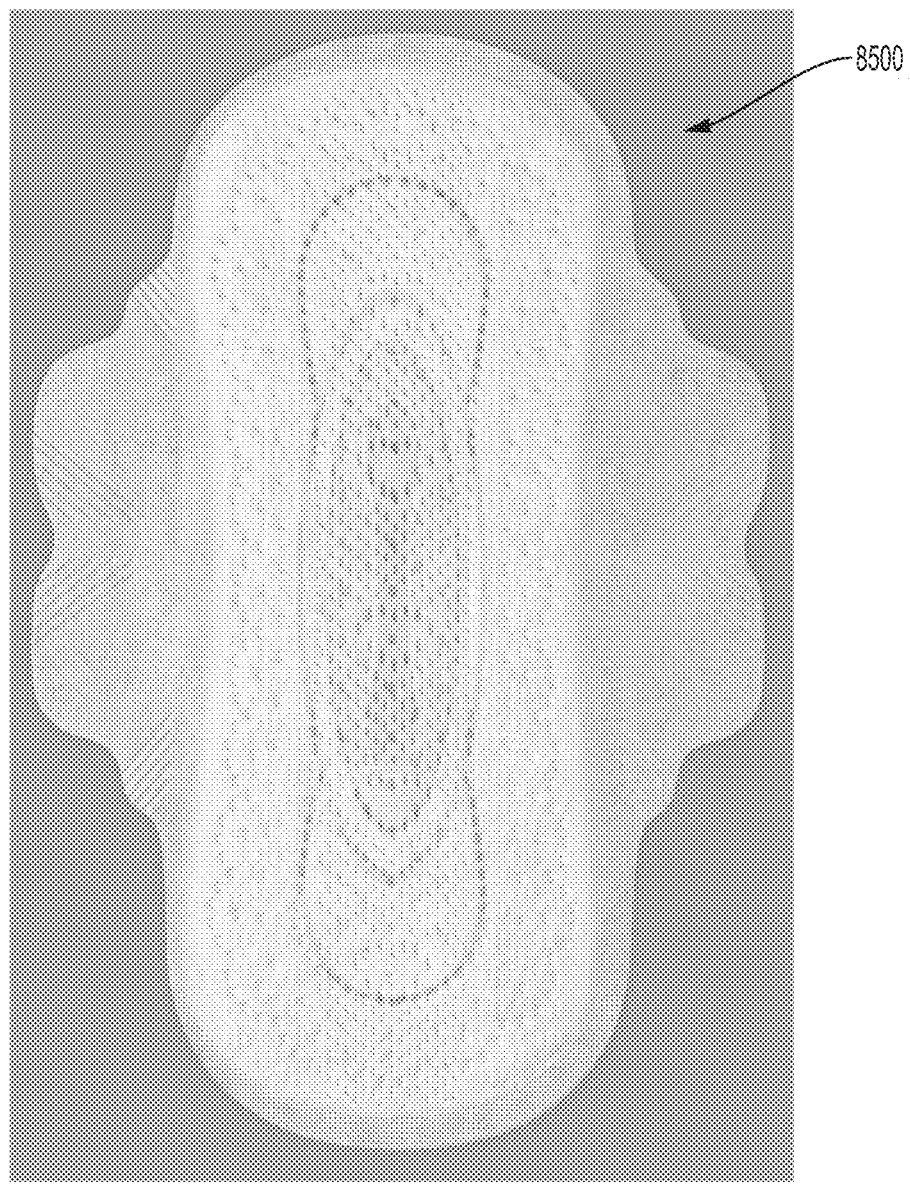
Figure 77:
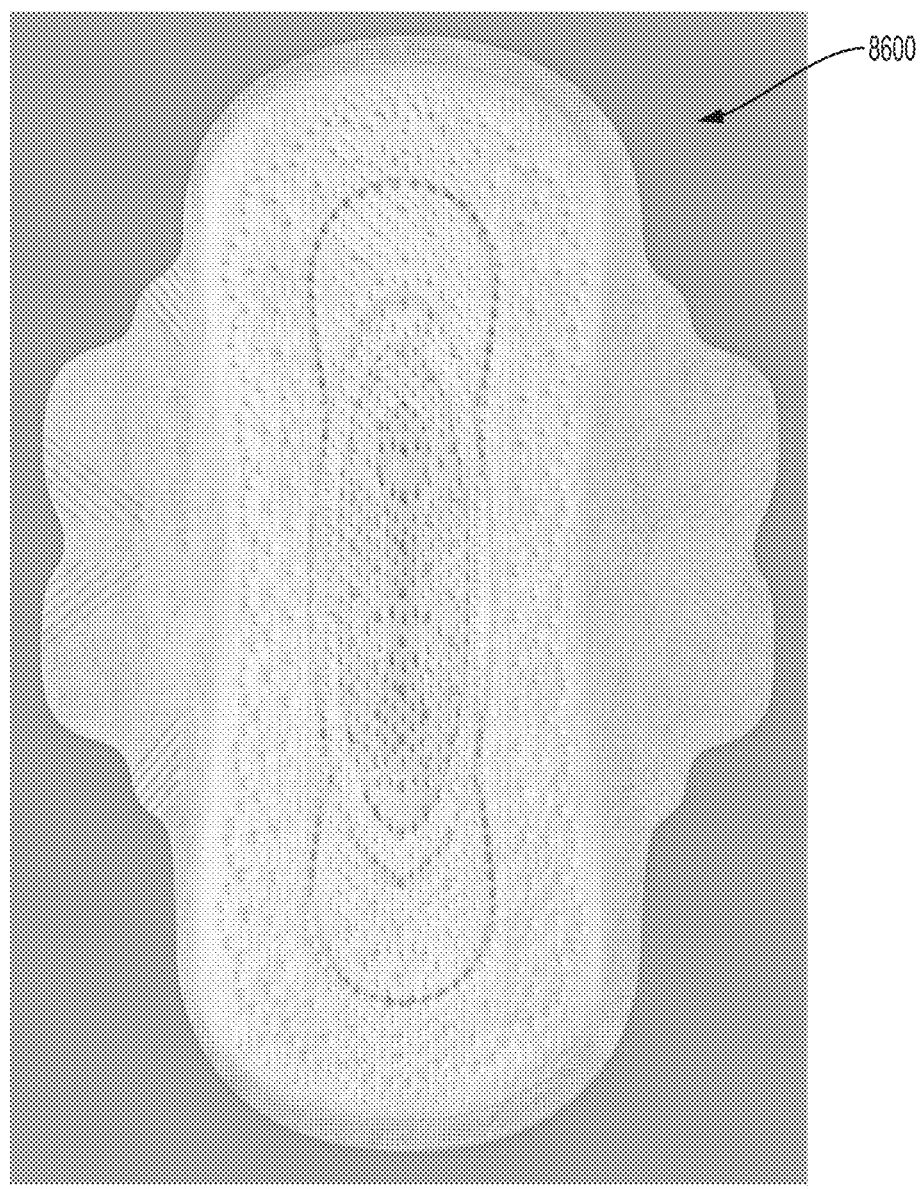

FIGS. 74 and 76-77 depict sanitary pads 8300, 8500, and 8600 respectively. Each of these pads comprise printing as described heretofore. Additionally, each of these pads may comprise a plurality of fusion bonds, a plurality of apertures, and a plurality of tufts configured as described heretofore.

Figure 75:
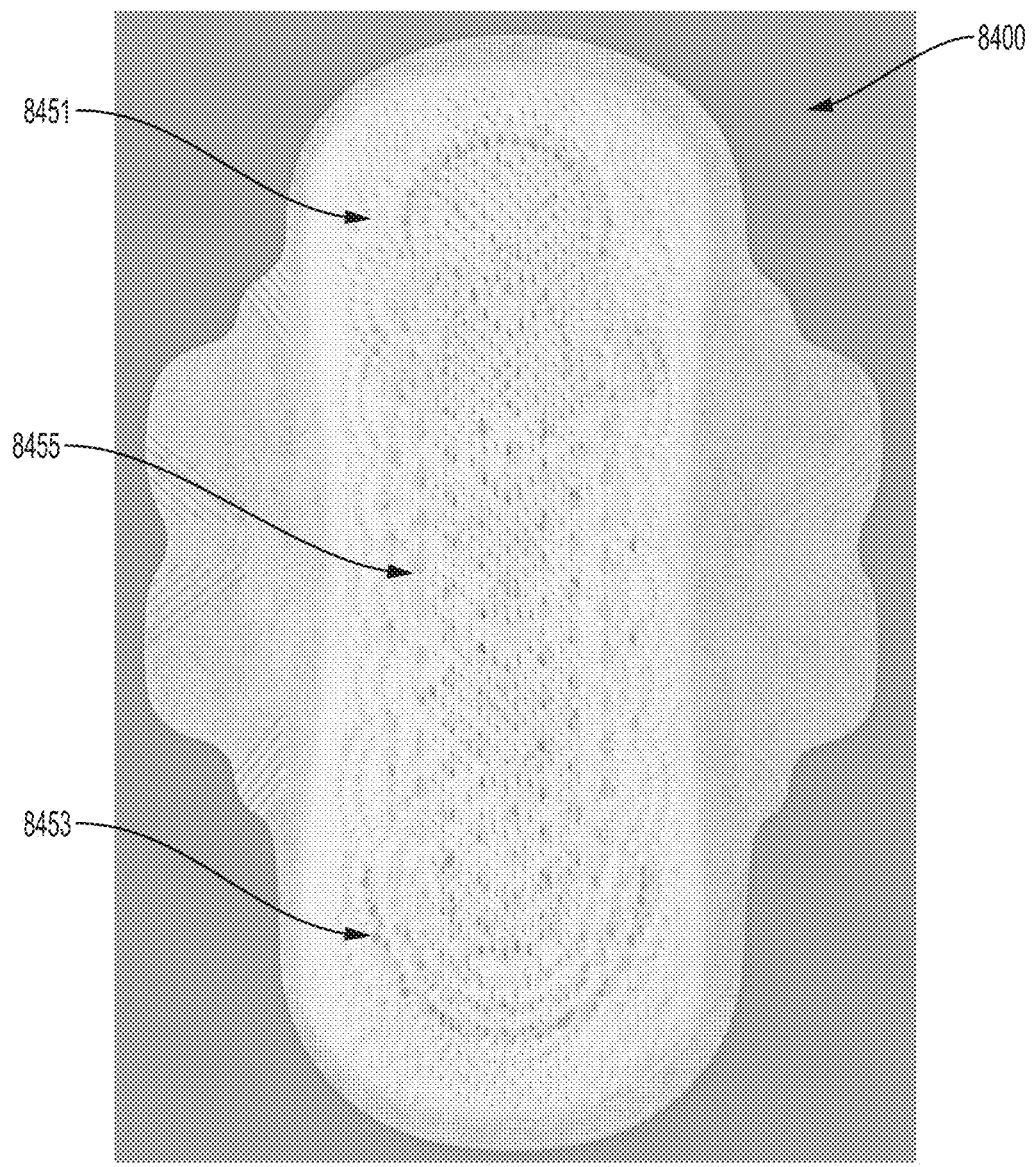

With regard to FIG. 75, sanitary pad 8400 is shown. The pad 8400 may comprise apertures, fusion bonds, tufts and printing as described herein. For example, the pad 8400 comprises printing which is coordinated throughout the pad 8400. At a first end portion 8451, printing may comprise, for example, a sun and cloud combination. An intermediate portion 8455, may comprise, for example, rain drops. And, a second end portion 8453 may comprise a rainbow. Because each of these depictions is related, the printing is considered to be coordinated.

Figure 78:

FIG. 78 depicts a sanitary pad 8700 comprising a laminated topsheet structure comprising a white upper layer and a blue lower layer. The fusion bond array, tuft array, and aperture array are similar to that described with regard to FIGS. 68 and 71A and 71B.

Figure 79:
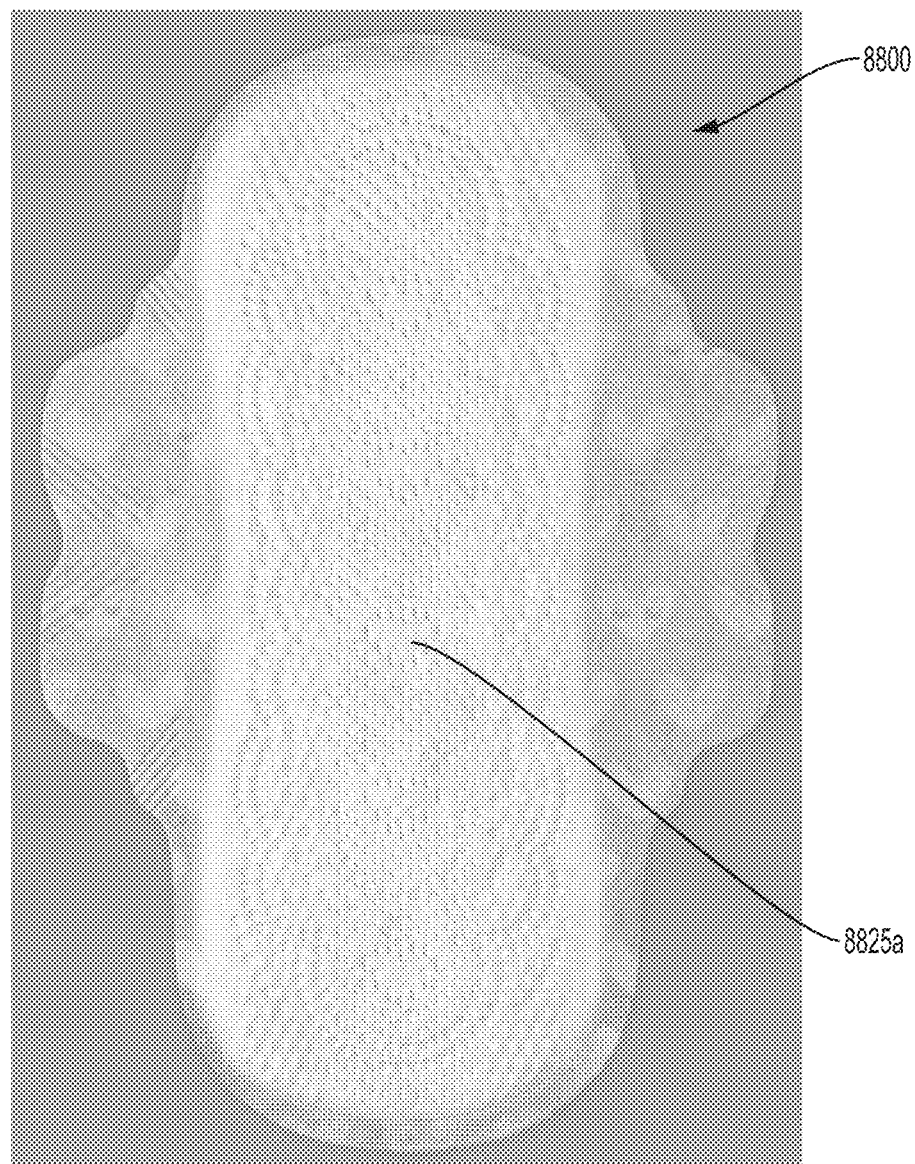

FIG. 79 depicts a sanitary pad 8800. The pad 8800 may comprise a plurality of apertures, a plurality of fusion bonds, and a plurality of tufts arranged as described heretofore. Additionally, as shown, at least a first array of apertures 8825a may be coordinated with printing that is associated with the backsheet, e.g. hearts.

Figure 80:
Figure 81:
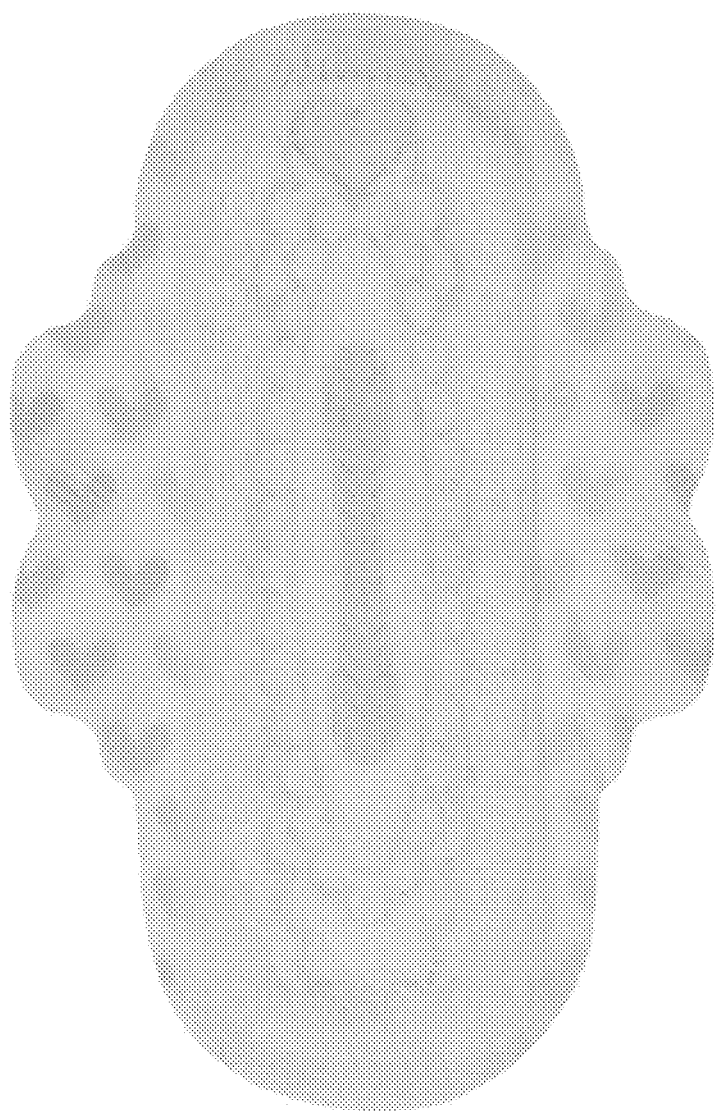
Figure 82:
Figure 83:
Figure 84:
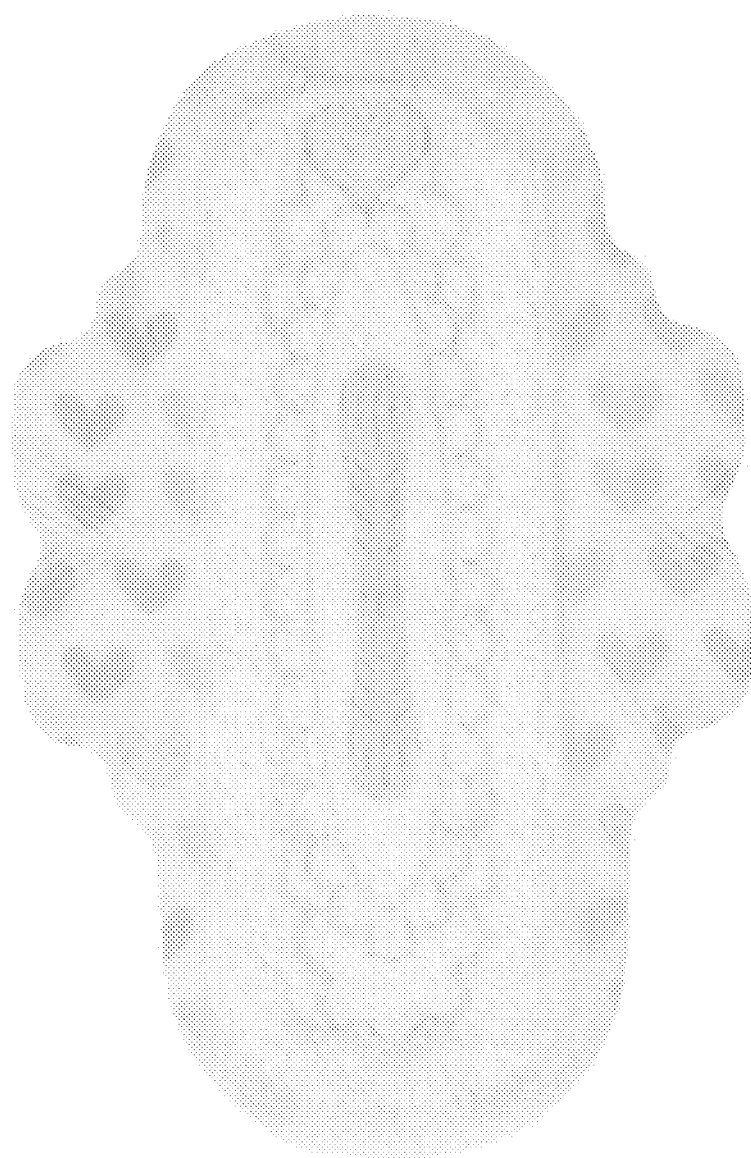
Figure 85:
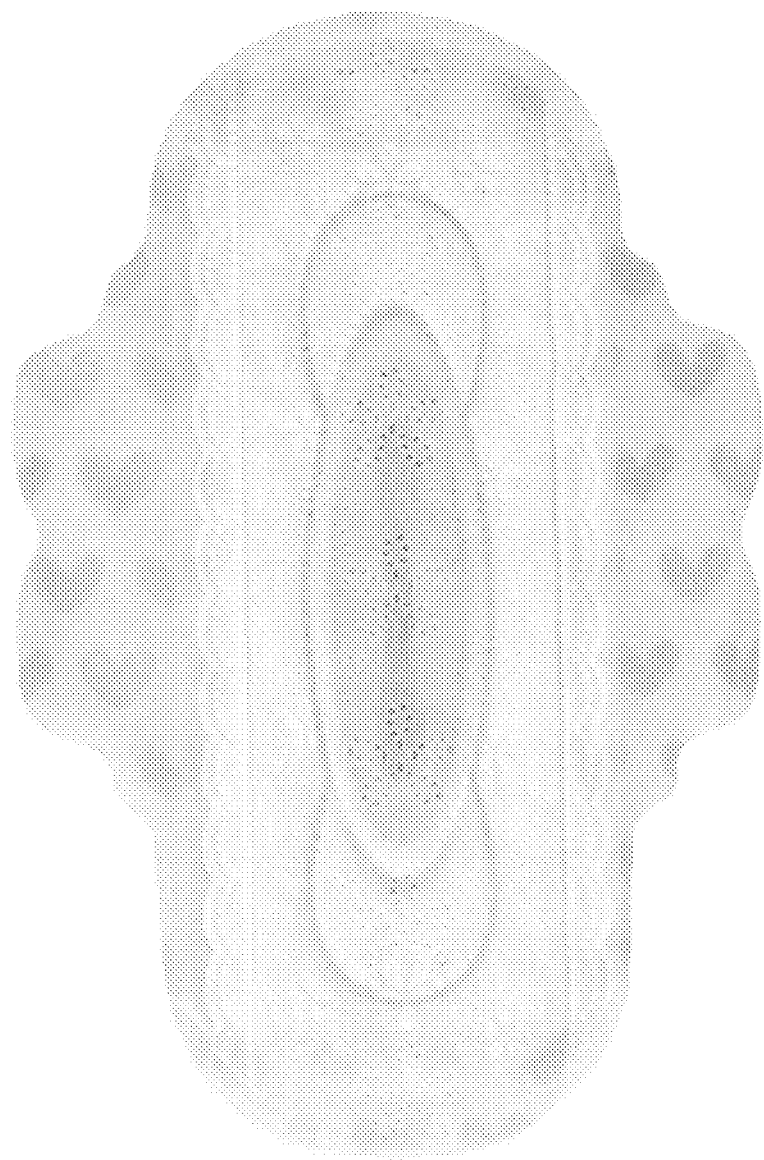

FIG. 80 depicts a sanitary pad 8900 which may be configured similar to the pad 8800 without the backsheet printing. Sanitary pad 8900 may comprise a plurality of apertures, a plurality of fusion bonds, and a plurality of tufts arranged as described heretofore.

FIGS. 81-85 depict sanitary pads constructed in accordance with the present disclosure. Each of these pads comprises a plurality of fusion bonds, a plurality of apertures, and a plurality of tufts as described herein. At least a portion of these pads include a colored topsheet or a portion thereof. At least a portion of these pads similarly include a printed backsheet, wherein the printing on the backsheet is viewable on a wearer-facing surface of the respective pad. In many of these pads, the printing on the backsheet is not necessarily coordinated with the arrays of apertures, fusion bonds, tufts, or printing on the topsheet. For example, some printed backsheets may include hearts while the apertures, for example, are arranged in the form of chevrons or clouds.

As noted in herein, registration between apertures and printing, tufting and printing, and/or fusion bonds and printing may occur in an absorbent article of the present invention. In some forms, the printing and feature to which the printing is to be registered, e.g. fusion bonds, apertures, tufts, etc., may be configured to increase the likelihood of registration.

Registration of features with other features and/or printing can prove difficult due to web tracking. Web tracking can cause the bond sites to track, for example, +/−1 or 3 or 5 or 10 mm in the machine direction and/or +/−1 or 3 or 5 or 10 mm in the cross machine direction. However, the shapes of the fusion bond pattern, shape of the aperture pattern/size of apertures, and/or tufting pattern may be configured to increase the likelihood of overlap. The examples below apply equally fusion bonds, tufts, embossed areas and apertures.

Referring to FIGS. 86-88C, as noted herein, any component/layer of a disposable absorbent article may comprise printing. Similarly, any component/layer of a disposable absorbent article may comprise bonds. In some specific forms, a topsheet may comprise bonds to join the topsheet to subjacent layers, e.g. secondary topsheets, acquisition layers, distribution layers, etc. In these forms, the subjacent layer may comprise printing or the topsheet may comprise printing. In other forms, a backsheet may comprise printing and/or bonds.

Figure 86:
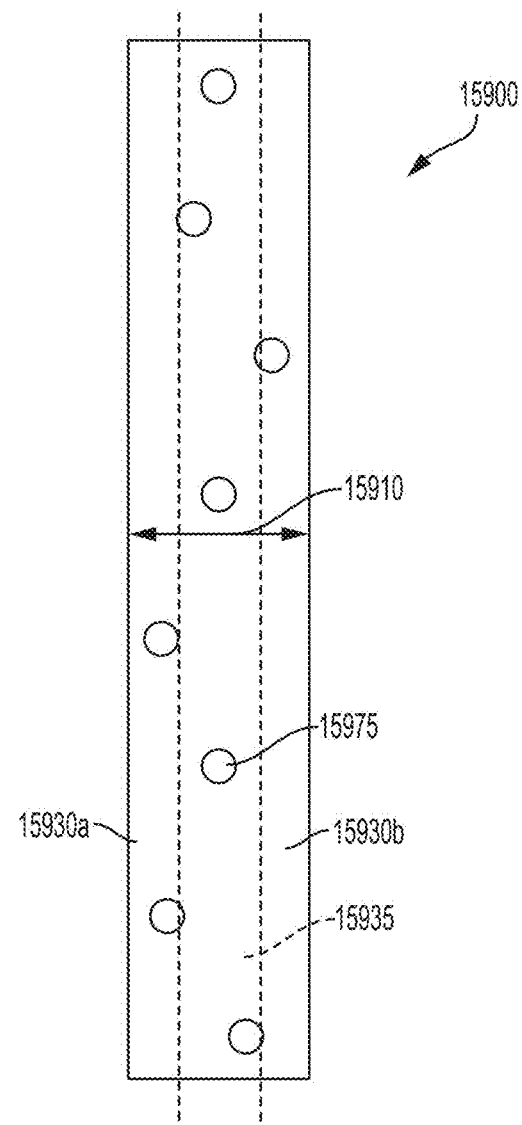
FIGS. 86-88C are schematic illustrations of print signals and fusion bonds.

Referring to FIG. 86, in some forms, printing may be thickened to accommodate web tracking. For example where web tracking is ±3 mm, a printed element 15900 may have a thickness of about 6 mm or greater. In this manner, if the target were to place fusion bond sites 15975 in the center of the element 15900, the thickness of the printed element 15900 could accommodate the web tracking variance of ±3 mm.

In some forms, in addition to the adjustment of the width of the printed element 15900, the printed element 15900 may be provided with a plurality of zones. As shown, the printed element 15900 may comprise a central zone 15935 and two flanking zones 15930a and 15930b. In some forms of the present invention, the central zone 15935 may comprise a darker color while the flanking zones comprise a lighter color, e.g. dark red/light red, dark blue/light blue, etc. For those bonds 15975 which associate with the central zone 15935 as well as the fusion bonds 15975 that associate with the flanking zones 15930a and 15930b, a visible color contrast can still be provided to the user.

Figure 87A:
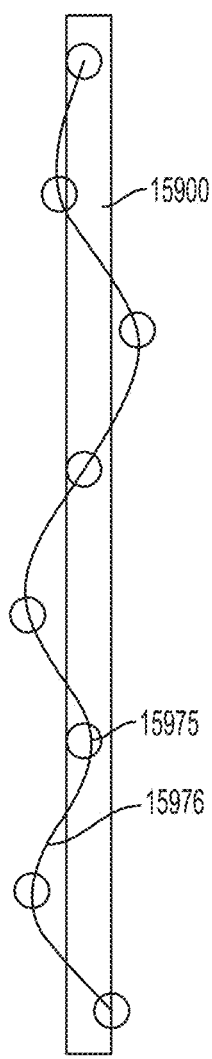
Figure 87B:
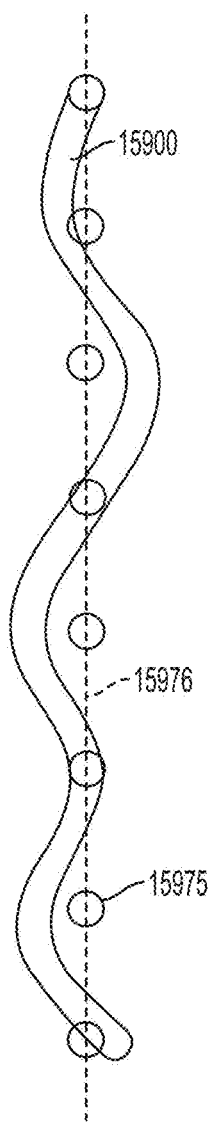
Figure 87C:
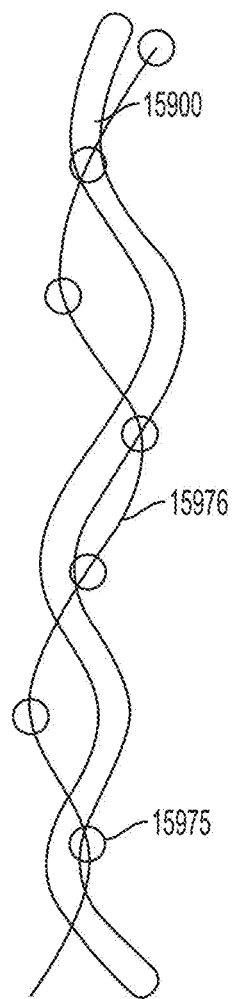

In some forms, the shape of the bonding pattern and the shape of the printing pattern can be coordinated to increase the likelihood of overlap between the two. For example, as shown in FIG. 87A, the shape of the bond pattern may be configured to exhibit variations in direction which are perpendicular to a major axis of the printed element 15900. As shown in FIG. 87A, a path 15976 of the fusion bonds 15975 generally varies perpendicular to length of the printed element 15900. In still another example, as shown in FIG. 87B, the printed element 15900 may vary perpendicular to the general length of the path 15976 of the fusion bonds 15975. While the path variance shown in FIGS. 87A and 87B are waves, additional patterns are contemplated. For example, zig-zag patterns, scalloped patterns—some examples of which are shown herein—may provide a similar benefit. As shown in FIG. 87C, both the fusion bonds 15975 and the print element 15900 may vary along one another's major axis, e.g. length.

Figure 88A:
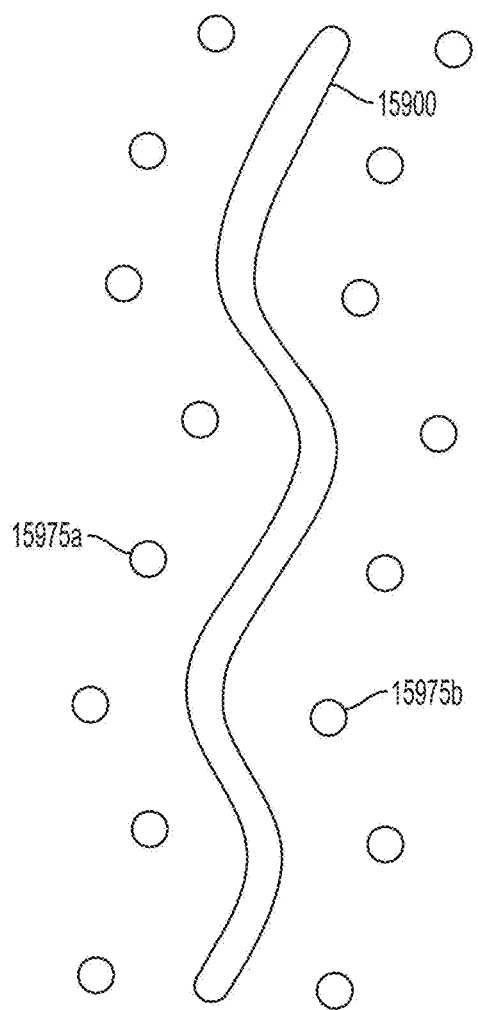

In some additional forms, as shown in FIG. 88A, the printed element 15900 may be disposed on a first layer between a first plurality of bonds 15975a and a second plurality of bonds 15975b. As such, a portion of the bonds of the first plurality 15975a and a portion of the bond of the second plurality 15975b may register with the print element 15900.

Figure 88B:
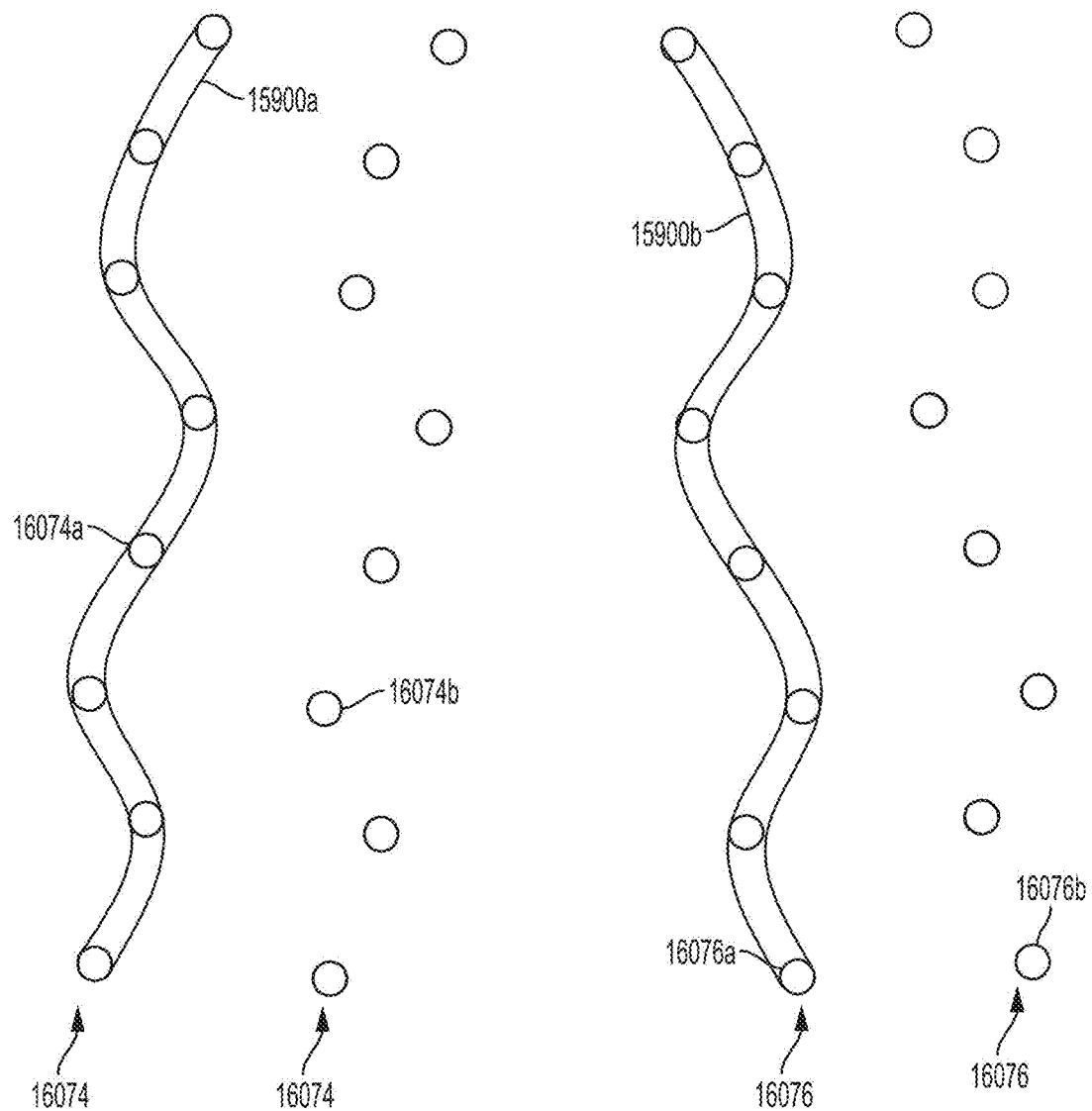

In other forms of the present invention, as shown in FIG. 88B, a first printed element 15900a may be registered with a first plurality of fusion bonds 16074a. An array of fusion bonds 16074 may comprise the first plurality of fusion bonds 16074a and a second plurality of fusion bonds 16074b. The second array of fusion bonds 16074b may be offset with respect to the first plurality of fusion bonds 16074a by about the distance of web tracking. Specifically, if the web tracking is ±5 mm, spacing between the first plurality 16074a and 16074b should be about 10 mm.

Figure 88C:
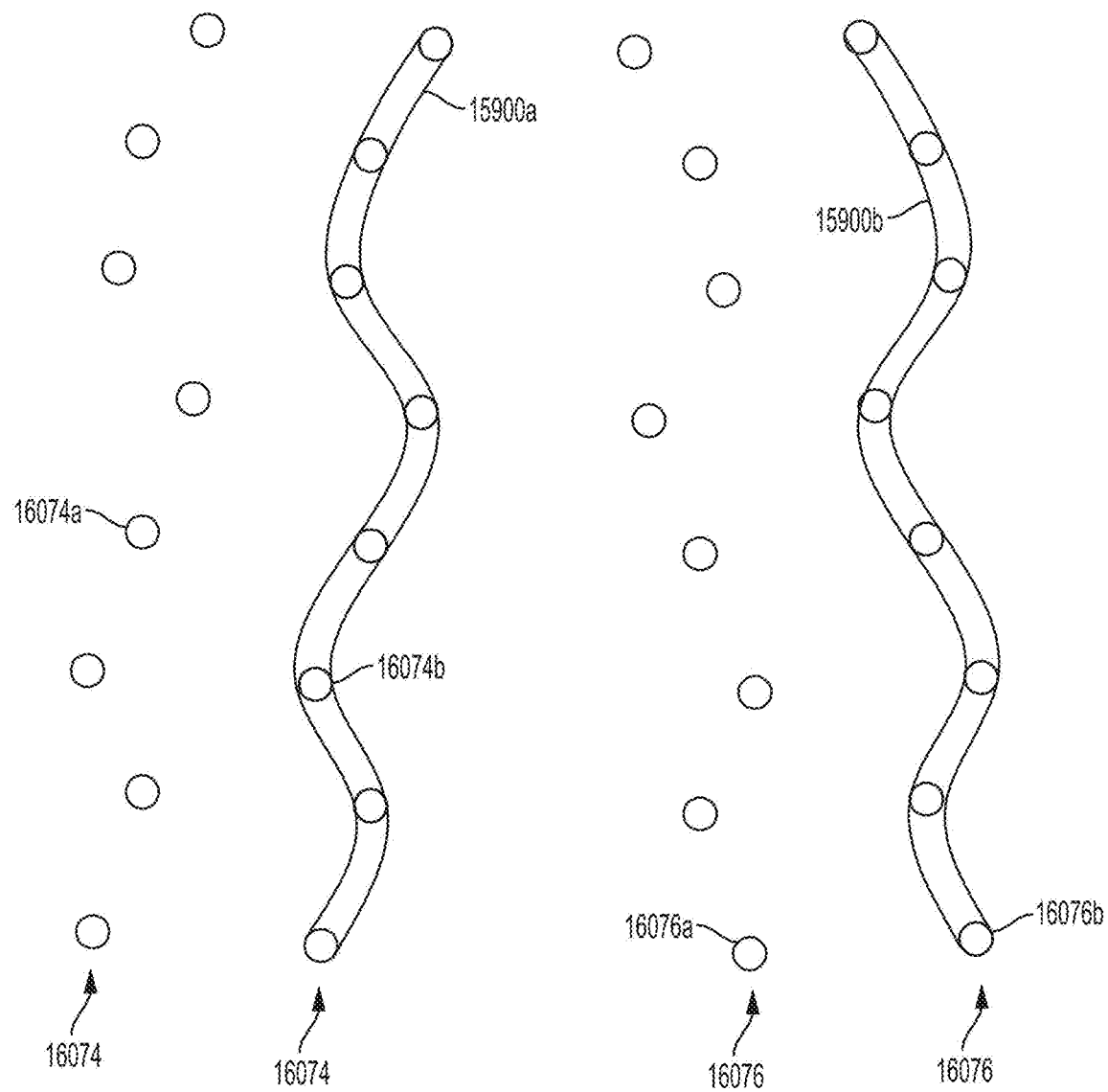

Similarly, a second array of fusion bonds 16076 comprises a first plurality of fusion bonds 16076a and a second plurality of fusion bonds 16076b. As shown, the arrays of fusion bonds 16074 and 16076 and the first print element 15900a and the second print element 15900b may be configured such that the first plurality of fusion bonds of each of the arrays is registered with its respective print stripe. As web tracking moves from left to right on FIG. 88B, the print stripes 15900a and 15900b can migrate between the fusion bonds to eventually be registered with the second plurality of fusion bonds 16074*b* and 16076*b* in each of the respective arrays as shown in FIG. 88C.

Additional arrangements are contemplated. For example, the first print element 15900*a* may be replaced by a first plurality of fusion bonds, and the second print element 15900*b* may be replaced by a second plurality of fusion bonds. The first array of fusion bonds 16074 may be replaced by an array of print elements, e.g. a first print element and a second print element. Similarly, the second array of fusion bonds 16076 may be replaced by an array of print stripes, e.g. a first print element and a second print element. And, similar to the above, the first print element in each of the arrays may be registered with their respective plurality of fusion bonds. As the web tracks from left to right, the fusion bonds may migrate to eventually be registered with the second print element in each of their respective arrays.

Forms of the present invention are contemplated where absorbent articles are arranged in an array. In such forms, the array of absorbent articles may comprise a first absorbent article comprising a first topsheet, a first backsheet, a first absorbent core disposed between the first topsheet and the first backsheet, and a first optional layer also disposed between the first topsheet and the first backsheet. The first topsheet may comprise fibers comprising a non-conventional white pigment that was not printed on and a plurality of mechanically-manipulated features, and at least one of the first absorbent core and the first optional layer comprises a first printed color to collectively create a first visual appearance.

The array further comprises a second absorbent article comprising a second topsheet, a second backsheet, a second absorbent core disposed between the second topsheet and the second backsheet, and a second optional layer also disposed between the second topsheet and the second backsheet, wherein at least one of the second topsheet, the second absorbent core, and the second optional layer comprises printing to create a second visual appearance that simulates the first appearance.

For such array, the mechanically manipulated feature may comprise apertures, tufts, ridges, fusion bond sites, and/or embossed areas. The array may further comprise a first package comprising a plurality of the first absorbent articles and comprising a first brand name, and a second package comprising a plurality of the second absorbent articles and comprising a second brand name that is different from the first brand name. In some forms, the second package may comprise the first brand name, e.g. in a comparative context.

A method of manufacturing an absorbent article may comprise the steps of analyzing a first absorbent article comprising a first topsheet, a first backsheet, a first absorbent core disposed between the first topsheet and the first backsheet, and a first fluid management layer also disposed between the first topsheet and the first backsheet, wherein the first topsheet comprises fibers comprising a non-white pigment that was not printed on and a plurality of mechanically-manipulated regions, and at least one of the first absorbent core and the first fluid management layer comprises a first printed color to collectively create a first visual appearance. The method may further comprise the steps of providing a second topsheet material; providing a second backsheet material; providing a second core material; providing a fluid management material; printing on at least one of the second topsheet, the second core material, and the second fluid management material; combining portions of the second topsheet, the second backsheet material, the second core material, and the second fluid management material to create a second visual appearance that approximates the first visual appearance.

Test Methods

Opacity Method

Opacity by contrast ratio measurements are made using a 0°/45° spectrophotometer suitable for making standard CIE L*a*b* color measurements (e.g. Hunterlab Labscan XE spectrophotometer, Hunter Associates Laboratory Inc., Reston Va. or equivalent). The diameter of the instrument's measurement port should be chosen such that only the region of interest is included within the measurement port. Analyses are performed in a room controlled at about 23° C.±2° C. and 50%±2% relative humidity. Samples are conditioned at the same condition for 2 hours before testing.

Calibrate the instrument per the vender instructions using the standard black and white tiles provided by the vendor. Set the spectrophotometer to use the CIE XYZ color space, with a D65 standard illumination and 10° observer. Using cryogenic spray and scissors carefully excise the specimen from the article for testing. Place the specimen flat against the instrument with the outward facing surface toward the spectrophotometer's measurement port and the region of interest within the port. Ensure that no tears, holes or apertures are within the measurement port. Place the white standard tile onto the opposing surface of the specimen such that it completely covers the measurement port. Take a reading for XYZ and record to 0.01 units. Without moving the specimen, remove the white plate and replace it with the black standard plate. Take a second reading for XYZ and record to 0.01 units. Repeat this procedure at a corresponding site for a total of ten (10) replicate specimens.

Opacity is calculated by dividing the Y value measured using the black tile as backing, divided by the Y value measured using the white tile as backing, then multiplying the ratio by 100. Record the opacity value to the nearest 0.01%. Calculate opacity for the 10 replicates and report the average opacity to the nearest 0.01%.

Aperture/Feret Angle Test

Aperture dimensions, Effective Open Area and Inter-Aperture Distance measurements are obtained from specimen images acquired using a flatbed scanner. The scanner is capable of scanning in reflectance mode at a resolution of 6400 dpi and 8 bit grayscale (a suitable scanner is an Epson Perfection V750 Pro from Epson America Inc., Long Beach Calif. or equivalent). The scanner is interfaced with a computer running an image analysis program (a suitable program is ImageJ v. 1.47 or equivalent, National Institute of Health, USA). The specimen images are distance calibrated against an acquired image of a ruler certified by NIST. A steel frame is used to mount the specimen, which is then backed with a black glass tile (P/N 11-0050-30, available from HunterLab, Reston, Va.) prior to acquiring the specimen image. The resulting image is then threshold, separating open aperture regions from specimen material regions, and analyzed using the image analysis program. All testing is performed in a conditioned room maintained at about 23±2° C. and about 50±2% relative humidity.

Sample Preparation:

To obtain a specimen, tape the absorbent article to a rigid flat surface in a planar configuration. Any leg elastics may be cut to facilitate laying the article flat. A rectilinear steel frame (100 mm square, 1.5 mm thick with an opening 60 mm square) is used to mount the specimen Take the steel frame and place double-sided adhesive tape on the bottom surface surrounding the interior opening. Remove the release paper of the tape, and adhere the steel frame to the apertured layer of the article. Align the frame so that it is parallel and perpendicular to the machine direction (MD) and cross direction (CD) of the apertured layer. Using a razor blade excise the apertured layer from the underlying layers of the article around the outer perimeter of the frame. Carefully remove the specimen such that its longitudinal and lateral extension is maintained to avoid distortion of the apertures. A cryogenic spray (such as Cyto-Freeze, Control Company, Houston Tex.) can be used to remove the specimen from the underlying layers if necessary. Five replicates obtained from five substantially similar articles are prepared for analysis. If the aperture layer of interest is too small to accommodate the steel frame, reduce the frame dimensions accordingly to accomplish the goals of removal of the specimen without distortion of the apertures while leaving an opening of sufficient size to allow for scanning a significant portion of the apertured layer. An apertured substrate raw material is prepared for testing by extending or activating it under the same process conditions, and to the same extent, as it would be for use on the absorbent article, and then in its extended state adhering it to the steel frame as described above for testing. Condition the samples at about 23° C.±2° C. and about 50%±2% relative humidity for 2 hours prior to testing.

Image Acquisition:

Place the ruler on the scanner bed, oriented parallel to the sides of the scanner glass, and close the lid. Acquire a calibration image of the ruler in reflectance mode at a resolution of 6400 dpi (approximately 252 pixels per mm) and 8 bit grayscale, with the field of view corresponding to the dimensions of the interior of the steel frame. Save the calibration image as an uncompressed TIFF format file. Lift the lid and remove the ruler. After obtaining the calibration image, all specimens are scanned under the same conditions and measured based on the same calibration file. Next, place the framed specimen onto the center of the scanner bed, lying flat, with the outward facing surface of the specimen facing the scanner's glass surface. Orient the specimen so that sides of the frame are aligned parallel with and perpendicular to the sides of the scanner's glass surface, so that the resulting specimen image will have the MD vertically running from top to bottom. Place the black glass tile on top of the frame covering the specimen, close the lid and acquire a scanned image. Scan the remaining four replicates in like fashion. If necessary, crop all images to a rectangular field of view circumscribing the apertured region, and resave the files.

Effective Open Area Calculation:

Open the calibration image file in the image analysis program and perform a linear distance calibration using the imaged ruler. This distance calibration scale will be applied to all subsequent specimen images prior to analysis. Open a specimen image in the image analysis program and set the distance scale. View the 8 bit histogram (0 to 255, with one bin per GL) and identify the gray level (GL) value for the minimum population located between the dark pixel peak of the aperture holes and the lighter pixel peak of the specimen material. Threshold the image at the minimum gray level value to generate a binary image. In the binary image the apertures appear as black, with a GL value of 255, and specimen as white, with a GL value of 0.

Using the image analysis program, analyze each of the discrete aperture regions. Measure and record all of the individual aperture areas to the nearest 0.01 mm², including partial apertures along the edges of the image. Discard any apertures with an area less than 0.3 mm². Apertures having a lower area than 0.3 mm² may prove difficult to measure particularly when stray fibers cross the boundary of the aperture. And such apertures with that small of an area are considered to contribute insignificantly to the Effective Open Area. Sum the remaining aperture areas (including whole and partial apertures), divide by the total area included in the image and multiply by 100. Record this value as the % Effective Open Area to the nearest 0.01%.

In like fashion, analyze the remaining four specimen images. Calculate and report the average % effective area values to the nearest 0.01% for the five replicates.

Effective Aperture Area and Absolute Feret Angle:

Open the calibration image (containing the ruler) file in the image analysis program. Resize the resolution of the original image from 6400 dpi to 640 dpi (approximately 25.2 pixels per mm) using a bicubic interpolation. Perform a linear distance calibration using the imaged ruler. This distance calibration scale will be applied to all subsequent specimen images prior to analysis. Open a specimen image in the image analysis program. Resize the resolution of the original image from 6400 dpi to 640 dpi (approximately 25.2 pixels per mm) using a bicubic interpolation. Set the distance scale. View the 8 bit histogram (0 to 255, with one bin per GL) and identify the gray level (GL) value for the minimum population located between the dark pixel peak of the aperture holes and the lighter pixel peak of the specimen material. Threshold the image at the minimum gray level value to generate a binary image. In the binary image the apertures appear as black, with a GL value of 255, and specimen as white, with a GL value of 0. Next, two morphological operations are performed on the binary image. First, a closing (a dilation operation followed by an erosion operation, iterations=1, pixel count=1), which removes stray fibers within an aperture hole. Second, an opening (an erosion operation followed by a dilation operation, iterations=1, pixel count=1), which removes isolated black pixels. Pad the edges of the image during the erosion step to ensure that black boundary pixels are maintained during the operation. Lastly, fill any remaining voids enclosed within the black aperture regions.

Using the image analysis program, analyze each of the discrete aperture regions. During the analysis exclude measurements of partial apertures along the edges of the image, so that only whole apertures are measured. Measure and record all of the individual aperture areas, perimeters, feret diameters (length of the apertures) along with its corresponding angle of orientation in degrees from 0 to 180, and minimum feret diameters (width of the apertures). Record the measurements for each of the individual aperture areas to the nearest 0.01 mm², the perimeters and feret diameters (length and width), to the nearest 0.01 mm, and angles to the nearest 0.01 degree. Discard any apertures with an area less than 0.3 mm². Record the number of remaining apertures, divide by the area of the image and record as the Aperture Density value. The angle of orientation for an aperture aligned with the MD (vertical in the image) will have an angle of 90 degrees. Apertures with a positive slope, increasing from left to right, will have an angle between zero and 90 degrees. Apertures with a negative slope, decreasing from left to right, will have an angle between 90 and 180 degrees. Using the individual aperture angles calculate an Absolute Aperture Angle by subtracting 90 degrees from the original angle of orientation and taking its absolute value. In addition to these measurements, calculate an Aspect Ratio value for each individual aperture by dividing the aperture length by its width. Repeat this analysis for each of the remaining four replicate images. Calculate and report the statistical mean and standard deviation for each of the effective aperture dimension measurements using all of the aperture values recorded from the replicates. Calculate and report the % relative standard deviation (RSD) for each of the aperture dimension measurements by dividing the standard deviation by the mean and multiplying by 100.

Inter-Aperture Distance Measurements:

The average, standard deviation, median, and maximum distance between the apertures can be measured by further analyzing the binary image that was analyzed for the aperture dimension measurements. First, obtain a duplicate copy of the resized binary image following the morphological operations, and using the image analysis program, perform a Voronoi operation. This generates an image of cells bounded by lines of pixels having equal distance to the borders of the two nearest pattern apertures, where the pixel values are outputs from a Euclidian distance map (EDM) of the binary image. An EDM is generated when each inter-aperture pixel in the binary image is replaced with a value equal to that pixel's distance from the nearest pattern aperture. Next, remove the background zeros to enable statistical analysis of the distance values. This is accomplished by using the image calculator to divide the Voronoi cell image by itself to generate a 32-bit floating point image where all of the cell lines have a value of one, and the remaining parts of the image are identified as Not a Number (NaN). Lastly, using the image calculator, multiply this image by the original Voronoi cell image to generate a 32-bit floating point image where the distance values along the cell lines remain, and all of the zero values have been replaced with NaN. Next, convert the pixel distance values into actual inter-aperture distances by multiplying the values in the image by the pixel resolution of the image (approximately 0.04 mm per pixel), and then multiply the image again by 2 since the values represent the midpoint distance between apertures. Measure and record the mean, standard deviation, median and maximum inter-aperture distances for the image to the nearest 0.01 mm. Repeat this procedure for all replicate images. Calculate the % relative standard deviation (RSD) for the inter-aperture distance by dividing the standard deviation by the mean and multiplying by 100.

Land Area Light Transmission Method

The land area light transmission method measures the average amount of light transmitted through specific regions of a specimen. A calibrated light transmission image is obtained using a flatbed scanner. A binary mask is generated to separate discrete aperture regions from the surrounding land area. The binary mask is then registered to the light transmission image, and used to exclude the apertures from the land area in the light transmission image. This enables the average light transmission value for the land area to be calculated.

Sample Preparation:

To obtain a specimen, tape the absorbent article to a rigid flat surface in a planar configuration. Any leg elastics may be cut to facilitate laying the article flat. A rectilinear steel frame (100 mm square, 1.5 mm thick with an opening 60 mm square) is used to mount the specimen. Take the steel frame and place double-sided adhesive tape on the bottom surface surrounding the interior opening. Remove the release paper of the tape, and adhere the steel frame to the apertured layer of the article. Align the frame so that it is parallel and perpendicular to the machine direction (MD) and cross direction (CD) of the apertured layer. Using a razor blade excise the apertured layer from the underlying layers of the article around the outer perimeter of the frame. Carefully remove the specimen such that its longitudinal and lateral extension is maintained to avoid distortion of the apertures. A cryogenic spray (such as Cyto-Freeze, Control Company, Houston Tex.) can be used to remove the specimen from the underlying layers if necessary. Five replicates obtained from five substantially similar articles are prepared for analysis. If the aperture layer of interest is too small to accommodate the steel frame, reduce the frame dimensions accordingly to accomplish the goals of removal of the specimen without distortion of the apertures while leaving an opening of sufficient size to allow for scanning a significant portion of the apertured layer. Condition the samples at about 23° C.±2° C. and about 50%±2% relative humidity for 2 hours prior to testing.

Light Transmission Image

The light transmission measurement is based on the CIE L*a*b* color system (CIELAB). A flatbed scanner capable of scanning a minimum of 24 bit color at 800 dpi and has manual control of color management (a suitable scanner is an Epson Perfection V750 Pro from Epson America Inc., Long Beach Calif. or equivalent) is used to acquire images. The scanner is interfaced with a computer running color management software (suitable color management software is MonacoEZColor available from X-Rite Grand Rapids, Mich. or equivalent). The scanner is calibrated against a color transparency target and corresponding reference file compliant with ANSI method IT8.7/1-1993 using the color management software to construct a calibrated color profile. The resulting calibrated scanner profile is used to color correct an image from a test specimen within an image analysis program that supports sampling in CIE L*a*b* (a suitable program is Photoshop S4 available from Adobe Systems Inc., San Jose, Calif. or equivalent). All testing is performed in a conditioned room maintained at about 23±2° C. and about 50±2% relative humidity.

Turn on the scanner for 30 minutes prior to calibration. Deselect any automatic color correction or color management options that may be included in the scanner software. If the automatic color management cannot be disabled, the scanner is not appropriate for this application. Place the IT8 target face down onto the scanner glass, close the scanner lid, acquire an image at 200 dpi and 24 bit color and remove the IT8 target. Open the image file on the computer with the color management software. Follow the recommended steps within the color management software to create and export a calibrated color profile. These steps may include, ensuring that the scanned image is oriented and cropped correctly. The calibrated color profile must be compatible with the image analysis program. The color management software uses the acquired image to compare with the included reference file to create and export the calibrated color profile. After the profile is created the scan resolution (dpi) for test specimens can be changed, but all other settings must be kept constant while imaging specimens.

Open the scanner lid and place the specimen flat against the scanner glass with the outward facing surface facing the glass. Acquire and import a scan of the specimen region within the interior of the frame into the image analysis software at 24 bit color and at 800 dpi in transparency mode. If necessary, crop image to a rectangular field of view circumscribing the apertured region. Transparency mode illuminates the specimen from one side with the sensor capturing the image from the opposite side. Assign the calibrated color profile to the image and change the color space mode to L*a*b* Color corresponding to the CIE L*a*b* standard. This produces a color corrected image for analysis. Save this color corrected image in an uncompressed format, such as a TIFF file.

Land Area Mask

The boundaries of the apertured areas and land area are identified by thresholding the L* channel image to generate a binary image, separating apertured areas from the surrounding land area. This binary image will then be used as a mask on the corresponding light transmission image to measure the average Light Transmission Value of only the land area.

To do this, first open the color corrected light transmission image in the image analysis software. To generate the land area mask, first separate the L*, a* and b* channels, and select only the L* channel for analysis. The L* channel represents the "Lightness" of the image and has values that range from 0-100. Threshold the L* channel image at a value of 90 to generate a binary image. By thresholding at the level described above, a binary mask image is produced with the discrete aperture areas assigned one value, and the surrounding land area assigned a different value. For example, the discrete aperture areas could appear black, and the surrounding land area could appear white. Save this binary mask image in an uncompressed format, such as a TIFF file.

Analysis of Light Transmission Image

Open both the color corrected light transmission image and the corresponding binary mask image in the image analysis software. To analyze the specimen light transmission image, first separate the L*, a* and b* channels, and select only the L* channel for analysis. Register the light transmission image and the binary mask image to each other. Use the binary mask to exclude the apertures from the light transmission image, and calculate an average L* value (Light Transmission Value) for the remaining surrounding land area. Record this value as the Land Area Light Transmission Value to the nearest 0.1 units. In like fashion, repeat this procedure on all of the replicate specimens. Calculate and report the average of the five individual Land Area Light Transmission Values to the nearest 0.1 units.

Color Measurement—L*, a*, b*

Measurement of Delta E*

The color difference measurement is based on the CIE L* a* b* color system (CIELAB). A flat-bed scanner capable of scanning a minimum of 24 bit color at 1200 dpi and has manual control of color management (a suitable scanner is an Epson Perfection V750 Pro from Epson America Inc., Long Beach Calif.) is used to acquire images. The scanner is calibrated against a color reflection target compliant to ANSI method IT8.7/2-1993 using color management software (a suitable package is i1Scanner for Epson available from X-Rite Grand Rapids, Mich.) to construct a scanner profile. The resulting calibrated scanner profile is opened within an imaging program that supports sampling in CIE L* a* b* (a suitable program is Photoshop CS4 available from Adobe Systems Inc., San Jose, Calif.) to measure colors seen at the user surface of the product.

Turn on the scanner for 30 minutes prior to calibration. Place the IT8 target face down onto the scanner glass and close the scanner lid. Open the Epson Scan software and for the Original options select Reflective mode as the Document Type, Document Table as the Document Source and Photo as the Auto Exposure Type. Acquire an image using the Epson software included with the scanner. Within the Epson software deselect the unsharp mask setting and any automatic color correction or color management options that may be included in the software. If the automatic color management cannot be disabled, the scanner is not appropriate for this application. Acquire a preview scan at 200 dpi and 24 bit color. Insure that the scanned image is straight and first outer surface facing side-up. Crop the image to the edge of the target, excluding all white space around the target, and acquire the final image. The X-Rite i1Scanner software uses this image to compare with included reference files to create and export a calibrated color profile compatible with Photoshop. After the profile is created the scan resolution (dpi) can be changed, but all other settings must be kept constant while imaging samples.

Open the X-Rite i1Scanner software. Select "Scanner Profiling" from the menu on the left side of the screen. Next select the target type as X-Rite Reflective. Load the image of the reference captured with the Epson scanner and then select "Next." Load the reference file that matches the scanner reference target.

Open the scanner lid and place the specimen onto the scanner glass with the first outer surface facing the glass. Cover the specimen with the white background (in this test method white is defined as having L*>94, −2<a*<2, and −2<b*<2) and close the lid. Acquire and import a scan of the specimen into Photoshop at 600 dpi and 24 bit color. Larger areas may be imported at 200 dpi and smaller areas may be imported at 1200 dpi. Assign the calibrated scanner profile to the image and change the mode to Lab Color ("Lab Color" in Photoshop corresponds to the CIE L* a* b* standard). Select the "eyedropper" color selection tool. Set the sampling size of the tool to include as many pixels as possible for the area to be measured. Using the eyedropper tool measure and record L* a* b* values in 8 different bonded areas in the product image. Average the 8 individual L* a* b* values and record as $L_1$, $a_1$, and $b_1$ respectively. Repeat the measure in like fashion for all areas of interest of the product. Calculate and report the color difference (delta E*) between the bonded and unbonded areas using the following equation:

$$\text{delta } E^* = \sqrt{(L^*_2 - L^*_1)^2 + (a^*_2 - a^*_1)^2 + (b^*_2 - b^*_1)^2}$$

and report to the nearest 0.01 units.

Other color analyses that may be useful are made using the calculations of delta Chroma (delta C*) and delta Hue (delta H*).

$$\text{Delta } C^* = \sqrt{a^{*2}_1 + b^{*2}_1} - \sqrt{a^{*2}_2 + b^{*2}_2}$$

$$\text{Delta } H^* = \sqrt{(a^*_2 - a^*_1)^2 + (b^*_2 - b^*_1)^2 - (\text{Delta} C^*)^2}$$

Basis Weight Method

Basis weight of the laminates may be determined by several available techniques, but a simple representative technique involves taking an absorbent article or other consumer product, removing any elastic which may be present and stretching the absorbent article or other consumer product to its full length. A punch die having an area of 45.6 cm² is then used to cut a piece of the laminate (e.g., topsheet, outer cover) from the approximate center of the absorbent article or other consumer product in a location which avoids to the greatest extent possible any adhesive which may be used to fasten the laminate to any other layers which may be present and removing the laminate from other layers (using cryogenic spray, such as Cyto-Freeze, Control Company, Houston, Tex., if needed). The sample is then weighed and dividing by the area of the punch die yields the basis weight of the laminate. Results are reported as a mean of 5 samples to the nearest 0.1 cm².

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article, comprising:
   a. a topsheet having a generally planar first surface comprising a plurality of out-of-plane features and wherein the topsheet has a first color, the topsheet further comprising a first layer and a second layer, wherein each of the first layer and second layer comprise side edges;
   b. a backsheet;
   c. an absorbent core disposed between the topsheet and the backsheet;
   d. an acquisition layer disposed between the topsheet and the absorbent core, the acquisition layer comprising a second color; and
   e. wherein the plurality of out-of-plane features have a feature color different than the first color and the second color, wherein the second layer is disposed between the first layer and the acquisition layer, wherein the first layer side edges are disposed outboard of the second layer side edges, wherein the first layer is more hydrophobic than the second layer, and wherein the first layer has an opacity of between 30 and 60 as determined via the Opacity Method disclosed herein.

2. The disposable absorbent article of claim 1 wherein the first surface is co-planar with a first plane, wherein the first plane comprises a land area color wherein the land area color is different than the feature color.

3. The disposable absorbent article of claim 1, wherein the topsheet further comprises a plurality of apertures, wherein the plurality of apertures have an aperture color which is different than the first color and the second color.

4. The disposable absorbent article of claim 2, wherein the first plane further comprises a melt lip color which is different than the first color and the second color.

5. The disposable absorbent article of claim 1, wherein the out-of-plane features are disposed in the positive Z-direction.

6. The disposable absorbent article of claim 1, wherein the out-of-plane features are disposed in the negative Z-direction.

7. The disposable absorbent article of claim 1, wherein a $\Delta E^*$ between the first color and the second color is between about 3 and about 10.

8. The disposable absorbent article of claim 1, wherein the first color is conventional white.

9. The disposable absorbent article of claim 1, wherein the second color is conventional white.

10. The disposable absorbent article of claim 1, further comprising a plurality of bonds at least between the topsheet and the layer between the topsheet and the absorbent core, wherein the plurality of bonds comprise a bond color, and wherein the bond color is different than the first color and the second color.

11. The disposable absorbent article of claim 3, wherein the apertures are disposed in a first zone between a second zone and a third zone.

12. The disposable absorbent article of claim 11, wherein each of the first zone, second zone, and third zone comprise land areas and wherein a $\Delta L^*$ between the first zone land areas and the second zone land areas is at least about 4.

13. The disposable absorbent article of claim 12, wherein the plurality of out-of-plane features are disposed in the second and third zones.

14. The disposable absorbent article of claim 1, wherein a $\Delta E^*$ between the first color and the feature color is greater than a $\Delta E^*$ between the second color and the feature color.

15. The disposable absorbent article of claim 1, wherein the topsheet comprises a first layer and a second layer, the first layer comprising the first color and the second layer comprising a third color, and wherein the first layer comprises a plurality of discontinuities and wherein the second layer extends through the plurality of discontinuities and forms the plurality of out-of-plane features.

16. The disposable absorbent article of claim 15, wherein a $\Delta E^*$ between the first color and the feature color is greater than a $\Delta E^*$ between the third color and the feature color.

17. The disposable absorbent article of claim 15, further comprising a plurality of apertures extending through both the first layer and second layer.

18. The disposable absorbent article of claim 15, wherein the second color is conventional white.

19. The disposable absorbent article of claim 1, wherein the topsheet comprises a first layer and a second layer, the first layer comprising a first color and the second layer comprising a third color, and wherein the first layer comprises a plurality of discontinuities and forms the plurality of out-of-plane features and wherein the second layer extends through the plurality of discontinuities.

20. The disposable absorbent article of claim 19, further comprising a plurality of apertures extending through both the first layer and second layer.

21. The disposable absorbent article of claim 19, wherein the second color is conventional white.

22. A disposable absorbent article, comprising:
   a topsheet having a first color, the topsheet further comprising a first layer and
   a second layer, wherein each of the first layer and second layer comprise side edges;
   a backsheet;
   an absorbent core disposed between the topsheet and the backsheet;
   an acquisition layer disposed between the topsheet and the absorbent core, the acquisition layer comprising a second color; and
   at least two of the following: a plurality of apertures having an aperture color which is different than the first color and the second color; a plurality of melt lips comprising a melt lip color different than the first color and the second color, a plurality of out-of-plane features comprising a feature color different than the first color and the second color, a plurality of bond sites comprising a bond color which is different than the first color and the second color, an embossed area comprising an embossed color which is different than the first color and the second color, or wing color which is different than the first color and the second color, and wherein the second layer is disposed between the first layer and the acquisition layer, wherein the first layer side edges are disposed outboard of the second layer side edges, wherein the first layer is more hydrophobic than the second layer, and wherein the first layer has an opacity of between 30 and 60 as determined via the Opacity Method disclosed herein.

* * * * *